US011434476B2

(12) United States Patent
Jaenisch et al.

(10) Patent No.: US 11,434,476 B2
(45) Date of Patent: Sep. 6, 2022

(54) METHODS OF EDITING DNA METHYLATION

(71) Applicant: Whitehead Institute for Biomedical Research, Cambridge, MA (US)

(72) Inventors: Rudolf Jaenisch, Brookline, MA (US); X Shawn Liu, Cambridge, MA (US); Hao Wu, Newton, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 481 days.

(21) Appl. No.: 16/326,700

(22) PCT Filed: Aug. 18, 2017

(86) PCT No.: PCT/US2017/047674
§ 371 (c)(1),
(2) Date: Feb. 19, 2019

(87) PCT Pub. No.: WO2018/035495
PCT Pub. Date: Feb. 22, 2018

(65) Prior Publication Data
US 2019/0359959 A1    Nov. 28, 2019

Related U.S. Application Data

(60) Provisional application No. 62/377,520, filed on Aug. 19, 2016.

(51) Int. Cl.
| | | |
|---|---|---|
| *C12N 9/22* | (2006.01) | |
| *A61K 35/30* | (2015.01) | |
| *A61K 35/33* | (2015.01) | |
| *C12N 9/10* | (2006.01) | |
| *C12N 15/11* | (2006.01) | |
| *C12N 15/86* | (2006.01) | |
| *C12N 15/90* | (2006.01) | |
| *A61P 3/10* | (2006.01) | |
| *A61P 9/00* | (2006.01) | |
| *A61P 9/10* | (2006.01) | |
| *A61P 9/12* | (2006.01) | |
| *A61P 11/00* | (2006.01) | |
| *A61P 25/00* | (2006.01) | |
| *A61P 25/16* | (2006.01) | |
| *A61P 25/28* | (2006.01) | |
| *A61P 35/00* | (2006.01) | |
| *A61P 37/06* | (2006.01) | |
| *A61K 38/46* | (2006.01) | |
| *C12N 15/00* | (2006.01) | |
| *C12N 15/113* | (2010.01) | |
| *A61K 31/7088* | (2006.01) | |

(52) U.S. Cl.
CPC ............ *C12N 9/22* (2013.01); *A61K 35/30* (2013.01); *A61K 35/33* (2013.01); *C12N 9/1007* (2013.01); *C12N 15/11* (2013.01); *C12N 15/86* (2013.01); *C12N 15/907* (2013.01); *C12Y 201/01037* (2013.01); *C12N 2310/20* (2017.05); *C12N 2740/15031* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 10,378,027 B2* | 8/2019 | Joung | .................... C12N 15/85 |
| 2015/0353885 A1 | 12/2015 | Sourdive | |
| 2016/0186208 A1 | 6/2016 | Jaenisch et al. | |
| 2019/0127713 A1* | 5/2019 | Gersbach | ............... C12N 15/86 |

FOREIGN PATENT DOCUMENTS

| | | |
|---|---|---|
| EP | 3 382 018 A1 | 10/2018 |
| WO | WO 2013/176772 A1 | 11/2013 |
| WO | WO 2014/172470 A2 | 10/2014 |
| WO | WO 2016/103233 A2 | 6/2016 |
| WO | WO 2016/130600 A2 | 8/2016 |
| WO | WO 2017/064546 A1 | 4/2017 |
| WO | WO 2017/208247 A1 | 12/2017 |

OTHER PUBLICATIONS

Choudhury et al. (CRISPR-dCas9 mediated TET1 targeting for selective DNA demethylation at BRCA1 promoter, Oncotarget, (published Jun. 23, 2016) vol. 7, No. 29, pp. 46545-46556).*
Votja et al. (Repurposing the CRISPR-Cas9 system for targeted DNA methylation, Nucleic Acids Research, 2016, vol. 44, No. 12 5615-5628, published on Mar. 11, 2016).*
Stelzer, Y., Shivalila, C.S., Soldner, F., Markoulaki, S., and Jaenisch, R. (2015). "Tracing dynamic changes of DNA methylation at single-cell resolution." Cell 163, 218-229.
Chen, W.G., Chang, Q., Lin, Y., Meissner, A., West, A.E., Griffith, E.C., Jaenisch, R., and Greenberg, M.E. (2003). "Derepression of BDNF transcription involves calcium-dependent phosphorylation of MeCP2." Science 302, 885-889.
Martinowich, K., Hattori, D., Wu, H., Fouse, S., He, F., Hu, Y., Fan, G., and Sun, Y.E. (2003). "DNA methylation-related chromatin remodeling in activity-dependent BDNF gene regulation." Science 302, 890-893.
Wu, H., and Zhang, Y. (2014). "Reversing DNA methylation: mechanisms, genomics, and biological functions." Cell 156, 45-68.
Schultz, M.D., He, Y., Whitaker, J.W., Hariharan, M., Mukamel, E.A., Leung, D., Rajagopal, N., Nery, J.R., Urich, M.A., Chen, H., et al. (2015). "Human body epigenome maps reveal noncanonical DNA methylation variation." Nature 523, 212-216.
Wang, H., Maurano, M.T., Qu, H., Varley, K.E., Gertz, J., Pauli, F., Lee, K., Canfield, T., Weaver, M., Sandstrom, R., et al. (2012). "Widespread plasticity in CTCF occupancy linked to DNA methylation." Genome Res 22, 1680-1688.

(Continued)

*Primary Examiner* — Suzanne M Noakes
*Assistant Examiner* — Jae W Lee
(74) *Attorney, Agent, or Firm* — Morse, Barnes-Brown & Pendleton, P.C.; Lisa M. Warren, Esq.; Erin E. Bryan, Esq.

(57) ABSTRACT

The invention relates to methods of modifying DNA methylation by contacting a catalytically inactive site specific nuclease fused to an effector domain having methylation or demethylation activity and one or more guide sequences.

16 Claims, 48 Drawing Sheets

Specification includes a Sequence Listing.

(56) References Cited

OTHER PUBLICATIONS

Sweatt, J.D. (2013). "The emerging field of neuroepigenetics." Neuron 80, 624-632.

Kang, J.Y., Song, S.H., Yun, J., Jeon, M.S., Kim, H.P., Han, S.W., and Kim, T.Y. (2015). "Disruption of CTCF/cohesin-mediated high-order chromatin structures by DNA methylation downregulates PTGS2 expression." Oncogene 34, 5677-5684.

Bell, A.C., and Felsenfeld, G. (2000). "Methylation of a CTCF-dependent boundary controls imprinted expression of the Igf2 gene." Nature 405, 482-485.

Rudolph Jaenish, Nuclear Cloning and the Reprogramming of the Genome, R01 HD045022 01-R01 HD045022 05; Funding date: Jul. 28, 2003-May 1, 2007.

Rudolph Jaenish, In Vitro Reprogramming of Somatic Cells Into Pluripotent ES-Like Cells, R01 HD045022 06-R01 HD045022 15; Funding date: Jun. 15, 2008-Jun. 1, 2017.

Vojta, Aleksandar, et al. "Repurposing the CRISPR-Cas9 system for targeted DNA methylation." *Nucleic acids research* 44.12 (2016): 5615-5628.

Xu, Xingxing, et al. "A CRISPR-based approach for targeted DNA demethylation." *Cell discovery* 2.1 (2016): 1-12.

Kungulovski, Goran, and Albert Jeltsch. "Epigenome editing: state of the art, concepts, and perspectives." *Trends in Genetics* 32.2 (2015): 101-113.

McDonald, James I., et al. "Reprogrammable CBISPR/Cas9-based system for inducing site-specific DNA methylation." *Biology open* 5.6 (2016): 866-874.

Xiong, Tina, et al. "Targeted DNA methylation in human cells using engineered dCas9-methyltransferases." *Scientific reports* 7.1 (2017): 1-14.

Morita, Sumiyo, et al."Targeted DNA demethylation in vivo using dCas9-peptide repeat and scFv-TET1 catalytic domain fusions." *Nature biotechnology* 34.10 (2016): 1060-1065.

Stepper, Peter, et al. "Efficient targeted DNA methylation with chimeric dCas9-Dnmt3a-Dnmt3L methyltransferase." *Nucleic acids research* 45.4 (2016): 1703-1713.

Lo, Albert, and Lei Qi. "Genetic and epigenetic control of gene expression by CRISPR-Cas systems." *F1000Research* 6 (2017): 747.

International Search Report for International Application No. PCT/US17/47674, dated Jan. 4, 2018.

Dávalos-Salas, Mercedes, et al. "Gain of DNA methylation is enhanced in the absence of CTCF at the human retinoblastoma gene promoter," *BMC cancer*11.1 (2011): 1-11.

Ishimaru, Naoki, et ai. "Differential epigenetic regulation of BDNF and NT-3 genes by trichostatin A and 5-aza-2'-deoxycytidine in Neuro-2a cells." *Biochemical and biophysical research communications*394.1 (2010): 173-177.

Brunk, Brian P., David J. Goldhamer, and Charles P. Emerson Jr. "Regulated demethylation of themyoddistal enhancer during skeletal myogenesis." *Developmental biology*177.2 (1996): 490-503.

* cited by examiner

2A
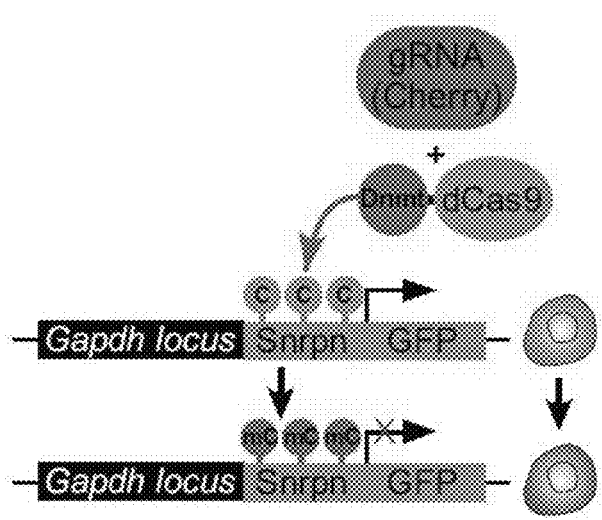
2B
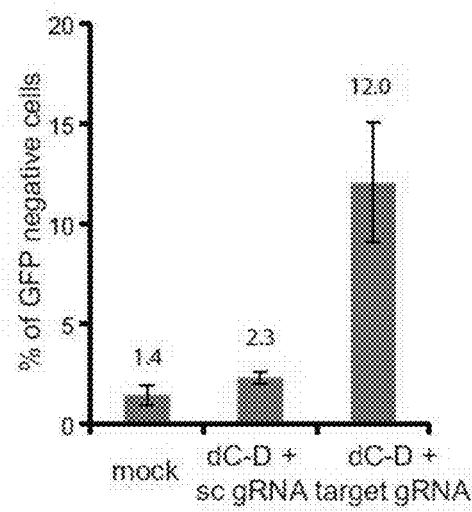
2C
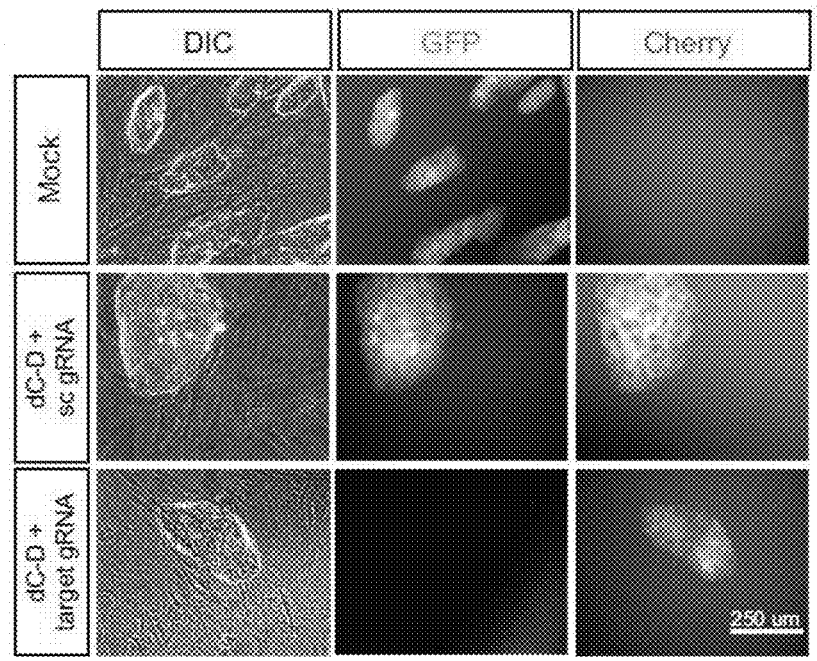
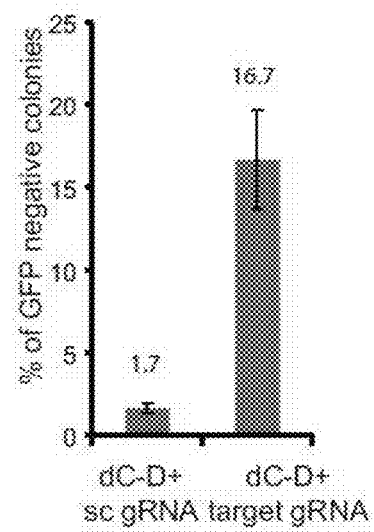
FIGS. 2A-2C

2G

2H

6C

6D

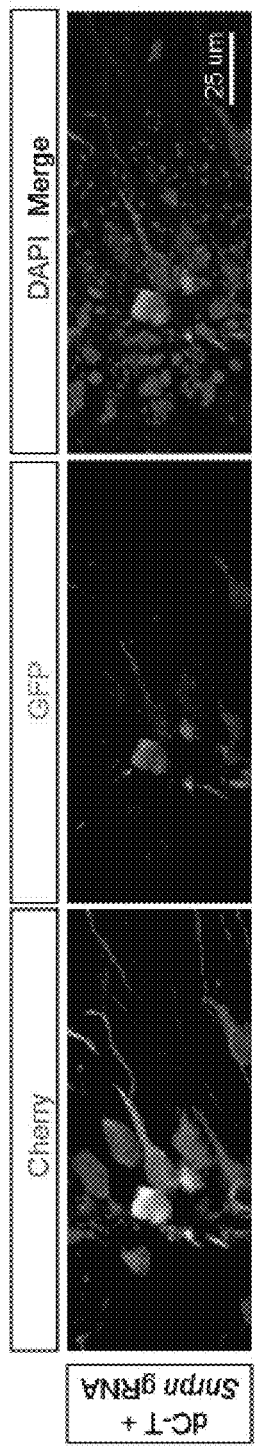
FIGS. 7F-7H

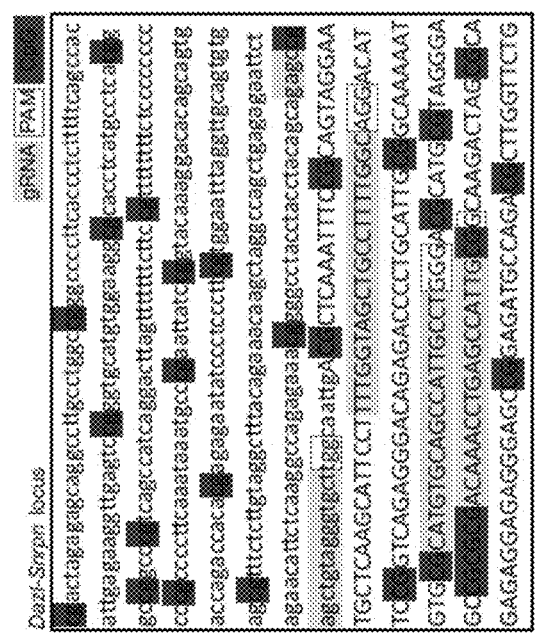
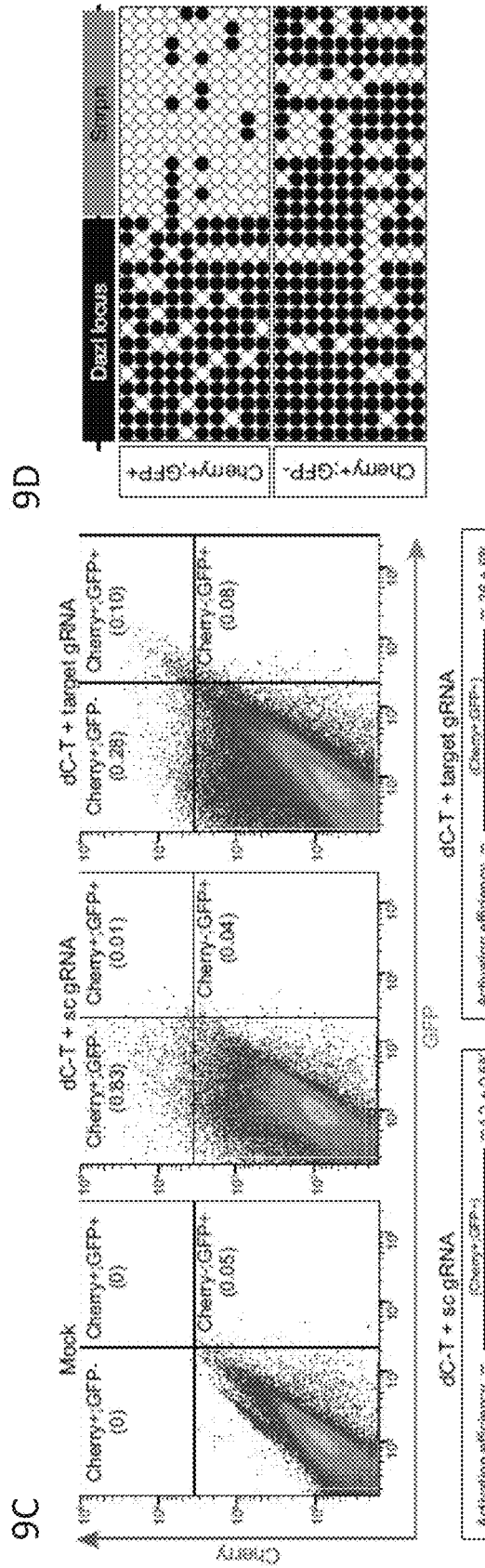
FIGS. 9A-9D

12A
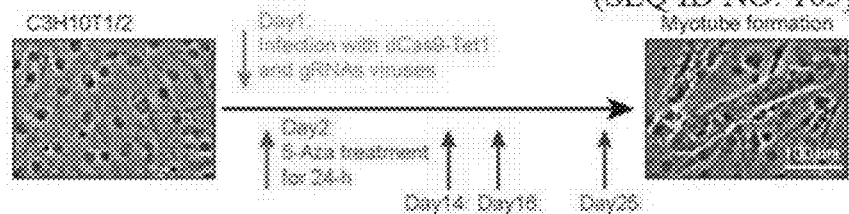
(SEQ ID NO: 165)
12B
12C
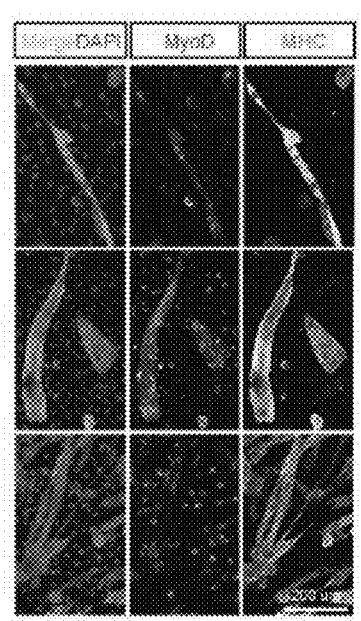
12D
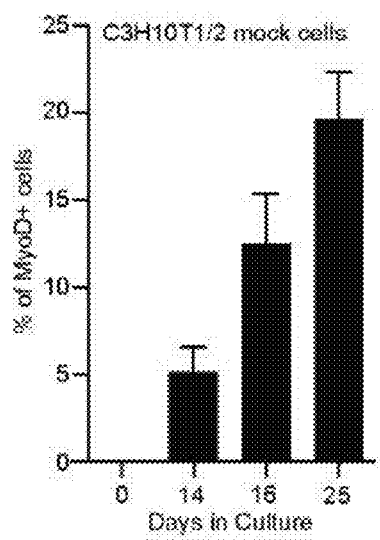
12E
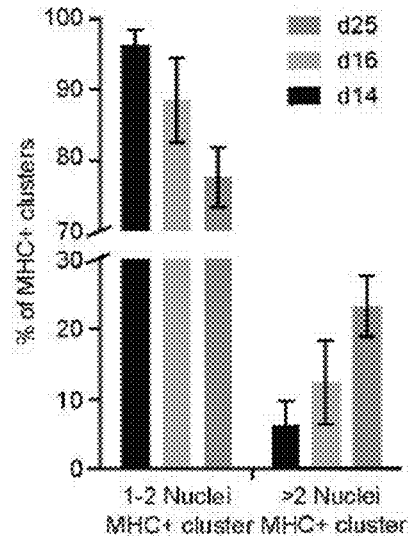
FIGS. 12A-12E

METHODS OF EDITING DNA METHYLATION

RELATED APPLICATIONS

This application claims the benefit of U.S. Provisional Application Ser. No. 62/377,520, filed Aug. 19, 2016, the contents of which is hereby incorporated by reference in its entirety.

GOVERNMENT SUPPORT

This application is a national stage filing under 35 U.S.C. 371 of International Application No. PCT/US2017/047674, filed Aug. 18, 2017, which claims the benefit of U.S. Provisional Application Ser. No. 62/377,520, filed Aug. 19, 2016, the contents of which are hereby incorporated by reference in their entirety.

BACKGROUND OF THE INVENTION

Mammalian DNA methylation at 5-cytosine plays critical roles in many biological processes, including genomic imprinting, cell fate determination, chromatin architecture organization, maintenance of cell identity, and regulation of gene expression (Bird, 2002; Cedar and Bergman, 2012; Jaenisch and Bird, 2003; Smith and Meissner, 2013). Genetic studies have revealed that DNA methylation is essential for mammalian development and adaptation to environmental signals (Jaenisch and Bird, 2003; Li et al., 1992; Smith and Meissner, 2013). Abnormal DNA methylation has been observed in cancer and neurological disorders (Laird and Jaenisch, 1996; Robertson, 2005). Owing to the advancement in sequencing technologies, single-nucleotide resolution methylation maps for many types of human and mouse cells and tissues have been depicted (Lister et al., 2009; Schultz et al., 2015). Importantly, these maps have allowed for the identification of differentially methylated regions (DMRs) at base pair resolution during different stages of normal development (Lister et al., 2013) as well as disease (De Jager et al., 2014; Doi et al., 2009; Landau et al., 2014). However, investigation of the functional significance of these DMRs remains a challenge due to lack of appropriate molecular tools that enable efficient editing of DNA methylation in a targeted manner.

SUMMARY OF THE INVENTION

Mammalian DNA methylation is a epigenetic mechanism orchestrating gene expression networks in many biological processes. However, investigation of the functions of specific methylation events remains challenging. It is demonstrated that fusion of Tet1 or Dnmt3a with a catalytically inactive Cas9 (dCas9) enables targeted DNA methylation editing. Targeting of the dCas9-Tet1 or -Dnmt3a fusion protein to methylated or unmethylated promoter sequences caused activation or silencing, respectively, of an endogenous reporter. Targeted demethylation of the BDNF promoter IV or the MyoD distal enhancer by dCas9-Tet1 induced BDNF expression in post-mitotic neurons or activated MyoD facilitating reprogramming of fibroblasts into myoblasts, respectively. Targeted de novo methylation of a CTCF loop anchor site by dCas9-Dnmt3a blocked CTCF binding and interfered with DNA looping, causing altered gene expression in the neighboring loop. Finally, it is shown that these tools can edit DNA methylation in mice demonstrating their wide utility for functional studies of epigenetic regulation. These tools will be useful to gain insight into the functional significance of DNA methylation in diverse biological processes such as gene expression, cell fate determination, and organization of high-order chromatin structures. Furthermore, these tools would be useful to build a screening platform to identify functionally specified differentially methylated regions (DMRs) when combined with different sgRNA libraries, and to generate transgenic mice to study specific DNA methylation events in vivo.

Disclosed herein are methods of modifying one or more genomic sequences in a cell, the methods comprising introducing into the cell a catalytically inactive site specific nuclease fused to an effector domain having methylation activity; and one or more guide sequences, thereby modifying one or more genomic sequences in the cell.

Also disclosed herein are methods of modifying one or more genomic sequences in a cell, the methods comprising introducing into the cell a catalytically inactive site specific nuclease fused to an effector domain having demethylation activity; and one or more guide sequences, thereby modifying one or more genomic sequences in the cell.

Also disclosed herein are methods of modulating the methylation of one or more genomic sequences in a cell, the methods comprising introducing into the cell a catalytically inactive site specific nuclease fused to an effector domain having methylation or demethylation activity; and a guide sequence or a nucleic acid that encodes a guide sequence, thereby modulating the methylation of one or more genomic sequences in a cell.

In certain aspects, the genomic sequence comprises a differentially methylated region, an enhancer (e.g., an enhancer of MyoD), a promoter (e.g., a BDNF promoter), or a CTCF binding site. In some aspects, the effector domain comprises Tet1. In other aspects, the effector domain comprises Dnmt3a.

In some aspects, the catalytically inactive site specific nuclease is a catalytically inactive Cas protein (e.g., a Cas9 protein or a Cpf1 protein). The guide sequences may be ribonucleic acid guide sequences. In certain aspects, the guide sequence is from about 10 base pairs to about 150 base pairs in length. The one or more guide sequences may comprise two or more guide sequences.

In some embodiments, 2, 3, 4, 5, 6, 7, 8, 9, 10, 11, 12, 13, 14, 15, 16, 17, 18, 19, or 20 genomic sequences are modified in the cell. The cell may be a stem cell, a neuron, a post-mitotic cell, or a fibroblast. In some aspects, the cell is a human cell or a mouse cell.

In some aspects, one or more nuclear localization sequences are fused between the catalytically inactive site specific nuclease and the effector domain. In certain aspects, one or more of the genomic sequences are associated with a disease or condition.

In certain aspects, the methods further comprise contacting the cell with an agent that inhibits or enhances DNA methylation. The agent may be a small molecule. For example, the agent is 5-azacytidine or 5-azadeoxycytidine.

In certain embodiments, the methods further comprise introducing the cell into a non-human mammal. The non-human mammal may be a mouse.

Also disclosed are isolated modified cell produced by the methods described herein.

Also disclosed herein are methods of treating a patient in need thereof, the method comprising administering a modified cell described herein to a patient in need of such cells.

Also disclosed are method of modulating the methylation of one or more genomic sequences that cause a disease in an individual in need thereof comprising introducing into the individual a catalytically inactive site specific nuclease fused to an effector domain having methylation or demethylation activity; and one or more guide sequences, thereby modulating the methylation of one or more genomic sequences that cause a disease in the individual.

Also disclosed are modified cells having a modified genome comprising a first genomic modification in which the methylation of a genomic sequence has been modulated, wherein the modulation occurs by contacting a cell with a catalytically inactive site specific nuclease fused to an effector domain having methylation or demethylation activity, and one or more guide sequences.

Also disclosed herein are methods of modulating the methylation of one or more genomic sequences in a cell, the methods comprising contacting the cell with a nucleic acid that encodes a polypeptide comprising a catalytically inactive site specific nuclease fused to an effector domain having methylation or demethylation activity; and a guide sequence or a nucleic acid that encodes a guide sequence.

Also disclosed herein, are methods of modulating the methylation of one or more genomic sequences in an individual, the methods comprising administering to the individual a nucleic acid that encodes a polypeptide comprising a catalytically inactive site specific nuclease fused to an effector domain having methylation or demethylation activity; and a guide sequence or a nucleic acid that encodes a guide sequence.

In some aspects, the guide sequence targets the polypeptide to the one or more genomic sequences. The genomic sequence may comprise a differentially methylated region, an enhancer, a promoter, or a CTCF binding site. In certain aspects, the method comprises modulating the methylation of at least two genomic sequences in a cell, wherein the genomic sequences are selected from differentially methylated regions, enhancers, promoters, and CTCF binding sites.

In some embodiments, the effector domain comprises Tet1 or Dnmt3a. In some aspects, the catalytically inactive site specific nuclease is a catalytically inactive Cas protein (e.g., a dCas9 protein).

In certain aspects, the methods further comprise administering to the individual an agent that inhibits or enhances DNA methylation. The agent may be a small molecule. For example, the agent is 5-azacytidine or 5-azadeoxycytidine.

Also disclosed herein, are methods of treating a patient in need thereof, the methods comprising administering to the patient a nucleic acid that encodes a polypeptide comprising a catalytically inactive site specific nuclease fused to an effector domain having methylation activity; and a guide sequence or a nucleic acid that encodes a guide sequence.

Also disclosed are methods of modulating the expression of one or more genes of interest in a cell, wherein a differentially methylated region is located within 50 kB of the transcription start site of the gene, the methods comprising contacting the cell with a nucleic acid that encodes a polypeptide comprising a catalytically inactive site specific nuclease fused to an effector domain having methylation or demethylation activity; a guide sequence or a nucleic acid that encodes a guide sequence, wherein the guide sequence targets the polypeptide to the differentially methylated region.

In some aspects, the differentially methylated region is hypermethylated in the cell and the effector domain (e.g., Tet1) has demethylation activity. In other aspects, the differentially methylated region is unmethylated in the cell and the effector domain (e.g., Dnmt3a) has methylation activity. In some embodiments, the cell is a stem cell, a post-mitotic cell, a neuron, or a fibroblast.

Also disclosed herein are methods of identifying a genomic sequence whose methylation status affects expression of a gene of interest, the methods comprising contacting a cell with a nucleic acid that encodes a polypeptide comprising a catalytically inactive site specific nuclease fused to an effector domain having methylation or demethylation activity; a guide sequence or a nucleic acid that encodes a guide sequence, wherein the guide sequence targets the polypeptide to a candidate genomic sequence; and measuring expression of the gene, wherein the genomic sequence is identified as one whose methylation status affects expression of the gene of interest if expression of the gene in the cell contacted with the nucleic acid differs from the level of methylation of said genomic region in a control cell not contacted with the nucleic acid.

In some aspects, the genomic sequence comprises a differentially methylated region, an enhancer, a promoter, or a CTCF binding site. In certain aspects, the method comprises modulating the methylation of at least two genomic sequences selected from: differentially methylated regions, enhancers, promoters, and CTCF binding sites. The one or more genomic sequences may be located within 50 kB of the transcription start site (TSS) of the gene.

In certain aspects, the effector domain has methylation activity. For example, the effector domain is Dnmt3a. In other aspects, the effector domain has demethylation activity. For example, the effector domain is Tet1. In some aspects, the cell is a stem cell, a post-mitotic cell, a neuron, or a fibroblast. In certain embodiments, one or more nuclear localization sequences is fused between the polypeptide comprising the catalytically inactive site specific nuclease and the effector domain.

Also disclosed herein are methods comprising identifying a genomic region whose methylation status affects expression of a gene of interest according to the method described herein; contacting a cell with a test agent; and measuring methylation of the identified genomic region in the cell, wherein the test agent is identified as a modulator of methylation of the genomic region if the level of methylation of the genomic region in the cell contacted with the test agent differs from the level of methylation of said genomic region in a control cell not contacted with the test agent (e.g., a small molecule).

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A Upper panel: provides schematic representation of a catalytic inactive mutant Cas9 (dCas9) fused with Tet1 for erasing DNA methylation, and with Dnmt3a for de novo methylation of specific sequences. Lower panel: shows optimized dCas9-effector construct with nuclear localization signal (NLS) linking dCas9 with Tet1, and a guide RNA construct with puro and Cherry cassettes. FIG. 1B is a schematic representation of targeting the Snrpn promoter region by dCas9-Tet1 with specific gRNAs to erase methylation and activate GFP expression. FIG. 1C shows Dazl-Snrpn-GFP mESCs were infected with lentiviruses expressing dCas9-Tet1 (dC-T) with a scrambled gRNA (sc gRNA) or 4 gRNAs targeting the Snrpn promoter region (target gRNA). Percentage of GFP positive cells were calculated by flow cytometric analysis of these cells 3-day post infection, and shown as the mean percentages of GFP positive cells ±SD of two biological replicates. Note that the percentages of GFP-positive cells are expressed as the fraction of infected Cherry-positive cells. FIG. 1D Left: shows representative fluorescence images of the sorted Cherry positive cells in FIG. 1C after culturing for 1 week. Scale bar: 250 um. Right: provides percentages of GFP positive colonies were quantified, and shown as the mean percentages of GFP positive cells ±SD of two biological replicates. FIG. 1E shows the bisulfite sequencing of cells described in FIG. 1C. FIG. 1F provides methylation levels of individual CpGs in the Snrpn promoter region and the adjacent Dazl locus. Shown is the mean percentage±SD of two biological replicates.

FIGS. 2A-2H depicts silencing of the Gapdh-Snrpn-GFP reporter by dCas9-Dnmt3a. FIG. 2A shows a schematic representation of targeting the Snrpn promoter region by dCas9-Dnmt3a with specific gRNAs to methylate the promoter and silence GFP expression. FIG. 2B shows Gapdh-Snrpn-GFP mESCs were infected with lentiviruses expressing dCas9-Dnmt3a (dC-D) with a scrambled gRNA (sc gRNA) or gRNAs targeting the Snrpn promoter region (target gRNA). Percentage of GFP negative cells was calculated by flow cytometric analysis 3-days after infection, and is shown as the mean percentages of GFP negative cells ±SD of two biological replicates. Note that the percentages of GFP-positive cells are expressed as the fraction of infected Cherry-positive cells. FIG. 2C Left: shows representative fluorescence images of the sorted Cherry-positive cells in B after culturing for 1 week. Scale bar: 250 um. Right: shows percentages of GFP negative colonies were quantified, and are shown as the mean percentages of GFP negative cells ±SD of two biological replicates. FIG. 2D provides bisulfite sequencing of cells described in FIG. 2B. FIG. 2E depicts methylation levels of individual CpGs in the Snrpn promoter region and the adjacent Gapdh locus. Shown is the mean percentage±SD of two biological replicates. FIG. 2F shows Gapdh-Snrpn-GFP mESCs with Doxycycline-inducible dCas9-Dnmt3a were infected with lentiviruses expressing gRNAs targeting the Snrpn promoter region in the presence of Doxycycline (2 ug/ml). Percentages of GFP negative cells were calculated by flow cytometric analysis 3-day after infection, and are shown as the mean percentages of GFP negative cells ±SD of two biological replicates. Note that the percentages of GFP-positive cells are expressed as the fraction of infected Cherry-positive cells. FIG. 2G Left: depicts representative fluorescence images of the sorted Cherry-positive population in FIG. 2F after culturing for 1 week with or without Doxycycline. Scale bar: 250 um. Right: shows percentages of GFP negative colonies were quantified, and are shown as the mean percentages of GFP negative cells ±SD of two biological replicates. FIG. 2H depicts methylation level of each individual CpG in the Snrpn promoter region and the adjacent Gapdh locus from cells in FIG. 2G. Shown is the mean percentage±SD of two biological replicates.

FIG. 3A provides a schematic representation of targeting BDNF promoter IV by dCas9-Tet1 (dC-T) with specific gRNAs to erase methylation and activate BDNF expression. FIG. 3B shows mouse cortical neurons cultured in vitro for 3 days (DIV3) were infected with lentiviruses expressing dC-T with or without gRNAs targeting the BDNF promoter IV, or a catalytic dead form of Tet1 (dC-dT, with mutations at H1672Y and D1674A) with BDNF gRNAs for 2 days, and then treated with or without KCl (50 mM) for 6 hours before harvesting for RT-qPCR analysis. Bars are mean+SD of three biological replicates. FIG. 3C provides representative confocal images for BDNF induction in FIG. 3B. Top panel: BDNF expression was induced by 50 mM KCl treatment for 6 hrs. Lower panels: BDNF expression was significantly induced when dC-T was co-expressed with gRNAs targeting BDNF promoter IV region. Note that co-expression of dC-dT with BDNF gRNAs did not activate BDNF expression. Stained in red for MAP2 (top two panels) or Cherry (bottom two panels), green for BDNF, blue for DAPI and grey for dCas9. Scale bar: 50 um. FIG. 3D depicts bisulfite sequencing of neurons in FIG. 3C. FIG. 3E shows methylation levels of each individual CpGs in the BDNF promoter IV region. Shown is the mean percentage±SD of two biological replicates.

FIG. 4A provides a schematic representation of targeting the MyoD distal enhancer (DE) region in DMR-5 by dCas9-Tet1 (dC-T) with specific gRNAs. FIG. 4B shows C3H10T1/2 mouse embryonic fibroblast cells were infected with lentiviruses expressing dC-T with target gRNAs, or a catalytic dead form of Tet1 (dC-dT) with target gRNAs for 2 days. Cherry positive cells were FACS sorted for RT-qPCR analysis. Bars represent mean±SD of three experimental replicates. FIG. 4C bisulfite sequencing of cells in FIG. 4B. FIG. 4D shows methylation level of individual CpGs in the MyoD DE region. Shown is the mean percentage±SD of two biological replicates. FIG. 4E shows representative confocal images for C3H10T1/2 cells on day 14 in the fibroblast-to-myoblast conversion assay. C3H10T1/2 cells were plated as 1×104 cells per well in 6-well plate, and then infected with lentiviruses expressing dC-T and gRNAs targeting DMR-5, or a catalytic dead form of Tet1 (dC-dT) with target gRNAs. 24-hour post infection, cells were treated with vehicle control (HEPES buffer) or 5-Azacytidine (1 uM) for 24-hour, and then harvested after 14 days for immunofluorescence staining. Stained in green for MyoD, magenta for MHC and blue for DAPI. Scale bar: 200 um. FIG. 4F provides quantification of MyoD positive cell ratio 14-day post infection with lentiviruses expressing dC-T alone, dC-T with gRNAs targeting DMR-5, and dC-dT with the target gRNAs. FIG. 4G shows a distribution profile of MHC positive cell clusters based on nuclei number per MHC+ cluster (grouped as 2-5, 6-10, 11-20 and >20 nuclei per MHC+ cluster) 14-days post infection. When treated with 5-Aza, co-expression of dC-T and the target gRNAs, but not of the other combinations significantly facilitates formation of more matured, larger MHC+ clusters compared to mock control or dC-T alone. FIG. 4H provides quantification of myotube density in MHC positive clusters with more than 2 or 5 nuclei at 14-days after infection. Addition of 5-Aza induces MHC+ myotube formation. Co-expression of dC-T and the target gRNAs synergizes with 5-Aza significantly, inducing more and larger myotubes (>5 nuclei MHC+ clusters). Data are quantified from 3-5 representative images for F-H. Bars represent mean±SD.

FIG. 5A provides a schematic representation of targeting the CTCF binding site by dCas9-Dnmt3a with specific gRNAs to induce de novo methylation, blocking CTCF recruitment, and opening CTCF loops which alters gene expression in the adjacent loop. FIG. 5B provides a schematic representation of CTCF target-1 (miR290 locus) with super-enhancer and miR290 in the loop, AU018091 gene in the left neighboring loop, and Nlrp12 gene in the right neighboring loop (close to the targeted CTCF binding site). The Myadm gene is in the adjacent loop right to the loop containing Nlrp12. The super-enhancer domain is indicated as a red bar. The targeted CTCF site is highlighted with a box. ChIP-seq binding profiles (reads per million per base pair) for CTCF in black and H3K27Ac (super-enhancer) in red, and methylation track in yellow with DMR in blue are also shown. FIGS. 5C-5E show doxycycline-inducible dCas9-Dnmt3a mESCs were infected with lentiviruses expressing a scrambled gRNA or CTCF target-1 gRNAs, and dC-dT with CTCF target-1 gRNAs for 3 days, and then Cherry-positive cells were FACS sorted. After cultured in the presence of Doxycycline for 3 day, these cells were plated on gelatin-coated plates for 1 hour to remove feeder cells and then harvested for RT-qPCR analysis in FIG. 5C, for bisulfite-sequencing analysis in FIG. 5D & FIG. 5E. Bars represent mean±SD of three experimental replicates. FIG. 5F provides a schematic representation of CTCF target-2 with super-enhancer and Pou5f1 gene in this loop, H2Q10 gene in the left neighboring loop (close to the targeted CTCF binding site), and Tcf19 in the right neighboring loop. The super-enhancer domain is indicated as a red bar. The targeted CTCF site is highlighted with a box. ChIP-seq binding profiles (reads per million per base pair) for CTCF in black and H3K27Ac (super-enhancer) in red, and methylation track in yellow with DMR in blue are also shown. FIGS. 5G-5I show the same set of experiments performed as described in FIGS. 5C-5E for CTCF target-2, and cells were harvested for RT-qPCR analysis as in FIG. 5C and for bisulfite sequencing as in FIG. 5D and FIG. 5E. Bars represent mean±SD of three experimental replicates.

FIG. 6A provides Quantitative Chromosome Conformation Capture (3C) analysis of cells described in C at the miR290 locus. The super-enhancer domain is indicated as a red bar. The targeted CTCF site is highlighted with a box. Arrows indicate the chromosomal positions between which the interaction frequency was assayed. Asterisk indicates the 3C anchor site. ChIP-seq binding profiles (reads per million base pair) for CTCF in black and H3K27Ac (super-enhancer) in red, and methylation track in yellow with DMR in blue are also shown. The interaction frequencies between the indicated chromosomal positions and the 3C anchor sites are displayed as a bar chart (mean±SD) on the bottom panel. qPCR reactions were run in duplicates, and values are normalized against the mean interaction frequency in cells with a scrambled gRNA. ($p<0.05$ for all three regions; Student's t test, ns stands for non-significant, NC stands for negative control.) FIG. 6B shows anti-CTCF ChIP experiment was performed using cells in FIG. 6A followed by quantitative PCR analysis. Bars represent mean±SD of three experimental replicates. FIG. 6C provides Quantitative Chromosome Conformation Capture (3C) analysis of cells described in FIG. 5G at the Pou5f1 locus. The super-enhancer domain is indicated as a red bar. The targeted CTCF site is highlighted with a box. Arrows indicate the chromosomal positions between which the interaction frequency was assayed. Asterisk indicates the 3C anchor site. ChIP-seq binding profiles (reads per million per base pair) for CTCF in black and H3K27Ac (super-enhancer) in red, and methylation track in yellow with DMR in blue are also shown. The interaction frequencies between the indicated chromosomal positions and the 3C anchor sites are displayed as a bar chart (mean±SD) on the bottom panel. qPCR reactions were run in duplicates, and values are normalized against the mean interaction frequency in cells with a scrambled gRNA. ($p<0.05$; Student's t test, ns stands for non-significant). FIG. 6D shows anti-CTCF ChIP experiment was performed using cells in C followed by quantitative PCR analysis. Bars represent mean±SD of three experimental replicates.

FIGS. 7A-7H depict targeted ex vivo and in vivo DNA methylation editing by dCas9-Tet1 to activate a silenced GFP reporter. FIG. 7A provides a schematic diagram illustrating the experimental procedure for the ex vivo activation of a silenced GFP reporter in mouse fibroblast cells. Mouse tail fibroblast cells were derived from a genetically modified mouse line carrying a paternal IG-DMR-Snrpn-GFP allele (IG-DMRGFP/Pat) in the Dlk1-Dio3 locus. The IG-DMR-Snrpn promoter on the paternal allele is hypermethylated so that the GFP reporter is constitutively silenced. The cultured fibroblast cells were infected with lentiviral vectors expressing dCas9-Tet1 and gRNAs to demethylate the Snrpn promoter and activate the GFP reporter. Cells are subject to imaging and FACS analysis. FIG. 7B shows representative immunohistochemical images of IG-DMR$^{GFP/Pat}$ fibroblasts infected with lentiviruses expressing dCas9-Tet1 (dC-T) with a sc gRNA, an inactive form of dCas9-Tet1 (dC-dT) with Snrpn target gRNA, or dCas9-Tet1 with Snrpn target gRNA. Stained in red for Cherry, green for GFP and DAPI for nuclei. Scale bar: 100 um. Note that in order to turn on the Snrpn-GFP methylation reporter, both dCas9-Tet1 and target gRNA lentiviral vectors have to be transduced into the same cells. Therefore, the number of Cherry-positive cells (target gRNA) is expected to be greater than the number of GFP-positive cells (demethylation of the Snrpn promoter) in this experiment. FIG. 7C provides quantification of the percentage of IG-DMR$^{GFP/Pat}$ mouse fibroblast cells with GFP activation in Cherry (gRNAs) positive cells. ~80% cells with the Snrpn target gRNAs expression turned on GFP expression. dC-T with a sc gRNA and an inactive form of dC-T (dC-dT) with Snrpn target gRNAs cannot turn on GFP reporter expression. Bars represent mean±SD of three experimental replicates. FIG. 7D provides a schematic diagram illustrating the experimental procedure for in vivo activation of GFP reporter in the IG-DMR$^{GFP/Pat}$ mouse brain. Lentiviral vectors expressing dC-T and sc gRNA, dC-dT and Snrpn target gRNAs, and dC-T and Snrpn target gRNAs were delivered with stereotaxic microinjection approach. Brains were sliced and analyzed by immunohistochemical approaches. FIG. 7E provides representative confocal micrographs for the IG-DMR$^{GFP/Pat}$ a mouse brains infected with dC-T and sc gRNA, dC-dT and Snrpn target gRNAs, and dC-T and Snrpn target gRNAs. Only dC-T with the target gRNAs activated the GFP expression. Scale bar: 100 um. FIGS. 7G-7H provide quantification of the percentage of IG-DMR$^{GFP/Pat}$ a cells with GFP activation in Cherry (gRNAs) positive cells in the in vivo lentiviral delivery experiment in the brain (FIG. 7G) and in the skin epidemis (FIG. 7H). About 70% neurons and 85% skin dermal cells transduced with the Snrpn target gRNAs expression turned on GFP expression in vivo. In contrast, dC-T with a scrambled gRNA and an inactive form of Tet1 (dC-dT) with Snrpn target gRNAs did not activate GFP reporter expression. Bars represent mean±SD of more than four representative images from 2 animals.

FIG. 8A depicts design of dCas9-effector constructs with nuclear localization signal (NLS) located at different positions, and guide RNA (gRNA) or enhanced guide RNA (E-gRNA) with CMV-driven puro-T2A-Cherry cassette. Ub: human Ubiquitin C promoter. FIG. 8B shows xxpression of dCas-NLS-Tet1 and NLS-dCas9-NLS-Tet1 was analyzed by immunoblotting with anti-Cas9 antibody after transfection with these constructs in HEK293T cells for 2 days. α-tubulin was used as a loading control. FIG. 8C provides comparison of the cellular localization of dCas9-NLS-Tet1 and NLS-dCas9-NLS-Tet1 in HEK293T cells with or without co-expression of a gRNA or E-gNRA targeting the same position in the MyoD locus. In the absence of sgRNAs, dCas9-NLS-Tet1 is predominantly excluded from the nuclear compartment, and NLS-dCas9-NLS-Tet1 shows weak nuclear localization in transfected HEK293T cells. Co-expression of either gRNA or E-gRNA induced cytoplasm-to-nucleus translocation of these two proteins. Stained in green for dCas9, red for Cherry and blue for DAPI in the merged images. The red dashed lines in the first two panels indicate the cross section of the images for GFP intensity quantification. Scale bar: 10 um. FIG. 8D provides quantification of the nuclear-cytoplasmic ratio of dCas9-NLS-Tet1 and NLS-dCas9-NLS-Tet1 in HEK293T cells in the absence or presence of a gRNA, or an E-gNRA in a Box and Whiskers plot. Average dCas9 intensity of cytoplasmic and nuclear domain along a cross-sectional line as illustrated in C was used for the quantification. "+" denotes mean value of the 20 data points in each group; the boxes indicate the extreme data points (top and bottom bars), the 25-75% interval (box), and the median (central line). FIG. 8E shows quantification of induction index (defined as the nuclear-cytoplasmic ratio with sgRNA normalized to that without sgRNA) for dCas9-NLS-Tet1 and NLS-dCas9-NLS-Tet1. gRNA and E-gRNA induced 3.17 and 3.22 folds of nuclear localization for dCas9-NLS-Tet1, and 1.73 and 1.77 folds for NLS-dCas9-NLS-Tet1, respectively. We reasoned that the combination with the highest induction index would result in the best signal-to-noise ratio for targeted DNA methylation editing.

FIGS. 9A-9J depict targeted promoter methylation editing to activate Dazle-Snrpn-GFP reporter by dCas9-Tet1 and repress Gapdh-Snrpn-GFP reporter by dCas9-Dnmt3a. FIG. 9A provides genomic sequence of the Dazl-Snrpn locus with gRNA sequences labeled in yellow and CpGs in green. PAM for each gRNA is highlighted by a red box. The Dazl sequence is in lower case, and the Snrpn sequence is in upper case. FIG. 9B provides fluorescence images of Dazl-Snrpn-GFP mESCs infected with lentiviruses expressing dCas9-Tet1 (dC-T) with or without target gRNAs for the Snrpn promoter for 3 days. Scale bar: 120 um. FIG. 9C provides flow cytometric analysis of Dazl-Snrpn-GFP mESCs 3-day after infection with lentiviruses to express dCas9-Tet1 (dC-T) with a scrambled gRNA or 4 gRNAs targeting the Snrpn promoter region. Activation efficiency was calculated by the listed equation and shown as the mean percentages of Cherry and GFP double positive cells ±SD of two biological replicates. FIG. 9D depicts bisulfite sequencing of the Dazl-Snrpn region in Cherry+; GFP+ or Cherry+; GFP− cell populations after FACS sorting of Dazl-Snrpn mouse ES cells infected with lentiviruses expressing dC-T and Snrpn gRNAs.

FIG. 9E provide genomic sequence of the Gapdh-Snrpn locus with gRNA sequences labeled in yellow and CpGs in green. PAM for each gRNA is highlighted by a red box. The Gapdh sequence is in lower case, and the Snrpn sequence is in upper case. FIG. 9F provide flow cytometric analysis of Gapdh-Snrpn-GFP mESCs at 3-days after infection with lentiviruses to express dCas9-Dnmt3a (dC-D) and 3 gRNAs targeting the Snrpn promoter region. Inactivation efficiency was calculated by the listed equation and shown as the mean percentage of Cherry positive and GFP negative cells ±SD of two biological replicates. FIG. 9G depict bisulfite sequencing of the Gapdh-Snrpn region in Cherry+; GFP+ or Cherry+; GFP− cell populations after FACS sorting of Gapdh-Snrpn mouse ES cells infected with lentiviruses expressing dC-D and Snrpn gRNAs. FIG. 9H shows mESCs with stably integrated Doxycycline-inducible dCas9-Dnmt3a cassette were analyzed by RT-qPCR after Doxycycline (2 ug/ml) treatment for 48 hours. Bars represent mean±SD of three experimental replicates. FIG. 9I provide flow cytometric analysis of Gapdh-Snrpn-GFP mESCs with Doxycycline-inducible dCas9-Dnmt3a after 3-day infection with lentiviruses expressing the same 3 gRNAs as in F in the presence of Doxycycline (2 ug/ml). Inactivation efficiency was calculated as shown at the bottom and is expressed as the mean percentage of Cherry positive and GFP negative cells ±SD of two biological replicates. FIG. 9J Left panel: shows a schematic diagram of dCas9-Dnmt3a-P2A-BFP construct and gRNA-Cherry constructs. Middle panel: provides percentages of BFP-positive only, Cherry-positive only, and double positive cell populations by FACS analysis of Gapdh-Snrpn-GFP mESCs after infection with lentiviruses expressing dCas9-Dnmt3a-P2A-BFP and Snrpn gRNAs. Right panel: depicts FACS analysis of the percentages of GFP− or GFP+ cells within BFP+; Cherry+ cell population.

FIG. 10A shows HeLa cells were transfected with dCas9-Dnmt3a and one p16 target gRNA (cherry) or TALE-Dnmt3a-GFP. Transfection positive cell populations (cherry+) or (GFP+) were FACS sorted 48-hour post-transfection. Methylation levels of each individual CpG in the p16 promoter region were analyzed by bisulfite sequencing. Shown is the mean percentage±SD of two biological replicates with a total of 34 single colonies sequenced for dCas9-Dnmt3a and 31 single colonies sequenced for TALE-Dnmt3a. Red arrow indicates the position of p16 target gRNA, and purple arrow indicates the binding site for TALE-Dnmt3a. FIG. 10B depicts HEK293T cells were co-transfected with dCas9-Tet1 and one RHOXF2 target gRNA (with puro cassette) or TALE-Tet1 with a puro cassette expressing plasmid. Puromycin (2 ug/ml) was added to the culture medium to select for transfection positive cells. Cells were harvested after 2-day selection for analysis of methylation levels for individual CpGs in the RHOXF2 promoter region by bisulfite sequencing. Shown is the mean percentage±SD of two biological replicates with a total of 34 single colonies sequenced for dCas9-Tet1 and 38 single colonies sequenced for TALE-Tet1. Red arrow indicates the position of RHOXF2 target gRNA, and purple arrow indicates the binding site for TALE-Dnmt3a. FIG. 10C provides a summary of methylation level analysis in A and B. The effective range was determined by the distance of CpGs that were significantly edited by dCas9-Dnmt3a/Tet1 (change of methylation greater than 10%) from the site of gRNA targeting. The resolution is defined as the effective range of dCas9-Dnmt3a/Tet with one single gRNA, and better resolution is referred to the shorter effective range of dCas9-Dnmt3a/Tet1 which will allow for more precise editing of DNA methylation. FIG. 10D shows Dox-inducible dCas9-Dnmt3a expression mouse ES cells described in FIG. 9H were infected with a scrambled gRNA or gRNAs targeting the miR290 locus or Dazl-Snrpn locus. FACS sorted Cherry-positive cells were cultured with Dox (2 ug/ml) for 3 days. Then these cells were harvested for anti-dCas9 ChIP-seq analysis. Peaks were called with the pairwise peak calling procedure described previously (Wu et al., 2014), and presented in a Manhattan plot depicting genome-wide ChIP-seq peaks. All peaks with p<0.001 are shown. Each dot represents a peak, with the X-axis showing genomic location and Y-axis showing the peak summit height output by Model-based Analysis of ChIP-Seq (MACS) (Zhang et al., 2008). The size of each dot is proportional to its Y-axis value, and individual chromosome is colored differently for visualization. FIG. 10E depicts ChIP-seq peaks at the targeted loci (miR290 or Dazl-Snrpn) with the highest level of signal and at two off-target loci with the second and third highest signals (Vac14 and Tenm4 loci for miR290 gRNAs; Vrk1 and Gm42619 loci for Dazl-Snrpn gRNAs) are illustrated with the nearby genes listed below. Note that the 4 Dazl-Snrpn gRNAs recognize the promoter sequences of Dazl and Snrpn as described in FIG. 9A, so the peaks for this group of gRNAs were mapped to both loci. FIG. 10F shows genomic DNA from cells used in FIG. 5C was subject to bisulfite sequencing of the off-target binding sites at Vac14 and Tenm4 loci. Shown is the mean percentage±SD of two biological replicates. FIG. 10G shows genomic DNA from cells used in FIG. 1D and FIG. 2C was subject to bisulfite sequencing of the off-target binding sites at Vrk1 and Gm42619 loci. Shown is the mean percentage±SD of two biological replicates.

FIG. 11A shows genomic sequence of the BDNF promoter IV region with gRNA sequences labeled in yellow and CpGs in green. PAM for each gRNA is highlighted by a red box. FIG. 11B Left panel: shows a schematic diagram depicting the KCl treatment and lentiviral delivery experiment on E17.5 mouse primary cortical neurons to investigate BDNF expression. Note that cultured neurons were treated with AraC on DIV2 to halt cell division in glial cells and neural progenitors. Right panel: shows DIV3 mouse cortical neurons were treated with 50 mM of KCl, and harvested at different time points for BDNF expression analysis by RT-qPCR. FIG. 11C provides EDU labeling analysis for the mouse primary neurons over the course of KCl treatment for 24 hrs. Note that extremely few EDU positive cells were observed. Stained in red for EDU, green for MAP2 and DAPI for nuclei. Scale bar: 500 um. FIG. 11D Upper panel: provides quantification of neuronal density over the course of KCl treatment. The post-mitotic neuron density remains steadily around 4.5×10$^4$/cm2 over time. Bars represent mean±SD of three experimental replicates. Lower panel: provides quantification of the EDU positive cells over the course of KCl treatment. Less than 2% of the cells are EDU-positive over 24 hrs. Bars represent mean±SD of three experimental replicates. FIG. 11E provides confocal micrographs of BDNF induction by ectopic expression of dCas9-Tet1 and a set of 4 gRNAs targeting BDNF promoter IV. Stained in green for BDNF, magenta for MAP2, red for Cherry and blue for DAPI. Note that the lentiviral infection efficiency is close to 100% in these neurons. Scale bar: 50 um. FIG. 11F shows neurons harvested from B and E were subjected to RT-qPCR analysis for Npas4 expression. Bars represent mean±SD of three experimental replicates. FIG. 11G shows DIV3 mouse cortical neurons were infected with dC-T alone or together with 4 gRNAs targeting BDNF promoter IV or individual BDNF gRNA, and then subject to qPCR analysis for BDNF expression. FIGS. 11H-11I shows Tet Assisted Bisulfite sequencing (TAB-Seq) analysis of neurons infected with lentiviruses expressing dC-T or dC-dT with 4 BDNF gRNAs for 40 and 60 hours in H, or neurons after KCl treatment for 6 hours in FIG. 11I. FIG. 11J depicts DIV3 mouse cortical neurons were treated with ABT (50 uM) for 6 hours and then treated with KCl (50 mM) for 6-hour before harvest for RT-qPCR analysis. Bars represent mean±SD of three experimental replicates. FIG. 11K depicts DIV3 mouse cortical neurons were treated with 2-Hydroxyglutarate (10 mM) for 2 hours and then treated with KCl (50 mM) for 6-hour before harvest for RT-qPCR analysis. Bars represent mean±SD of three experimental replicates. FIG. 11L depicts DIV3 mouse cortical neurons derived from wild-type or Tet1 knockout E17.5 embryos were subject to time course KCl treatment experiments (6, 9 and 12 h). Bars represent mean±SD of three experimental replicates.

FIGS. 12A-12J depict targeted demethylation of the MyoD DMR-5 by dCas9-Tet1 and conversion of fibroblasts to myoblasts. FIG. 12A shows genomic sequence of the MyoD distal enhancer region with gRNA sequences labeled in yellow and CpGs in green. PAM for each sgRNA is highlighted by a red box. FIG. 12B provides experimental scheme of the fibroblast-to-myoblast conversion assay. Briefly, C3H10T1/2 mouse embryonic fibroblast cells were plated as 1×10$^4$ cells per well in 6-well plate, and then infected with lentiviruses expressing dCas9-Tet1 and target gRNAs. 24-hour post infection, cells were optionally treated with 5-Azacytidine (1 uM) for 24-hour (labeled in red), and harvested for immunofluorescence staining at different time points (day-14, -16 and -25, labeled in dark blue) with medium change every other day. Scale bar: 100 um. FIG. 12C shows representative confocal micrographs of myotube formation for C3H10T1/2 fibroblast cells after 5-Aza treatment. Upper panel: shows a clonal field contains sparsely distributed small and mid-size myotubes. Middle panel: shows a clonal field contains sparsely distributed large size myotubes. Bottom panel: shows a clonal field contains high density of myotubes with heterogeneous size. Stained in green for MHC, red for MyoD and blue for DAPI. Scale bar: 200 um. FIG. 12D depicts a fraction of mock C3H10T1/2 cells expressing MyoD at different times after 5-Aza treatment. The fraction of cells expressing MyoD increases from around 6% at day 14 to around 13% at day 16 and reached around 20% at day 25. Bars represent mean±SD. FIG. 12E provides number of nuclei in MHC+ cell clusters (grouped as 1-2 and >2 nuclei per MHC+ cluster). Formation of larger myotubes was observed at later time points after 5-Aza treatment. Bars represent mean±SD. Data was quantified from 3-5 representative images for each group in FIG. 12D and FIG. 12E. FIG. 12F shows C3H10T1/2 cells were infected with lentiviruses expressing dC-T with MyoD gRNAs for 24-hour, and treated with or without 5-Aza for 48-hour before harvested for qPCR analysis. Bars represent mean±SD of three experimental replicates. FIG. 12G provides representative images for C3H10T1/2 cells 16 days after infection with lentiviruses expressing dC-T and gRNAs targeting DMR-5 (MyoD distal enhancer) in a fibroblast-to-myoblast conversion assay as described in FIG. 12B. Note that a modest level of MyoD activation (compared to the cells treated by 5-Aza) was observed in cells with dC-T and target gRNA, but not myosin heavy chain (MHC) expression or myotube formation. Stained in magenta for MHC, green for MyoD and blue for DAPI. Scale bar: 200 um. FIG. 12H depicts a fraction of MyoD positive cells 16 days after infection with lentiviruses expressing dC-T alone or with gRNAs targeting DMR-5. FIG. 12I show a number of nuclei in MHC+ cell clusters (grouped as 2-5, 6-10, 11-20 and >20 nuclei per MHC+ cluster) 16 days after infection. When treated with 5-Aza, co-expression of gRNAs and dC-T significantly facilitated formation of larger and more maturated MHC+ clusters compared to mock control or dC-T alone. FIG. 12J shows myotube density of MHC positive clusters with more than 2 or 5 nuclei 16 days after infection. Addition of 5-Aza induces MHC+ myotube formation. Co-expression of dC-T and gRNAs significantly induced more and larger myotubes (>5 nuclei MHC+ clusters). Data are quantified from 3-5 representative images for FIGS. 12H-12J. Bars represent mean±SD.

FIG. 13A provides genomic sequence of the CTCF target 1 region (miR290 locus) with gRNA sequences labeled in yellow and CpGs in green. PAM for each sgRNA is highlighted by a red box, predicted CTCF binding motif is highlighted in a blue box. FIG. 13B provides genomic sequence of the CTCF target 2 region (H2Q10-Pou5f1 locus) with gRNA sequences labeled in yellow and CpGs in green. PAM for each sgRNA is highlighted by a red box, predicted CTCF binding motif is highlighted in blue boxes.

FIG. 14A provides a schematic diagram illustrating the experimental procedure for ex vivo activation of the silenced GFP reporter in IG-DMR$^{GFP/Pat}$ mouse fibroblasts. The cultured fibroblasts were infected with lentiviral vectors expressing dCas9-Tet1 and gRNAs to demethylate the Snrpn promoter and activate the GFP reporter. FIG. 14B provides FACS analysis of the infected IG-DMR$^{GFP/Pat}$ mouse fibroblasts. FIG. 14C shows quantification of the percent of GFP+ cells in Cherry positive cell population in FIG. 14B. FIG. 14D provides a schematic diagram illustrating the lentiviral delivery approach for each site on the ventral side of the IG-DMR$^{GFP/pat}$ mouse. FIG. 14E provides representative confocal micrographs for the IG-DMR$^{GFP/Pat}$ mouse skin infected with dCas9-Tet1 and sc gRNA, an inactive form of Tet1 (dC-dT) and the Snrpn gRNAs, and dCas9-Tet1 with Snrpn gRNAs. Arrowheads indicate that only dC-T with Snrpn gRNAs activated the GFP expression. Note red auto-fluorescence on the left edges of the epidermis. FIG. 14F provides representative confocal micrographs of 2 hair follicles with lentiviral delivery for dC-T and Snrpn gRNAs to activate the GFP expression.

FIG. 19A demonstrates the demethylation of Dazl-Snrpn-GFP reporter and methylation of Gapdh-Snrpn-GFP reporter. FIG. 19B demonstrates targeted demethylation of BDNF promoter IV by dCas9-Tet1 to activate BDNF. FIG. 19C demonstrates targeted demethylation of the MyoD distal enhancer by dCas9-Tet1 to facilitate muscle cell transdifferentiation. FIG. 19D demonstrates targeted methylation of CTCF binding sites. FIG. 19E demonstrates targeted in vivo DNA methylation editing by dCas9-Tet1 to activate a silenced GFP reporter.

FIG. 23A demonstrates a three-dimensional structure of a chromosome. FIG. 23B shows gene expression level of the indicated genes in wild type and CTCF site-deleted cells measured by qRT-PCR. FIG. 23C shows anti-CTCF ChIP experiment was performed using cells in C followed by quantitative PCR analysis. Bars represent mean+SD of three experimental replicates.

DETAILED DESCRIPTION OF THE INVENTION

Figures 1A, 1B:
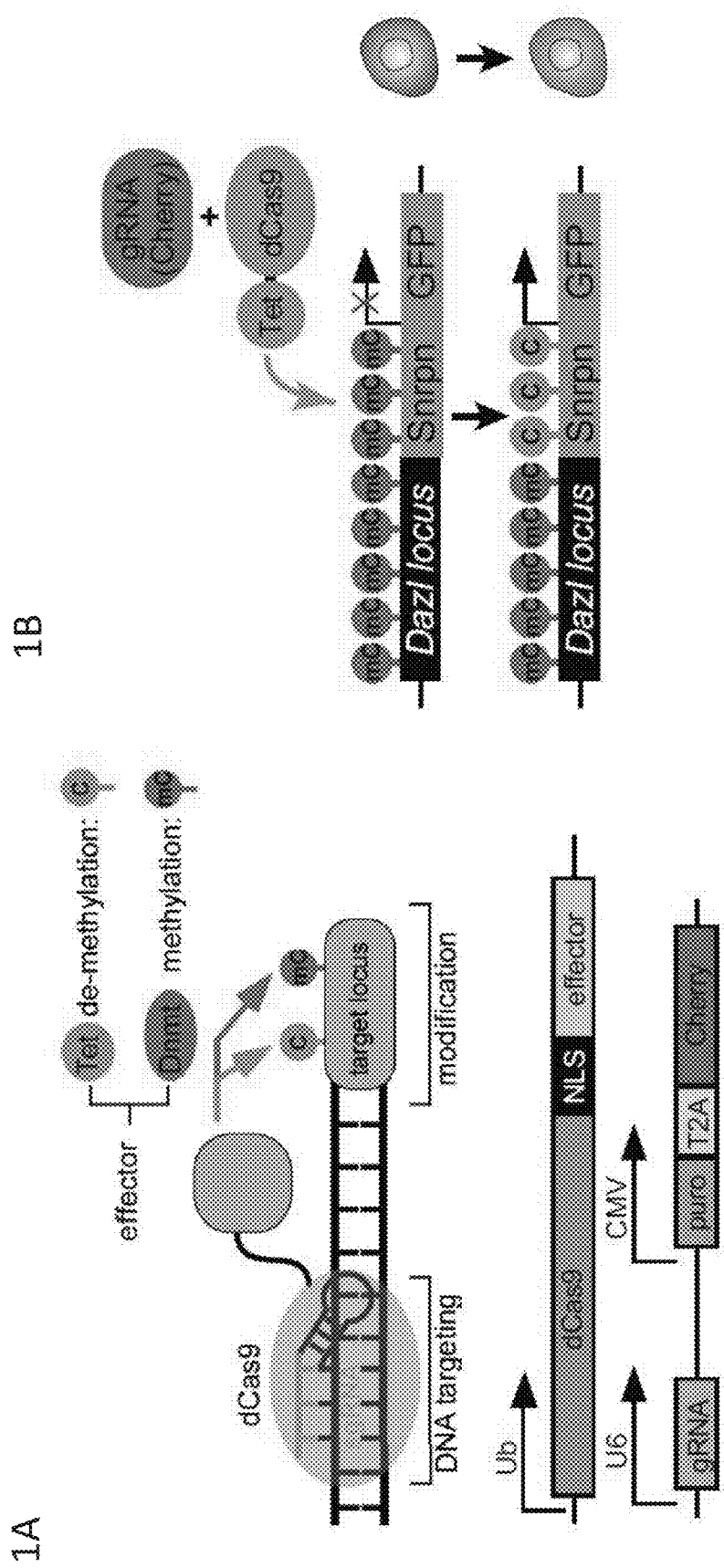
FIGS. 1A-1F depict activation of the Dazl-Snrpn-GFP reporter by dCas9-Tet1.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In one aspect, the invention is directed to a method of modifying or modulating one or more genomic sequences in a cell comprising introducing into the cell a catalytically inactive site specific nuclease fused to an effector domain having methylation activity or demethylation activity, and one or more guide sequences. The method can result in the modification of the one or more genomic sequences in the cell. An isolated modified cell may be produced by the described method. The catalytically inactive site specific nuclease may bind to each of the one or more guide sequences and the effector domain modulates the methylation or demethylation (e.g., DNA methylation or DNA demethylation) of the genomic sequence. One or more guide sequences, catalytically inactive site specific nucleases and effector domains can be introduced into a cell, zygote, embryo or non-human mammal.

In other aspects, the invention is directed to a method of modulating the methylation of one or more genomic sequences in a cell. The method may comprise contacting the cell with a nucleic acid that encodes a polypeptide comprising a catalytically inactive site specific nuclease fused to an effector domain having methylation or demethylation activity. The cell is further contacted with a guide sequence or a nucleic acid that encodes a guide sequence. In some aspects, the guide sequence targets the polypeptide to the one or more genomic sequences. In some embodiments, the contacting of the cell may include introducing directly into the cell. In other aspects, the contacting of the cell includes expressing in the cell or inducing expression in the cell. Reporters of genomic methylation are described in U.S. application Ser. No. 15/078,851, which is incorporated herein by reference in its entirety.

There are various ways that a polypeptide comprising a catalytically inactive site specific nuclease fused to an effector domain having methylation or demethylation activity can be delivered to a cell or subject, e.g., by administering a nucleic acid that encodes the polypeptide, which nucleic acid may be, e.g., a viral vector or may be a translatable nucleic acid (e.g, synthetic modified mRNA. Examples of modified mRNA are described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624). Additional examples are found in numerous PCT and US applications and issued patents to Moderna Therapeutics, e.g., PCT/US2011/046861; PCT/US2011/054636, PCT/US2011/054617, U.S. Ser. No. 14/390,100 (and additional patents and patent applications mentioned in these.) Also, the guide sequence can be delivered as a nucleic acid that encodes the guide sequence. For example, administration can be performed by direct administration to a tissue or organ (e.g., skin, heart, liver, lung, kidney, brain, eye, muscle, bone, nerve) or tumor. Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. The nucleic acids may be encapsulated, e.g., in liposomes, polymeric particles (e.g., PLGA particles).

The methods described herein can be used to modify or modulate one or more genomic sequences in a variety of cells, which includes somatic cells, stem cells, mitotic or post-mitotic cells, neurons, fibroblasts, or zygotes. A cell, zygote, embryo, or post-natal mammal can be of vertebrate (e.g., mammalian) origin. In some aspects, the vertebrates are mammals or avians. Particular examples include primate (e.g., human), rodent (e.g., mouse, rat), canine, feline, bovine, equine, caprine, porcine, or avian (e.g., chickens, ducks, geese, turkeys) cells, zygotes, embryos, or post-natal mammals. In some embodiments, the cell, zygote, embryo, or post-natal mammal is isolated (e.g., an isolated cell; an isolated zygote; an isolated embryo). In some embodiments, a mouse cell, mouse zygote, mouse embryo, or mouse post-natal mammal is used. In some embodiments, a rat cell, rat zygote, rat embryo, or rat post-natal mammal is used. In some embodiments, a human cell, human zygote or human embryo is used. The methods described herein can be used to modify or modulate one or more genomic sequences (e.g., methylate or demethylate a genomic sequence) in a mammal (e.g., a mouse) in vivo.

Stem cells may include totipotent, pluripotent, multipotent, oligopotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc.

In some aspects, one or more guide sequences include sequences that recognize DNA in a site-specific manner. For example, guide sequences can include guide ribonucleic acid (RNA) sequences utilized by a CRISPR system or sequences within a TALEN or zinc finger system that recognize DNA in a site-specific manner. The guide sequences comprise a portion that is complementary to a portion of each of the one or more genomic sequences and comprise a binding site for the catalytically inactive site specific nuclease. In some embodiments, the RNA sequence is referred to as guide RNA (gRNA) or single guide RNA (sgRNA).

In some aspects, a single RNA sequence can be complementary to one or more (e.g., all) of the genomic sequences that are being modulated or modified. In one aspect, a single RNA is complementary to a single target genomic sequence. In a particular aspect in which two or more target genomic sequences are to be modulated or modified, multiple (e.g., 2, 3, 4, 5, 6, 7, 8, 9, 10, or more) RNA sequences are introduced wherein each RNA sequence is complementary to (specific for) one target genomic sequence. In some aspects, two or more, three or more, four or more, five or more, or six or more RNA sequences are complementary to (specific for) different parts of the same target sequence. In one aspect, two or more RNA sequences bind to different sequences of the same region of DNA. In some aspects, a single RNA sequence is complementary to at least two target or more (e.g., all) of the genomic sequences. It will also be apparent to those of skill in the art that the portion of the RNA sequence that is complementary to one or more of the genomic sequences and the portion of the RNA sequence that binds to the catalytically inactive site specific nuclease can be introduced as a single sequence or as 2 (or more) separate sequences into a cell, zygote, embryo or nonhuman animal. In some embodiments the sequence that binds to the catalytically inactive site specific nuclease comprises a stem-loop.

In some embodiments, an RNA sequence used to modify gene expression in a nonhuman mammal is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications (e.g., RNA comprising one or more non-standard and/or non-naturally occurring bases) to the RNA sequence (e.g., modifications to the backbone and or sugar). Methods of modifying bases of RNA are well known in the art. Examples of such modified bases include those contained in the nucleosides 5-methylcytidine (5mC), pseudouridine ($\Psi$), 5-methyluridine, 2'0-methyluridine, 2-thiouridine, N-6 methyladenosine, hypoxanthine, dihydrouridine (D), inosine (I), and 7-methylguanosine (m7G). It should be noted that any number of bases in a RNA sequence can be substituted in various embodiments. It should further be understood that combinations of different modifications may be used.

In some aspects, the RNA sequence is a morpholino. Morpholinos are typically synthetic molecules, of about 25 bases in length and bind to complementary sequences of RNA by standard nucleic acid base-pairing. Morpholinos have standard nucleic acid bases, but those bases are bound to morpholine rings instead of deoxyribose rings and are linked through phosphorodiamidate groups instead of phosphates. Morpholinos do not degrade their target RNA molecules, unlike many antisense structural types (e.g., phosphorothioates, siRNA). Instead, morpholinos act by steric blocking and bind to a target sequence within a RNA and block molecules that might otherwise interact with the RNA.

Each RNA sequence can vary in length from about 8 base pairs (bp) to about 200 bp. In some embodiments, the RNA sequence can be about 9 to about 190 bp; about 10 to about 150 bp; about 15 to about 120 bp; about 20 to about 100 bp; about 30 to about 90 bp; about 40 to about 80 bp; about 50 to about 70 bp in length.

The portion of each genomic sequence to which each RNA sequence is complementary can also vary in size. In particular aspects, the portion of each genomic sequence to which the RNA is complementary can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each RNA sequence can be at least about 70%, 75%, 80%, 85%, 90%, 95%, 100%, etc. identical or similar to the portion of each genomic sequence. In some embodiments, each RNA sequence is completely or partially identical or similar to each genomic sequence. For example, each RNA sequence can differ from perfect complementarity to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more RNA sequences are perfectly complementary (100%) across at least about 10 to about 25 (e.g., about 20) nucleotides of the genomic sequence.

The one or more guide sequences (e.g., RNA sequences) can be complementary to any of a variety of all or a portion of a target genomic sequence that is to be modified. In some aspects, the target genomic sequence comprises a differentially methylated region, an enhancer (e.g., MyoD distal enhancer), a promoter (e.g., BDNF promoter), a reporter, or a CTCF binding site.

In some aspects of the invention, the method of modulating one or more genomic sequences comprises introducing one or more guide sequences that are complementary to all or a portion of a (one or more) regulatory region, an open reading frame (ORF; a splicing factor), an intronic sequence, a chromosomal region (e.g., telomere, centromere) of the one or more genomic sequences into a cell. In some aspects, the genomic sequence is all or a portion of a plasmid or linear double stranded DNA (dsDNA). In some aspects, the regulatory region targeted by the one or more genomic sequences is a promoter, enhancer, and/or operator region. In some aspects, all or a portion of the regulatory region is targeted by the one or more genomic sequences. All or a portion of the region targeted by the one or more genomic sequences may be a differentially methylated region. In some aspects, the differentially methylated region is exactly or within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases or more upstream to the one or more genes (e.g., endogenous genes; exogenous genes) or a (one or more) transcription start site (TSS). In some aspects, the differentially methylated region is exactly or within about 25 bases, 50 bases, 100 bases, 200 bases, 300 bases, 400 bases, 500 bases, 600 bases, 700 bases, 800 bases, 900 bases, 1000 bases, 1500 bases, 2000 bases, 5000 bases, 10000 bases, 20000 bases, 50000 bases, or more downstream to the one or more genes (e.g., endogenous genes; exogenous genes) or a TSS. As will be appreciated by one of ordinary skill in the art, the regulatory region targeted by one or more genomic sequences can be entirely or partially found at or about the 5' end of the gene (e.g., endogenous or exogenous) or a TSS. The 5' end of a gene can include untranscribed (flanking) regions (e.g., all or a portion of a promoter) and a portion of the transcribed region.

As will be apparent to those of ordinary skill in the art, the one or more RNA sequences can further comprise one or more expression control elements. For example, in some embodiments the RNA sequences comprises a promoter, suitable to direct expression in cells, wherein the portion of the RNA sequence is operably linked to the expression control element(s). The promoter can be a viral promoter (e.g., a CMV promoter) or a mammalian promoter (e.g., a PGK promoter). The RNA sequence can comprise other genetic elements, e.g., to enhance expression or stability of a transcript. In some embodiments the additional coding region encodes a selectable marker (e.g., a reporter gene such as green fluorescent protein (GFP)).

As described herein, the one or more RNA sequences also comprise a (one or more) binding site for a (one or more) catalytically inactive site specific nuclease. The catalytically inactive site specific nuclease may be a catalytically inactive CRISPR associated (Cas) protein. In a particular aspect, upon hybridization of the one or more RNA sequences to the one or more genomic sequences, the catalytically inactive site specific nuclease binds to the one or more RNA sequences.

In some aspects, the method of modulating one or more genomic sequences comprises adjusting the level of modulation of one or more genomic sequences by adjusting the amount (e.g. grams, milligrams, micrograms, nanograms, moles, millimoles, micromoles, nanomoles, stoichiometric amount, molar ratio) of the one or more guide sequences introduced into the cell or zygote. In some aspects, the level of modulation of one genomic sequence is the same or different compared to the level of modulation of another genomic sequence in the same cell or zygote. In one aspect, multiple genomic sequences are modulated (e.g. multiplexed activation).

In one aspect, the method further comprises introducing one or more catalytically inactive Cas (dCas) nucleic acid or variant thereof into the cell, embryo, zygote, or non-human mammal. In some aspects, a dCas protein or variant thereof is introduced into the cell, embryo, zygote, or non-human mammal. In some aspects, a cell, e.g., post-mitotic cell, neuron, fibroblast, stem cell (ES or iPS cell), zygote, embryo, or animal may already harbor a nucleic acid that encodes dCas (may be constitutive or inducible) and/or may already contain dCas protein. For example, in some embodiments a cell, zygote, embryo, or animal, may be descended from a cell or organism into which a nucleic acid encoding a dCas protein has been introduced by a process involving the hand of man.

A variety of CRISPR associated (Cas) genes or proteins which are known in the art can be used in the methods of the invention and the choice of Cas protein will depend upon the particular conditions of the method (e.g., ncbi.nlm.nih.gov/gene/?term=cas9). Specific examples of Cas proteins include Cas1, Cas2, Cas3, Cas4, Cas5, Cas6, Cas7, Cas8, Cas9 and Cas10. In a particular aspect, the Cas nucleic acid or protein used in the methods is Cas9. In some embodiments a Cas protein, e.g., a Cas9 protein, may be from any of a variety of prokaryotic species. In some embodiments a particular Cas protein, e.g., a particular Cas9 protein, may be selected to recognize a particular protospacer-adjacent motif (PAM) sequence. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a *Streptococcus*, (e.g., a *S. pyogenes*, a *S. thermophilus*) a *Crptococcus*, a *Corynebacterium*, a *Haemophilus*, a *Eubacterium*, a *Pasteurella*, a *Prevotella*, a *VeiUonella*, or a *Marinobacter*. In some embodiments nucleic acids encoding two or more different Cas proteins, or two or more Cas proteins, may be introduced into a cell, zygote, embryo, or animal, e.g., to allow for recognition and modification of sites comprising the same, similar or different PAM motifs.

In some embodiments, the Cas protein is Cpf1 protein or a functional portion thereof. In some embodiments, the Cas protein is Cpf1 from any bacterial species or functional portion thereof. In certain embodiments, a Cpf1 protein is a *Francisella novicida* U112 protein or a functional portion thereof, a *Acidaminococcus* sp. BV3L6 protein or a functional portion thereof, or a Lachnospiraceae bacterium ND2006 protein or a function portion thereof. Cpf1 protein is a member of the type V CRISPR systems Cpf1 protein is a polypeptide comprising about 1300 amino acids. Cpf1 contains a RuvC-like endonuclease domain.

In some embodiments a Cas9 nickase may be generated by inactivating one or more of the Cas9 nuclease domains. In some embodiments, an amino acid substitution at residue 10 in the RuvC I domain of Cas9 converts the nuclease into a DNA nickase. For example, the aspartate at amino acid residue 10 can be substituted for alanine (Cong et al, Science, 339:819-823). Other amino acids mutations that create a catalytically inactive Cas9 protein includes mutating at residue 10 and/or residue 840. Mutations at both residue 10 and residue 840 can create a catalytically inactive Cas9 protein, sometimes referred herein as dCas9. For example, a D10A and a H840A Cas9 mutant is catalytically inactive.

Modulating one or more genomic sequences may comprise introducing one or more effector domains. As used herein an "effector domain" is a molecule (e.g., protein) that modulates the expression and/or activation of a genomic sequence (e.g., gene). The effector domain may have methylation activity or demethylation activity (e.g., DNA methylation or DNA demethylation activity). In some aspects, the effector domain targets one or both alleles of a gene. The effector domain can be introduced as a nucleic acid sequence and/or as a protein. In some aspects, the effector domain can be a constitutive or an inducible effector domain. In some aspects, a Cas (e.g., dCas) nucleic acid sequence or variant thereof and an effector domain nucleic acid sequence are introduced into the cell as a chimeric sequence. In some aspects, the effector domain is fused to a molecule that associates with (e.g., binds to) Cas protein (e.g., the effector molecule is fused to an antibody or antigen binding fragment thereof that binds to Cas protein). In some aspects, a Cas (e.g., dCas) protein or variant thereof and an effector domain are fused or tethered creating a chimeric protein and are introduced into the cell as the chimeric protein. In some aspects, the Cas (e.g., dCas) protein and effector domain bind as a protein-protein interaction. In some aspects, the Cas (e.g., dCas) protein and effector domain are covalently linked. In some aspects, the effector domain associates non-covelently with the Cas (e.g., dCas) protein. In some aspects, a Cas (e.g., dCas) nucleic acid sequence and an effector domain nucleic acid sequence are introduced as separate sequences and/or proteins. In some aspects, the Cas (e.g., dCas) protein and effector domain are not fused or tethered.

As shown herein, fusions of a catalytically inactive (D10A; H840A) Cas9 protein (dCas9) tethered with all or a portion of (e.g., biologically active portion of) an (one or more) effector domain create chimeric proteins that can be guided to specific DNA sites by one or more RNA sequences (sgRNA) to modulate activity and/or expression of one or more genomic sequences (e.g., exert certain effects on transcription or chromatin organization, or bring specific kind of molecules into specific DNA loci, or act as sensor of local histone or DNA state). In specific aspects, fusions of a dCas9 tethered with all or a portion of an effector domain create chimeric proteins that can be guided to specific DNA sites by one or more RNA sequences to modulate or modify methylation or demethylation of one or more genomic sequences. As used herein, a "biologically active portion of an effector domain" is a portion that maintains the function (e.g. completely, partially, minimally) of an effector domain (e.g., a "minimal" or "core" domain). The fusion of the Cas9 (e.g., dCas9) with all or a portion of one or more effector domains created a chimeric protein.

Examples of effector domains include a transcription(al) activating domain, a coactivator domain, a transcription factor, a transcriptional pause release factor domain, a negative regulator of transcriptional elongation domain, a transcriptional repressor domain, a chromatin organizer domain, a remodeler domain, a histone modifier domain, a DNA modification domain, a RNA binding domain, a protein interaction input devices domain (Grunberg and Serrano, Nucleic Acids Research, 3 '8 (8): '2663-267'5 (2010)), and a protein interaction output device domain (Grunberg and Serrano, Nucleic Acids Research, 3 '8 (8): '2663-267'5 (2010)). As used herein a "protein interaction input device" and a "protein interaction output device" refers to a protein-protein interaction (PPI). In some embodiments the PPI is regulatable, e.g., by a small molecule or by light. In some aspect, binding partners are targeted to different sites in the genome using the inactive Cas protein. The binding partners interact, thereby bringing the targeted loci into proximity. A protein interaction output device is a system for detecting/monitoring occurrence of a PPI, generally by producing a detectable signal when the PPI occurs (e.g., by reconstituting a fluorescent protein) or to trigger specific cellular responses {e.g., by reconstituting a caspase protein to induce apoptosis). The idea in this context is to target different sites in the genome with the components of the "output device". If the interaction occurs, the "output device" generates a signal. This can be used to determine or monitor the proximity of the targeted loci. In some aspects, cells are treated with an agent and the effect of the agent on the cell is determined. Other examples of effector domains include histone marks readers/interactors (cell.com/abstract/S0092-8674(10)00951-7) and DNA modification readers/interactors.

In some aspects, the effector domain is a DNA modifier. Specific examples of DNA modifiers include 5hmc conversion from 5mC such as Tet1 (Tet1CD); DNA demethylation by Tet1, ACID A, MBD4, Apobec1, Apobec2, Apobec3, Tdg, Gadd45a, Gadd45b, ROS1; DNA methylation by Dnmt1, Dnmt3a, Dnmt3b, CpG Methyltransferase M.SssI, and/or M.EcoHK31I. In specific aspects, an effector domain is Tet1. In other specific aspects, as effector domain is Dmnt3a. In some embodiments, dCas9 is fused to Tet1. In other embodiments, dCas9 is fused to Dnmt3a.

DNA methylation is established by two de novo DNA methyltransferases (Dnmt3a/b), and is maintained by Dnmt1 (Smith and Meissner, 2013). Gene activation during development is associated with demethylation of promoter and enhancer sequences. In addition, demethylation can be achieved through oxidation of the methyl group by TET (ten-eleven translocation) dioxygenases to form 5-hydroxymethylcytosine (5-hmC), and then restoration into unmodified cytosines by either DNA replication-dependent dilution or DNA glycosylase-initiated base excision repair (BER), a process termed as active demethylation and proposed to operate during specific developmental stages such as preimplantation embryos or in post-mitotic neurons (Wu and Zhang, 2014).

In one aspect of the invention, fusion of the dCas9 to an effector domain can be to that of a single copy or multiple/tandem copies of full-length or partial-length effectors. Other fusions can be with split (functionally complementary) versions of the effector domains. Effector domains for use in the methods include any one of the following classes of proteins: proteins that mediate drug inducible looping of DNA and/or contacts of genomic loci, proteins that aid in the three-dimensional proximity of genomic loci bound by dCas9 with different sgRNA.

Other examples of effector domains are described in PCT Application No. PCT/US2014/034387 and U.S. application Ser. No. 14/785,031, which are incorporated herein by reference in their entirety.

In some aspects the invention is directed to (e.g., a composition comprising, consisting essentially of, consisting of) a nucleic acid sequence that encodes a fusion protein (chimeric protein) comprising all or a portion of a Cas (e.g., dCas) protein fused to all or a portion of an effector domain. In some aspects, the invention is directed to (e.g., a composition comprising, consisting essentially of, consisting of) a fusion protein comprising all or a portion of a Cas (e.g., dCas) protein fused to all or a portion of an effector domain. In some aspects all or a portion of the Cas (e.g., dCas) protein targets but does not cleave a nucleic acid sequence. In some aspects, the Cas (e.g., dCas) protein can be fused to the N-terminus or C-terminus of the effector domain. In some aspects, the portion of the effector domain modulates the methylation of the genomic sequence (e.g., demethylates or methylates the genomic sequence).

In some aspects, the nucleic acid sequence encoding the fusion protein and/or the fusion protein are isolated. An "isolated," "substantially pure," or "substantially pure and isolated" nucleic acid sequence, as used herein, is one that is separated from nucleic acids that normally flank the gene or nucleotide sequence (as in genomic sequences) and/or has been completely or partially purified from other transcribed sequences (e.g., as in an RNA or cDNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. An "isolated," "substantially pure," or "substantially pure and isolated" protein (e.g., chimeric protein; fusion protein), as used herein, is one that is separated from or substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an isolated nucleic acid molecule comprises at least about 50%, 80%, 90%, 95%, 98% or 99% (on a molar basis) of all macromolecular species present.

In one aspect, fusion of Cas9 with all or a portion of one or more effector domains comprise one or more linkers. As used herein, a "linker" is something that connects or fuses two or more effector domains (e.g see Hermanson, Bioconjugate Techniques, $2^{nd}$ Edition, which is hereby incorporated by reference in its entirety). As will be appreciated by one of ordinary skill in the art, a variety of linkers can be used. In one aspect, a linker comprises one or more amino acids. In some aspects, a linker comprises two or more amino acids. In one aspect, a linker comprises the amino acid sequence GS. In some aspects, fusion of Cas9 (e.g., dCas9) with two or more effector domains comprises one or more interspersed linkers (e.g., GS linkers) between the domains. In some aspects, one or more nuclear localization sequences may be located between the catalytically inactive nuclease (e.g., dCas9) and the effector domain. For example, a fusion protein may include dCas9-NLS-Tet1 or dCas9-NLS-Dnmt3a.

In some aspects of the invention, the method of modulating one or more genomic sequences in a cell can further comprise introducing an effector molecule. As used herein, an "effector molecule" is a molecule (e.g., nucleic acid sequence; protein; organic molecule; inorganic molecule, small molecule) or physical trigger that associates with (e.g., binds to; specifically binds to) the effector domain to modulate the methylation or demethylation of a genomic sequence (e.g., an inducer molecule; a trigger molecule). The effector molecule can be contacted with the cell and/or introduced into the cell (e.g., as a nucleic acid sequence or as protein sequence). In some embodiments, the effector molecule is endogenous. In other embodiments, the effector molecule is exogenous. For example, an exogenous effector molecule can be introduced to the cell. In some aspects, the effector molecule binds to the effector domain. In some aspects, the effector molecule is a nucleic acid, protein, drug, small organic molecule and derivatives/variants thereof. In some aspects of the invention, the effector molecule is an antibiotic or derivatives/variants thereof.

As will be apparent to those of skill in the art, the method can further comprise introducing other molecules or factors into the cell to facilitate methylation or demethylation of the genomic sequence. An agent that inhibits or enhances DNA methylation may be an inhibitor of an endogenous DNA methylase or DNA demethylase. For example, an inhibitor of DNA methylation may be a small molecule, e.g., a cytidine analog, such as 5-azacytidine (azacitidine) and 5-azadeoxycytidine (decitabine). In other methods, the agent that inhibits or enhances DNA methylation may be administered to an individual.

A variety of genomic sequences can be modulated or modified using the methods described herein and will depend upon the desired results. In one aspect, the target genomic sequence is a gene sequence. In particular aspects, the methods described herein can be used to genetically modify two or more different genes in the same gene family, two or more genes that have a redundant function (e.g., redundant may mean that one needs to inactivate at least two of the genes to produce a particular phenotype, e.g., a detectable phenotype), two or more genes at least 80%, 85%, 90%, 95%, 96%, 97%, 98%, 99%, or more identical, two or more copies of the same gene, two or more genes in same biological pathway (e.g., signaling pathway, metabolic pathway), two or more genes that share at least one biological activity and/or act on at least one common substrate and/or are part of the same protein or protein-nucleic acid complex (e.g., a heteroligomeric protein, spliceosome, proteasome, RISC, transcription complex, replication complex, kinetochore, channel, transporter). In some aspects, two or more guide sequences may guide a polypeptide comprising a catalytically inactive site specific nuclease fused to an effector domain to different sites located within the genomic sequence.

"Modulate" or "modify" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" or "modifier" is an agent that causes or facilitates a qualitative or quantitative change, alteration, or modification in a process, pathway, or phenomenon of interest.

In some aspects, "modulating" or "modifying" the methylation of a genomic sequence refers to any of a variety of alterations to the methylation status of the one or more genomic sequences. For example, the method of modulating the methylation of the one or more genomic sequences includes methylating or demethylating the genomic sequence (e.g., the genomic sequence may be methylated or the genomic sequence may be demethylated).

The methods provided herein can also be used to modify or modulate one or more genomic sequences in cells that are present in cell compositions such as embryos, zygotes, fetuses, and post-natal mammals. In some embodiments, a cell (e.g., a post-mitotic cell, a neuron, a fibroblast, a stem cell, etc.), zygote, embryo, or post-natal mammal is already genetically modified (already harbors one or more genetic modifications, e.g., epigenetic modifications) prior to being subjected to the methods described herein. For example, the cell, zygote, embryo, or post-natal mammal may be one into which an exogenous nucleic acid has been introduced by a process involving the hand of man (or may be descended at least in part from a cell or organism into which an exogenous nucleic acid has been introduced by a process involving the hand of man). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. In some embodiments, a cell, zygote, embryo, or post-natal mammal is not already genetically modified (does not already harbor one or more genetic modifications) prior to being subjected to the methods described herein.

In some aspects, the invention is directed to a method of producing a nonhuman mammal carrying modifications in one or more genomic sequences comprising introducing into a zygote or an embryo a catalytically inactive site specific nuclease fused to an effector domain having methylation or demethylation activity, and one or more guide sequences. The zygote or the embryo is maintained under conditions in which the guide sequence hybridizes to a portion of each of the one or more genomic sequences, and the catalytically inactive site specific nuclease fused to an effector domain either methylates or demethylates the genomic sequence, thereby producing an embryo having one or more modified genomic sequences. The embryo having one or more modified genomic sequences may be transferred into a foster nonhuman mammalian mother. The foster nonhuman mammalian mother is maintained under conditions in which one or more offspring carrying the one or more modified genomic sequences are produced, thereby producing a nonhuman mammal carrying modifications in one or more genomic sequences.

As will be apparent to those of skill in the art, the nonhuman mammals can also be produced using methods described herein and/or with conventional methods, see for example, U.S. Published Application No. 2011/0302665. A method of producing a non-human mammalian embryo can comprise injecting non-human mammalian ES cells (e.g., iPSCs) into non-human tetraploid blastocysts and maintaining said resulting tetraploid blastocysts under conditions that result in formation of embryos, thereby producing a non-human mammalian embryo. In some embodiments, said non-human mammalian cells are mouse cells and said non-human mammalian embryo is a mouse. In some embodiments, said mouse cells are mutant mouse cells and are injected into said non-human tetraploid blastocysts by microinjection. In some embodiments laser-assisted micromanipulation or piezo injection is used. In some embodiments, a non-human mammalian embryo comprises a mouse embryo.

Another example of such conventional techniques is two step cloning which involves introducing embryonic stem (ES) and/or induced pluripotent stem (iPS) cells comprising the one or more mutations into a blastocyst (e.g., a tetraploid blastocyst) and maintaining the blastocyst under conditions that result in development of an embryo. The embryo is then transferred (impregnated) into an appropriate foster mother, such as a pseudopregnant female (e.g., of the same species as the embryo). The foster mother is then maintained under conditions that result in development of live offspring that harbor the one or more mutations.

Another example is the use of the tetraploid complementation assay in which cells of two mammalian embryos are combined to form a new embryo (Tarn and Rossant, Develop, 750:6156-6163 (2003)). The assay involves producing a tetraploid cell in which every chromosome exists fourfold. This is done by taking an embryo at the two-cell stage and fusing the two cells by applying an electrical current. The resulting tetraploid cell continues to divide, and all daughter cells will also be tetraploid. Such a tetraploid embryo develops normally to the blastocyst stage and will implant in the wall of the uterus. In the tetraploid complementation assay, a tetraploid embryo (either at the morula or blastocyst stage) is combined with normal diploid embryonic stem cells (ES) from a different organism. The embryo develops normally; the fetus is exclusively derived from the ES cell, while the extraembryonic tissues are exclusively derived from the tetraploid cells.

Another conventional method used to produce nonhuman mammals includes pronuclear microinjection. DNA is introduced directly into the male pronucleus of a nonhuman mammal egg just after fertilization. Similar to the two-step cloning described above, the egg is implanted into a pseudopregnant female. Offspring are screened for the integrated transgene. Heterozygous offspring can be subsequently mated to generate homozygous animals.

A variety of nonhuman mammals can be used in the methods described herein. For example, the nonhuman mammal can be a rodent (e.g., mouse, rat, guinea pig, hamster), a nonhuman primate, a canine, a feline, a bovine, an equine, a porcine or a caprine.

In some aspects, various mouse strains and mouse models of human disease are used in conjunction with the methods of producing a nonhuman mammal carrying mutations in one or more target nucleic acid sequences described herein. One of ordinary skill in the art appreciates the thousands of commercially and non-commercially available strains of laboratory mice for modeling human disease. Mice models exist for diseases such as cancer, cardiovascular disease, autoimmune diseases and disorders, inflammatory diseases, diabetes (type 1 and 2), neurological diseases, and other diseases. Examples of commercially available research strains include, and is not limited to, 11BHSD2 Mouse, GSK3B Mouse, 129-E Mouse HSD1 1B1 Mouse, AK Mouse Immortomouse®, Athymic Nude Mouse, LCAT Mouse, B6 Albino Mouse, Lox-1 Mouse, B6C3F1 Mouse, Ly5 Mouse, B6D2F1 (BDF1) Mouse, MMP9 Mouse, BALB/c Mouse, NIH-III Nude Mouse, BALB/c Nude Mouse, NOD Mouse, NOD SCID Mouse, Black Swiss Mouse, NSE-p25 Mouse, C3H Mouse, NU/NU Nude Mouse, C57BL/6-E Mouse, PCSK9 Mouse, C57BL/6N Mouse, PGP Mouse (P-glycoprotein Deficient), CB6F1 Mouse, repTOP™ ERE-Luc Mouse, CD-I® Mouse, repTOP™ mitoIRE Mouse, CD-I® Nude Mouse, repTOP™ PPRE-Luc Mouse, CD1-E Mouse, Rip-HAT Mouse, CD2F1 (CDF1) Mouse, SCID Hairless Congenic (SHC™) Mouse, CF-1™ Mouse, SCID Hairless Outbred (SHO™) Mouse, DBA/2 Mouse, SJL-E Mouse, Fox Chase CB 17™ Mouse, SKH1-E Mouse, Fox Chase SCID® Beige Mouse, Swiss Webster (CFW®) Mouse, Fox Chase SCID® Mouse, TARGAT™ Mouse, FVB Mouse, THE POUND MOUSE™, and GLUT 4 Mouse. Other mouse strains include BALB/c, C57BL/6, C57BU10, C3H, ICR, CBA, A/J, NOD, DBA/1, DBA/2, MOLD, 129, HRS, MRL, NZB, NIH, AKR, SJL, NZW, CAST, KK, SENCAR, C57L, SAMR1, SAMP1, C57BR, and NZO.

In some aspects, the method of producing a nonhuman mammal carrying modifications in one or more genomic sequences further comprises mating one or more commercially and/or non-commercially available nonhuman mammal with the nonhuman mammal carrying modifications in one or more genomic sequences produced by the methods described herein. The invention is also directed to nonhuman mammals produced by the methods described herein.

In some aspects, the genomic sequence is associated with a disease or condition (e.g., see van der Weyden et al, Genome Biol, 12:224 (2011)). Specific examples of genetic modifications of interest include modifying sequence(s), (e.g., gene(s)) to match sequence in different species (e.g., change mouse sequence to human sequence for any gene(s) of interest), alter sites of potential or known post-translational modification of proteins (e.g., phosphorylation, glycosylation, lipidation, acylation, acetylation), alter sites of potential or known epigenetic modification, alter sites of potential or known protein-protein or protein-nucleic acid interaction, inserting tag, e.g., epitope tag, and/or inserting or deleting splice sites.

In some aspects, one copy of the one or more genomic sequences is modified. In some aspects, both copies of one or more of the genomic sequences in the cell are modified. In some aspects, the one or more genomic sequences that are modified are endogenous to the cell.

In particular aspects, at least two of the genomic sequences are endogenous genomic sequences. In some aspects, at least two of the genomic sequences are exogenous genomic sequences. In some aspects where there are at least two genomic sequences, at least one of the genomic sequences is an endogenous genomic sequence and at least one of the genomic sequences is an exogenous genomic sequence. In some aspects, at least two of the genomic sequences are endogenous genes. In some aspects, at least two of the genomic sequences are exogenous genes. In some aspects where there are at least two genomic sequences, at least one of the genomic sequences is an endogenous gene and at least one of the genomic sequences is an exogenous gene. In some aspects, at least two of the genomic sequences are at least 1 kB apart. In some aspects, at least two of the genomic sequences are on different chromosomes. A genomic sequence may comprises a tag (e.g., an epitope tag or a fluorescent tag) or a transgene (e.g., a reporter gene).

The methods provided herein provide for multiplexed genome editing in cells, embryos, zygotes and nonhuman mammals. As shown herein, cells, embryos, zygotes and non-human mammals carrying modifications in multiple genes can be generated in a single step. In some aspects, the methods described herein allow for the modification of 1, 2, 3, 4, 5, 6, 7, 8, 9, 10, 11, 12, 13, 14, 15, 16, 17, 18, 19, 20 21, 22, 23, 24, 25, 26, 27, 28, 29, 30, etc. genomic sequences (e.g., genes) in a (single) cell, zygote, embryo or nonhuman mammal using the methods described herein. In a particular aspect, one genomic sequence is modified in a (single) cell, zygote, embryo or nonhuman mammal. In some aspects, two genomic sequences are modified in a (single) cell, zygote, embryo or nonhuman mammal. In some aspects, three genomic sequences are modified in a (single) cell, zygote, embryo or nonhuman mammal. In some aspects, four genomic sequences are modified in a (single) cell, zygote, embryo or nonhuman mammal. In some aspects, five genomic sequences are modified in a (single) cell, zygote, embryo or nonhuman mammal, etc.

As will be apparent to those of skill in the art, a variety of methods can be used to introduce nucleic acid and/or protein into a cell, zygote, embryo, and or mammal. Suitable methods include calcium phosphate or lipid-mediated transfection, electroporation, injection, and transduction or infection using a vector (e.g., a viral vector such as an adenoviral vector). In some aspects, the nucleic acid and/or protein is complexed with a vehicle, e.g., a cationic vehicle, that facilitates uptake of the nucleic acid and/or protein, e.g., via endocytosis.

The method described herein can further comprise isolating the cell or zygote produced by the methods. Thus, in some aspects, the invention is directed to a cell or zygote (an isolated cell or zygote) produced by the methods described herein. In some aspects, the disclosure provides a clonal population of cells harboring the modification(s), replicating cultures comprising cells harboring the modification(s) and cells isolated from the generated animals.

The methods described herein can further comprise crossing the generated animals with other animals harboring genetic modifications (optionally in same strain background) and/or having one or more phenotypes of interest (e.g., disease susceptibility—such as NOD mice). In addition, the methods may comprise modifying a cell, zygote, and/or animal from a strain that harbors one or more genetic modifications and/or has one or more phenotypes of interest (e.g., disease susceptibility). In some aspects, the genetic modifications are epigenetic modifications.

The methods described herein can further comprise assessing whether the one or more target nucleic acids have been modified and/or modulated using a variety of known methods.

In some embodiments methods described herein are used to produce multiple genetic modifications in a cell, zygote, embryo, or animal, wherein at least one of the genetic modifications methylates or demethylates a gene, and at least one of the genetic modifications is in a different gene or genomic location. In some embodiments, a genetic modification further includes epigenetic modifications. The resulting cell, zygote, embryo, or animal, or a cell, zygote, embryo, or animal generated therefrom, is analyzed. In some embodiments at least one of the genetic modifications may be conditional (e.g., the effect of the modification, such as gene methylation or demethylation, only becomes manifest under certain conditions, which are typically under control of the artisan). In some embodiments animals are permitted to develop at least to post-natal stage, e.g., to adult stage. The appropriate conditions for the modification to produce an effect (sometimes termed "inducing conditions") are imposed, and the phenotype of the animal is subsequently analyzed. A phenotype may be compared to that of an unmodified animal or to the phenotype prior to the imposition of the inducing conditions.

Analysis may comprise any type of phenotypic analysis known in the art, e.g., examination of the structure, size, development, weight, or function, of any tissue, organ, or organ system (or the entire organism), analysis of behavior, activity of any biological pathway or process, level of any particular substance or gene product, etc. In some embodiments analysis comprises gene expression analysis, e.g., at the level of mRNA or protein. In some embodiments such analysis may comprise, e.g., use of microarrays (e.g., oligonucleotide microarrays, sometimes termed "chips"), high throughput sequencing (e.g., RNASeq), ChIP on Chip analysis, ChIPSeq analysis, etc. In some embodiments high content screening may be used, in which elements of high throughput screening may be applied to the analysis of individual cells through the use of automated microscopy and image analysis (see, e.g., Zanella et al, (2010). High content screening: seeing is believing. Trends Biotechnol. 28:237-245). In some embodiments analysis comprises quantitative analyses of components of cells such as spatiotemporal distributions of individual proteins, cytoskeletal structures, vesicles, and organelles, e.g., when contacted with test agents, e.g., chemical compounds. In some embodiments activation or inhibition of individual proteins and protein-protein interactions and/or changes in biological processes and cell functions may be assessed. A range of fluorescent probes for biological processes, functions, and cell components are available and may be used, e.g., with fluorescence microscopy. In some embodiments cells or animals generated according to methods herein may comprise a reporter, e.g., a fluorescent reporter or enzyme (e.g., a luciferase such as *Gaussia, Renilla*, or firefly luciferase) that, for example, reports on the expression or activity of particular genes. Such reporter may be fused to a protein, so that the protein or its activity is rendered detectable, optionally using a non-invasive detection means, e.g., an imaging or detection means such as PET imaging, MRI, fluorescence detection. Multiplexed genome editing according to the invention may allow installation of reporters for detection of multiple proteins, e.g., 2-20 different proteins, e.g., in a cell, tissue, organ, or animal, e.g., in a living animal.

Multiplexed genome editing according to the present invention may be useful to determine or examine the biological role(s) and/or roles in disease of genes of unknown function. For example, discovery of synthetic effects caused by modifications in first and second genes may pinpoint a genetic or biochemical pathway in which such gene(s) or encoded gene product(s) is involved.

In some embodiments it is contemplated to use, in methods described herein, cells or zygotes generated in or derived from animals produced in projects such as the International Knockout Mouse Consortium (IKMC), the website of which is knockoutmouse.org). In some embodiments it is contemplated to cross animals generated as described herein with animals generated by or available through the IKMC. For example, in some embodiments a mouse gene to be modified according to methods described herein is any gene from the Mouse Genome Informatics (MGI) database for which sequences and genome coordinates are available, e.g., any gene predicted by the NCBI, Ensembl, and Vega (Vertebrate Genome Annotation) pipelines for mouse Genome Build 37 (NCBI) or Genome Reference Consortium GRCm38.

In some embodiments a gene or genomic location to be modified is included in a genome of a species for which a fully sequenced genome exists. Genome sequences may be obtained, e.g., from the UCSC Genome Browser (genome.ucsc.edu/index.html). For example, in some embodiments a human gene or sequence to be modified according to methods described herein may be found in Human Genome Build hg19 (Genome Reference Consortium). In some embodiments a gene is any gene for which a Gene ID has been assigned in the Gene Database of the NCBI (ncbi.nlm.nih.gov/gene). In some embodiments a gene is any gene for which a genomic, cDNA, mRNA, or encoded gene product (e.g., protein) sequence is available in a database such as any of those available at the National Center for Biotechnology Information (ncbi.nih.gov) or Universal Protein Resource (uniprot.org). Databases include, e.g., GenBank, RefSeq, Gene, UniProtKB/SwissProt, UniProtKB/Trembl, and the like.

In some embodiments it is of interest to genetically modify a known or suspected differentially methylated region (DMR). There are various examples of differentially methylated regions. A differentially methylated region may be differentially methylated between cells of different cell types (e.g., muscle cells vs neuron or skin cells vs hepatocytes). A differentially methylated region may also be differentially methylated between diseased vs non-diseased cells (e.g., cancer vs non-cancer cells). A differentially methylated region may also be differentially methylated between differentiation states (e.g., progenitor cells vs terminally differentiated cells). The effect on expression of one or more genes (e.g., within up to about 0.5, 1, 2, 5, 10, 20, 50, 100, 500 kb or within about 1, 2, 5, or 10 MB from the modification) may be assessed. A genetic modification may be made in the sequence to determine whether such genetic modification alters the phenotype of a cell or animal or affects product of an RNA or protein or alters susceptibility to a disease. A genetic modification may include epigenetic modifications. In some aspects, the differentially methylated region may be hypermethylated or unmethylated.

In some aspects, it is of interest to demethylate a genomic sequence that is aberrantly hypermethylated or to methylate a genomic sequence that is aberrantly unmethylated. In some aspects, an aberrantly hypermethylated sequence or aberrantly unmethylated sequence may occur in a disease or disorder. In other aspects, it is of interest to methylate a CTCF site (e.g., a CTCF binding site) that is aberrantly unmethylated or remove methylation of a CTCF site that is aberrantly methylated. Modifying the methylation or demethylation of the CTCF site may treat or prevent a disease or disorder that exhibits an aberrantly unmethylated sequence or region or an aberrantly hypermethylated sequence or region. For example, a CTCF loop may be opened by methylating a CTCF binding site and thereby bring a gene that is outside the loop under control of an enhancer inside the loop if one wanted to increase expression of that gene (e.g., if expression of the gene is aberrantly low and/of if increased expression is desired for therapeutic or other purposes).

In some aspects, methods described herein may be used to produce cells having a modification in a promoter sequence. Targeting of dCas9-Tet1 or dCas9-Dnmt3a fusion proteins to methylated or unmethylated promoter sequences causes activation or silencing, respectively, of an endogenous reporter. For example, dCas9-Tet1 fusion protein targets the BDNF promoter IV and demethylates the promoter, thereby inducing BDNF expression in post-mitotic neurons.

In some aspects, methods described herein may be used to produce cells having a modification in an enhancer sequence. Targeting of dCas9-Tet1 or dCas9-Dnmt3a fusion proteins to methylated or unmethylated enhancer sequences causes activation or silencing, respectively, of an endogenous enhancer. For example, dCas9-Tet1 fusion protein targets the MyoD distal enhancer in fibroblasts and demethylates the enhancer, thereby facilitating reprogramming of fibroblasts into myoblasts.

In other aspects, methods described herein may be used to produce cells having a modification in a CTCF binding site. Targeting of dCas9-Tet1 or dCas9-Dnmt3a fusion proteins to CTCF binding sites may affect CTCF binding and interfere with DNA looping. For example, dCas9-Dnmt3a fusion protein performs targeted de novo methylation of a CTCF loop anchor site blocks CTCF binding and interferes with DNA looping, thereby causing altered gene expression in the neighboring loop.

In some embodiments any method described herein may comprise isolating one or more cells, samples, or substances from an animal generated according to methods described herein, e.g., any genetically modified animal generated as described herein. In some embodiments a method may further comprise analyzing the one or more cells, samples, or substances. Such analysis may, for example assess the effect of a genetic modification(s) introduced according to the methods. Genetic modifications may include the methylation or demethylation of a genomic sequence and/or may include epigenetic modifications.

In some embodiments animals generated according to methods described herein may be useful in the identification of candidate agents for treatment of disease and/or for testing agents for potential toxicity or side effects. In some embodiments any method described herein may comprise contacting an animal generated according to methods described herein, e.g., any genetically modified animal generated as described herein, with a test agent (e.g., a small molecule, nucleic acid, polypeptide, lipid, etc.). In some embodiments contacting comprises administering the test agent. Administration may be by any route (e.g., oral, intravenous, intraperitoneal, gavage, topical, transdermal, intramuscular, enteral, subcutaneous), may be systemic or local, may include any dose (e.g., from about 0.01 mg/kg to about 500 mg/kg), may involve a single dose or multiple doses. In some embodiments a method may further comprise analyzing the animal. Such analysis may, for example assess the effect of the test agent in an animal having a genetic modification(s) introduced according to the methods. In some embodiments a test agent that reduces or enhances an effect of one or more genetic modification(s) may be identified. In some embodiments if a test agent reduces or inhibits development of a disease associated with or produced by the genetic modification(s), (or reduces or inhibits one or more symptoms or signs of such a disease) the test agent may be identified as a candidate agent for treatment of a disease associated with or produced by the genetic modification(s) or associated with or produced by naturally occurring mutations in a gene or genomic location harboring the genetic modification.

In some embodiments a cell may be a diseased cell or may originate from a subject suffering from a disease, e.g., a disease affecting the cell or organ from which the cell was obtained. In some embodiments a mutation is introduced into a genomic region of the cell that is associated with a disease (e.g., any disease of interest, such as diseases mentioned herein). For example, in some embodiments it is of interest to methylate or demethylate a gene or genomic location that is known or suspected to be involved in disease pathogenesis and/or known or suspected to be associated with increased or decreased risk of developing a disease or particular manifestation(s) of a disease. In some embodiments it is of interest to methylate or demethylate a gene or genomic location and determine whether such modification alters the risk of developing a disease or one or more manifestations of a disease, alters progression of the disease, or alters the response of a subject to therapy or candidate therapy for a disease. In some embodiments it is of interest to modify an abnormal or disease-associated nucleotide or sequence to one that is normal or not associated with disease. In some embodiments this may allow production of genetically matched cells or cell lines (e.g., iPS cells or cell lines) that differ only at one or more selected sites of genetic modification. Multiplexed genome editing as described herein may allow for production of cells or cell lines that are isogenic except with regard to, e.g., between 2 and 20 selected sites of genetic alterations. This may allow for the study of the combined effect of multiple modifications that are suspected of or known to play a role in disease risk, development or progression.

The terms "disease", "disorder" or "condition" are used interchangeably and may refer to any alteration from a state of health and/or normal functioning of an organism, e.g., an abnormality of the body or mind that causes pain, discomfort, dysfunction, distress, degeneration, or death to the individual afflicted. Diseases include any disease known to those of ordinary skill in the art. In some embodiments a disease is a chronic disease, e.g., it typically lasts or has lasted for at least 3-6 months, or more, e.g., 1, 2, 3, 5, 10 or more years, or indefinitely. Disease may have a characteristic set of symptoms and/or signs that occur commonly in individuals suffering from the disease. Diseases and methods of diagnosis and treatment thereof are described in standard medical textbooks such as Longo, D., et al. (eds.), Harrison's Principles of Internal Medicine, 18th Edition; McGraw-Hill Professional, 2011 and/or Goldman's Cecil Medicine, Saunders; 24 edition (Aug. 5, 2011). In certain embodiments a disease is a multigenic disorder (also referred to as complex, multifactorial, or polygenic disorder). Such diseases may be associated with the effects of multiple genes, sometimes in combination with environmental factors (e.g., exposure to particular physical or chemical agents or biological agents such as viruses, lifestyle factors such as diet, smoking, etc.). A multigenic disorder may be any disease for which it is known or suspected that multiple genes (e.g., particular alleles of such genes, particular polymorphisms in such genes) may contribute to risk of developing the disease and/or may contribute to the way the disease manifests (e.g., its severity, age of onset, rate of progression, etc.) In some embodiments a multigenic disease is a disease that has a genetic component as shown by familial aggregation (occurs more commonly in certain families than in the general population) but does not follow Mendelian laws of inheritance, e.g., the disease does not clearly follow a dominant, recessive, X-linked, or Y-linked inheritance pattern. In some embodiments a multigenic disease is one that is not typically controlled by variants of large effect in a single gene (as is the case with Mendelian disorders). In some embodiments a multigenic disease may occur in familial form and sporadically. Examples include, e.g., Parkinson's disease, Alzheimer's disease, and various types of cancer. Examples of multigenic diseases include many common diseases such as hypertension, diabetes mellitus (e.g., type II diabetes mellitus), cardiovascular disease, cancer, and stroke (ischemic, hemorrhagic). In some embodiments a disease, e.g., a multigenic disease is a psychiatric, neurological, neurodevelopmental disease, neurodegenerative disease, cardiovascular disease, autoimmune disease, cancer, metabolic disease, or respiratory disease. In some embodiments at least one gene is implicated in a familial form of a multigenic disease.

In some embodiments a disease is cancer, which term is generally used interchangeably to refer to a disease characterized by one or more tumors, e.g., one or more malignant or potentially malignant tumors. The term "tumor" as used herein encompasses abnormal growths comprising aberrantly proliferating cells. As known in the art, tumors are typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclearxytoplasmic ratio, atypical mitoses, etc.); invasion of adjacent tissues (e.g., breaching a basement membrane); and/or metastasis. Malignant tumors have a tendency for sustained growth and an ability to spread, e.g., to invade locally and/or metastasize regionally and/or to distant locations, whereas benign tumors often remain localized at the site of origin and are often self-limiting in terms of growth. The term "tumor" includes malignant solid tumors, e.g., carcinomas (cancers arising from epithelial cells), sarcomas (cancers arising from cells of mesenchymal origin), and malignant growths in which there may be no detectable solid tumor mass (e.g., certain hematologic malignancies). Cancer includes, but is not limited to: breast cancer; biliary tract cancer; bladder cancer; brain cancer (e.g., glioblastomas, medulloblastomas): cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma, oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors, thyroid cancer including thyroid adenocarcinoma and medullary carcinoma. It will be appreciated that a variety of different tumor types can arise in certain organs, which may differ with regard to, e.g., clinical and/or pathological features and/or molecular markers. Tumors arising in a variety of different organs are discussed, e.g., the WHO Classification of Tumours series, $4^{th}$ ed, or $3^{rd}$ ed (Pathology and Genetics of Tumours series), by the International Agency for Research on Cancer (IARC), WHO Press, Geneva, Switzerland, all volumes of which are incorporated herein by reference. In some embodiments a cancer is one for which mutation or overexpression of particular genes is known or suspected to play a role in development, progression, recurrence, etc., of a cancer. In some embodiments such genes are targets for genetic modification according to methods described herein. In some embodiments a gene is an oncogene, proto-oncogene, or tumor suppressor gene. The term "oncogene" encompasses nucleic acids that, when expressed, can increase the likelihood of or contribute to cancer initiation or progression. Normal cellular sequences ("proto-oncogenes") can be activated to become oncogenes (sometimes termed "activated oncogenes") by mutation and/or aberrant expression. In various embodiments an oncogene can comprise a complete coding sequence for a gene product or a portion that maintains at least in part the oncogenic potential of the complete sequence or a sequence that encodes a fusion protein. Oncogenic mutations can result, e.g., in altered (e.g., increased) protein activity, loss of proper regulation, or an alteration (e.g., an increase) in RA or protein level. Aberrant expression may occur, e.g., due to chromosomal rearrangement resulting in juxtaposition to regulatory elements such as enhancers, epigenetic mechanisms, or due to amplification, and may result in an increased amount of proto-oncogene product or production in an inappropriate cell type. Proto-oncogenes often encode proteins that control or participate in cell proliferation, differentiation, and/or apoptosis. These proteins include, e.g., various transcription factors, chromatin remodelers, growth factors, growth factor receptors, signal transducers, and apoptosis regulators. A TSG may be any gene wherein a loss or reduction in function of an expression product of the gene can increase the likelihood of or contribute to cancer initiation or progression. Loss or reduction in function can occur, e.g., due to mutation or epigenetic mechanisms. Many TSGs encode proteins that normally function to restrain or negatively regulate cell proliferation and/or to promote apoptosis. Exemplary oncogenes include, e.g., MYC, SRC, FOS, JUN, MYB, RAS, RAF, ABL, ALK, AKT, TRK, BCL2, WNT, HER2/NEU, EGFR, MAPK, ERK, MDM2, CDK4, GLI1, GLI2, IGF2, TP53, etc. Exemplary TSGs include, e.g., RB, TP53, APC, NF1, BRCA1, BRCA2, PTEN, CDK inhibitory proteins (e.g., p16, p21), PTCH, WT1, etc. It will be understood that a number of these oncogene and TSG names encompass multiple family members and that many other TSGs are known.

In some embodiments a disease is a cardiovascular disease, e.g., atherosclerotic heart disease or vessel disease, congestive heart failure, myocardial infarction, cerebrovascular disease, peripheral artery disease, cardiomyopathy.

In some embodiments a disease is a psychiatric, neurological, or neurodevelopmental disease, e.g., schizophrenia, depression, bipolar disorder, epilepsy, autism, addiction. Neurodegenerative diseases include, e.g., Alzheimer's disease, Parkinson's disease, amyotrophic lateral sclerosis, frontotemporal dementia. [00162] In some embodiments a disease is an autoimmune diseases e.g., acute disseminated encephalomyelitis, alopecia areata, antiphospholipid syndrome, autoimmune hepatitis, autoimmune myocarditis, autoimmune pancreatitis, autoimmune polyendocrine syndromesautoimmune uveitis, inflammatory bowel disease (Crohn's disease, ulcerative colitis), type I diabetes mellitus (e.g., juvenile onset diabetes), multiple sclerosis, scleroderma, ankylosing spondylitis, sarcoid, pemphigus vulgaris, pemphigoid, psoriasis, myasthenia gravis, systemic lupus erythemotasus, rheumatoid arthritis, juvenile arthritis, psoriatic arthritis, Behcet's syndrome, Reiter's disease, Berger's disease, dermatomyositis, polymyositis, antineutrophil cytoplasmic antibody-associated vasculitides (e.g., granulomatosis with polyangiitis (also known as Wegener's granulomatosis), microscopic polyangiitis, and Churg-Strauss syndrome), scleroderma, Sjogren's syndrome, anti-glomerular basement membrane disease (including Goodpasture's syndrome), dilated cardiomyopathy, primary biliary cirrhosis, thyroiditis (e.g., Hashimoto's thyroiditis, Graves' disease), transverse myelitis, and Guillane-Barre syndrome.

In some embodiments a disease is a respiratory disease, e.g., allergy affecting the respiratory system, asthma, chronic obstructive pulmonary disease, pulmonary hypertension, pulmonary fibrosis, and sarcoidosis.

In some embodiments a disease is a renal disease, e.g., polycystic kidney disease, lupus, nephropathy (nephrosis or nephritis) or glomerulonephritis (of any kind).

In some embodiments a disease is vision loss or hearing loss, e.g., associated with advanced age.

In some embodiments a disease is an infectious disease, e.g., any disease caused by a virus, bacteria, fungus, or parasite.

In some embodiments, a disease exhibits hypermethylation (e.g., aberrant hypermethylation) or unmethylation (e.g., aberrant unmethylation) in a genomic sequence. For example, Fragile X Syndrome exhibits hypermethylation of FMR-1. A dCas9-Tet1 fusion protein may be used to specifically demethylate CCG hypermethylation and to reactivate FMG-1, thereby treating Fragile X Syndrome. The methods described herein may be used to treat or prevent diseases or disorders exhibiting aberrant methylation (e.g., hypermethylation or unmethylation).

It will be understood that classification of diseases herein is not intended to be limiting. One of ordinary skill in the art will appreciate that various diseases may be appropriately classified in multiple different groups.

In some embodiments a disease is one for which at least one genome-wide association (GWA) study (GWAS) has been performed. In some embodiments a GWAS types multiple "cases" (subjects having a disease of interest or particular manifestations thereof) and "controls" (subjects not having the disease or manifestations) for several thousand to millions, e.g., 1 million or more, e.g., 1-5 million or more, alleles (e.g., single nucleotide polymorphisms) positioned throughout the genome or a substantial portion thereof (e.g., at least 80%0, 90%, 95%, or more of the genome). It will be understood that control data may be obtained from historical data. Genotyping may be performed using microarrays or other methods. Alleles associated (e.g., in a statistically significant manner) with increased (or decreased) risk of a disease (or particular manifestations) may thereby be identified. It will be appreciated that statistical results may be corrected for multiple hypothesis testing, e.g., using methods known in the art. In some embodiments a p value of less than about $10^{-7}$, $10^{-8}$, or $10^{-9}$ is considered evidence of association. In some embodiments a gene or allele or polymorphism has been identified as contributing to disease risk or severity in at least one GWAS. See, e.g., genome.gov/gwastudies for examples of GWAS studies and genetic variants (alleles, polymorphisms) associated with various diseases. In some embodiments a gene (or any sequence) is one for which an allele or polymorphism is associated with an increased or decreased risk of developing a disease of at least 1.1, 1.2, 1.5, 2, 3, 4, 5, 7.5, 10, or more, relative to individuals not having the allele or polymorphism. In some embodiments an allele or polymorphism is associated with an increased or decreased risk of developing a disease of at least 1.1, 1.2, 1.5, 2, 3, 4, 5, 7.5, 10, or more, relative to individuals not having the allele or polymorphism. Genes, alleles, polymorphisms, or genetic loci that may contribute to any phenotypic trait of interest such as longevity, weight, resistance to infection, response or lack thereof to various therapeutic agents, resistance or susceptibility to potentially harmful substances such as toxins or infectious agents (e.g., viruses, bacteria, fungi, parasites), are of interest. A phenotypic trait may be a physical sign (such as blood pressure), a biochemical marker, which in some embodiments may be detectable in a body fluid such as blood, saliva, urine, tears, etc., such as level of a metabolite, LDL, etc., wherein an abnormally low or high level of the marker may correlate with having or not having the disease or with susceptibility to or protection from a disease.

In some embodiments a sequence to be inserted into a genome encodes a tag. The sequence may be inserted into a gene in an appropriate position such that a fusion protein comprising the tag is produced. The term "tag" is used in a broad sense to encompass any of a wide variety of polypeptides. In some embodiments, a tag comprises a sequence useful for purifying, expressing, solubilizing, and/or detecting a polypeptide. In some embodiments a tag may serve multiple functions. In some embodiments a tag is a relatively small polypeptide, e.g., ranging from a few amino acids up to about 100 amino acids long. In some embodiments a tag is more than 100 amino acids long, e.g., up to about 500 amino acids long, or more. In some embodiments, a tag comprises an HA, TAP, Myc, 6×His, Flag, V5, or GST tag, to name few examples. A tag (e.g., any of the aforementioned tags) that comprises an epitope against which an antibody, e.g., a monoclonal antibody, is available (e.g., commercially available) or known in the art may be referred to as an "epitope tag". In some embodiments a tag comprises a solubility-enhancing tag (e.g., a SUMO tag, NUS A tag, SNUT tag, a Strep tag, or a monomeric mutant of the Ocr protein of bacteriophage T7). See, e.g., Esposito D and Chatterjee D K. Curr Opin BiotechnoL; 17(4):353-8 (2006). In some embodiments, a tag is cleavable, so that at least a portion of it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., PCT/US05/05763. In some embodiments, a tag comprises a fluorescent polypeptide (e.g., GFP or a derivative thereof such as enhanced GFP (EGFP)) or an enzyme that can act on a substrate to produce a detectable signal, e.g., a fluorescence or colorimetric signal. Luciferase (e.g., a firefly, *Renilla*, or *Gaussia* luciferase) is an example of such an enzyme. Examples of fluorescent proteins include GFP and derivatives thereof, proteins comprising chromophores that emit light of different colors such as red, yellow, and cyan fluorescent proteins, etc. A tag, e.g., a fluorescent protein, may be monomeric. In certain embodiments a fluorescent protein is e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mK02, mOrange, mOrange2, TagRFP, TagRFP-T, mStrawberry, mRuby, mCherry, mRaspberry, mKate2, mPlum, niNeptune, mTomato, T-Sapphire, mAmetrine, mKeima. See, e.g., Chalfie, M. and Kain, SR (eds.) Green fluorescent protein: properties, applications, and protocols (Methods of biochemical analysis, v. 47). Wiley-Interscience, Hoboken, N.J., 2006, and/or Chudakov, D M, et al, Physiol Rev. 90(3): 1103-63, 2010 for discussion of GFP and numerous other fluorescent or luminescent proteins. In some embodiments a tag may comprise a domain that binds to and/or acts a sensor of a small molecule (e.g., a metabolite) or ion, e.g., calcium, chloride, or of intracellular voltage, pH, or other conditions. Any genetically encodable sensor may be used; a number of such sensors are known in the art. In some embodiments a FRET-based sensor may be used. In some embodiments different genes are modified to incorporate different tags, so that proteins encoded by the genes are distinguishably labeled. For example, between 2 and 20 distinct tags may be introduced. In some embodiments the tags have distinct emission and/or absorption spectra. In some embodiments a tag may absorb and/or emit light in the infrared or near-infrared region. It will be understood that any nucleic acid sequence encoding a tag may be codon-optimized for expression in a cell, zygote, embryo, or animal into which it is to be introduced.

In some embodiments it may be of interest to express fragments or domains of a protein, which may act in a dominant negative manner and may, for example, disrupt normal function or interaction of the protein.

In some embodiments a gene of interest encodes a protein the aggregation of which is associated with one or more diseases, which may be referred to as protein misfolding diseases. Examples include, e.g., alpha-synuclein (Parkinson's disease and related disorders), amyloid beta or tau (Alzheimer's disease), TDP-43 (frontotemporal dementia, ALS).

In some embodiments a gene of interest encodes a transcription factor, a transcriptional co-activator or co-repressor, an enzyme, a chaperone, a heat shock factor, a heat shock protein, a receptor, a secreted protein, a transmembrane protein, a histone (e.g., H1, H2A, H2B, H3, H4), a peripheral membrane protein, a soluble protein, a nuclear protein, a mitochondrial protein, a growth factor, a cytokine (e.g., an interleukin, e.g., any of IL-1-IL-33), an interferon (e.g., alpha, beta, or gamma), a chemokine (e.g., a CXC, CX3C, C (or XC), or CX3C chemokine). A chemokine may be CCL1-CCL28, CXCL1-CXCL17, XCL1 or XCL2, or CXC3L1). In some embodiments a gene encodes a colony-stimulating factor, a hormone (e.g., insulin, thyroid hormone, growth hormone, estrogen, progesterone, testosterone), an extracellular matrix protein (e.g., collagen, fibronectin), a motor protein (e.g., dynein, myosin), cell adhesion molecule, a major or minor histocompatibility (MHC) gene, a transporter, a channel (e.g., an ion channel), an immunoglobulin (Ig) superfamily (IgSF) gene (e.g., a gene encoding an antibody, T cell receptor, B cell receptor), tumor necrosis factor, an NF-kappaB protein, an integrin, a cadherin superfamily member (e.g., a cadherin), a selectin, a clotting factor, a complement factor, a plasminogen, plasminogen activating factor. Growth factors include, e.g., members of the vascular endothelial growth factor (VEGF, e.g., VEGF-A, VEGF-B, VEGF-C, VEGF-D), epidermal growth factor (EGF), insulin-like growth factor (IGF; IGF-1, IGF-2), fibroblast growth factor (FGF, e.g., FGF1-FGF22), platelet derived growth factor (PDGF), or nerve growth factor (NGF) families. It will be understood that the aforementioned protein families comprise multiple members. Any such member may be used in various embodiments. In some embodiments a growth factor promotes proliferation and/or differentiation of one or more hematopoietic cell types. For example, a growth factor may be CSF1 (macrophage colony-stimulating factor), CSF2 (granulocyte macrophage colony-stimulating factor, GM-CSF), or CSF3 (granulocyte colony-stimulating factors, G-CSF). In some embodiments a gene encodes erythropoietin (EPO). In some embodiments, a gene encodes a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the protein is a factor that promotes neurite outgrowth. In some embodiments, the protein is ciliary neurotrophic factor (CNTF) or brain-derived neurotrophic factor (BDNF).

In some embodiments a gene of interest encodes a polypeptide that is a subunit of any protein that is comprised of multiple subunits.

An enzyme may be any protein that catalyzes a reaction of a type that has been assigned an Enzyme Commission number (EC number) by the Nomenclature Committee of the International Union of Biochemistry and Molecular Biology (NC-IUBMB). Enzymes include, e.g., oxidoreductases, transferases, hydrolases, lyases, isomerases, ligases. Examples include, e.g., kinases (protein kinases, e.g., Ser/Thr kinase, Tyr kinase), lipid kinases (e.g., phosphatidylmositide 3-kinases (PI 3-kinases or PI3Ks)), phosphatases, acetyltransferases, methyltransferases, deacetylases, demethylases, lipases, cytochrome P450s, glucuronidases, recombinases (e.g., Rag-1, Rag-2). An enzyme may participate in the biosynthesis, modification, or degradation of nucleotides, nucleic acids, amino acids, proteins, neurotransmitters, xenobiotics (e.g., drugs) or other macromolecules.

The mammalian genome encodes at least about 500 different kinases. Kinases can be classified based on the nature of their typical substrates and include protein kinases (i.e., kinases that transfer phosphate to one or more protein(s)), lipid kinases (i.e., kinases that transfer a phosphate group to one or more lipid(s)), nucleotide kinases, etc. Protein kinases (PKs) are of particular interest in certain aspects of the invention. PKs are often referred to as serine/threonine kinases (S/TKs) or tyrosine kinases (TKs) based on their substrate preference. Serine/threonine kinases (EC 2.7.11.1) phosphorylate serine and/or threonine residues while TKs (EC 2.7.10.1 and EC 2.7.10.2) phosphorylate tyrosine residues. A number of "dual specificity" kinases (EC 2.7.12.1) that are capable of phosphorylating both serine/threonine and tyrosine residues are known. The human protein kinase family can be further divided based on sequence/structural similarity into the following groups: (1) AGC kinases—containing PKA, PKC and PKG; (2) CaM kinases—containing the calcium/calmodulin-dependent protein kinases; (3) CK1—containing the casein kinase 1 group; (4) CMGC—containing CDK, MAPK, GSK3 and CLK kinases; (5) STE—containing the homologs of yeast Sterile 7, Sterile 11, and Sterile 20 kinases; (6) TK—containing the tyrosine kinases; (7) TKL—containing the tyrosine-kinase like group of kinases. A further group referred to as "atypical protein kinases" contains proteins that lack sequence homology to the other groups but are known or predicted to have kinase activity, and in some instances are predicted to have a similar structural fold to typical kinases.

Receptors include, e.g., G protein coupled receptors, tyrosine kinase receptors, serine/threonine kinase receptors, Toll-like receptors, nuclear receptor, immune cell surface receptor. In some embodiments a receptor is a receptor for any of the hormones, cytokines, growth factors, or secreted proteins mentioned herein. Numerous G protein coupled receptors (GPCRs) are known in the art. See, e.g., Vroling B, GPCRDB: information system for G protein-coupled receptors. Nucleic Acids Res. 2011 January; 39(Database issue): D309-19. Epub 2010 Nov. 2. The GPCRDB can be found online at gpcr.org/7tm/. G protein coupled receptors include, e.g., adrenergic, cannabinoid, purinergic receptors, neuropeptide receptors, olfactory receptors. Transcription factors (TFs) (sometimes called sequence-specific DNA-binding factors) bind to specific DNA sequences and (alone or in a complex with other proteins), regulate transcription, e.g., activating or repressing transcription. Exemplary TFs are listed, for example, in the TRANSFAC® database, Gene Ontology (geneonlology.org/) or DBD (transcriptionfactor.org) (Wilson, et al, DBD—taxonomically broad transcription factor predictions: new content and functionality Nucleic Acids Research 2008 doi: 10.1093/nar/gkm964). TFs can be classified based on the structure of their DNA binding domains (DBD). For example in certain embodiments a TF is a helix-loop-helix, helix-turn-helix, winged helix, leucine zipper, bZIP, zinc finger, homeodomain, or beta-scaffold factor with minor groove contacts protein. Transcription factors include, e.g., p53, STAT3, PAS family transcription factors (e.g., HIF family: HIF1A, HIF2A, HIF3A), aryl hydrocarbon receptor.

Other methods of modifying or modulating nucleic acids in a cell or nonhuman mammal are described in PCT Application No. PCT/US2014/034387 and U.S. application Ser. No. 14/785,031, which are incorporated herein by reference in their entirety.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

Specific examples of these methods are set forth below in the Examples.

EXAMPLES

In this study, we demonstrate that fusion of dCas9 with the Tet1 enzymatic domain or Dnmt3a allows for targeted erasure or establishment of DNA methylation, respectively. As a proof of principle, we first induced alterations to DNA methylation in two synthetic methylation reporters integrated in mouse embryonic stem cells (mESCs). With application of dCas9-Tet1, we re-visited some long-standing questions in the DNA methylation field. Our results show that targeted demethylation of BDNF promoter IV is sufficient to activate its expression in mouse cortical neurons, and that targeted demethylation of a MyoD distal enhancer promotes reprogramming of fibroblasts into myoblasts and facilitates myotube formation. With dCas9-Dnmt3a, we demonstrate that targeted methylation at CTCF binding sites is able to block CTCF recruitment and to alter the expression of genes in the neighborhood loop by increasing their interaction frequencies with the super-enhancers insulated in the targeted loops. Furthermore, lentiviral delivery of dCas9-Tet1 with target gRNAs into mice enabled in vivo activation of a methylation reporter by demethylation of its promoter. Thus, dCas9-Tet1 and dCas9-Dnmt3a provide powerful tools to investigate the functional significance of DNA methylation in a locus-specific manner.

A Modified CRISPR System to Edit DNA Methylation

Figures 8A, 8B:
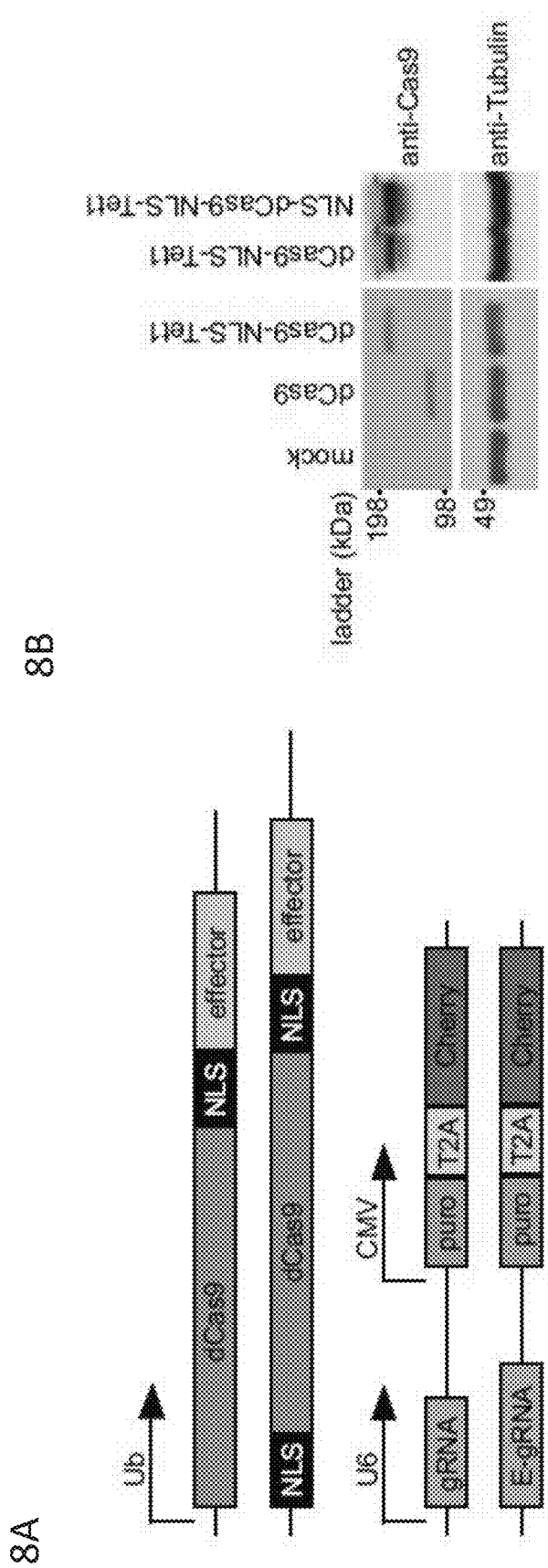
FIGS. 8A-8E depict a modified CRISPR system for editing 5-cytosine DNA methylation in the mammalian genome.
Figure 8C:
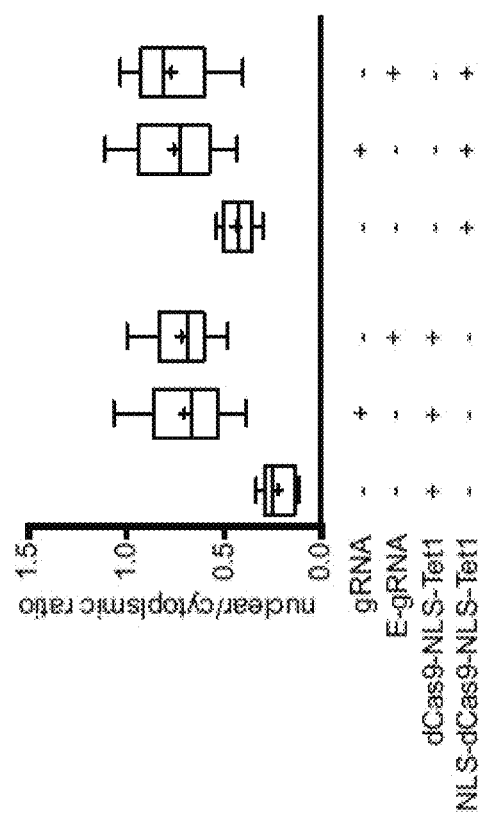
Figure 8D:
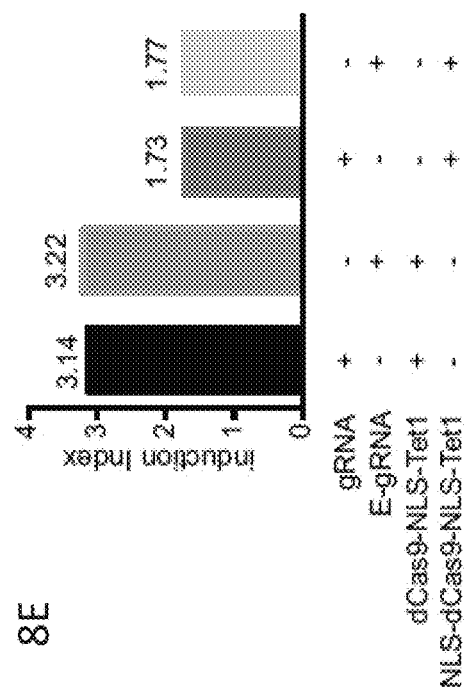
Figure 8E:
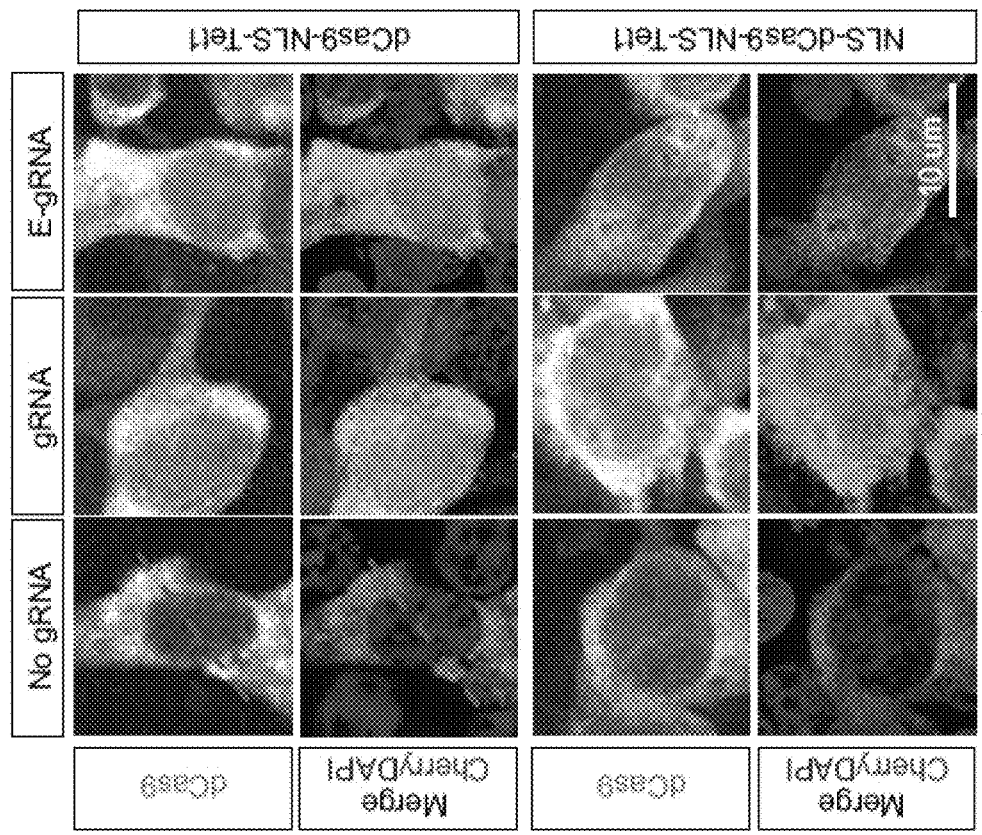

To achieve targeted editing of DNA methylation, we fused dCas9 with enzymes in the methylation/demethylation pathway (FIG. 1A). Based on previous studies using the TALE system to target specific CpGs (Bernstein et al., 2015; Maeder et al., 2013), Tet1 and Dnmt3a were chosen as the effectors in our system. Co-expression of sequence-specific guide RNA (gRNA) would be expected to target dCas9-Tet1 or dCas9-Dnmt3a to the specific locus and mediate modification of DNA methylation status without altering the DNA sequence. To optimize this chimeric CRISPR/dCas9-effector system, we tested two types of dCas9-Tet1 lentiviral constructs with nuclear localization signal (NLS) at different positions: dCas9-NLS-Tet1 and NLS-dCas9-NLS-Tet1 (FIGS. 8A and 8B). We also tested two types of gRNA lentiviral constructs, a widely used chimeric single-guide RNA referred as gRNA (Jinek et al., 2012) and a modified guide RNA with enhanced capacity to guide Cas9 to the designed genomic locus referred as E-gRNA (Chen et al., 2013). Both gRNA constructs contain a puro selection cassette and a Cherry fluorescence protein cassette driven by an independent CMV promoter that allows for Fluorescence Activated Cell Sorting (FACS) of gRNA-expressing cells after lentiviral transduction (FIG. 8A). Characterization of these constructs showed a robust gRNA-induced nuclear translocation for the dCas9-NLS-Tet1 construct (FIGS. 8C-8E), and thus this construct was chosen for all experiments in order to minimize non-specific modifications of DNA. Two types of gRNA behaved similarly (FIGS. 8C-8E) and thus were used interchangeably.

dCas9-Tet1 and dCas9-Dnmt3a Enable Targeted Alterations of CpG Methylation State To assess whether the dCas9-Tet1 and -Dnmt3a fusion constructs would induce demethylation or de novo methylation, respectively, of specific sequences, we utilized a methylation reporter system previously developed in our laboratory (Stelzer et al., 2015). This reporter system consists of a synthetic methylation-sensing promoter (conserved sequence elements from the promoter of an imprinted gene, Snrpn) that controls the expression of a green fluorescence protein (GFP). Insertion of this reporter construct into a genomic locus was shown to faithfully report on the methylation state of the adjacent sequences (Stelzer et al, 2015).

Figures 1C, 1D:
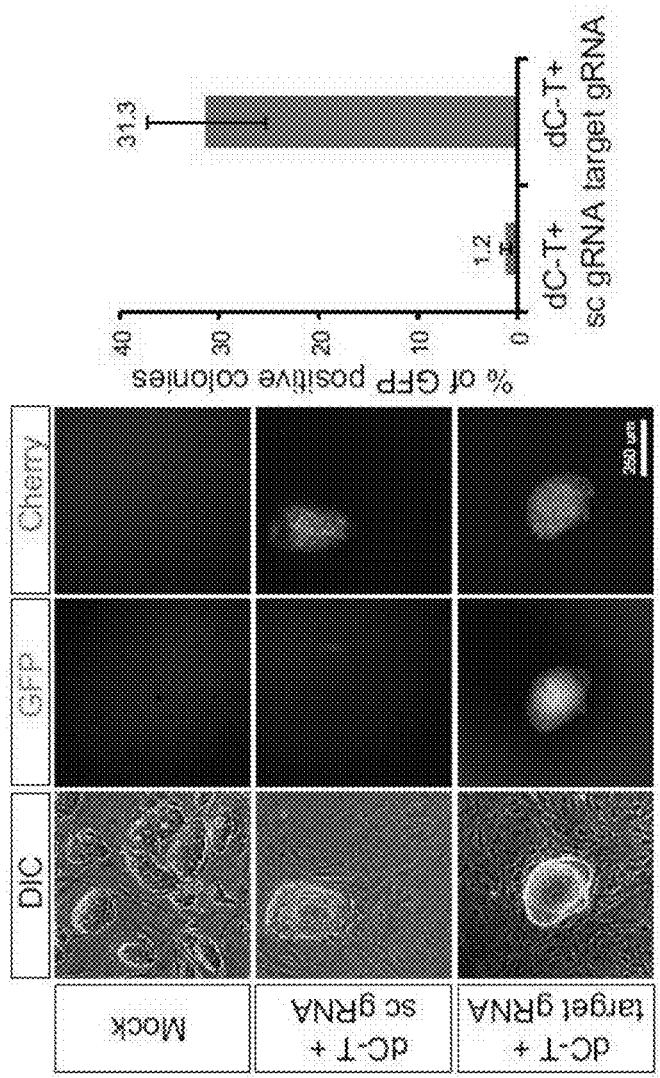
Figure 1E:
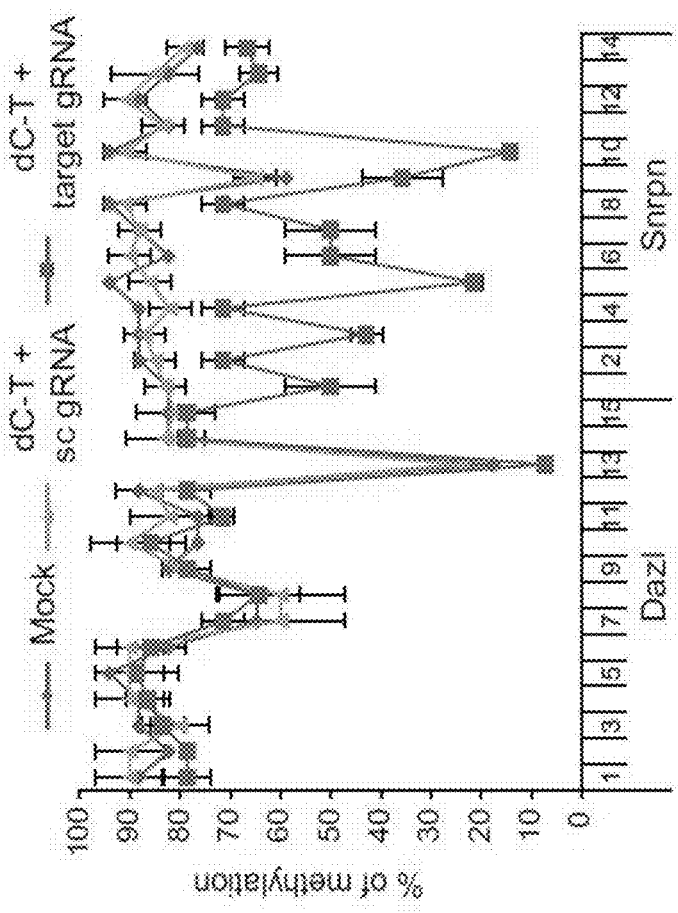
Figure 1F:
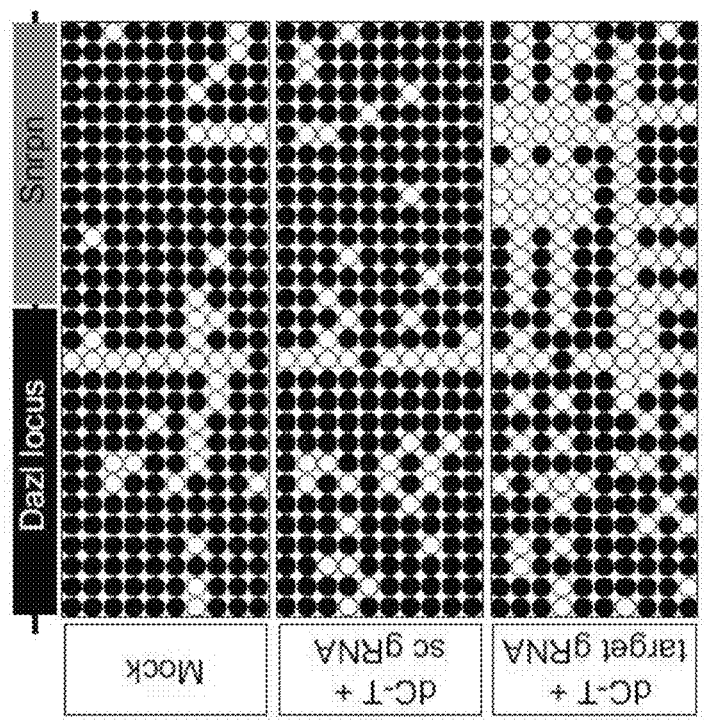

Demethylation of specific CpGs: To test whether defined sequences could be demethylated, we introduced the dCas9-Tet1 construct in combination with gRNAs to target the Snrpn-GFP reporter inserted into the Dazl promoter (FIG. 1B and FIG. 9A). Dazl is a germ cell specific gene, which is hypermethylated and not active in ES cells, and thus the GFP reporter is not expressed. To activate GFP expression by dCas9-Tet1 we designed 4 gRNAs targeting all 14 CpGs in the Snrpn promoter region. After infection with lentiviral vectors co-expressing dCas9-Tet1 and the 4 gRNAs for three days, some infection-positive cells as labeled by Cherry positive signal expressed from gRNA construct began to turn on GFP (FIG. 9B). To assess the activation efficiency by dCas9-Tet1 with target gRNAs, we analyzed the cells infected by both viruses using FACS. Among the Cherry positive population, about 26% of cells with target gRNAs activated GFP, whereas only 1% of cells with a scrambled gRNA were GFP positive (FIG. 1C and FIG. 9C). These Cherry positive single cells were further cultured to allow for formation of ES cell colonies. Cells with target gRNAs, but not the scrambled gRNA, expressed GFP (FIG. 1D). To confirm that the activation of GFP in these cells is caused by demethylation of the Snrpn promoter, we performed bisulfite sequencing of genomic DNA from these samples. As illustrated in FIGS. 1E and 1F, samples from cells with target gRNAs showed robust demethylation only in the Snrpn promoter region but not the adjacent Dazl locus, and samples from the cells with the scrambled gRNA showed a similar methylation status to the uninfected (Mock) control. We further analyzed the GFP-positive and -negative populations within infected Cherry-positive cells. As shown in FIG. 9D, a more robust demethylation of the Snrpn promoter region was observed in double positive cells (Cherry+; GFP+). These results confirm the targeted erasure of DNA methylation by dCas9-Tet1 with gRNAs in proliferative cells.

Figure 2D:
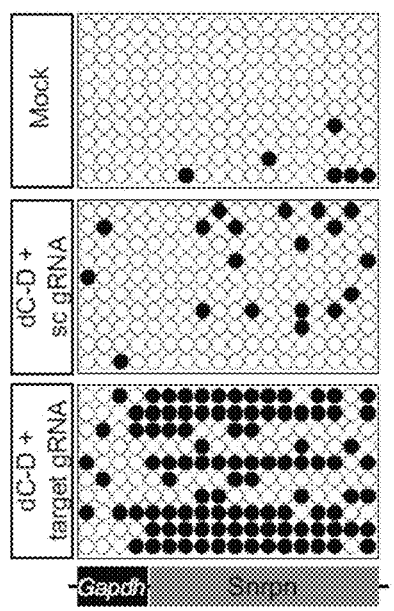
Figure 2E:
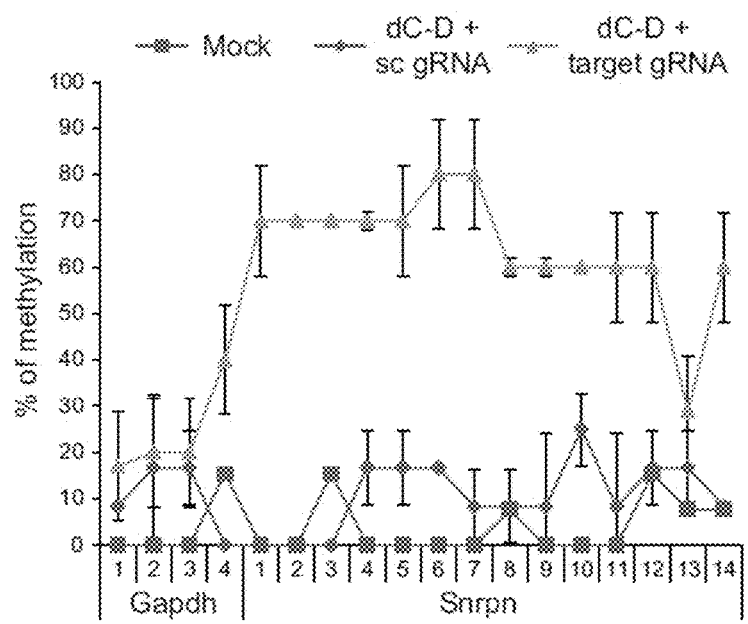
Figure 2F:
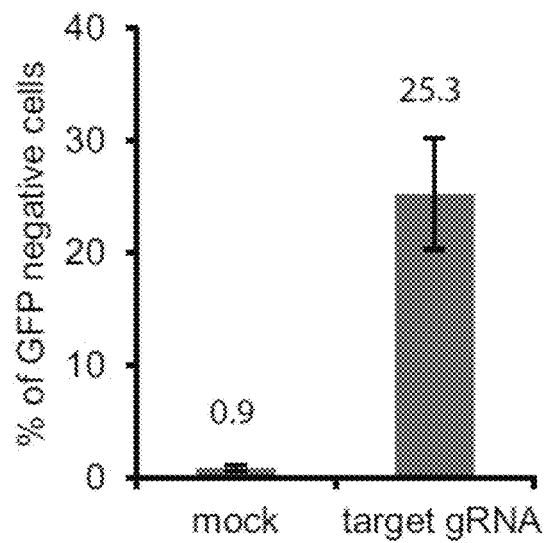
Figure 2G:
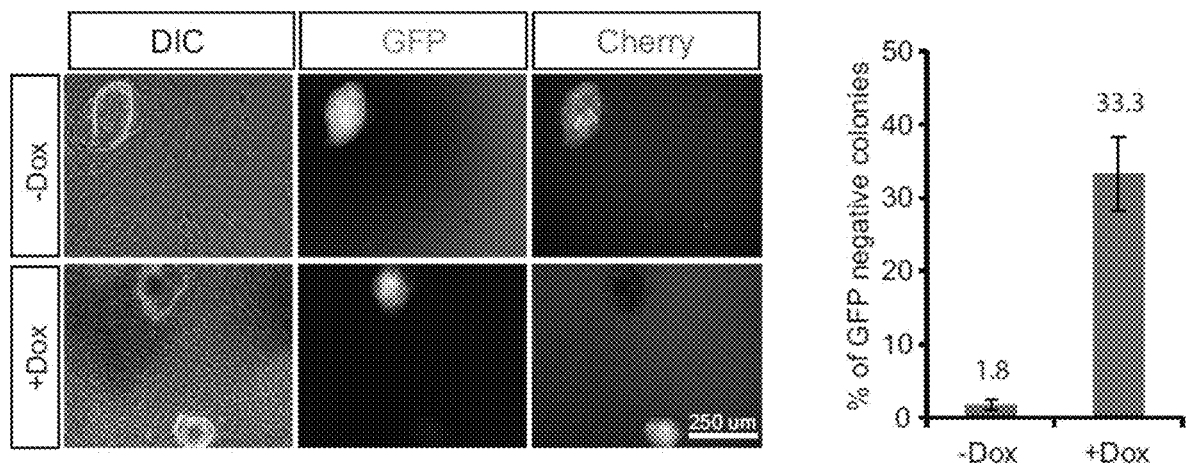
Figure 2H:
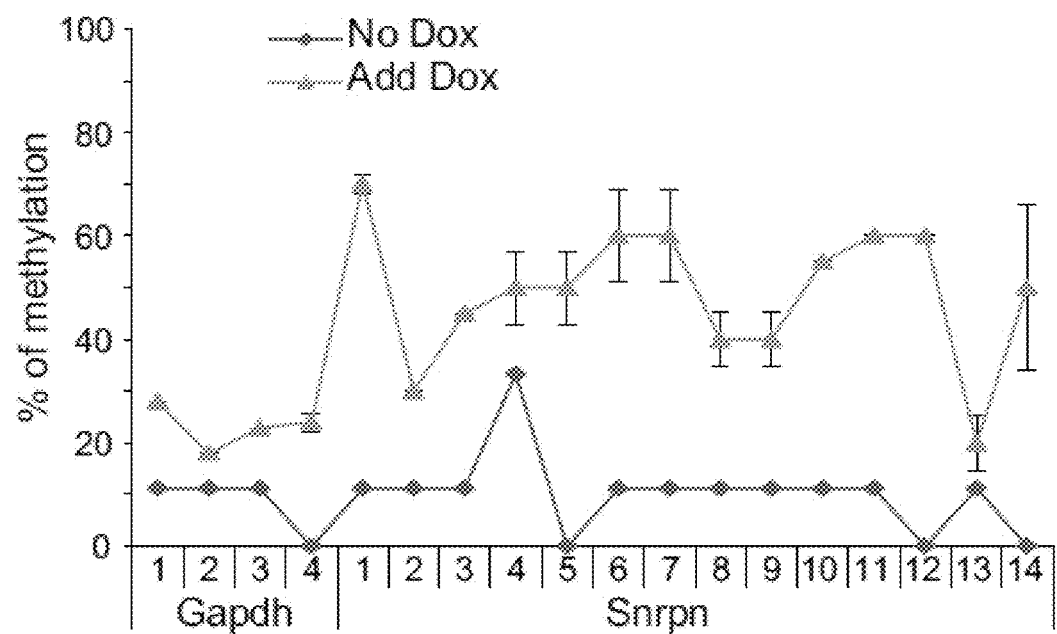
Figures 9E, 9F, 9G, 9H, 9I:
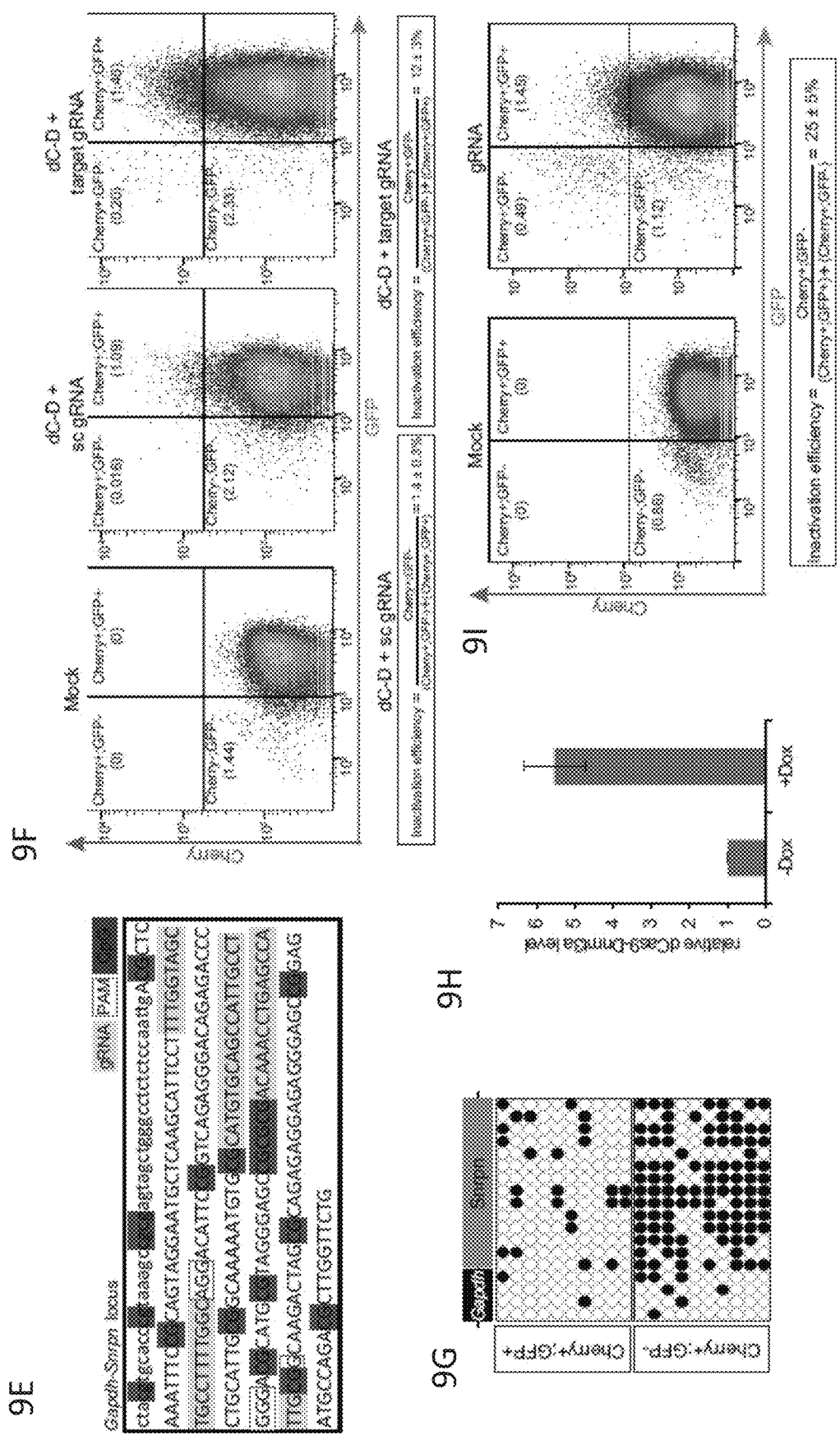
Figure 9J:
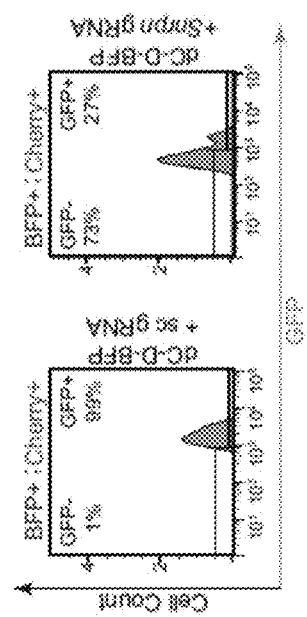
Figure 9J:
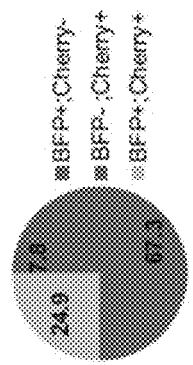
Figure 9J:
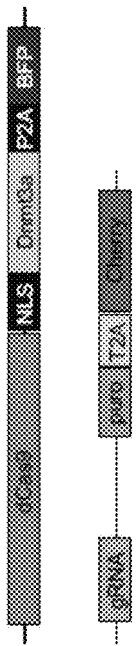

De Novo Methylation of Specific CpGs:

To assess whether a dCas9-Dnmt3a fusion protein could de novo methylate promoter sequences and silence gene expression, we used cells carrying the Snrpn-GFP reporter in the Gapdh promoter. These cells are GFP positive because Gapdh is unmethylated and expressed in ES cells (Stelzer et al., 2015). We infected the Gapdh-Snrpn-GFP ESCs with lentiviruses expressing dCas9-Dnmt3a and gRNAs targeting the Snrpn promoter or a scrambled gRNA (FIG. 2A and FIG. 9E), followed by FACS analysis. Among infection-positive (Cherry positive) population, about 12% of cells with target gRNAs inactivated GFP, whereas only 2% of cells with the scrambled gRNA were GFP negative (FIG. 2B and FIG. 9F). When the Cherry positive cells were grown in culture, GFP expression of cells with target gRNAs remained off whereas cells with the scrambled gRNA and mock controls remained GFP positive (FIG. 2C). Furthermore, bisulfite sequencing showed that transduction of dCas9-Dnmt3a/gRNAs resulted in a significant increase of DNA methylation in the Snrpn promoter region but not in the adjacent Gapdh region (FIGS. 2D-2E). Further analysis of the GFP-positive and -negative populations within infected Cherry-positive cells showed a more robust methylation of the Snrpn promoter region in Cherry+; GFP− cells (FIG. 9G). To overcome the possible limitation caused by low co-transduction efficiency of both dCas9-Dnmt3a and gRNA lentiviruses, a Doxycycline-inducible dCas9-Dnmt3a expression cassette was integrated into the Gapdh-Snrpn-GFP mES cell line by using a PiggyBac transposon system (FIG. 9H). After delivery of the same group of target gRNAs, FACS analysis showed that GFP inactivation efficiency was increased to 25% (FIG. 2F and FIG. 9I). Sorted Cherry-positive cells showed loss of GFP expression upon Doxycycline treatment (FIG. 2G) and were robustly methylated in the Snrpn promoter region (FIG. 2H). We also generated a new construct of dCas9-Dnmt3a-P2A-BFP which enables isolation of dCas9-Dnmt3a expressing cells by FACS. ~70% of GFP inactivation efficiency was achieved in FACS sorted double positive cells (BFP+; Cherry+) after lentiviral delivery of this construct together with gRNAs (FIG. 9J).

In summary, our results indicate that the dCas9 fusion constructs described above either efficiently demethylate methylated sequences (dCas9-Tet1) or de novo methylate unmethylated sequences (dCas9-Dnmt3a) in dividing cells when targeted by specific guide RNAs.

Comparison of dCas9- and TALE-Based Methylation Editing

Figures 10A, 10B, 10C, 10D:
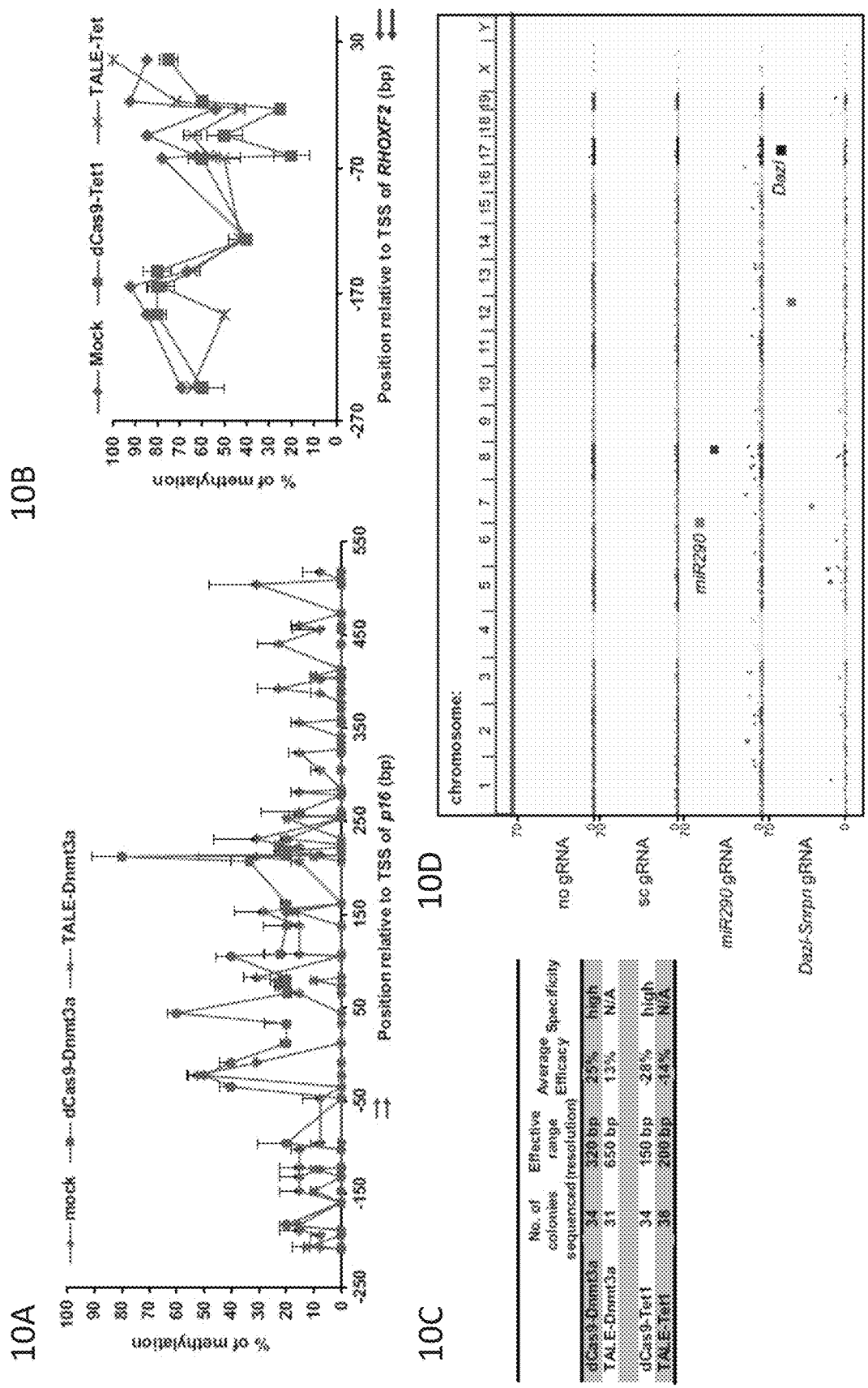
FIGS. 10A-10G depict comparison of TALE- and dCas9-based methylation editing.

To compare the methylation editing efficacy and effective range by dCas9-Tet1/Dnmt3a with TALE-based methods, we chose two previously reported loci edited by TALE-based method (Bernstein et al., 2015; Maeder et al., 2013) and designed a single gRNA targeting dCas9-Tet1/Dnmt3 to the same site bound by the TALE-Tet1/Dnmt3a. As shown in FIG. 10A and FIG. 10C, dCas9-Dnmt3a with one single gRNA targeting the p16 locus induced an average of 25% increase of methylation within a 320 bp region of the p16 promoter whereas TALE-Dnmt3a only induced 13% increase within a 650 bp region. Similarly, dCas9-Tet1 with one single gRNA targeting the RHOXF2 locus induced an average of 28% decrease of methylation within a 150 bp region of the RHOXF2 promoter whereas TALE-Tet1 only induced 14% decrease within a 200 bp region (FIGS. 10B-10C). These results suggest that dCas9-Tet1/Dnmt3a system has higher efficacy and resolution for methylation editing than TALE-based method.

Figures 10E, 10F, 10G:
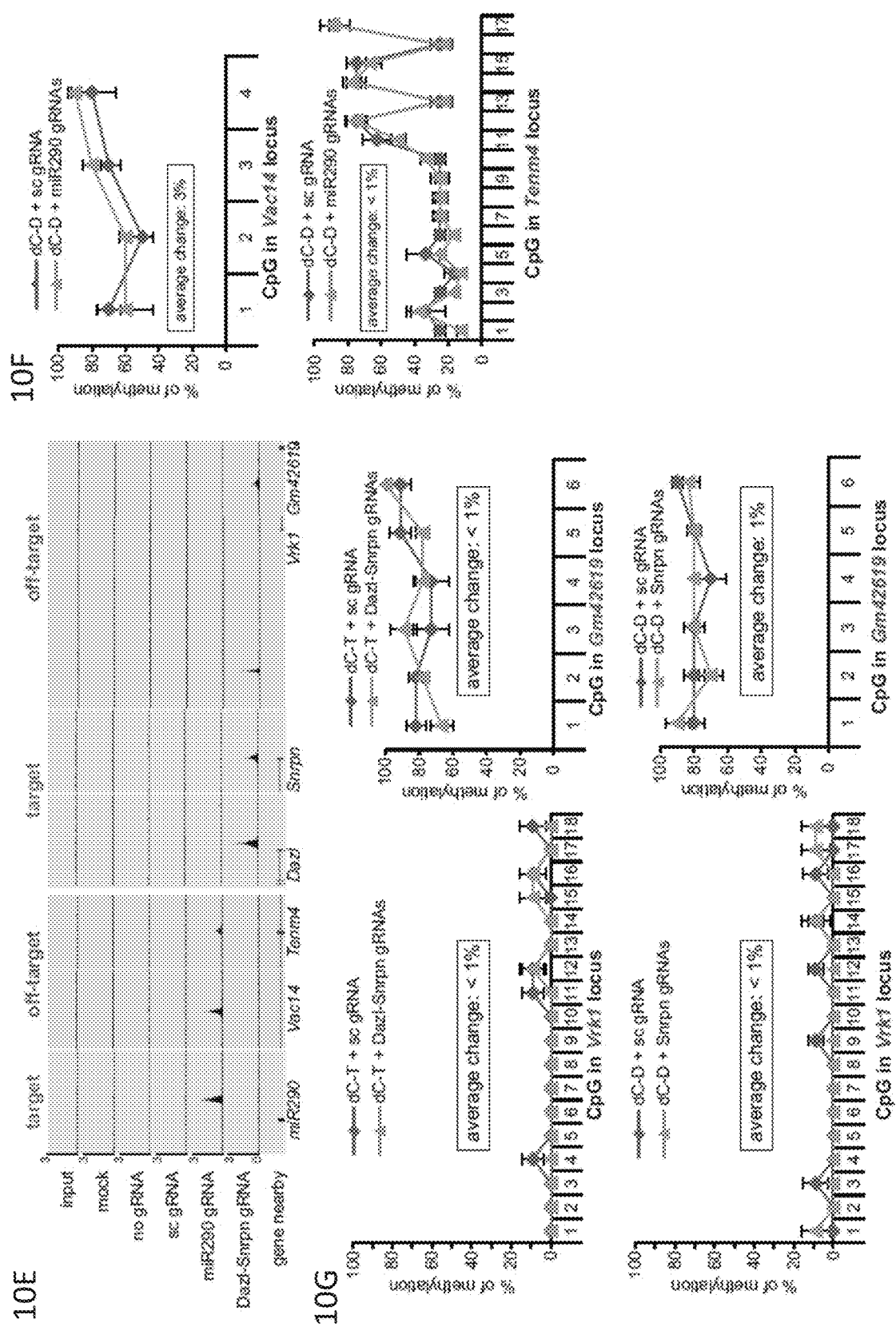
Figure 13A:
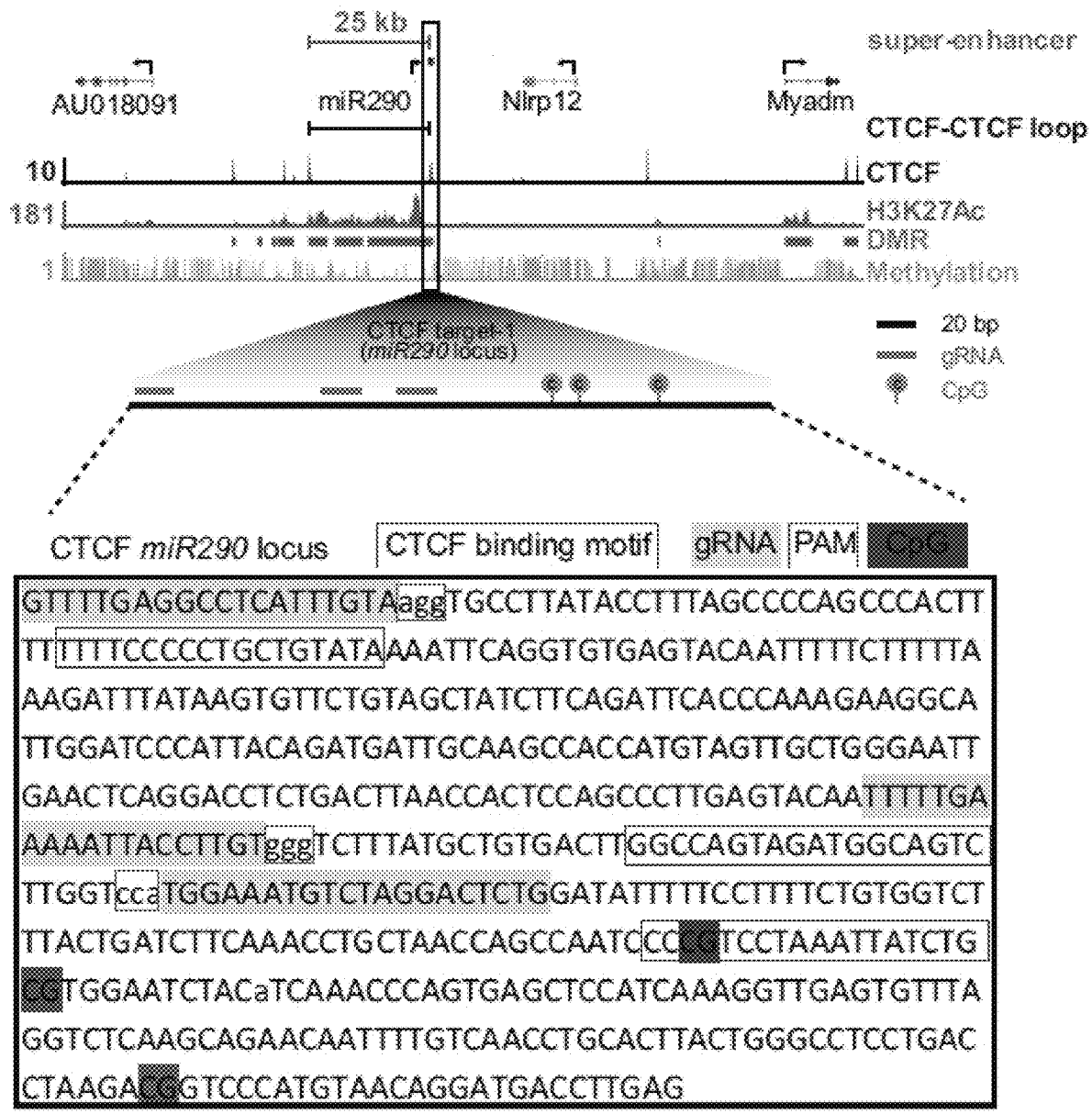
FIGS. 13A-13B depict gRNA design for targeted methylation of CTCF binding sites for miR290 and Pou5f1 loci.
Figure 18:
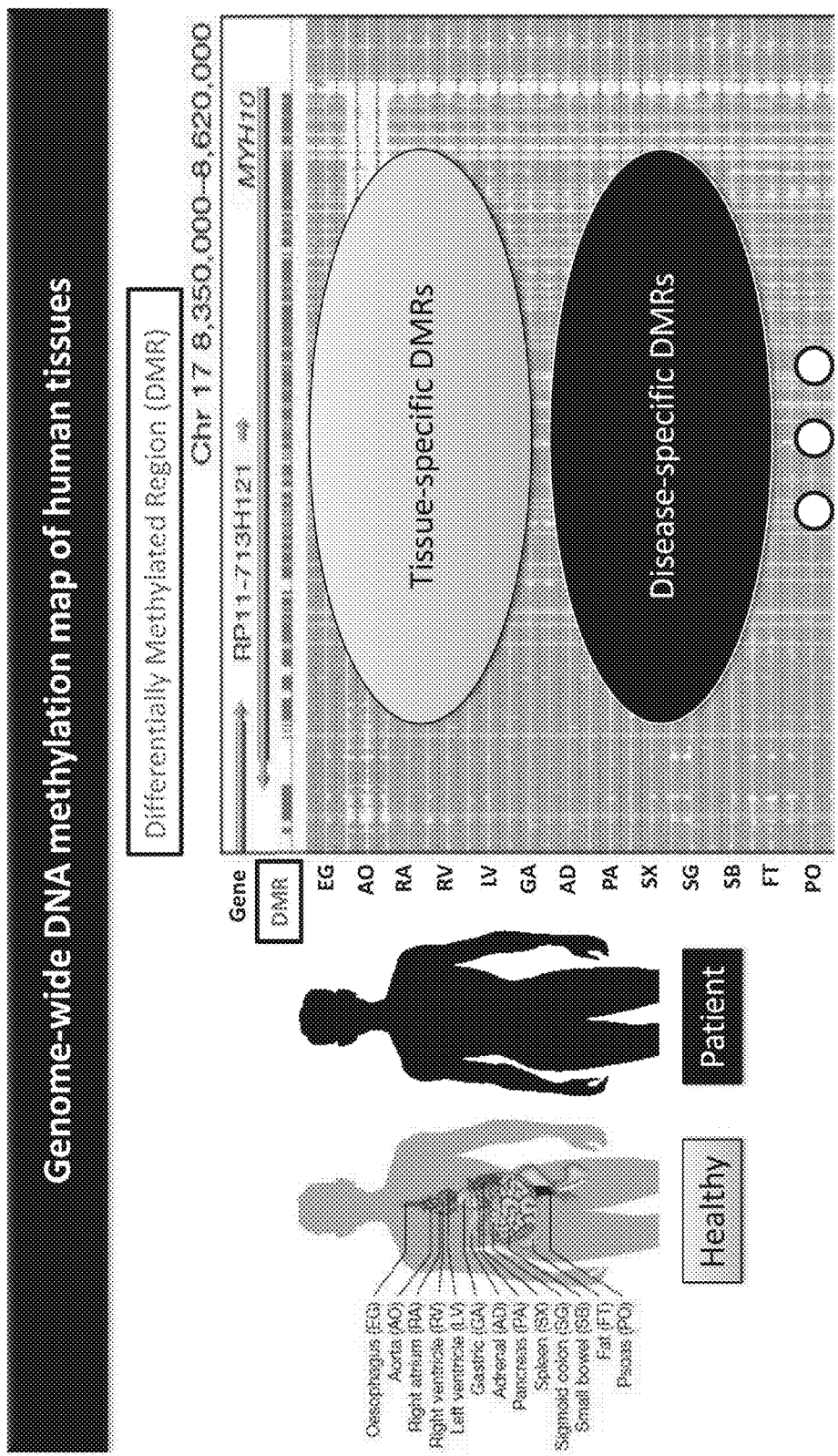
FIG. 18 provides an example of a DNA methylation map of human tissues.
Figure 19A:
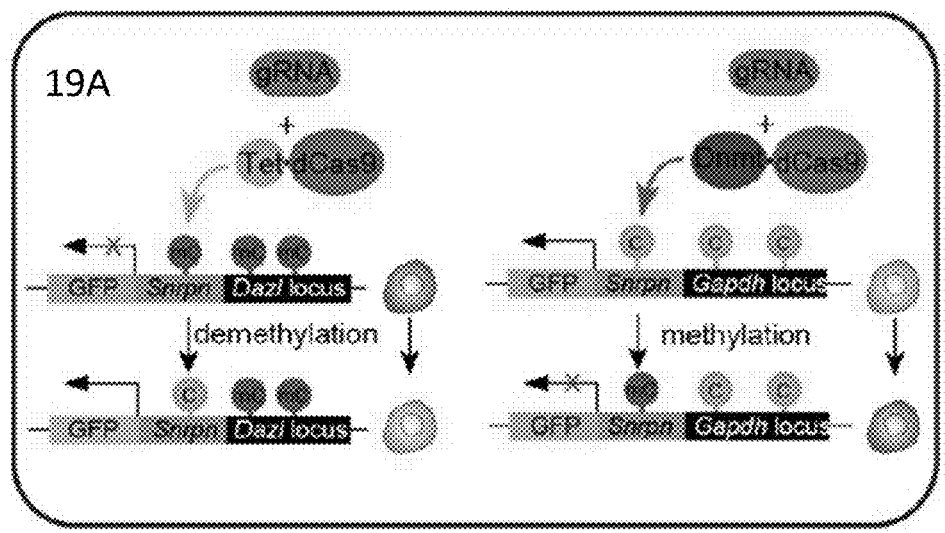
FIGS. 19A-19E depict a summary of methylation and demethylation activities.
Figure 19B:
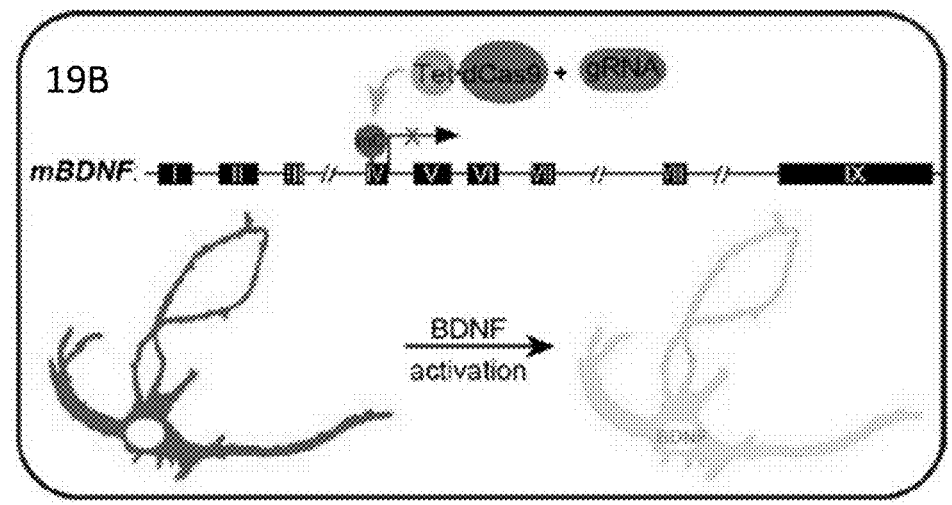
Figure 19C:
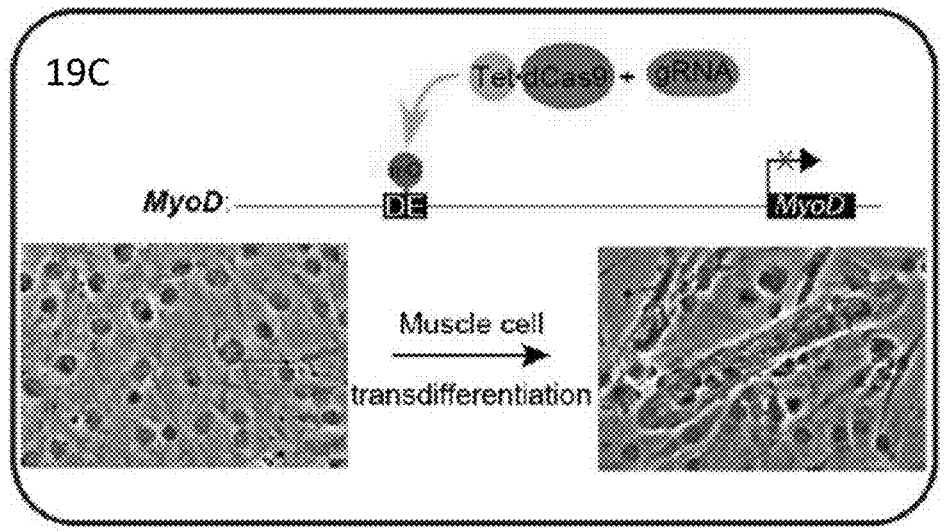
Figure 19D:
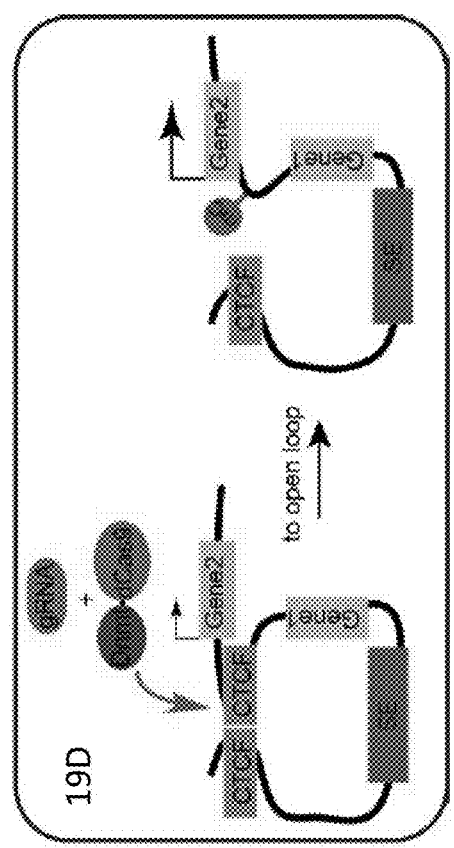
Figure 19E:
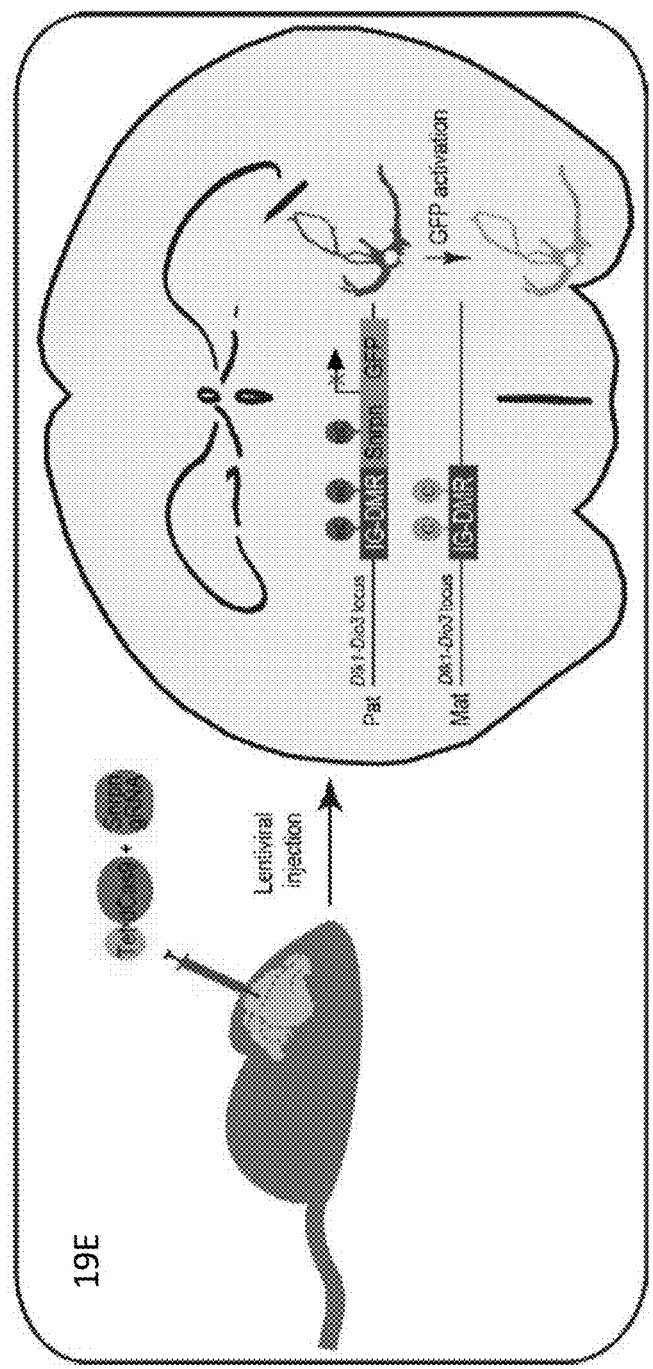
Figure 20:
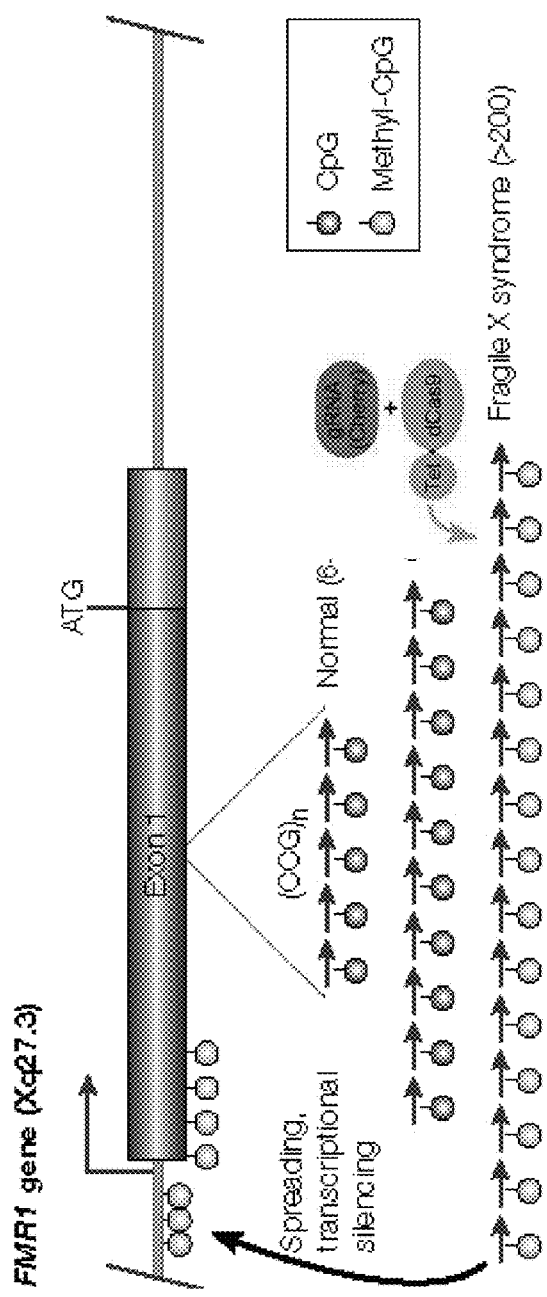
FIG. 20 depicts the reversal of hypermethylation of FMR-1 in Fragile X Syndrome. A cell exhibiting Fragile X Syndrome is contacted with dCas9-Tet1 fusion protein to specifically demethylate CCG hypermethylation so as to reactivate FMR-1.
Figure 21:
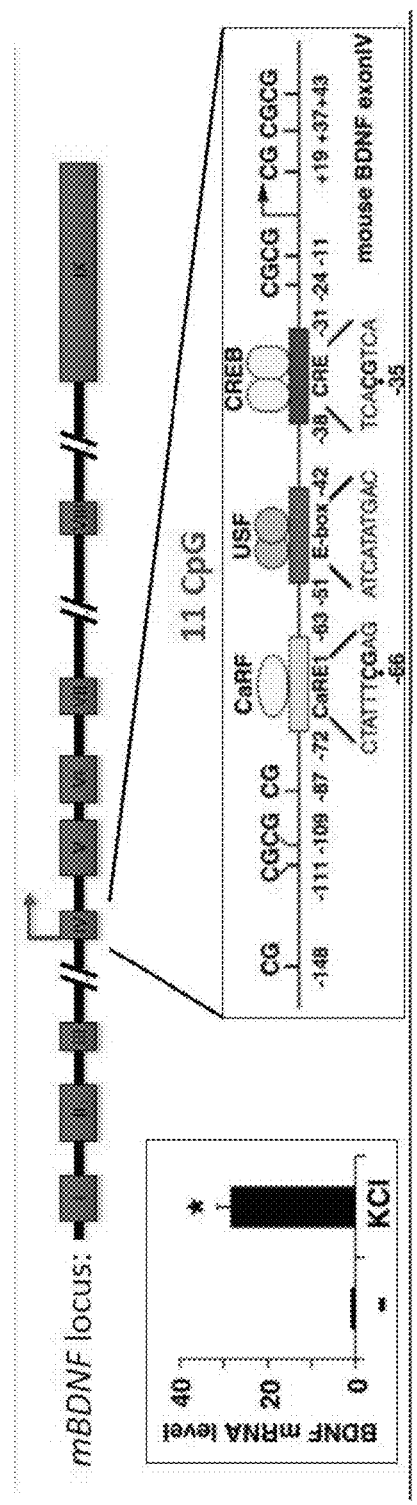
FIG. 21 demonstrates proposal of demethylation of BDNF to operate in post-mitotic neurons.
Figure 22:
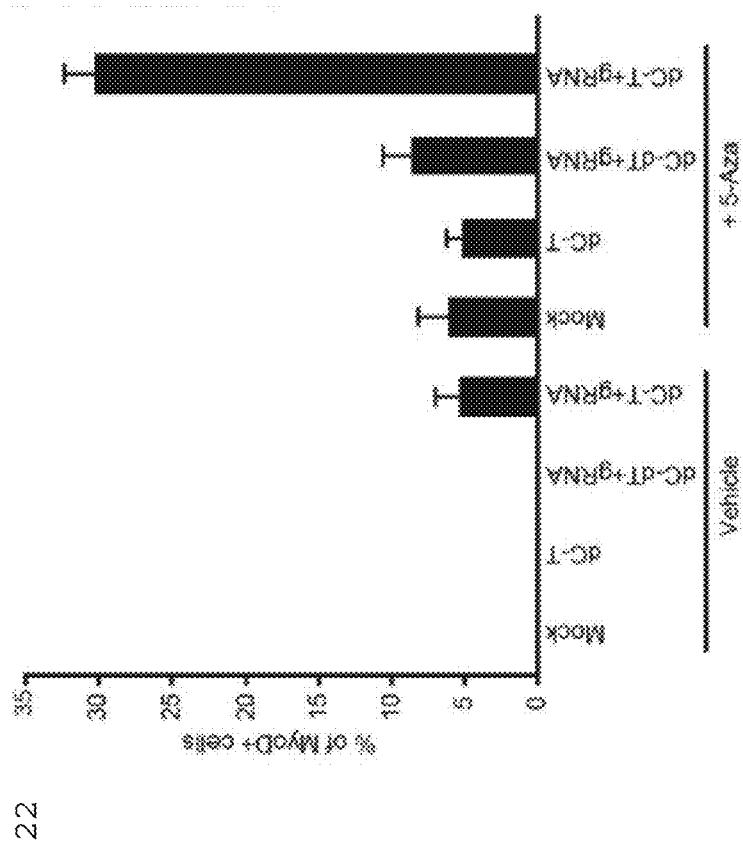
FIG. 22 depicts quantification of MyoD positive cell ratio after infection with lentiviruses expressing dC-T alone, dC-T with target gRNA, and dC-dT with target gRNAs.
Figure 23A:
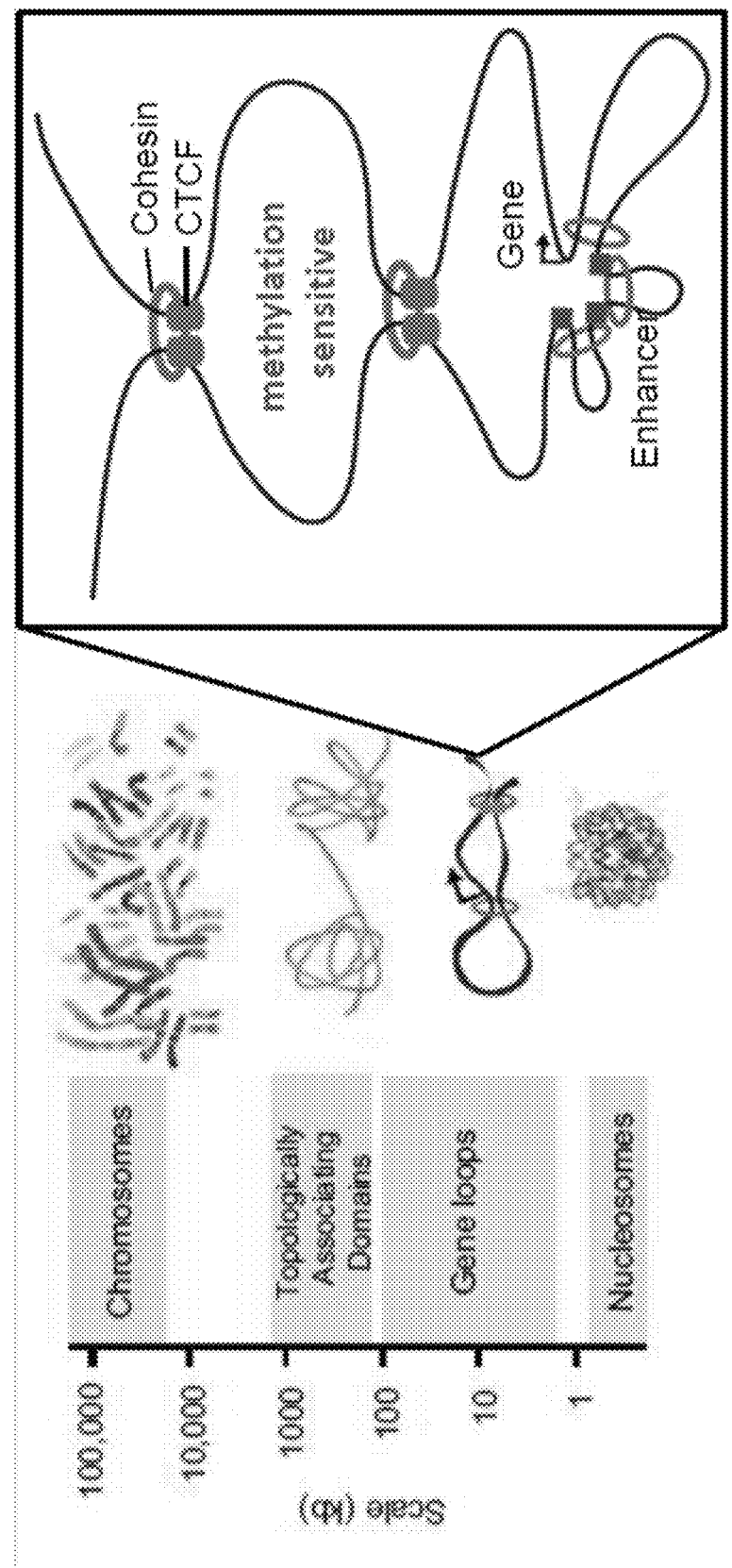
FIGS. 23A-23C depict targeted methylation of CTCF binding sites.
Figures 23B, 23C:
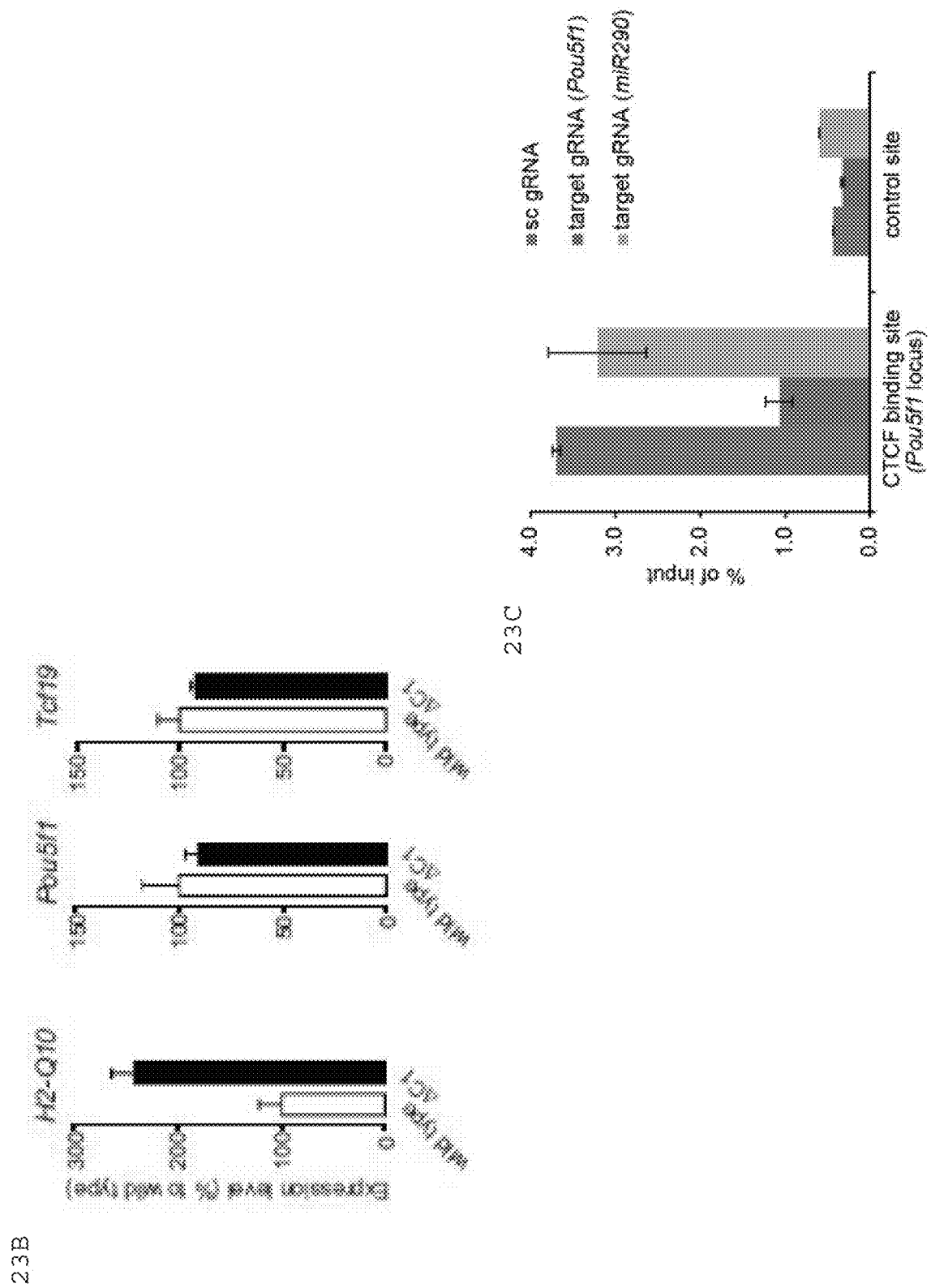

To evaluate the specificity of dCas9-Tet1/Dnmt3a-mediated methylation editing, we performed dCas9 ChIP-seq assay and identified 9 binding sites in the presence of gRNAs targeting the Dazl-Snrpn region described in FIG. 9A and 18 binding sites in the presence of gRNAs targeting CTCF binding sites adjacent to the miR290 locus (see below FIG. 13A). FIG. 10D shows that among the identified binding sites for each group of gRNAs, the targeted locus (Dazl-Snrpn or miR290) showed the highest level of binding for dCas9-Dnmt3a (Table S1). The second and third strongest binding sites for each targeted locus were illustrated in FIG. 10E, and bisulfite sequencing analysis of these loci showed only marginal change in methylation level (FIGS. 10F-10G), likely due to the significantly lower binding affinity of dCas9-Dnmt3a/Tet1 at these off-target loci compared to the targeted loci. These results indicate that dCas9-based epigenetic editing can be highly specific.

Targeted Demethylation of BDNF Promoter IV Activates BDNF in Neurons

Figure 3A:
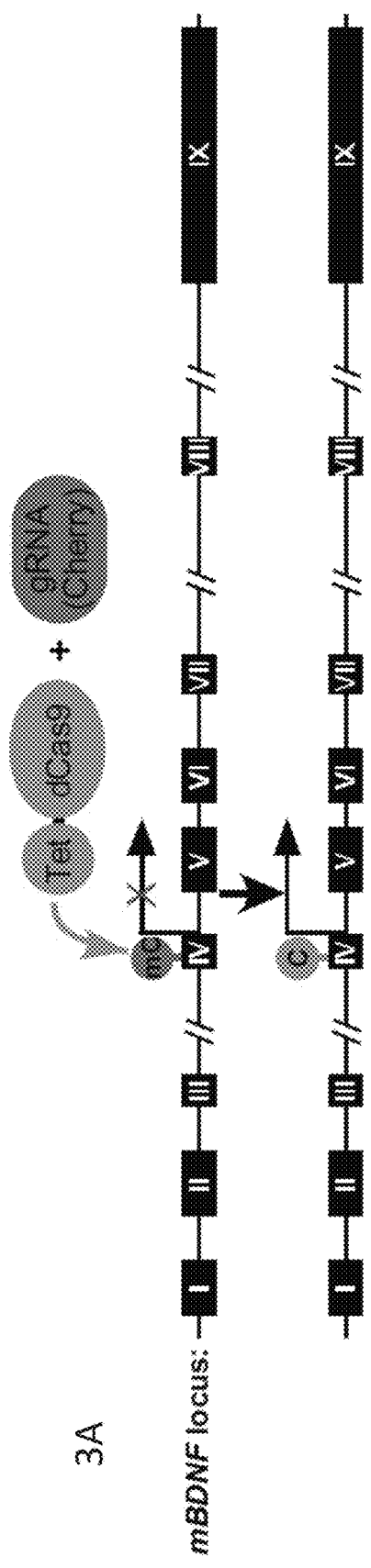
FIGS. 3A-3E depict targeted demethylation of BDNF promoter IV by dCas9-Tet1 to activate BDNF in neurons.
Figure 3B:
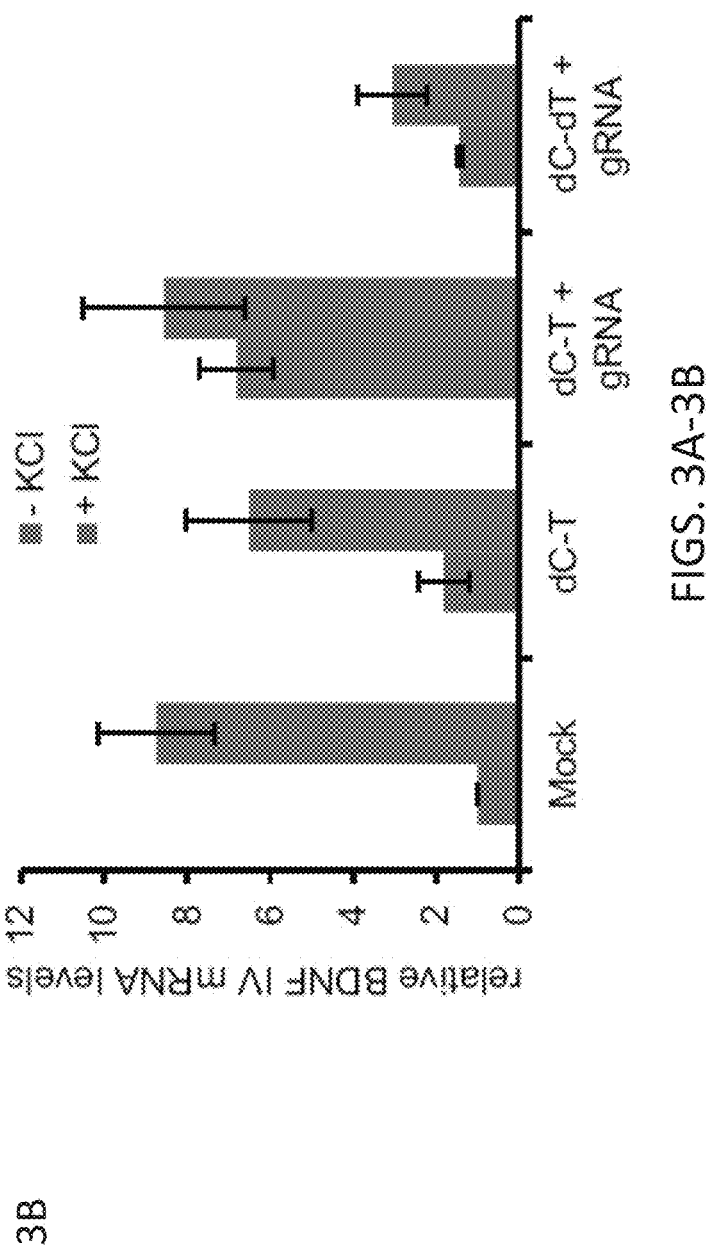
Figure 3C:
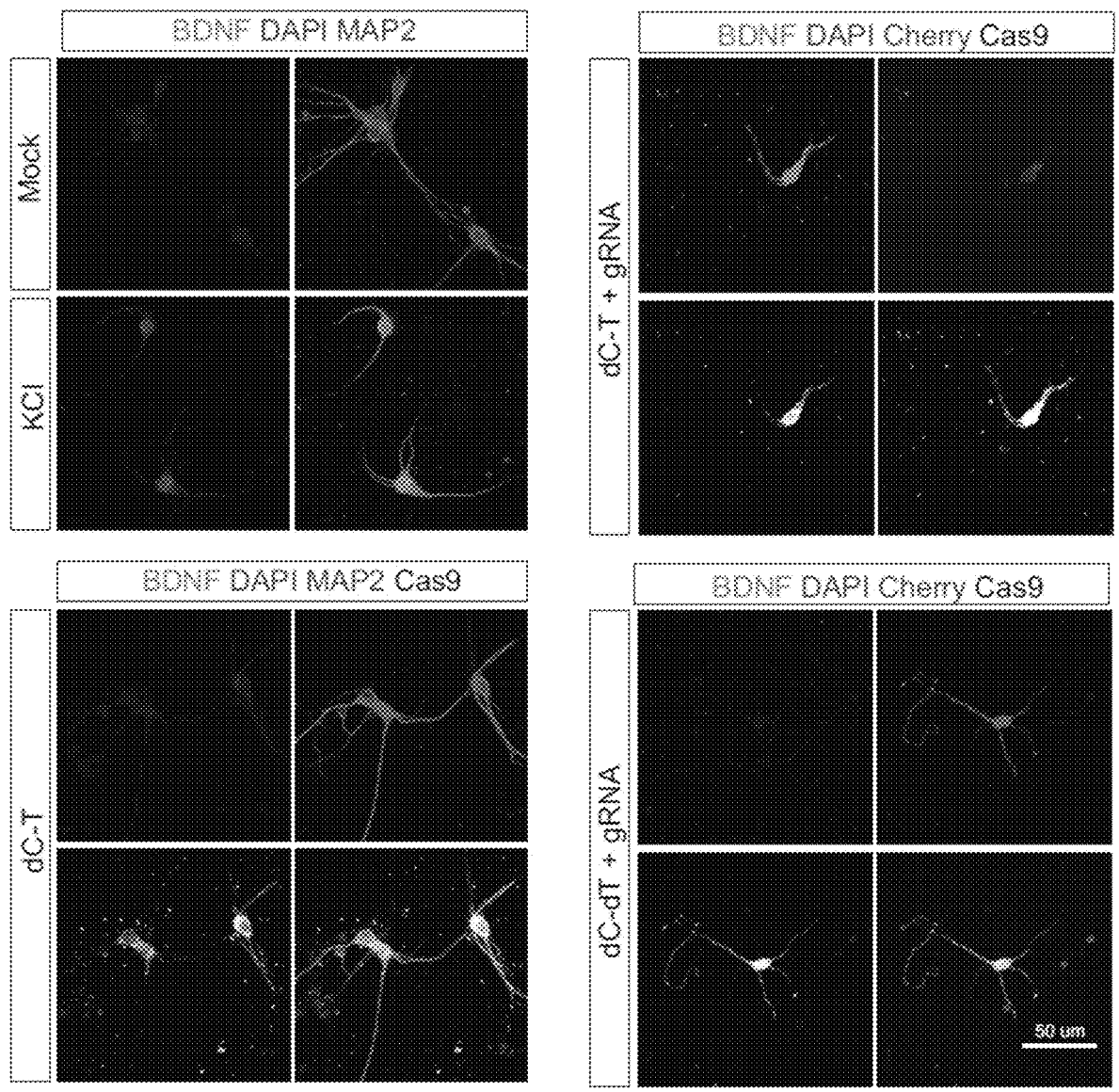
Figure 3D:
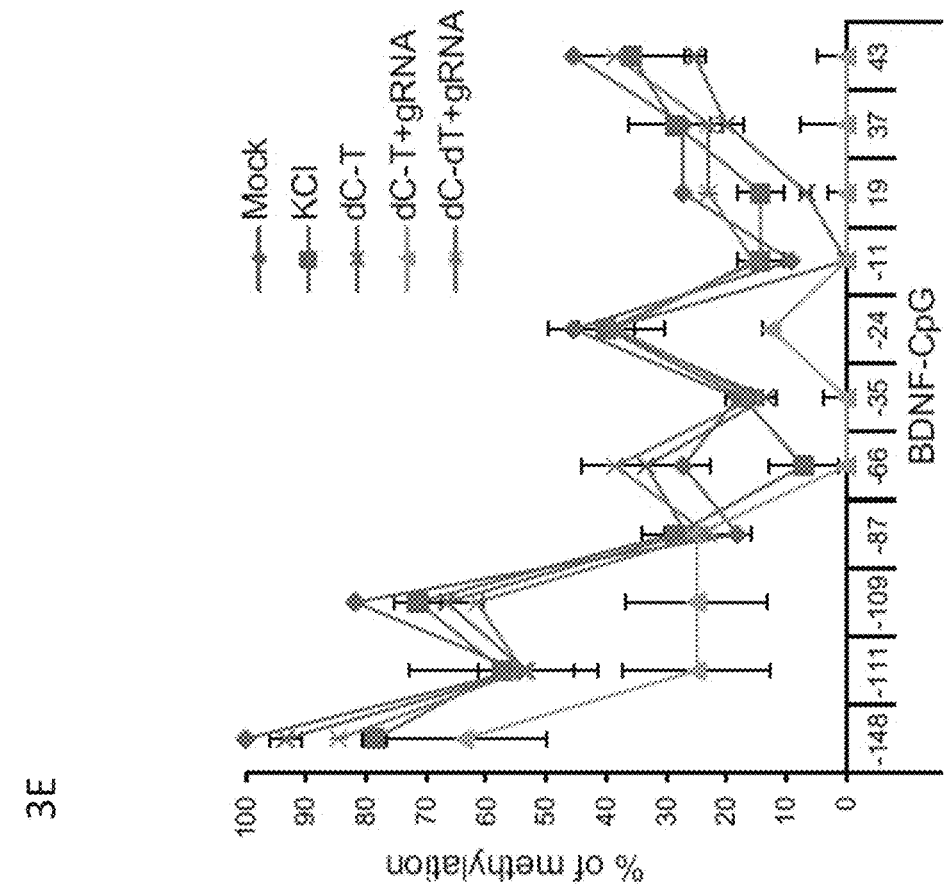
Figure 3E:
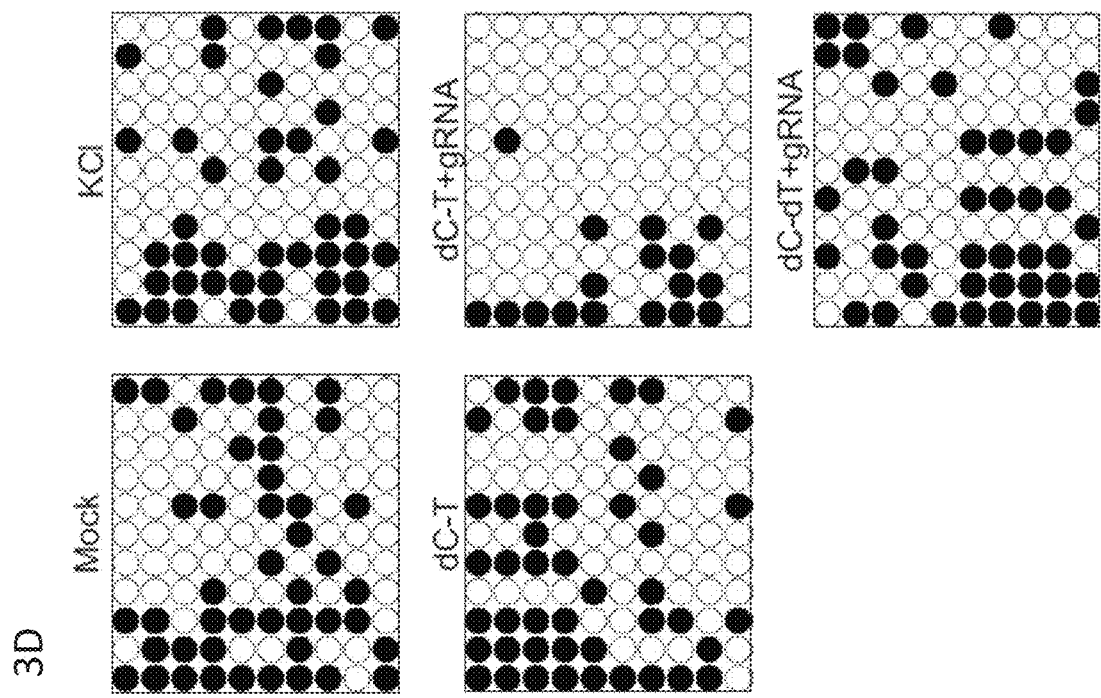
Figures 11A, 11B, 11C, 11D, 11E:
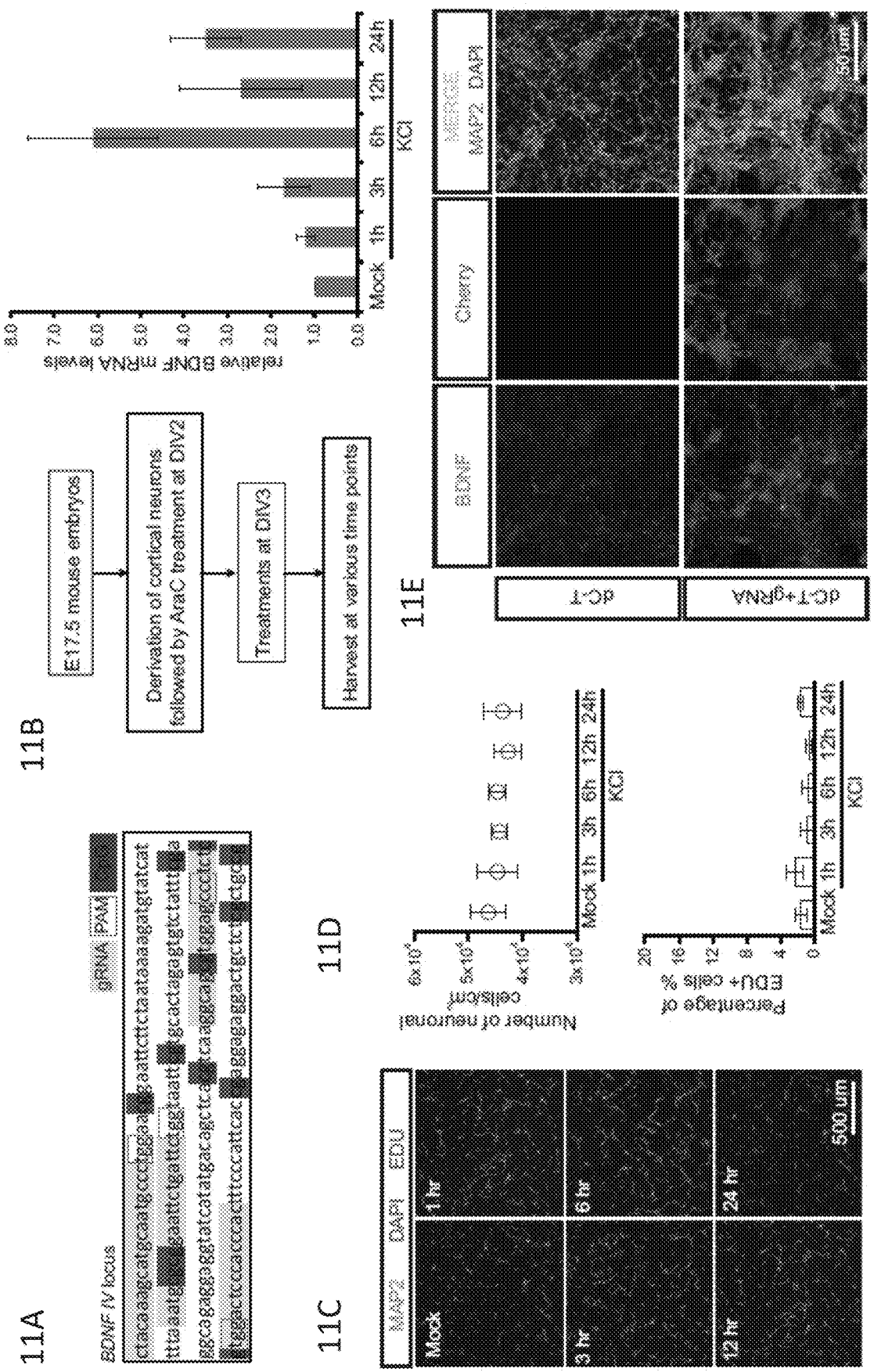
FIGS. 11A-11L depict targeted demethylation of BDNF promoter IV by dCas9-Tet1 in neurons.
Figures 11F, 11G, 11H, 11I:
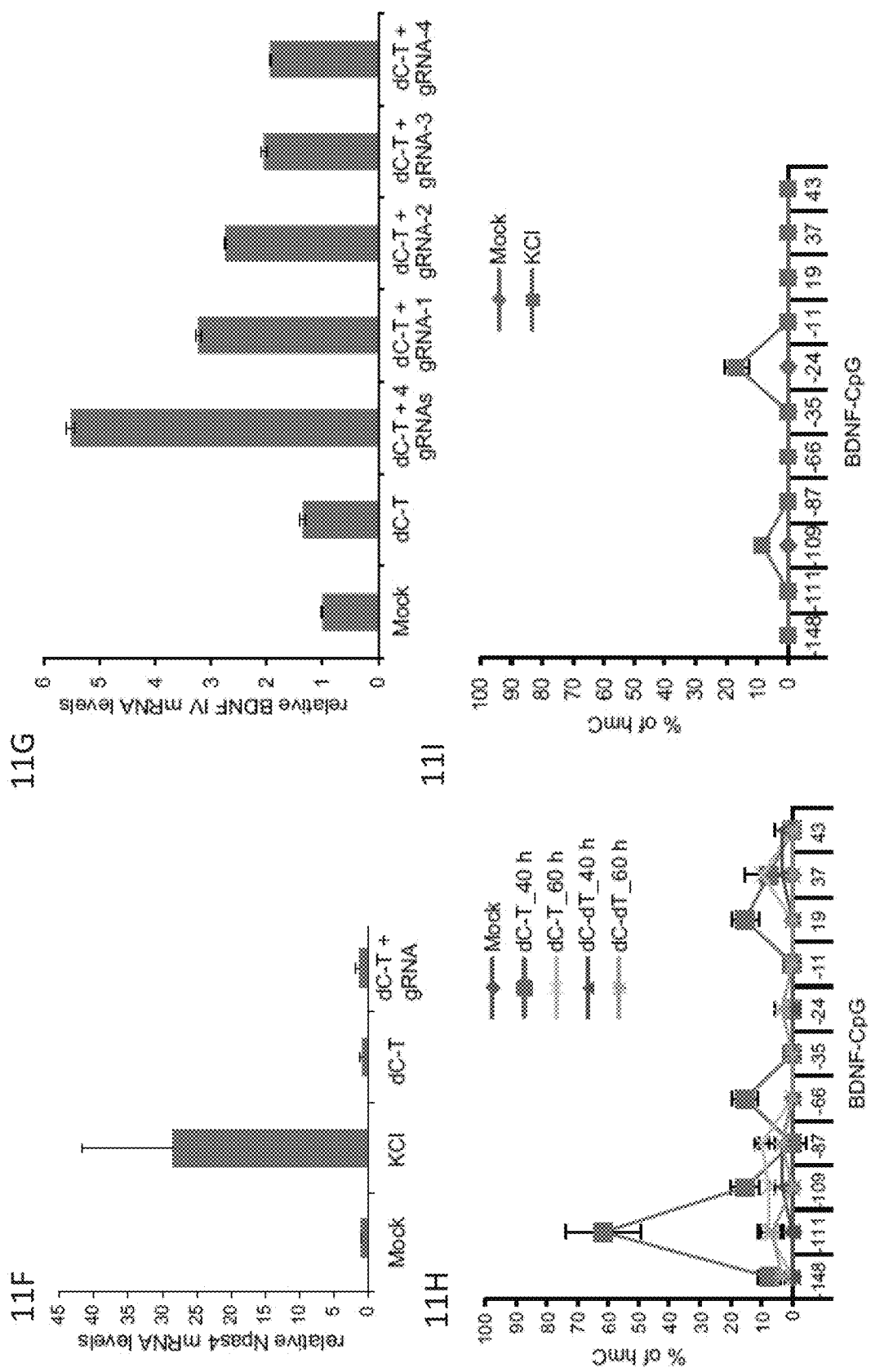

DNA replication-independent active demethylation has been proposed to operate in post-mitotic neurons (Guo et al., 2011; Martinowich et al., 2003). To test whether active demethylation can be induced in post-mitotic neurons, we applied the dCas9-Tet1 system to study the regulation of the BDNF gene. BDNF expression can be induced by neuronal activity accompanied by demethylation of its promoter IV (Chen et al., 2003; Martinowich et al., 2003). We designed 4 gRNAs targeting 11 CpGs in BDNF promoter IV (FIG. 11A) to determine whether dCas9-Tet1 can activate BDNF by inducing demethylation of this promoter (FIG. 3A). Mouse cortical neurons were isolated from E17.5 embryos and cultured for two days in vitro (DIV2) following a well-established experimental procedure for producing primary neuronal culture (Ebert et al., 2013). As shown in FIGS. 11B-11D, KCl treatment induced BDNF expression in these neurons with no detectable cell proliferation. Neurons at day 3 in culture (DIV3) were infected with lentiviral vectors expressing dCas9-Tet1 with or without the 4 gRNAs at almost 100% transduction efficiency (FIG. 11E). At 48-hour post infection some of the cultures were treated with KCl to induce neuronal activity. As shown in FIGS. 3B-3C, dCas9-Tet1/gRNAs induced BDNF expression by about 6-fold, whereas dCas9-Tet1 in the absence of gRNAs showed only a slight induction (less than 2-fold) and a catalytically dead form of Tet1 (dC-dT) showed no induction. Importantly, the same group of dCas9-Tet1/gRNAs did not induce Npas4 expression (FIG. 11F), another neuronal activity-inducible gene (Lin et al., 2008). Co-transduction of dCas9-Tet1 with each individual gRNA targeting the BDNF promoter IV showed a 2-3 fold induction of BDNF (FIG. 11G). We performed bisulfite sequencing to examine the methylation state of BDNF promoter IV. As shown in FIGS. 3D-3E, dCas9-Tet1/gRNAs significantly reduced methylation in this region in contrast to gRNA negative controls while KCl treatment also induced demethylation of CpGs at positions of −148, −66 and 19 (relative to transcription start site).

Figure 11J:
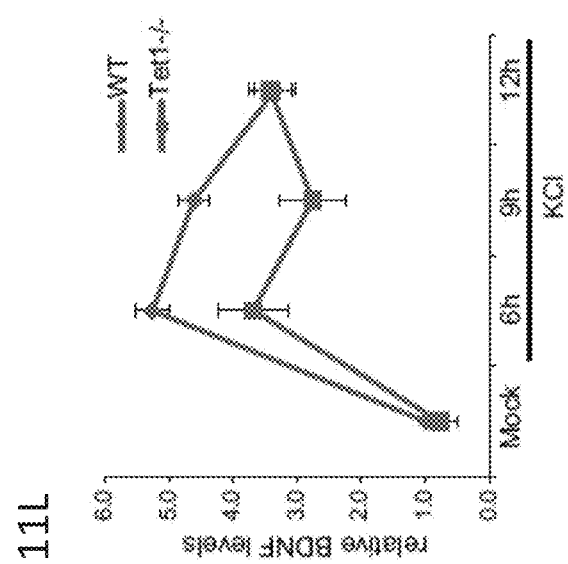

Our results demonstrate that demethylation of the BDNF promoter IV can be induced by dCas9-Tet1/gRNAs and is sufficient to activate BDNF expression. Because post-mitotic neurons were used for these experiments, loss of methylation was likely due to active demethylation. To further support this conclusion, we examined 5-hmC level in the BDNF promoter IV during the time course of dCas9-Tet1 induced demethylation by Tet-assisted Bisulfite sequencing (TAB-seq) analysis. As shown in FIG. 11H, 5-hmC was detected 40-hour post infection with dCas9-Tet1 and gRNA lentiviruses and diminished after 60 hours. Similarly, 5-hmC was also detected after KCl treatment (FIG. 11I). As bisulfite sequencing method does not distinguish unmethylated 5-cytosine (5-C) and 5-formlycytosine/5-carboxylcytosin (5-fC/5-caC) generated from 5-hmC, it is possible that some CpGs were 5-fC/5-caC modified after targeting with dCas9-Tet1/gRNA. Nevertheless, inhibition of the base excision repair pathway by treatment with ABT-888 (an inhibitor of PARP) reduced the activation of BDNF by KCl treatment (FIG. 11J), suggesting that demethylation of BDNF promoter IV contributes to BDNF activation.

Figure 11K:
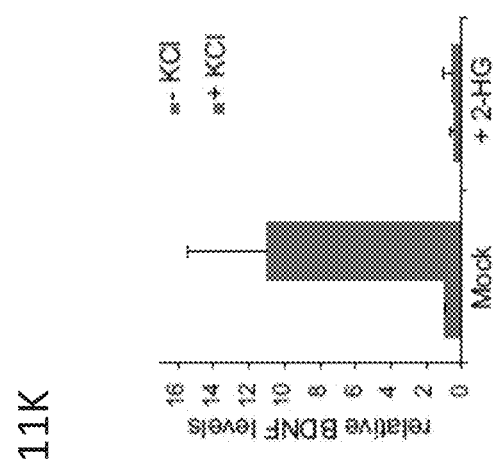
Figure 11L:
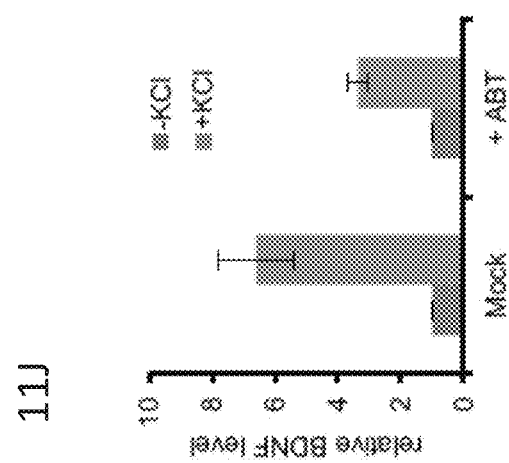

To test whether endogenous Tet activity was required to regulate BDNF expression upon neuronal activity stimulation, we treated DIV3 neurons with 2-hydroxygluterate, a competitive inhibitor for α-ketoglutarate-dependent dioxygenases including Tet enzymes (Xu et al., 2011). As shown in FIG. 11K, pharmacological inhibition of Tet enzymatic activity completely abolished the induction of BDNF expression by KCl treatment. Furthermore, mouse primary cortical neurons carrying a Tet1 null mutant showed significantly attenuated activation kinetics of BDNF (FIG. 11L), supporting a role of endogenous Tet for induction of neuronal activity.

Figures 4A, 4B, 4C:
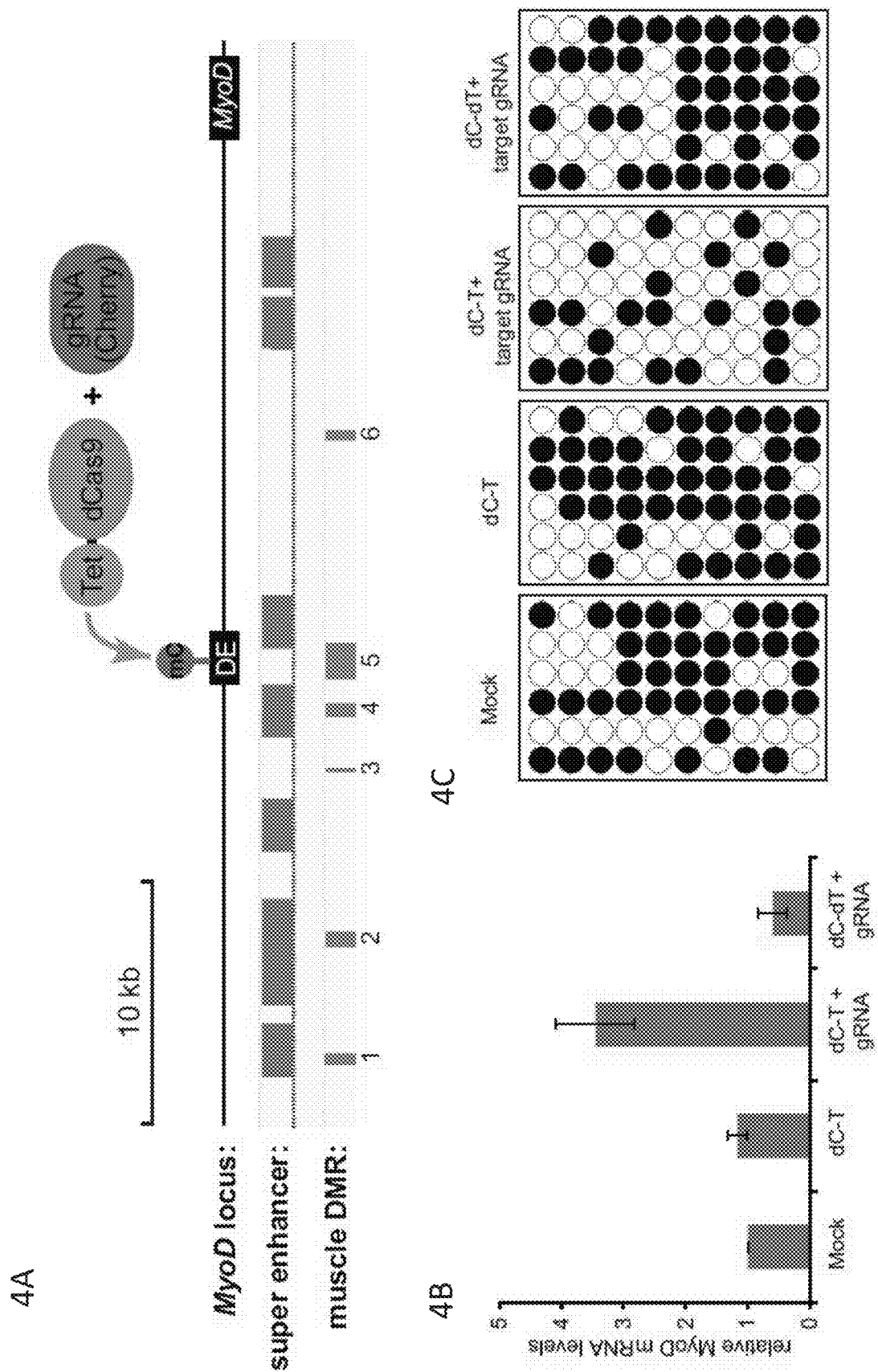
FIGS. 4A-4H depict targeted demethylation of the MyoD distal enhancer by dCas9-Tet1 to facilitate conversion of fibroblasts to myoblasts.
Figure 4D:
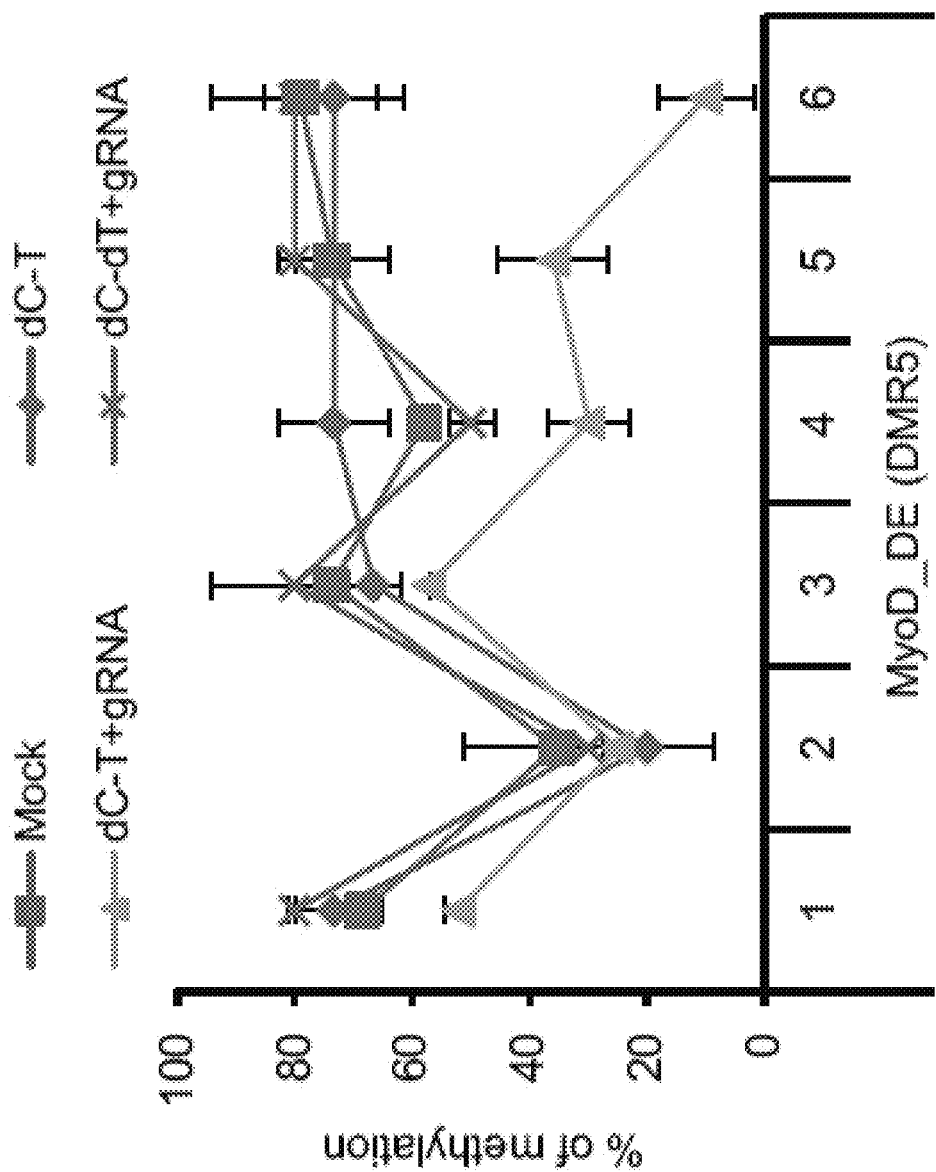
Figure 4E:
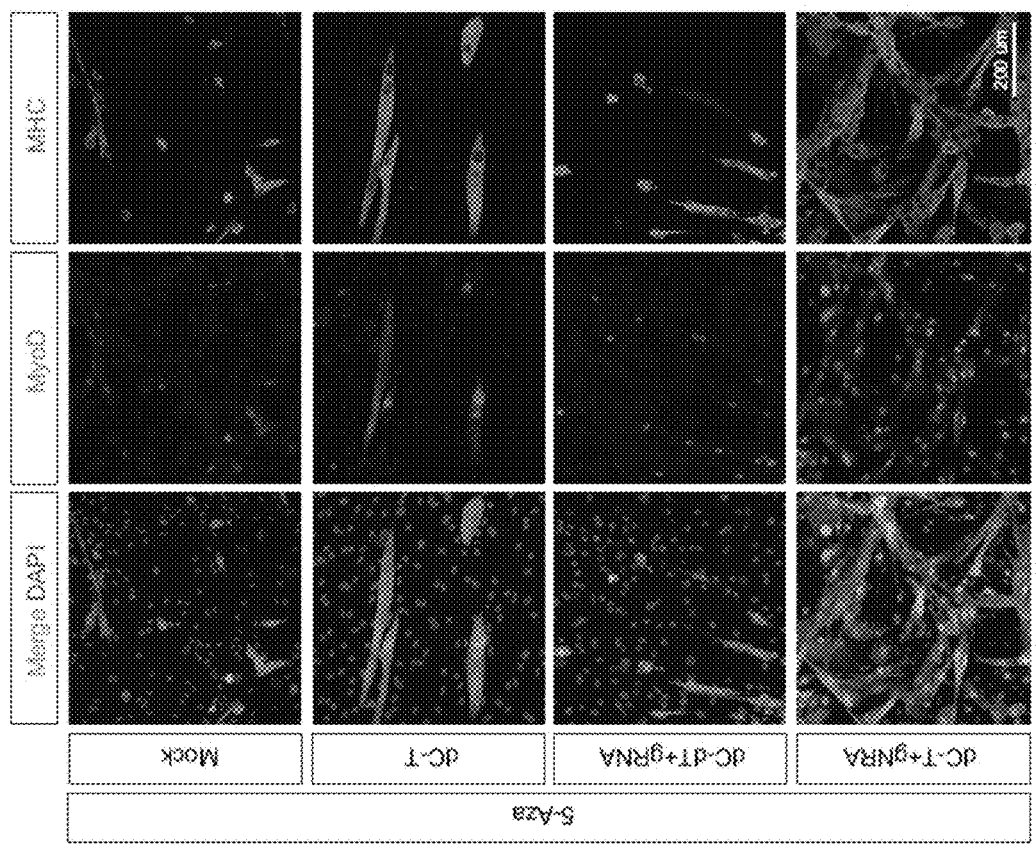
Figure 4E:
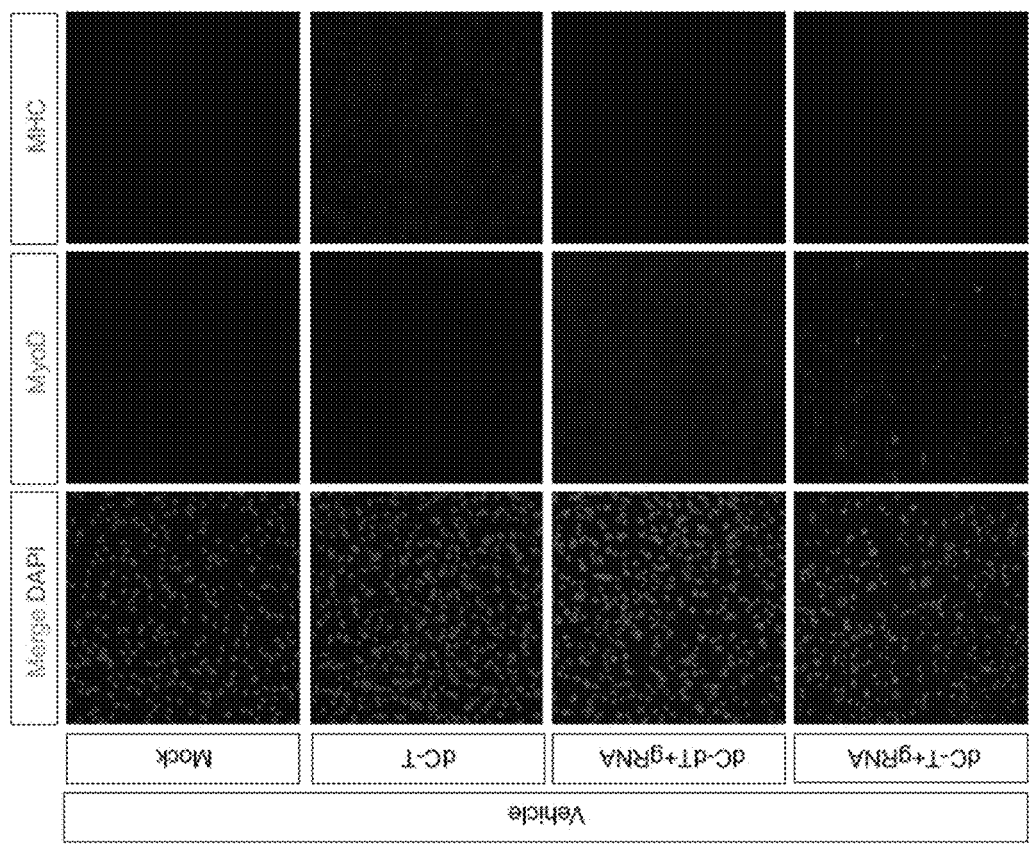
Figures 4F, 4G, 4H:
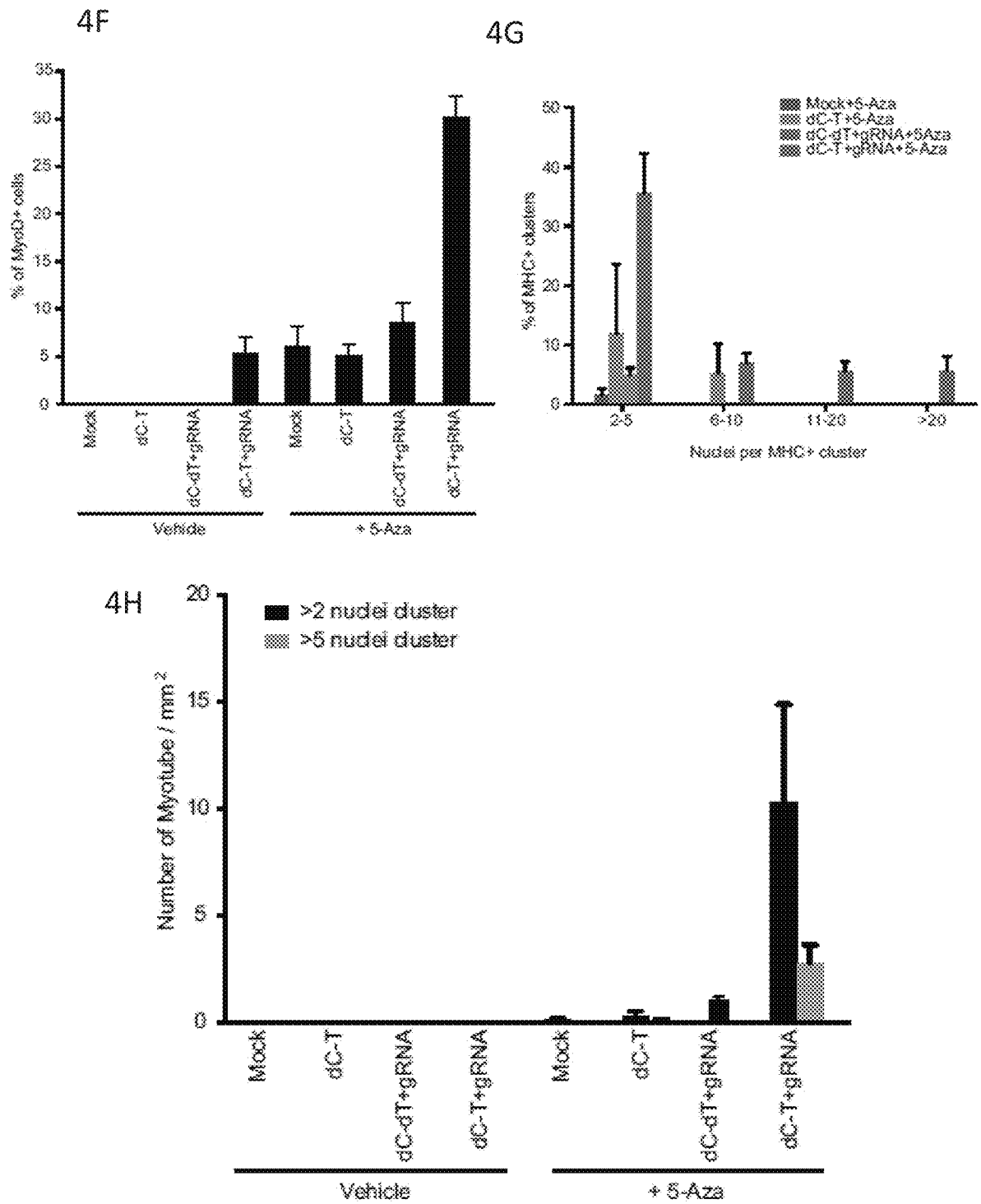
Figures 12F, 12G:
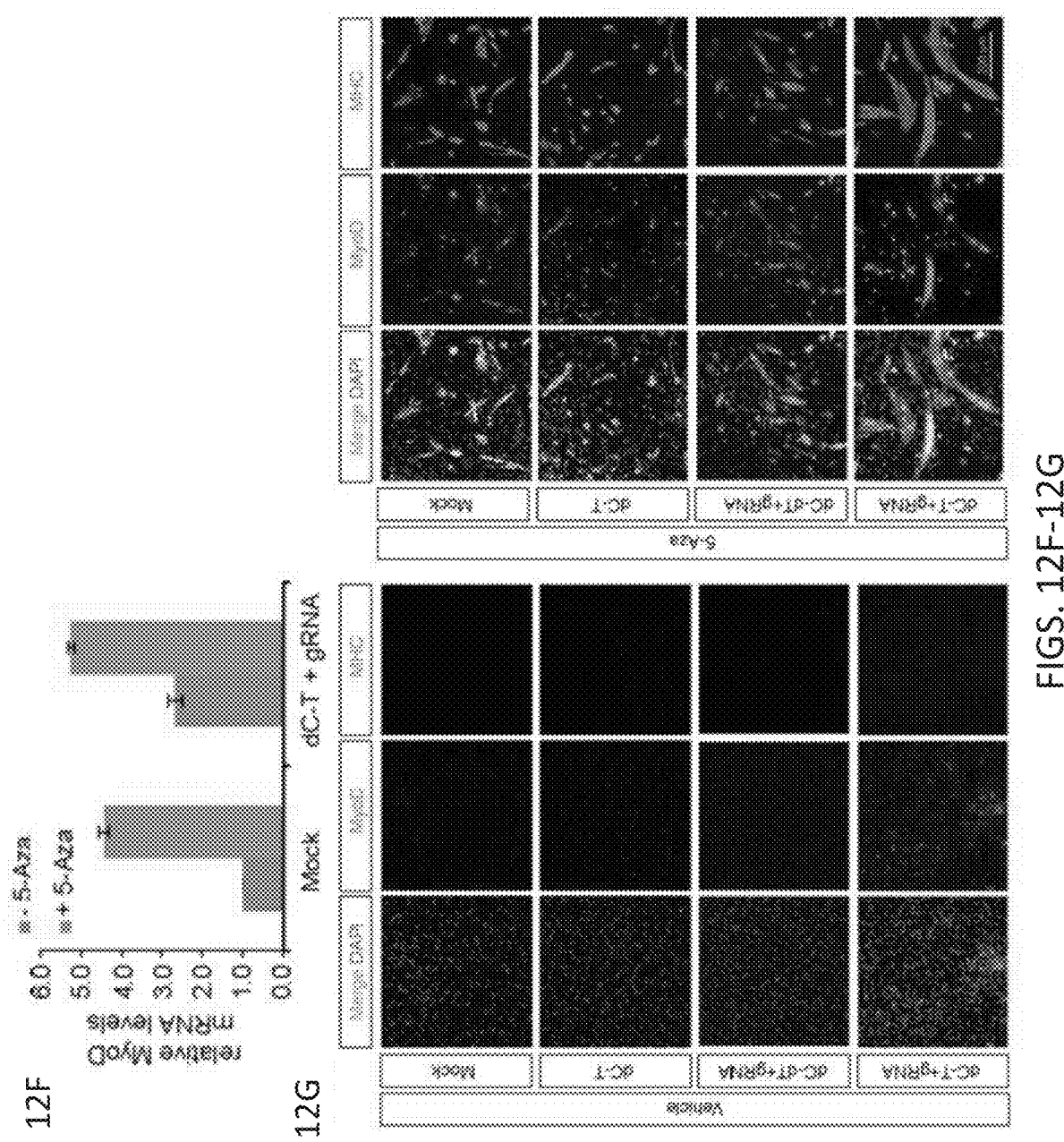
Figures 12H, 12I, 12J:
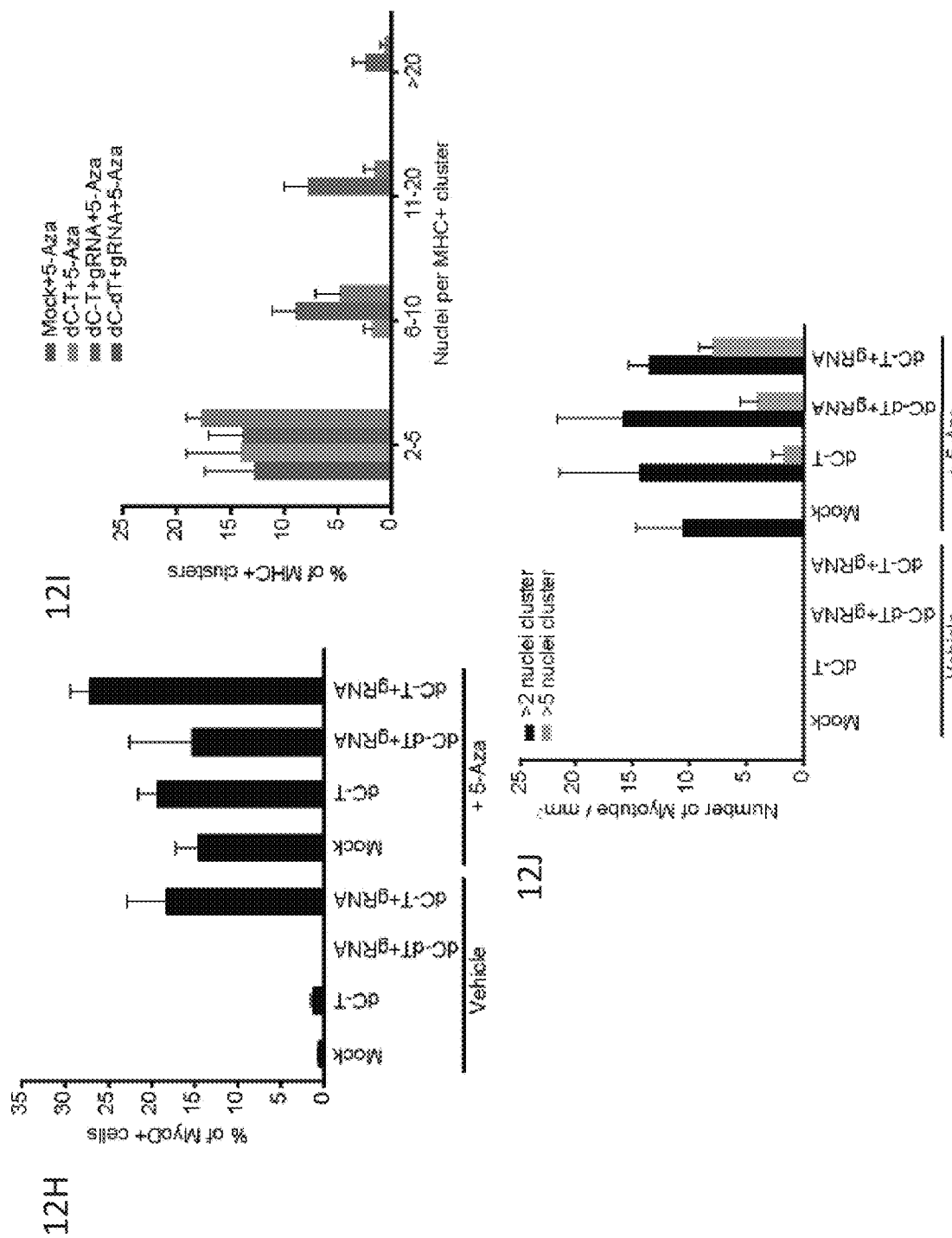

Targeted Demethylation of the MyoD Distal Enhancer Facilitates Myogenic Reprogramming of Fibroblasts The role of MyoD as a master regulator for muscle development was initially defined by the observations that demethylation of DNA in fibroblasts by 5-Aza (5-Aza-2'-deoxycytidine) treatment resulted in activation of MyoD and subsequent myoblast conversion and myotube formation (Constantinides et al., 1977; Davis et al., 1987; Lassar et al., 1986). Six muscle-specific DMRs have been described within the 50 kb upstream region ofMyoD gene (Schultz et al., 2015), and DMR-5 overlaps with a known distal enhancer of MyoD (Brunk et al., 1996) as shown in FIG. 4A. To test whether demethylation of DMR-5 would activate MyoD in fibroblasts, we designed 4 gRNAs targeting this DMR (FIG. 12A). Co-expression of dCas9-Tet1 with these gRNAs in C3H10T1/2 cells, a sub-clone from mouse embryonic fibroblasts previously used for 5-Aza mediated MyoD activation (Constantinides et al., 1977), resulted in a moderate induction of MyoD expression (3-fold) as shown in FIG. 4B. Combination of dCas9-Tet1/MyoD DMR-5 gRNAs with 5-Aza treatment resulted in a higher induction of MyoD as shown in FIG. 12F. Bisulfite sequencing showed a substantial reduction of methylation in the DMR-5 region of sorted infection-positive cells transduced with dCas9-Tet1 and target gRNAs lentiviruses, but not with a catalytically dead Tet1 (dC-dT) or a scrambled gRNA (FIGS. 4C-4D). To investigate whether demethylation of the MyoD distal enhancer region could reprogram fibroblasts into muscle cells, we infected C3H10T1/2 cells with lentiviruses expressing dCas9-Tet1 and gRNAs. The cells were cultured for 14 days and analyzed for MyoD and MHC (Myosin Heavy chain, a myotube specific marker) expression. As shown in FIGS. 4E-4F, co-expression of dCas9-Tet1 with gRNAs targeting DMR-5 induced a moderate expression level of MyoD, but was not sufficient to induce myotube formation in the absence of 5-Aza treatment.

We then investigated whether targeted demethylation of DMR-5 would synergize with 5-Aza treatment to induce myotube formation (FIG. 12B). To follow the process of myotube formation after 5-Aza treatment, a time-course experiment was performed. Multi-nucleated myotube (MHC-positive) with heterogeneous sizes began to form 14 days post treatment, and both MyoD-positive cell ratio and myotube density and size then increased up to day-25 (FIGS. 12C-12E). Co-expression of dCas9-Tet1 with gRNAs targeting MyoD DMR-5 facilitated the myotube formation 14 days post-treatment as evidenced by significantly more mature, multi-nucleated MHC+ clusters (>2 nuclei per MHC+ cluster) compared to cells expressing only dCas9-Tet1 or dC-dT with MyoD DMR-5 gRNAs (FIG. 4E, FIGS. 4G-4H). A similar observation was made when the cells were analyzed at a later time point (16-day) post-treatment (FIGS. 12G-12J). Our results suggest that demethylation of the MyoD distal enhancer by dCas9-Tet1/gRNA synergizes with 5-Aza in C3H10T1/2 cells to substantially facilitate myoblast conversion and myotube formation.

Figure 5A:
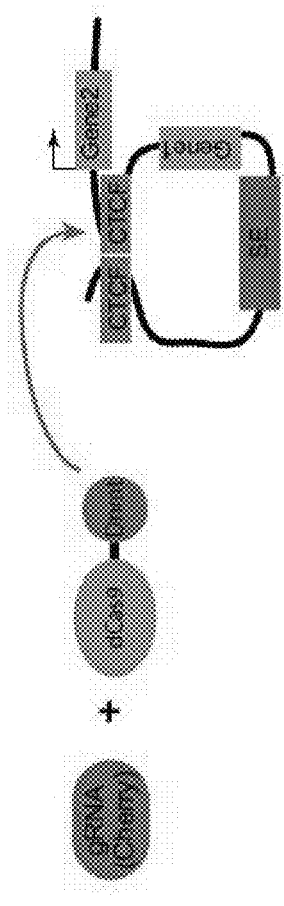
FIGS. 5A-5I depict targeted methylation of CTCF binding sites.
Figure 5B:
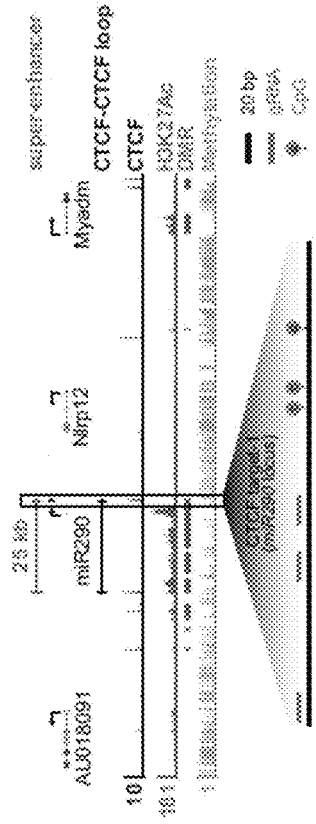
Figure 5C:
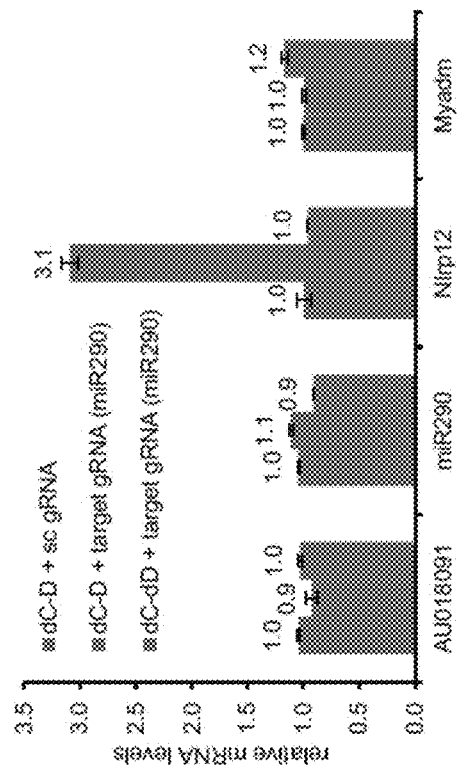
Figures 5D, 5E, 5F:
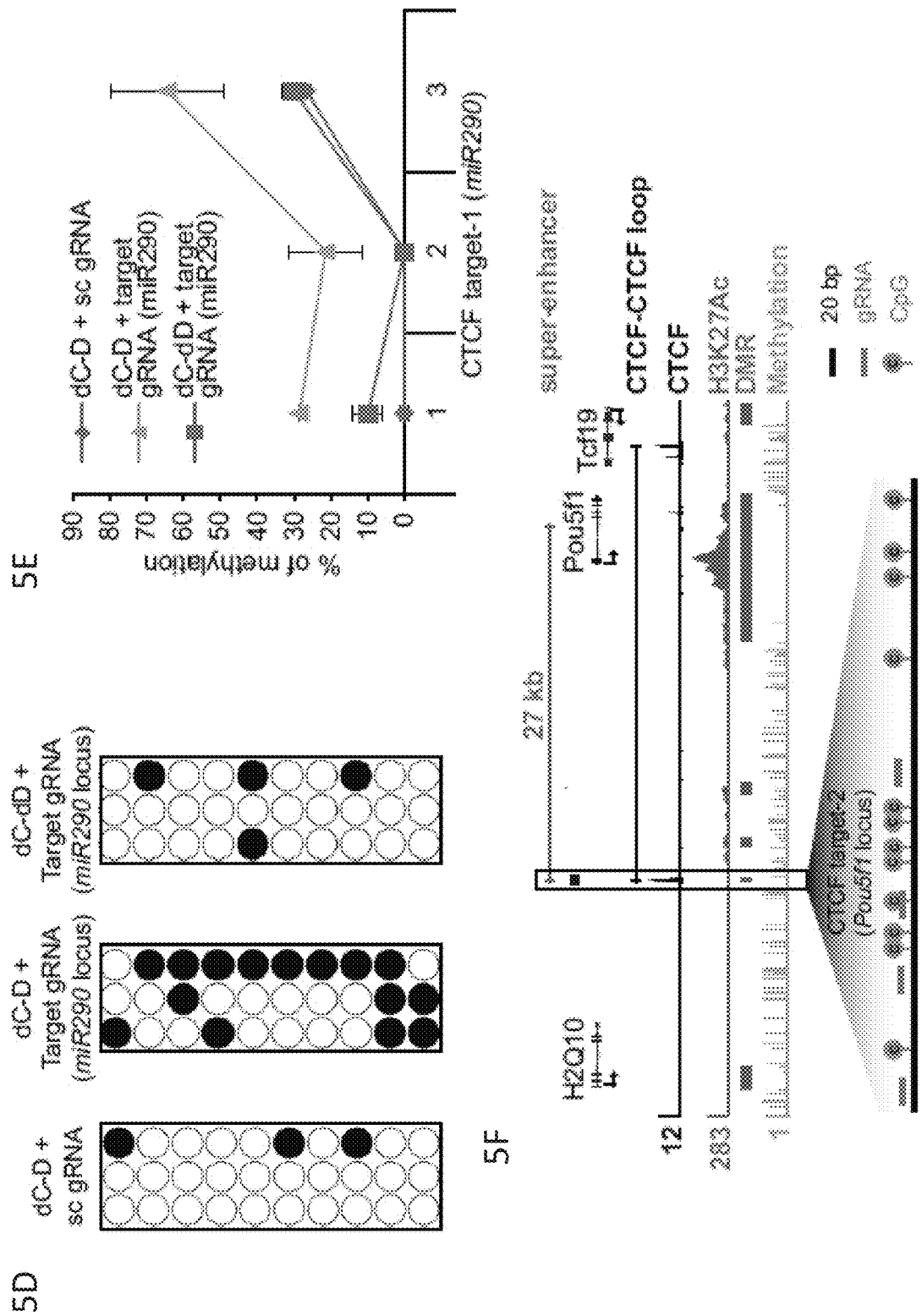
Figure 13B:
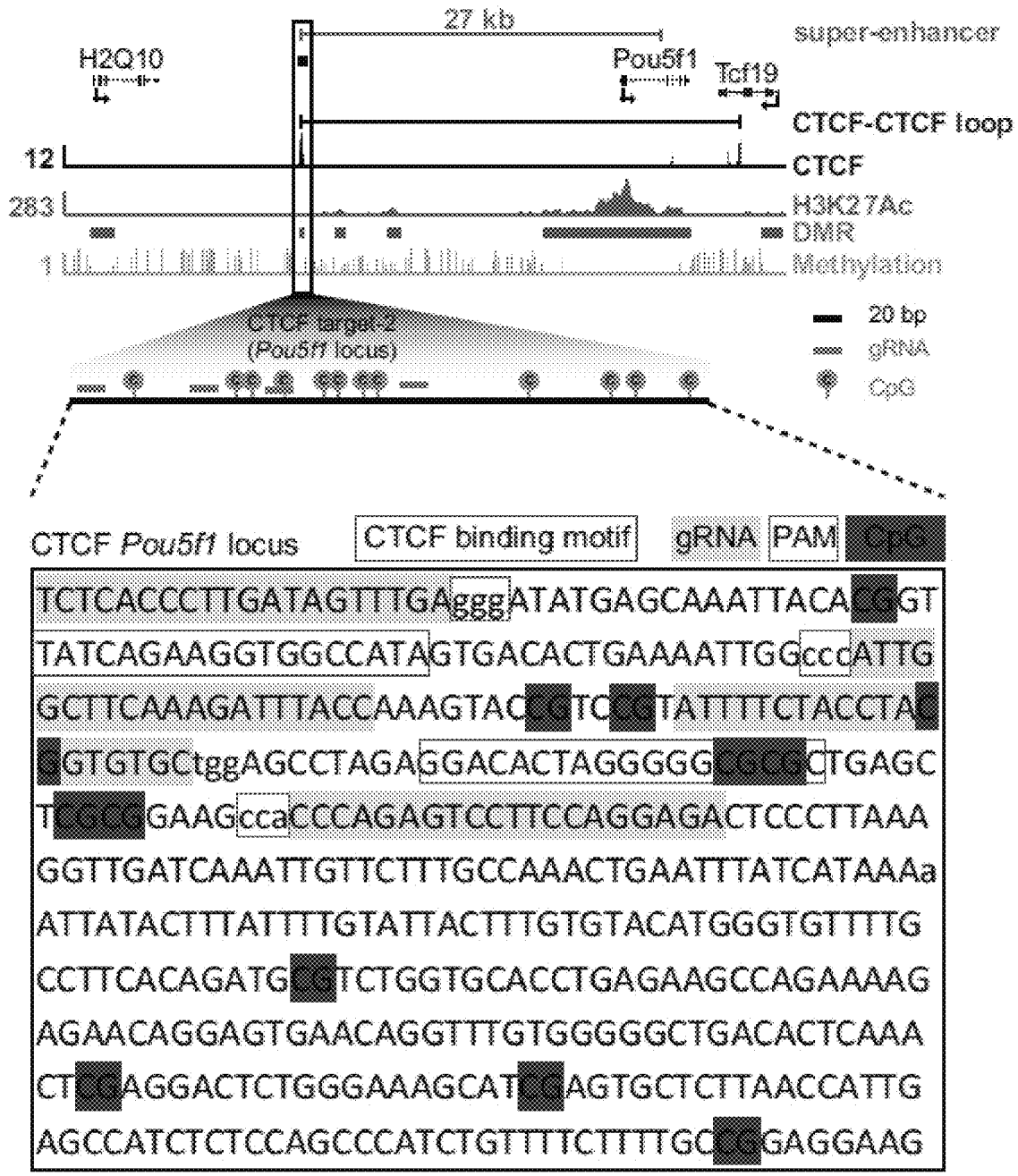

Targeted De Novo Methylation of CTCF Binding Sites Alters CTCF-Mediated Chromatin Loops CTCF is a highly conserved zinc finger protein that plays a primary role in the global organization of chromatin architecture (Phillips and Corces, 2009). Transcriptional enhancers normally interact with their target genes through the formation of DNA loops (Gibcus and Dekker, 2013; Gorkin et al., 2014; Kagey et al., 2010), which typically are constrained within larger CTCF-mediated loops called insulated neighborhoods (Dowen et al., 2014; Ji et al., 2016; Phillips-Cremins et al., 2013), which in turn can form clusters of loops that contribute to topologically associating domains (TADs) (Dixon et al., 2012; Nora et al., 2012). Deletion of the CTCF loop anchor sites of insulated neighborhoods can cause enhancers to interact inappropriately with genes located outside the loop and thus increase their expression (Dowen et al., 2014). Interestingly, methylation of the DNA recognition site of CTCF has been reported to block CTCF binding (Bell and Felsenfeld, 2000; Wang et al., 2012). To study whether methylation of specific CTCF sites could alter CTCF-mediated chromatin loops, we applied the dCas9-Dnmt3a system to target CTCF anchor sites (FIG. 5A). We designed specific gRNAs (FIG. 13) targeting dCas9-Dnmt3a to two CTCF sites to investigate whether de novo methylation would interfere with the looping function of CTCF (FIG. 5B and FIG. 5F). Doxycycline-inducible dCas9-Dnmt3a mES cells (FIG. 9H) were infected with lentiviruses expressing the gRNAs and transduced cells were FACS sorted for subsequent analysis.

Figures 5G, 5H, 5I:
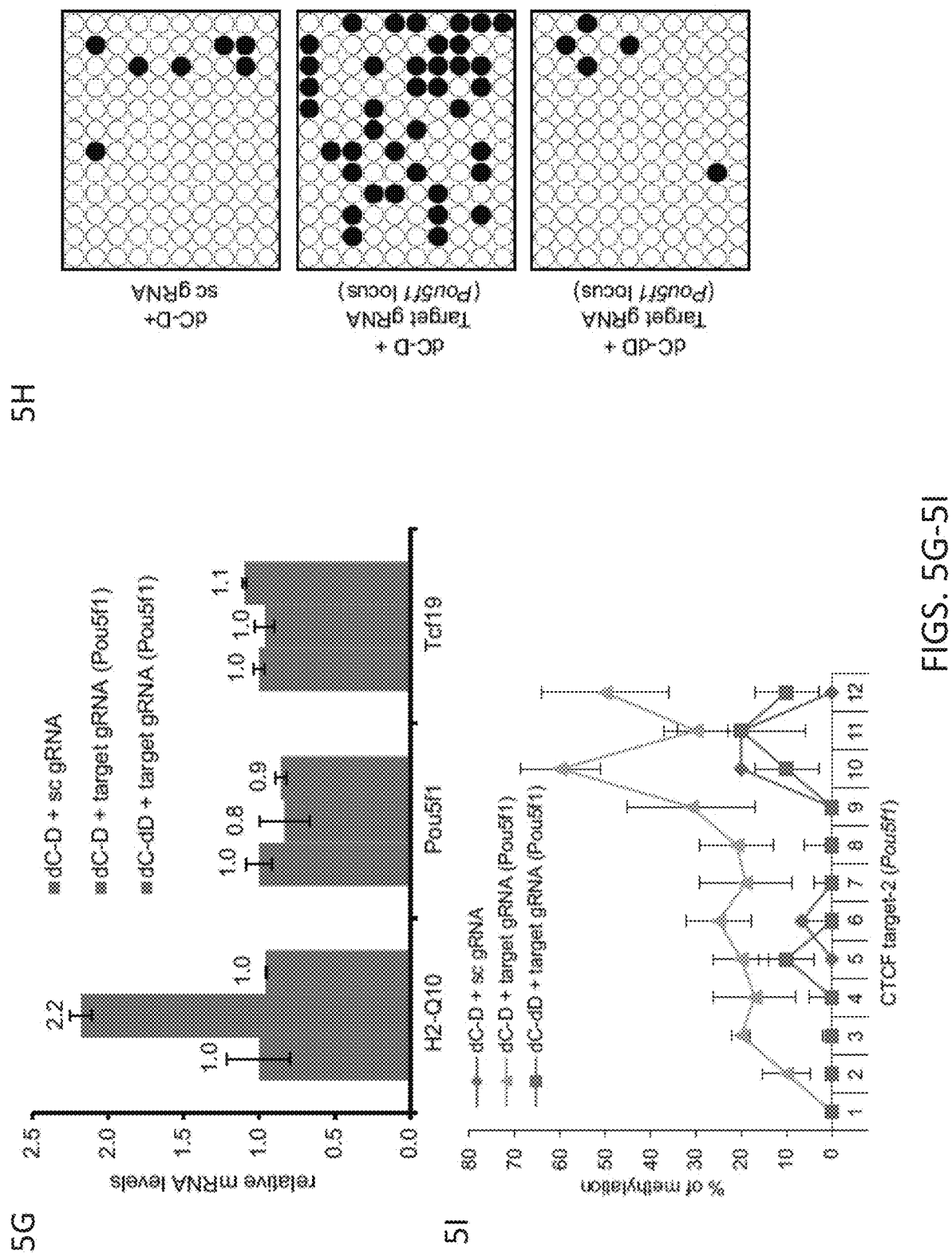

Targeting of dCas9-Dnmt3a to the CTCF binding site bordering the miR290 loop that harbors a super-enhancer (FIG. 5B) induced de novo methylation of CpGs at this site (FIGS. 5D-5E). Gene expression analysis of transduced cells showed a significant elevation of Nlrp12 gene, which is outside of this super-enhancer-containing insulated neighborhood and next to the targeted CTCF site, but did not affect the expression of genes that are located inside the miR290 loop or of genes in other neighboring loops including AU01801 and Myadm (FIG. 5C). Similarly, targeting of dCas9-Dnmt3a to the CTCF binding site bordering the Pou5f1 gene loop that harbors another super-enhancer (FIG. 5F) induced methylation of CpGs in the CTCF binding sequence (FIGS. 5H-5I), and increased the expression of H2Q10, which is located in a neighboring loop and next to the targeted CTCF site, but did not affect the expression of Pou5f1 gene itself or Tcf19 gene in the other neighboring loop (FIG. 5G). For either targeted CTCF sites, a catalytically inactive Dnmt3a form (dC-dD) did not induce changes in methylation level or gene expression as did by dC-D (FIGS. 5C-5E and FIGS. 5G-5I). These observations are consistent with the results obtained when these CTCF sites were deleted (Dowen et al., 2014), and support the notion that methylation of the CTCF binding site interferes with its insulator function.

Figure 6A:
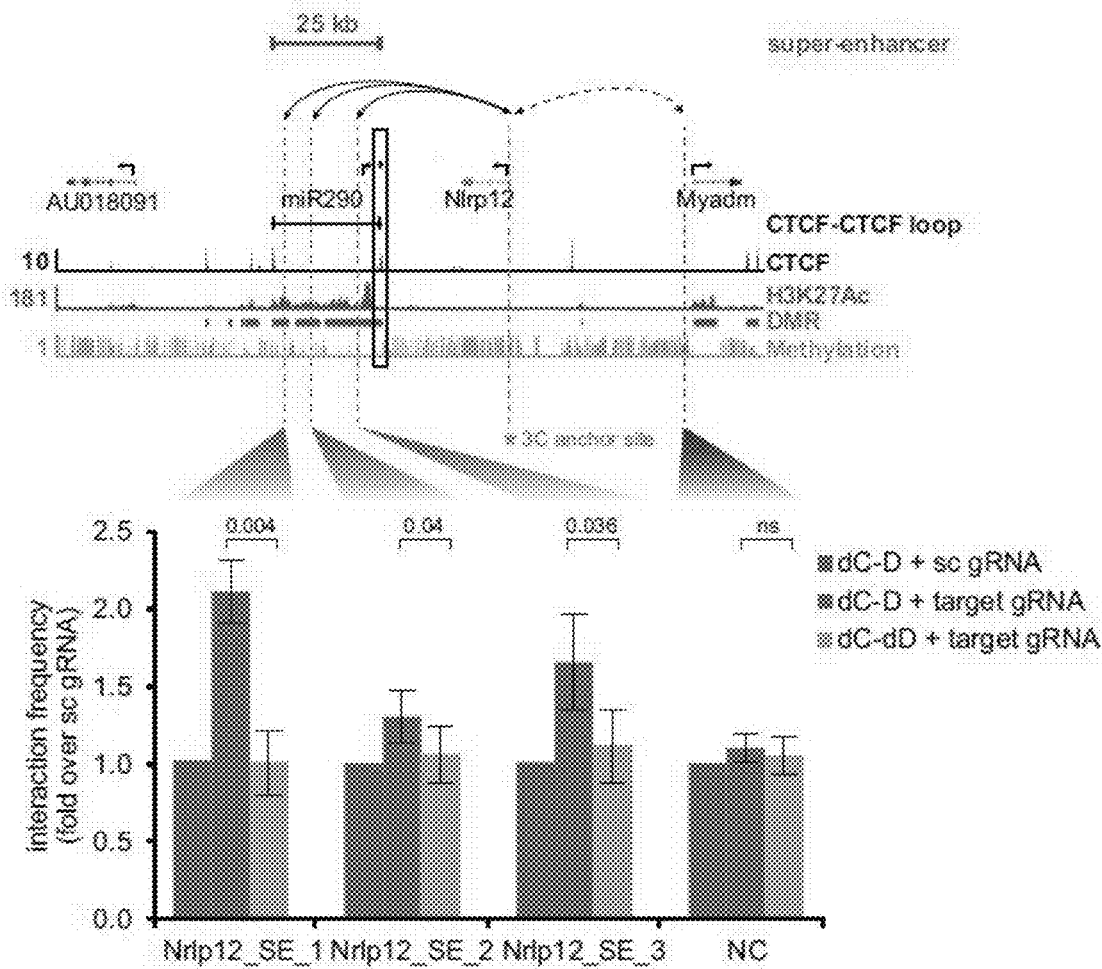
FIGS. 6A-6D depict targeted methylation of CTCF binding sites to manipulate CTCF loops.
Figure 6B:
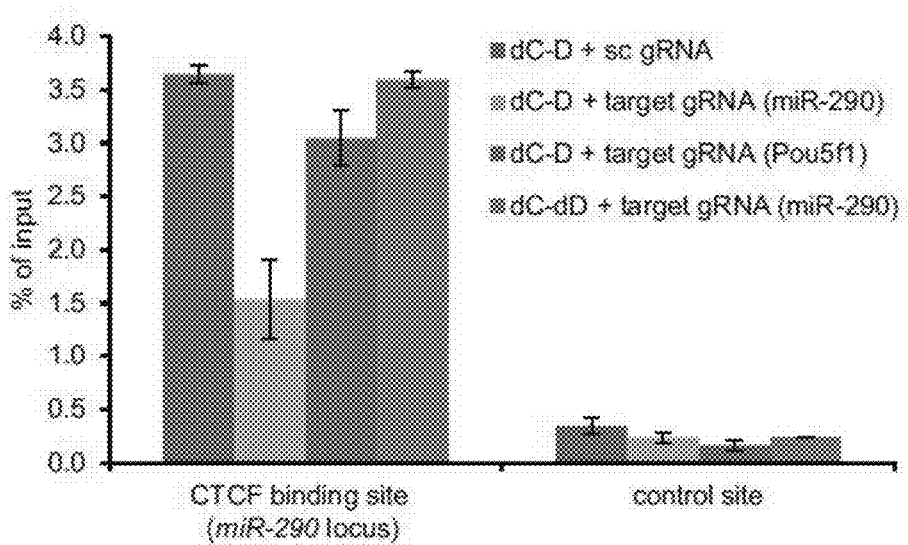
Figure 6C:
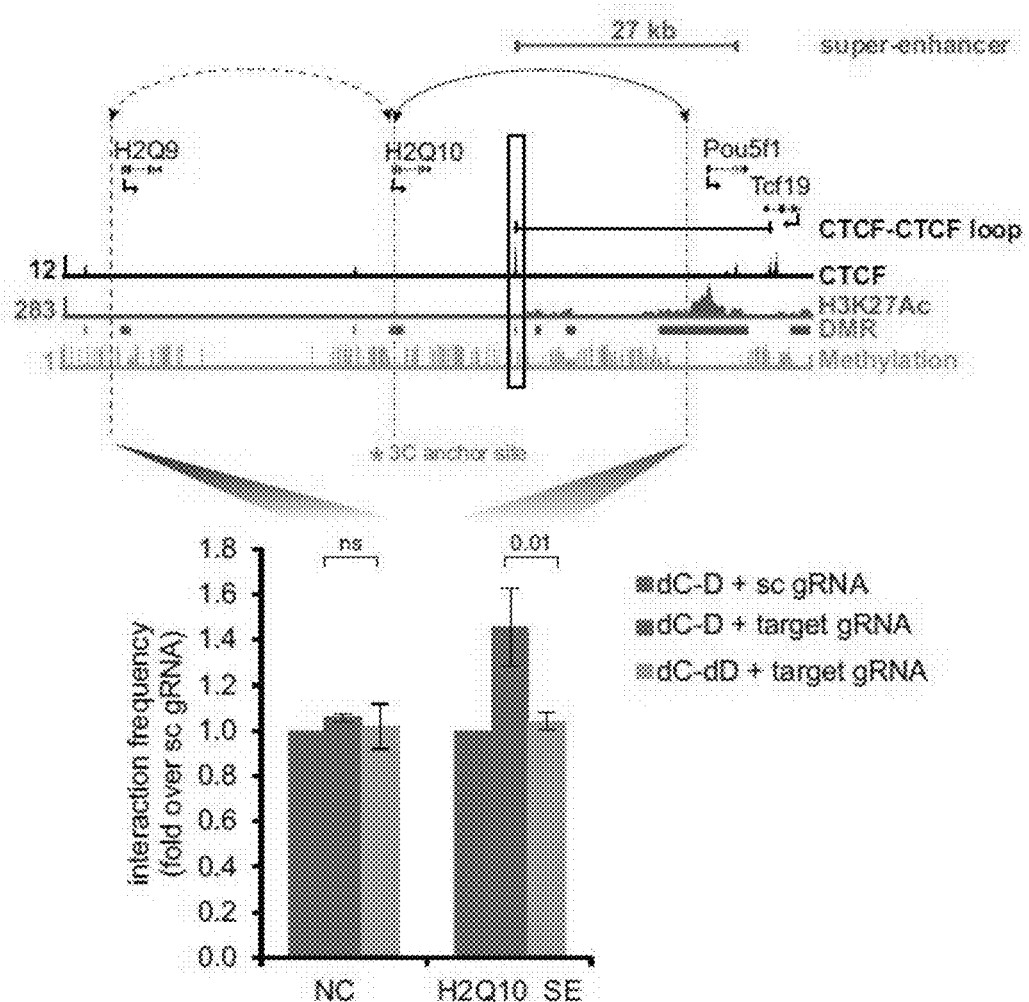
Figure 6D:
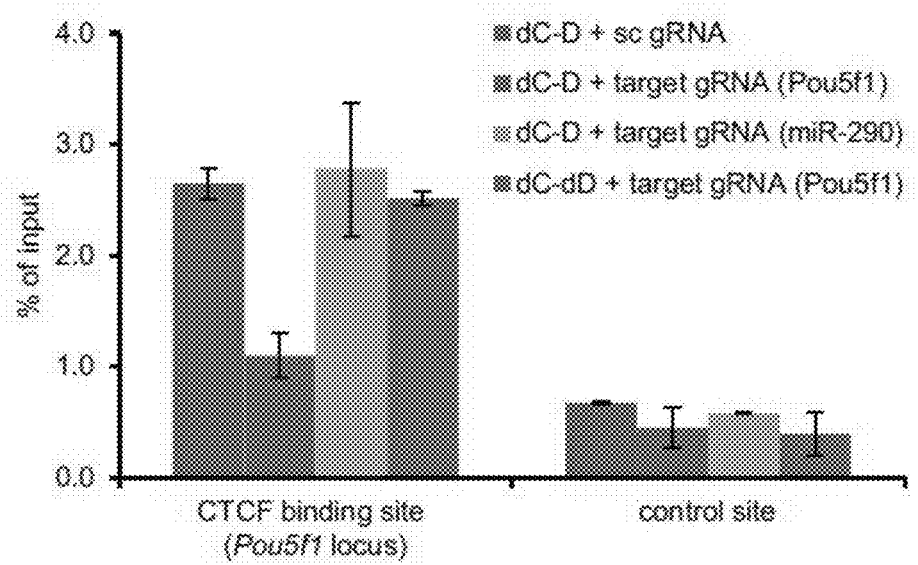

To test whether targeted methylations of CTCF binding sites would result in increased interaction frequencies between insulated super-enhancers and activated genes, Chromosome Conformation Capture (3C) assay was performed at these loci. As shown in FIG. 6A, the interaction frequency between super-enhancers in the miR290 loop and the newly activated gene (Nlrp12) in the neighboring loop was significantly increased but the interaction between Nlrp12 and Myadm genes remained the same, indicating an open conformation for this targeted CTCF loop. To confirm that the increased interaction frequency was due to blocking CTCF anchoring, we performed a CTCF ChIP assay. Binding of CTCF to the targeted genomic site was significantly reduced in the sample with miR290 target gRNAs as compared to the sample with a scrambled gRNA, gRNAs targeting other CTCF binding sites or a catalytically inactive dC-dD with miR290 target gRNAs (FIG. 6B), supporting the notion that DNA methylation blocks CTCF anchoring and thus alters the CTCF loop conformation. A similar set of experiments was performed for the second CTCF loop (Pou5f1 loop) demonstrating increased interaction frequency between the insulated super-enhancers and the newly activated gene (H2Q10), and decreased binding of CTCF after targeted methylation of its binding site (FIGS. 6C-6D).

In summary, our results demonstrate that the dCas9-Dnmt3a system can be used to change the methylation state of specific CTCF anchor sites and thus to interfere with the CTCF looping function.

In Vivo Demethylation of an Endogenous Locus for Gene Activation by dCas9-Tet1

Figures 7A, 7B, 7C:
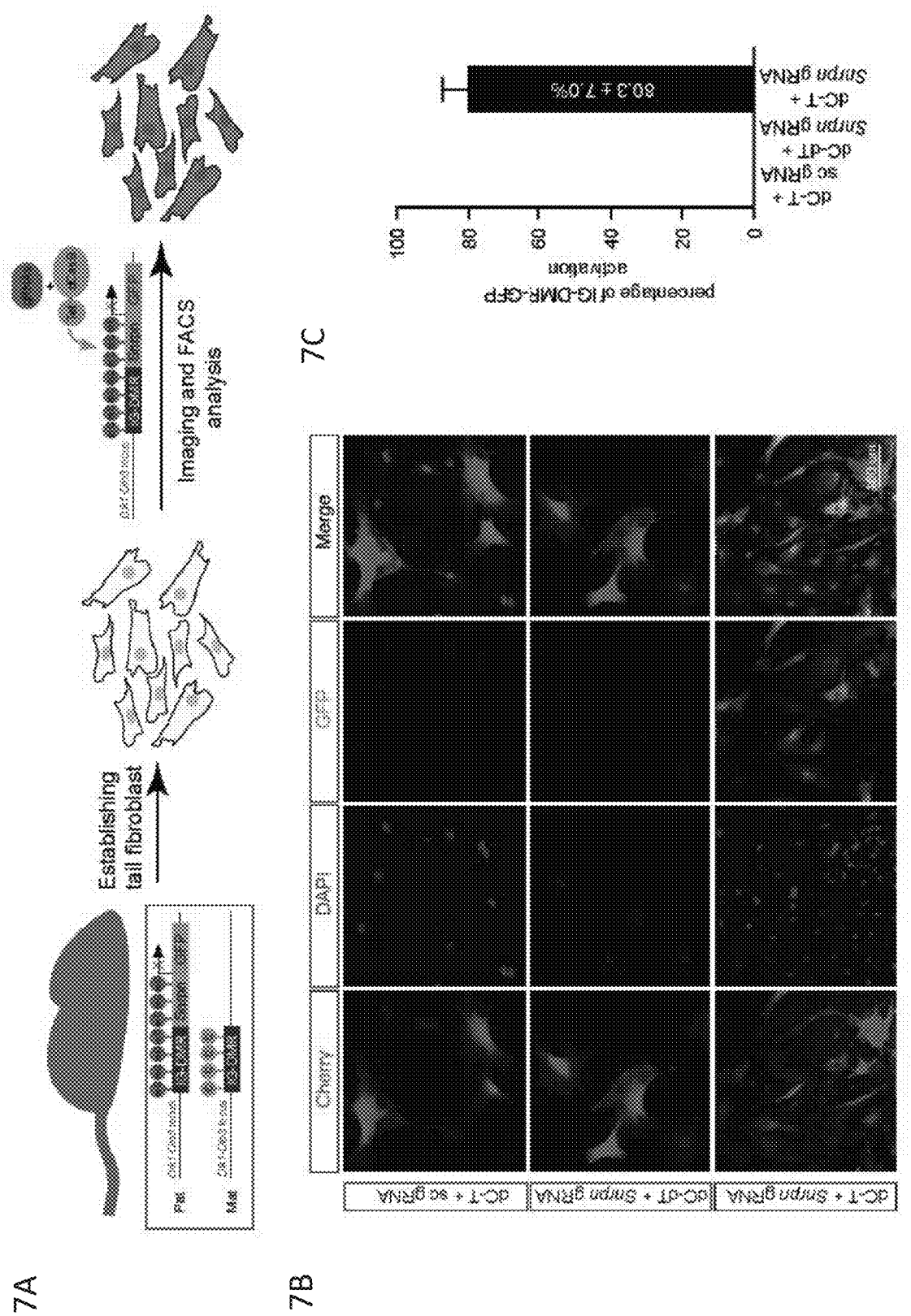

To test whether the dCas9-mediated DNA methylation-editing tools could be used to alter methylation in vivo we utilized a methylation sensitive reporter mouse previously generated (FIG. 7A, Ref: Stelzer et al., Parent-of-origin DNA methylation dynamics during mouse development, Developmental Cell, under editorial consideration). In these transgenic mice, a methylation sensitive Snrpn-GFP cassette was inserted into the Dlk1-Dio3 locus to report the methylation status of its intergenic-differentially methylated region (IG-DMR). As the IG-DMR of this locus acquires paternal methylation during spermatogenesis, the GFP reporter (IG-DMR$^{GFP/Pat}$) is constitutively repressed in heterozygous mice carrying the paternal Snrpn-GFP allele (See the Ref: Stelzer et al., Parent-of-origin DNA methylation dynamics during mouse development, Developmental Cell, under editorial consideration). As shown above the GFP reporter in the Dazl locus was activated by targeted promoter demethylation in mES cells (FIG. 1). To assess whether the Dlk1-Dio3 locus GFP reporter could be activated by dCas9-Tet1 in differentiated cells we derived adult mouse skin fibroblast cells from the tails of IG-DMR$^{GFP/Pat}$ transgenic mice, which were then transduced by lentiviruses expressing dCas9-Tet1 with Snrpn target gRNAs or a scrambled gRNA, or a catalytically dead form of Tet1 (dC-dT) with Snrpn target gRNAs (FIG. 7A). The results in FIGS. 7B-7C reveal GFP reporter activation in about 80% of Cherry (gRNA) positive fibroblasts but only when transduced by both dCas9-Tet1 and Snrpn gRNAs lentiviruses. FACS analysis of these cells further confirmed this notion (FIGS. 14A-14C).

Figures 7D, 7E:
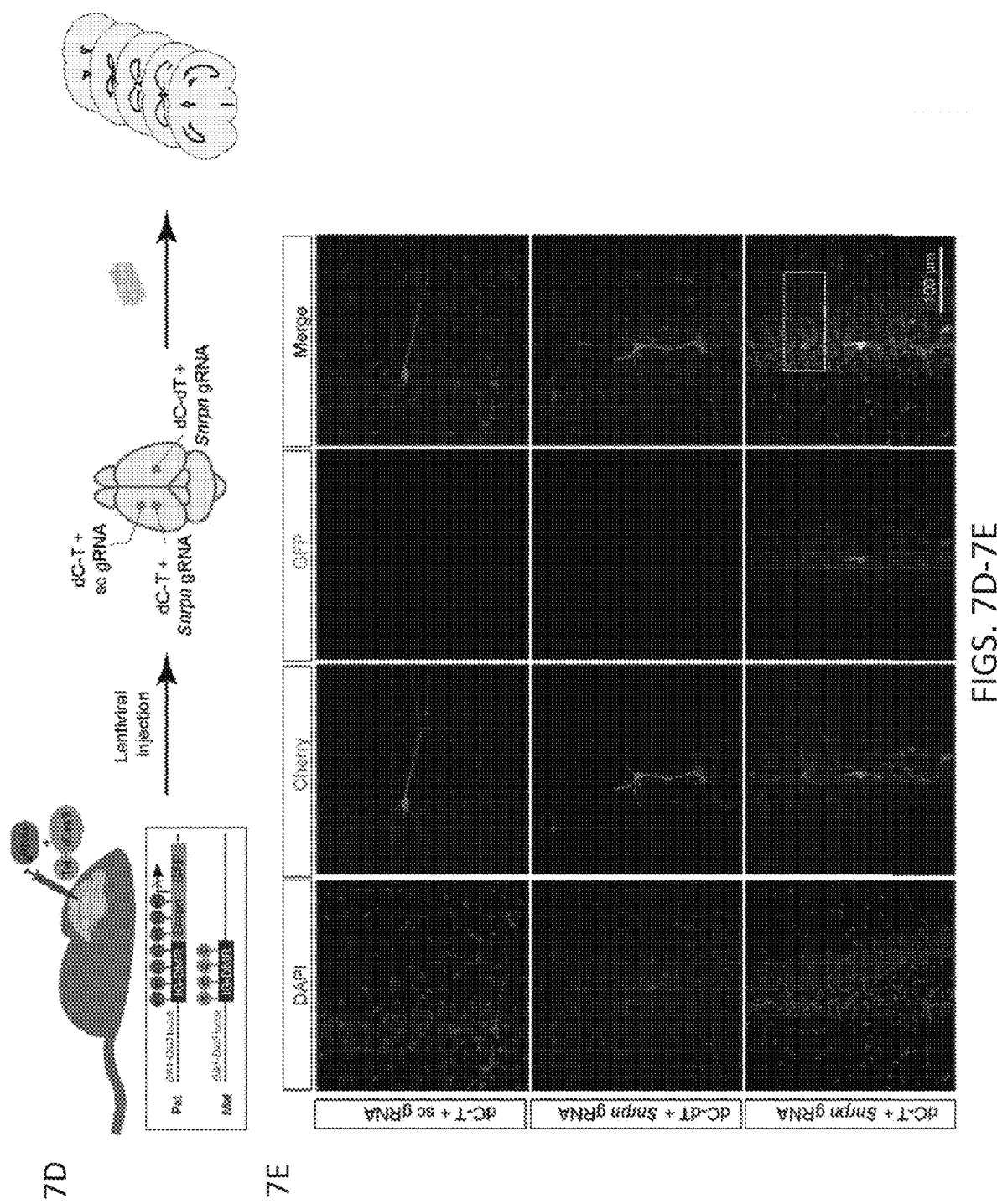
Figures 14A, 14B, 14C, 14D:
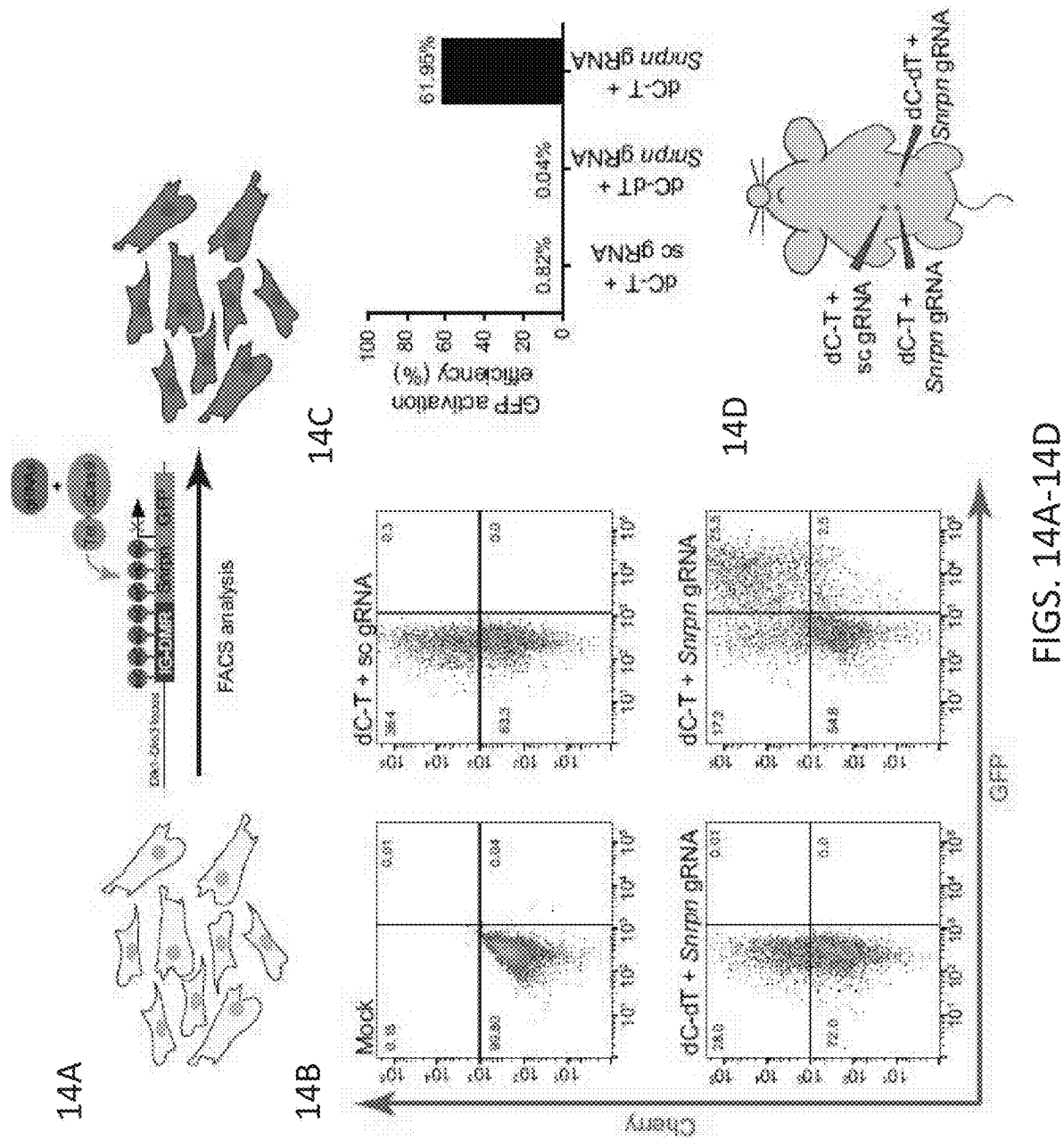
FIGS. 14A-14F depict activation of IG-DMR$^{GFP/Pat}$ reporter in mouse skin cells by dCas9-Tet1 mediated demethylation.
Figures 14E, 14F:
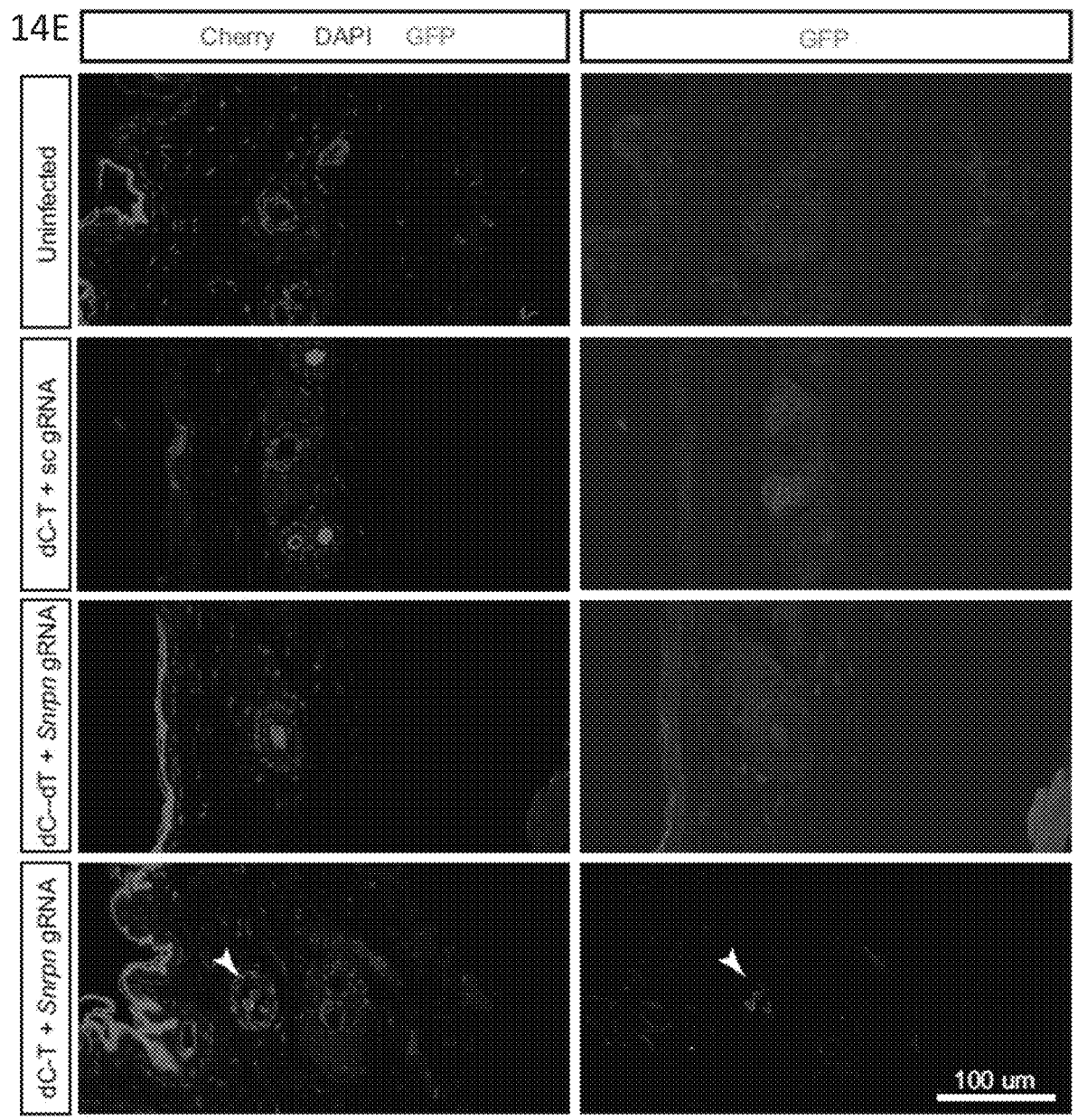
Figure 15:
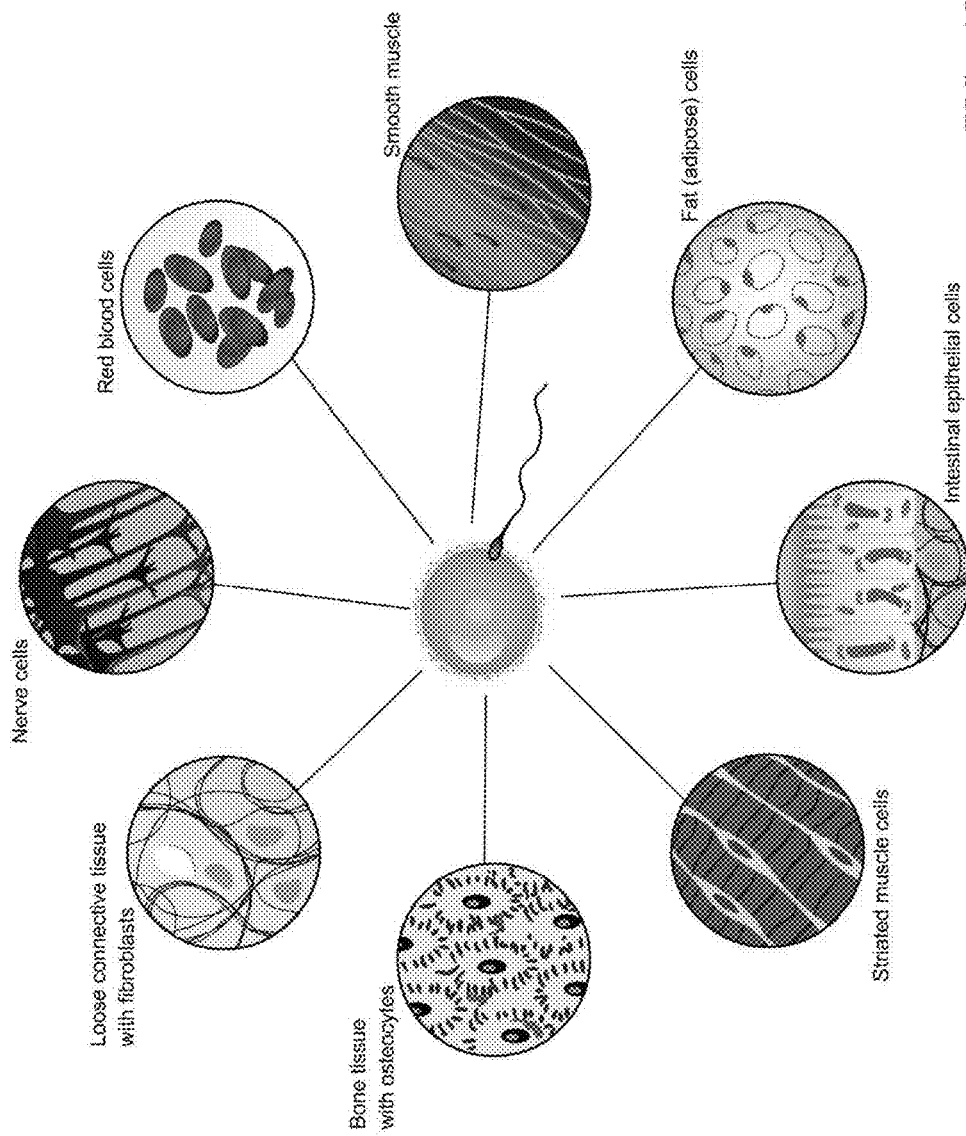
FIG. 15 demonstrates various examples of cell types.
Figure 16:
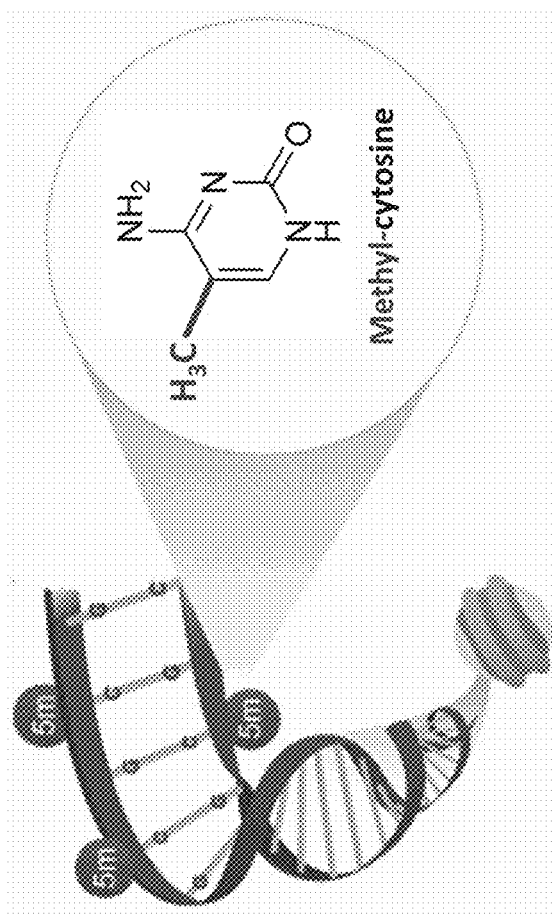
FIG. 16 depicts DNA methylation.
Figure 17:
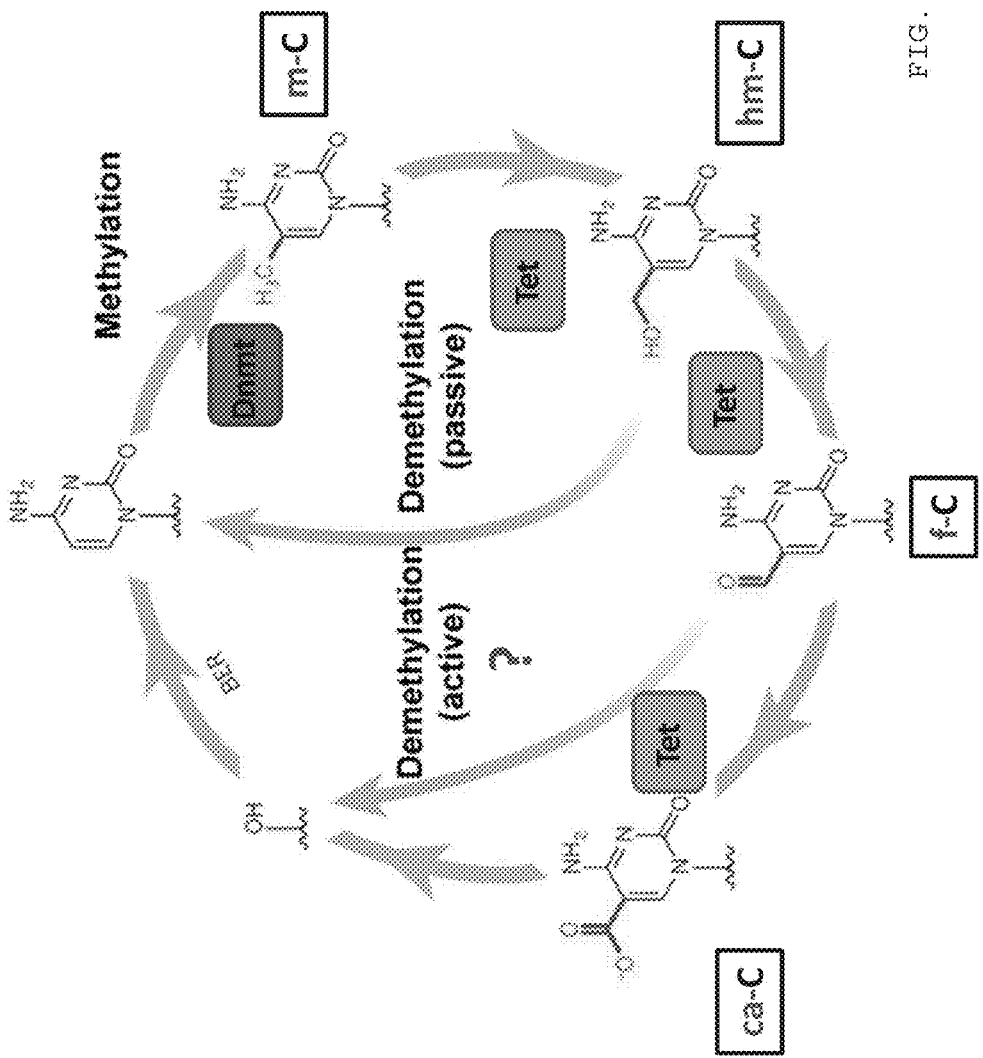
FIG. 17 shows a DNA methylation cycle including DNA methylation and reversing DNA methylation.

To investigate whether the DNA methylation status can be modified in vivo, we infected 3 epidermal sites on the ventral side of an IG-DMR$^{GFP/Pat}$ transgenic mouse with the dCas9-Tet1 and Snrpn gRNAs (FIG. 14D). Cells were sparsely infected with cherry expression seen only in some of the hair follicles. dCas9-Tet1 with Snrpn gRNAs, but not dCas9-Tet1 with the scrambled gRNA or dC-dT with Snrpn gRNAs, was able to activate GFP reporter expression in about 85% infected skin dermal cells in vivo (FIG. 7H, FIGS. 14E-14F). In addition we infected the brain of an IG-DMR$^{GFP/Pat}$ transgenic mouse with lentiviral vectors using a stereotaxic setup and analyzed the effect on targeted DNA methylation in brain slices by confocal microscopy. To eliminate possible inter-individual variability, we injected lentiviral vectors expressing dCas9-Tet1 and Snrpn gRNAs, as well as the two negative control vector combinations into different regions of the same brain (FIG. 7D). As shown in FIGS. 7E-7F, after infection with all three lentiviral combinations as indicated by Cherry expression, only lentiviral vectors expressing dCas9-Tet1 with Snrpn gRNAs, but not vectors expressing dCas9-Tet1 with sc gRNA or dC-dT with Snrpn gRNAs, activated the GFP reporter with an activation efficiency of about 70% (FIG. 7G).

DISCUSSION

In this study we have repurposed the CRISPR/Cas9 system to edit the methylation status of genomic sequences. The catalytically inactive Cas9 protein (dCas9) was fused either to the catalytic domain of Tet1 (dCas9-Tet1) or to Dnmt3a (dCas9-Dnmt3a) to predictably alter the epigenetic state of target sequences. A GFP reporter inserted into the promoter region of the methylated and silenced Dazl gene was demethylated and activated when targeted by dCas9-Tet1 whereas the GFP reporter inserted into the promoter region of the active and unmethylated Gapdh gene was de novo methylated and silenced when targeted by dCas9-Dnmt3a. When the dCas9-Tet1 was targeted to the inactive BDNF promoter IV in post-mitotic neurons, the promoter became demethylated and activated. Importantly, this tool predictably altered the methylation state and activity of regulatory regions: Targeted demethylation of the inactive distal enhancer of MyoD activated the gene and facilitated muscle differentiation and targeted methylation of CTCF anchor sites inhibited CTCF binding and interfered with its function as an insulator between chromatin loops. Finally, the editing tools can in vivo alter the methylation state of regulatory sequences as injection of the lentiviral vectors of dCas9-Tet1 with target gRNAs into the dermis or brain of transgenic mice demethylated the methylated Snrpn promoter in the Dlk1-Dio3 imprinted locus and activated the methylation-sensing GFP reporter.

Dynamic DNA methylation has been proposed to decode neuronal activities (Sweatt, 2013). For instance, treatment of neurons with KCl has been shown to de-silence promoter IV of BDNF and induce BDNF expression associated with demethylation of some methylated CpGs in the promoter region (Chen et al., 2003; Martinowich et al., 2003). When the BDNF promoter IV was targeted by dCas9-Tet1, extensive demethylation of methylated CpGs was observed, and BDNF was activated to a similar level as when the cultures were treated with KCl. Because the neurons were post-mitotic, the dCas9-Tet1-mediated demethylation of the promoter sequences was likely the result of active demethylation as has been proposed previously (Wu and Zhang, 2014). Although it is possible that some CpGs in the BDNF promoter were 5-fC/5-caC modified after targeting with dCas9-Tet1/gRNA, blocking restoration of 5-fC/5-caC into unmethylated cytosine by inhibition of the BER pathway reduced BDNF expression, suggesting that demethylation of the BDNF promoter IV contributes to the activation of BDNF. Importantly, our results establish a causal relationship between demethylation of BDNF promoter IV and gene activation.

The role of DNA methylation as a barrier between cell lineages is consistent with the previous observation that demethylation of DNA in fibroblasts by treatment with 5-Aza can activate MyoD and mediate myotube formation (Constantinides et al., 1977; Davis et al., 1987; Lassar et al., 1986). Targeting of dCas9-Tet1 to the methylated distal enhancer of MyoD in fibroblasts induced demethylation of CpGs and resulted in a moderate activation of MyoD but failed to generate myoblasts. However, when dCas9-Tet1/gRNA lentiviral transduction was combined with 5-Aza treatment, a significantly enhanced myoblast and myotube formation was observed as compared to 5-Aza treatment alone. Additional DMRs upstream of MyoD have been identified (Schultz et al., 2015) and it is possible that demethylation of these sites in combination with the distal enhancer may be required to induce efficient conversion of fibroblasts to myoblasts.

Recent studies of mammalian chromosome structure reveal that chromatin is organized in topologically associating domains and gene loops mediated by chromatin architecture proteins such as Cohesin and CTCF (Ji et al., 2016; Seitan et al., 2013; Sofueva et al., 2013; Tang et al., 2015; Zuin et al., 2014). Emerging data suggest that higher-order chromatin structures confer epigenetic information during development and are frequently altered in cancer (Flavahan et al., 2016; Ji et al., 2016; Narendra et al., 2015). It has been reported that binding of CTCF is inhibited when its recognition sequence is methylated (Bell and Felsenfeld, 2000; Kang et al., 2015; Wang et al., 2012). Targeting of dCas9-Dnmt3a to two CTCF binding sites induced de novo methylation of CpGs in these sites and interfered with the insulator function of the protein as evidenced by increased interaction frequencies between insulated super-enhancers in the targeted loop and genes in the neighboring loop causing up-regulation of these genes. This suggests that the dCas9-Dnmt3a system is a useful tool to manipulate chromatin structure and to assess its functional significance during development and in disease context.

Our results indicate that dCas9 fused to the epigenetic effectors Tet1 and Dnmt3a represent a powerful toolbox to edit DNA methylation of specific genomic sequences. Comparison of these tools with TALE-based method showed a higher efficacy and resolution for methylation editing, and dCas9 ChIP-seq followed by bisulfite sequencing of potential off-target binding loci revealed marginal changes in methylation levels, suggesting that high specificity can be achieved with properly designed gRNAs. These dCas9-Dnmt3a/Tet1 tools will be useful to gain insight into the functional significance of DNA methylation in diverse biological processes such as gene expression, cell fate determination, and organization of high-order chromatin structures.

EXPERIMENTAL PROCEDURES

Plasmid Design and Construction

PCR amplified Tet1 catalytic domain from pJFA344C7 (Addgene plasmid: 49236), Tet1 inactive catalytic domain from MLM3739 (Addgene plasmid: 49959), or Dnmt3a from pcDNA3-hDNMT3A (Addgene plasmid: 35521) were cloned in modified pdCas9 plasmid (Addgene plasmid: 44246) with BamHI and EcoRI sites. Then dCas9-NLS-Tet1 or dCas9-NLS-Dnmt3a were PCR amplified and cloned into FUW vector (Addgene plasmid: 14882) with AscI and EcoRI to package lentiviruses. NLS-dCas9-NLS-Tet1 was cloned by inserting annealed oligos (NLS) into FUW-dCas9-NLS-Tet1 with XbaI and AscI. The gRNA expression plasmids were cloned by inserting annealed oligos into modified pgRNA plasmid (Addgene plasmid: 44248) with AarI site. The PiaggyBac-dCas9-Tet1 and -dCas9-Dnmt3a were cloned by ligation of PCR– amplified dCas9-NLS-Tet1 or dCas9-NLS-Dnmt3a from FUW constructs with modified PiggyBac transposon vector (Wilson et al., 2007) with NheI and EcoRI. All constructs were sequenced before transfection. Primer information for gRNA design and construction is listed in Supplemental Table S2. Related plasmids have been deposited into Addgene plasmid database. TALE-Dnmt3a construct targeting p16 locus is a gift from Dr. Klaus Kaestner, and TALE-Tet1 targeting RHOXF2 locus is from Addgene (Plasmid #49943). Full length protein sequences of dCas9-Dnmt3a and dCas9-Tet1CD and their mutants are listed in Supplemental Table S6.

Cell Culture, Lentivirus Production, and Stable Cell Line Generation

Mouse embryonic stem cells (mESCs) were cultured on irradiated mouse embryonic fibroblasts (MEFs) with standard ESCs medium: (500 ml) DMEM supplemented with 10% FBS (Hyclone), 10 ug recombinant leukemia inhibitory factor (LIF), 0.1 mM ß-mercaptoethanol (Sigma-Aldrich), penicillin/streptomycin, 1 mM L-glutamine, and 1% nonessential amino acids (all from Invitrogen). C3H10T1/2 cells were cultured in standard DEME medium with 10% FBS. Lentiviruses expressing dCas9-Tet1, dCas9-Dnmt3a, and gRNAs were produced by transfecting HEK293T cells with FUW constructs or pgRNA constructs together with standard packaging vectors (pCMV-dR8.74 and pCMV-VSVG) followed by ultra-centrifugation-based concentration. Virus titer (T) was calculated based on the infection efficiency for 293T cells, where T=(P*N)/(V), T=titer (TU/ul), P=% of infection positive cells according to the fluorescence marker, N=number of cells at the time of transduction, V=total volume of virus used. Note TU stands for transduction unit. To generate stable cell lines with integrated Doxycycline-inducible dCas9-Tet1 or dCas9-Dnmt3a transgenes, PiggyBac-dCas9-Tet1 or -dCas9-Dnmt3a construct, with a helper plasmid expressing transposase, were transfected into C3H10T1/2 cell using X-tremeGENE 9 transfection reagent (Roche) or into mESCs cells using Xfect transfection reagent (Clontech), according to the provider's protocol. Stably integrated cells were selected with G418 (400 ug/ml) for 10 days. Adult mouse fibroblasts were derived from tails of IG-DMR$^{GFP/Pat}$ reporter mice. Briefly, ~2 cm-long mouse tail was obtained from 3 month old mouse carrying paternally transmitted IG-DMR-Snrpn-GFP methylation reporter, and sterilized by 70% EtOH. ~2 mm×2 mm minced tail pieces were digested with 5 ml of 1 mg/ml Collagenase IV at 37° C. for 90 min in a 15 ml Falcon tube. 5 ml MEF medium were added into the tube to terminate the digestion. Dissociated cells were extruded through a 40 um cell strainer with gentle grind using a syringe plug. Cells were then collected and cultured for viral infection. Cells were analyzed 3 days post-infection in this study.

Mouse Lines and Breeding Strategies

Tet1 mutant mice were previously generated in our lab (Dawlaty et al., 2011). Tet1 KO mice in the study were maintained in a mixed 129 and C57BU6 background. To obtain Tet1 KO mice, male and female mice heterozygous for Tet1 were crossed. To obtain wild type mouse primary cortical neurons, male and female C57BL/6 mice were mated. IG-DMR$^{GFP/Pat}$ methylation reporter mouse line was generated as described (Ref: Stelzer et al., Parent-of-origin DNA methylation dynamics during mouse development, Developmental Cell, under editorial consideration). Male mice with IG-DMR$^{GFP/Pat}$ reporter allele were crossed with C57BL/6 females to generate adult offsprings carrying the paternally transmitted allele for in vivo DNA methylation editing analysis. Mice were handled in accordance with institutional guidelines and approved by the Committee on Animal Care (CAC) and Department of Comparative Medicine (DCM) of Massachusetts Institute of Technology.

Viral Infection of Mice and Tissue Sample Preparation

Mice were infected with appropriate lentiviral cocktails in accordance with institutional guidelines and approved by the Committee on Animal Care (CAC) and Department of Comparative Medicine (DCM) of Massachusetts Institute of Technology. Specifically, to infect mouse skin, lentiviruses expressing dCas9-Tet1 with sc gRNA, an inactive mutant of dC-dT with target gRNAs, and dCas9-Tet1 with target gRNAs were delivered by Hamilton syringe into multiple dermal sites on the ventral side of the deeply anesthetized mouse carrying the Paternal IG-DMR reporter allele (FIG. 14D). To infect mouse brain, various lentiviral mixtures were delivered by stereotaxic setup (Leica BIOSYSTEMS, BenchMark Digital Stereotaxic with Manual Fine Drive) into the following locations (relative to the Franklin and Paxinos mouse brain atlas) of the deeply anesthetized mouse carrying the paternal IG-DMR$^{GFP/Pat}$ reporter allele (FIG. 7D): dCas9-Tet1 with sc gRNA (A-P 0.70 mm, M-L 1.50 mm, D-V 1.50 mm), an inactive mutant of dC-dT with Snrpn gRNAs (A-P −1.90 mm, M-L −1.50 mm, D-V 1.50 mm), and dCas9-Tet1 with Snrpn gRNAs (A-P—1.90 mm, M-L 1.50 mm, D-V 1.50 mm). The titers for dC-T/dC-dT and gRNA lentiviruses are 1.2×104 TU/ul and 1.2×105 TU/ul respectively. Mice were sacrificed 3 days after infection. The animals were fixed by transcardial perfusion with 4% paraformaldehyde (PFA)/PBS. Fixed skin pads and brain samples were dissected and post fixed with 4% paraformaldehyde (PFA)/PBS overnight at 4° C. The brain samples were sectioned with a vibratome (Leica VT1100) at 150 um thickness and the skin samples were sectioned with a cryostat (Leica) at 10 um thickness followed by immunohistochemical analysis. For vibratome sectioning, tissues were embedded in 3% agarose gel. For cryosectioning, tissues were equilibrated in 30% sucrose/PBS prior to embedding in Optimal Cutting Temperature (OCT) compound.

Immunohistochemistry, Microscopy, and Image Analysis

Neurons, HEK293T cells, mouse ES cells and C3H10T1/2 cells were fixed with 4% paraformaldehyde (PFA) for 10 min at room temperature. Cells were permeablized with PBST (1×PBS solution with 0.1% Triton X-100) before blocking with 10% Normal Donkey Serum (NDS) in PBST. Cells were then incubated with appropriately diluted primary antibodies in PBST with 5% NDS for 1 hours at room temperature or 12 hours at 4° C., washed with PBST for 3 times at room temperature and then incubated with desired secondary antibodies in TBST with 5% NDS and DAPI to counter stain the nuclei. Cells were washed 3 times with PBST before mounted onto slides with Fluoromount G (SouthernBiotech). Immunostaining procedures for tissue sections were previously described (Wu et al., 2014a). Briefly, sections were permeablized with PBST (1×PBS solution with 0.5% Triton X-100) for 1 hour at RT before blocking with 10% Normal Donkey Serum (NDS) in PBST. Slices were then incubated with desired primary antibodies in PBST with 5% NDS for 24 hours at 4° C., washed with PBST for 3 times at room temperature and then incubated with secondary antibodies in TBST with 5% NDS and DAPI to counter stain the nuclei. Sections were washed 3 times with PBST before slide mounting. The following antibodies were used in this study: Chicken anti-GFP (1:1000, Aves Labs), Mouse anti-Cas9 (7A9, 1:1000, EMD Millipore), Rabbit anti-BDNF (1:1000, Thermo Fisher), Chicken anti-MAP2 (1:1000, Sigma Aldrich), Mouse antiTuj 1 (1:1000, R&D system), Rabbit anti-MyoD (C-20, 1:1000, Santa Cruz Biotechnology), Mouse anti-MHC (MF20, 1:1000, Fisher Scientific), Mouse anti-MyoG (F5G, 1:1000, Life Technologies). Images were captured on a Zeiss LSM710 confocal microscope and processed with Zen software, ImageJ/Fiji, and Adobe Photoshop. For imaging based quantification, unless otherwise specified, 3-5 representative images were quantified and data were plotted as mean+SD with Excel or Graphpad.

FACS Analysis

To assess the proportion of GFP and/or Cherry positive cells after treatment, the treated cells were dissociated with trypsin and single-cell suspensions were prepared in growth medium subject to a BD FACSAria cell sorter according to the manufacture's protocol at the Whitehead Institute Flow Cytometry Core. Data were analyzed with FlowJo software.

Mouse Primary Cortical Neuron Culture, EDU Labeling and Neural Induction

Dissociated E17.5 cortical neuron cultures were generated from wild type or Tet1 KO mouse embryos as described previously (Ebert et al., 2013). Briefly, E17.5 cortices were dissected in ice-cold 1×HBSS (Gibco 14185-052) containing 1×pen/strep (Gibco: 15140122), 1×pyruvate (Gibco: 11360070) and 30 mM Glucose. Tissues were minced into around 1 mm3 and dissociated with Papain neural tissue dissociation system (Worthington Biochemicals) following the manufacturer's instruction. Cells were resuspended in NM5 media (%5 FBS (Hyclone), 2% B27 supplement (Gibco 17504044), 1×pen/strep and 1× glutamax I (Gibco 35050-061)). 1×10$^6$ cells were plated per well of a 6-well plate coated with poly-D-lysine (PDL, Sigma). On DIV2, cells were treated with 2.5 uM AraC overnight (Sigma C-6645) to eliminate the excessive cell division of mitotic astrocytes and neural progenitor cells. Cultures were fed at DIV3 with fresh NM5 media and subsequently membrane depolarized with 50 mM KCl or infected with preferred lentivirus. We started the treatment at the very beginning of the in vitro culture so the step of AP5 and TTX (tetrodotoxin) treatment to silence basal activity in the culture before KCl treatment was omitted. For EDU labeling, primary neuronal culture were treated with EDU at a final concentration of 10 uM for 24 hours followed by Click-it EDU labeling procedure according to the manufacturer's instruction (Thermo Fisher Scientific). Cells were fixed for immunohistochemical analysis, lysed in Trizol to extract total RNA for RT-qPCR or lysed to extract DNA for bisulfite sequencing analysis.

Fibroblast-to-Myoblast Conversion Assay

Myoblast conversion assay was described previously (Constantinides et al., 1977). Briefly, C3H10T1/2 mouse embryonic fibroblast cells were plated as $1 \times 10^4$ cells per well in 6-well plate, and then infected with lentiviruses expressing dCas9-Tet1 and target gRNAs. 24-hour post infection, cells were treated with vehicle control (HEPES buffer) or 5-Azacytidine (1 uM) for 24-hour, and harvested at different time points for subsequently analysis. DMRs upstream of mouse MyoD gene were defined based on human/mouse genome homology (Schultz et al., 2015).

Western Blot

HEK293T cells were transfected with various constructs by X-tremeGENE 9 reagent following manufacturer's protocol. 2-day post transfection, cells were lysed by RIPA buffer with proteinase inhibitor (Invitrogen), and subject to standard immunoblotting analysis. Mouse anti-Cas9 (1:1000, Active Motif) and mouse α-Tubulin (1:1000, Sigma) antibodies were used.

RT-qPCR

Cells were harvested using Trizol followed by Direct-zol (Zymo Research), according to manufacturer's instructions. RNA was converted to cDNA using First-strand cDNA synthesis (Invitrogen SuperScript III). Quantitative PCR reactions were prepared with SYBR Green (Invitrogen), and performed in 7900HT Fast ABI instrument. Primer information for RT-qPCR is listed in Supplemental Table S3.

ChIP Assay

ChIP experiment was performed as previously described (Dowen et al., 2014). Briefly, cells were cross-linked by 1% formaldehyde in the medium for 10 min in room temperature, and then quenched by adding 0.125 M Glycine for 5 min. Collected cells were washed with PBS twice, and then re-suspended in 3.5 ml of sonication buffer. Sonication was performed for 10 cycles with 0.5 min pulse on and 1 min rest, and 24 watts in ice-water mixture. Then cell lysate was spun down with 14,000×rpm for 10 min at 4° C. 50 ul of supernatant was saved as input for gDNA. 10 ul of anti-CTCF antibody (EMD Millipore: 07729) or anti-Cas9 antibody (Active Motif) was added and incubate overnight at 4° C. 50 ul protein G dynabeads was added into antibody-cell lysate mixture and incubate overnight at 4° C. Then beads were washed with sonication buffer, sonication buffer with high salt (500 mM NaCl), LiCl wash buffer, and TE buffer. Bound protein-DNA complex was eluted from beads by incubation in a 65° C. oven for 15 min, and then reverse cross-linked under 65° C. over-night. The bound DNA was purified with Qiagen QIAquick PCR Purification Kit, and then subject to qPCR analysis or sequencing.

ChIP-Seq Data Analysis

Sequencing data was analyzed with a previously reported method (Wu et al., 2014b). Reads are de-multiplexed and the first 25 bases are mapped to mouse genome (mm10) using STAR (Dobin et al., 2013), requiring unique mapping allowing one mismatch. Mapped reads are collapsed and the same number of reads (about 15 million) are randomly sampled from each sample to match sequencing depth. Peaks are called using MACS (Zhang et al., 2008) with default settings. For each sample, the other five samples are each used as a control and only peaks called over all five controls are defined as candidate peaks. Candidate peaks are filtered by fold of enrichment over background and the threshold is chosen such that no peaks pass this threshold in the four control samples (input, mock IP, dCas9 alone, and scrambled gRNA). Note that six candidate peaks in input mapped to 45S rRNA and mitochondria DNA are excluded from the analysis. Raw data is available in the following link: ncbi.nlm.nih.gov/geo/queryacc.cgi?token=ktohskmgnhudhud&acc=GSE83890.

Bisulfite Conversion, PCR and Sequencing

Bisulfite conversion of DNA was established using the EpiTect Bisulfite Kit (Qiagen) following the manufacturer's instructions. The resulting modified DNA was amplified by first round of nested PCR, following a second round using loci specific PCR primers (Supplemental Table S3). The first round of nested PCR was done as follows: 94° C. for 4 min; 55° C. for 2 min; 72° C. for 2 min; Repeat steps 1-3 1×; 94° C. for 1 min; 55° C. for 2 min; 72° C. for 2 min; Repeat steps 5-7 35×; 72° C. for 5 min; Hold 12° C. The second round of PCR was as follows: 95° C. for 4 min; 94° C. for 1 min; 55° C. for 2 min; 72° C. for 2 min; Repeat steps 2-4 35×; 72° C. for 5 min; Hold 12° C. The resulting amplified products were gel-purified, sub-cloned into a pCR2.1-TOPO-TA cloning vector (Life technologies), and sequenced. Primer information for bisulfite sequencing is listed in Supplemental Table S4.

Locus-Specific TAB-Seq

TAB-Seq was performed as described previously (Yu et al., 2012). Briefly, 1 ug of genomic DNA from treated mouse cortical neuron was glucosylated in a solution containing 50 mM HEPES buffer (pH 8.0), 25 mM $MgCl_2$, 100 ng/ml model DNA, 200 mM UDP-Glc, and 1 mM bGT at 37C for 1 hr. After the reaction, the DNA was column purified. The oxidation reactions were performed in a solution containing 50 mM HEPES buffer (pH 8.0), 100 mM ammonium iron (II) sulfate, 1 mM a-ketoglutarate, 2 mM ascorbic acid, 2.5 mM DTT, 100 mM NaCl, 1.2 mM ATP, 15 ng/ml glucosylated DNA, and 3 mM recombinant mTet1. The reactions were incubated at 37C for 1 hr. After proteinase K treatment, the DNA was column purified and then applied to EpiTect Bisulfite Kit (QIAGEN) following the supplier's instruction. The resulting modified DNA was amplified by first round of nested PCR, following a second round using loci specific PCR primers (Supplemental Table S3). The resulting amplified products were gel-purified, sub-cloned into a pJET cloning vector (Life technologies), and sequenced. Primer information for bisulfite sequencing is listed in Supplemental Table S4.

Chromosome Conformation Capture (3C) Assay $5 \times 10^6$ mESCs were fixed with 1% formaldehyde for 20 min at room temperature, and the reaction was quenched by 0.125 M glycine for 5 min at room temperature. Cross-linked cells were collected and washed with 1 ml ice cold PBS. Cell pellet was re-suspended with 550 μl lysis buffer (10 mM Tris-HCl with pH 8.0, 10 mM NaCl, and 0.2% IGEPAL CA630 with proteinase inhibitor), and incubated on ice for 20 min. Cell pellet was then washed twice with 1×NEB buffer 2 (NEB, B7002S), then incubated with 50 μl 0.5% SDS for 10 min at 62° C. After heating, 145 μl $H_2O$ and 25 μl 10% Triton X-100 were added into the mixture and incubate for 15 min at 37° C. 25 µl 10×NEB buffer 2 and 100 U BglII (NEB, R0144S) were added to digest chromatin over night at 37° C. The digest reaction was inactivated by incubation for 20 min at 62° C. Then 713 µl H₂O, 120 µl 10×T4 DNA ligase buffer (NEB, B0202), 100 µl 10% Triton X-100, 12 µl 10 mg/ml BSA, and 5 µl T4 DNA ligase (NEB, M0202) were added and incubated for 22 hour at 16° C. The chromatin was reverse cross-linked, and DNA was purified by phenol:chloroform:isoamyl alcohol (Sigma, P3803) extraction. The 3C interactions at the miR290 and Pou5f1 loci (FIG. 6A and FIG. 6C) were analyzed by quantitative real-time PCR using custom Taqman probes. The amount of DNA in the qPCR reactions was normalized across 3C libraries using a custom Taqman probe directed against the Actb locus. Primer and probe sequences are listed in Supplemental Table S5.

Supplemental Tables:

SUPPLEMENTAL TABLE S1 dCas9 ChIP-Seq (SEQ ID NOs: 1-35)

| | position | start | end | guide_match | guide_match + NGG | peak_score | peak_summit_height | relative binding |
|---|---|---|---|---|---|---|---|---|
| peak (miR290) | | | | | | | | |
| 1 | chr7 (miR290) | 3221169 | 3222647 | 20 | GTTTTGAGGCCTCATTTGTAAGG, TTTTTGAAAAATTACCTTGTGGG, CAGAGTCCTAGACATTTCCATGG | 3100 | 65 | 1.00 |
| 2 | chr8 (Vac14) | 110658179 | 110659329 | 16, 12 | GgagaGAGGCCTCATTTGTAGGG, gTTgTcAgAgcaTAgCTTGTAGG | 3147 | 52 | 0.80 |
| 3 | chr16 (Tenm4) | 92920310 | 92920851 | 9 | CtaAagCgatGttccTTCCAGGG | 1240 | 27 | 0.42 |
| 4 | chr7 | 96797181 | 96798058 | 13 | ttGctctCaAGACATTTCCAGGG | 1371 | 23 | 0.35 |
| 5 | chr8 | 47748476 | 47743820 | 9 | ttGctTtCcAttttcTTCCAGGG | 346 | 17 | 0.26 |
| 6 | chr8 | 119843496 | 119843845 | 10 | agcTTctAgctcTACCTTcTAGG | 582 | 17 | 0.26 |
| 7 | chr2 | 60720846 | 60721662 | 12 | tcTgcGAGtCCTtAaTTtTAGGG | 779 | 17 | 0.26 |
| 8 | chr4 | 134701902 | 134702180 | 8 | aAagcattTtcttcTTTCCAGGG | 212 | 15 | 0.23 |
| 9 | chr3 | 35405566 | 35406124 | 6 | agttGctgctctttTgTCCAGGG | 447 | 15 | 0.23 |
| 10 | chr3 | 116425072 | 116425343 | 9 | acGcaaCtgcGAgcTTTCaAAGG | 220 | 15 | 0.23 |
| 11 | chr11 | 113612406 | 113612812 | 7 | tttAaagCccttccTTCCAGGG | 227 | 15 | 0.23 |
| 12 | chr15 | 58022874 | 58023158 | 10 | acTgTcttcAAcTtCCTTGgGGG | 143 | 14 | 0.22 |
| 13 | chr3 | 116748072 | 116748683 | 12 | ggactaCtgAGACATTTCCAGGG | 793 | 13 | 0.20 |
| 14 | chr2 | 122357139 | 122357691 | 13 | tcaAccCtgAGACATTTCCAGGG | 326 | 13 | 0.20 |
| 15 | chr1 | 191708537 | 191708741 | 14 | CCaAGattgAGACATTTCCAGGG | 205 | 13 | 0.20 |
| 16 | chr8 | 84471283 | 84471659 | 12 | tAaAGTCCcAGtCcccTCCcTGG | 345 | 12 | 0.18 |
| 17 | chr4 | 125502945 | 125503352 | 10 | CtaAGctCTgtgttgTTCCAGGG | 219 | 12 | 0.18 |
| 18 | chr2 | 152112091 | 152112284 | 9 | GTagaGcatgtTgAgcTGTAGGG | 84 | 12 | 0.18 |
| peak (Dazl-Snrpn) | | | | | | | | |
| 1 | chr17 (Dazl) | 50293768 | 50295107 | 20 | GAGCCGAGCTGTAGGGTGCTTGG | 3100 | 64 | 1.00 |
| 2 | chr12 (Vrk1) | 105962219 | 105963255 | 14, 5 | cgGgCagcCTGTAGGGTGCTGGG, gcgcaagGgttgtcgTGCCTTGG | 3100 | 64 | 1.00 |
| 3 | chr7 (Snrpn) | 60004839 | 60005472 | 20, 20, 20 | CGCATGTGCAGCCATTGCCTGGG, TTTGGTAGCTGCCTTTTGGCAGG, ACAAACCTGAGCCATTGCGG | 1251 | 35 | 0.55 |
| 4 | chr5 (Gm42619) | 148500582 | 148501113 | 14, 8 | ccctgcAGCTGTAGGGTGCTAGG, tctcTtcagtGtaATTGgCTTGG | 657 | 21 | 0.33 |
| 5 | chr5 | 103341125 | 103341731 | 13, 10 | tccatttGCTGTAGGGTGCTAGG, TgctaatGtccCCaTTTGGCAGG | 1073 | 19 | 0.30 |

SUPPLEMENTAL TABLE S1-continued dCas9 ChIP-Seq (SEQ ID NOs: 1-35)

|   | position | start | end | guide_match | guide_match + NGG | peak_score | peak_summit_height | relative binding |
|---|----------|-------|-----|-------------|-------------------|------------|--------------------|-----------------|
| 6 | chr18 | 82149068 | 82149284 | 15 | GcaCaGcaCTGTAGGGTGCTGGG | 377 | 17 | 0.27 |
| 7 | chr1  | 127220317 | 127220836 | 13 | ccatCtctCTGTAGGGTGCTGGG | 521 | 17 | 0.27 |
| 8 | chr19 | 46897110 | 46897668 | 15 | GtGagctGCTGTAGGGTGCTAGG | 386 | 13 | 0.20 |
| 9 | chr6  | 93599579 | 93599815 | 16 | GAatgGAcCTGTAGGGTGCTTGG | 205 | 12 | 0.19 |

Table legends:
chr: chromosome
start: start coordinate of the peak
end: end coordinate of the peak
guide_match: number of base match to the guide
guide_match + NGG: guide match sequence + NGG within the peak (mismatched sequence in lower case)
peak_score: MACS peak score (log-transformed: $-10^6 \log_{10}(p\ value)$)
peak_summit_height: MACS peak summit height
relative binding: normalized to peak summit heigh of target gRNAs

SUPPLEMENTAL TABLE S2

Primer sequences to construct guide RNAs

5' to 3' scrambled gRNA

| | |
|---|---|
| SL-289_dCas9-effector_scramble gRNA_For | TTGG cccccgggggaaaaattttt (SEQ ID NO: 36) |
| SL-290_dCas9-effector_scramble gRNA_Rev | AAAC aaaaattttttcccccgggg (SEQ ID NO: 37) | gRNAs targeting the BDNF promoter IV

| | |
|---|---|
| SL-64_mBDNF_Exon IV_gRNA-1_For | TTGG ctacaaagcatgcaatgccc (SEQ ID NO: 38) |
| SL-65_mBDNF_Exon IV_gRNA-1_Rev | AAAC gggcattgcatgctttgtag (SEQ ID NO: 39) |
| SL-66_mBDNF_Exon IV_gRNA-2_For | TTGG aatgcgcggaattctgattc (SEQ ID NO: 40) |
| SL-67_mBDNF_Exon IV_gRNA-2_Rev | AAAC gaatcagaattccgcgcatt (SEQ ID NO: 41) |
| SL-68_mBDNF_Exon IV_gRNA-3_For | TTGG gtgggtgggagtccacgaga (SEQ ID NO: 42) |
| SL-69_mBDNF_Exon IV_gRNA-3_Rev | AAAC tctcgtggactcccacccac (SEQ ID NO: 43) |
| SL-70_mBDNF_Exon IV_gRNA-4_For | TTGG ggcagcgtggagccctctcg (SEQ ID NO: 44) |
| SL-71_mBDNF_Exon IV_gRNA-4_Rev | AAAC cgagagggctccacgctgcc (SEQ ID NO: 45) | gRNAs targeting the Snrpn promoter

| | |
|---|---|
| SL-127_mSnrpn_gRNA-1_For | TTGG GAGCCGAGCTGTAGGGTGCT (SEQ ID NO: 46) |
| SL-128_mSnrpn_gRNA-1_Rev | AAAC AGCACCCTACAGCTCGGCTC (SEQ ID NO: 47) |
| SL-129_mSnrpn_gRNA-2_For | TTGG TTTGGTAGCTGCCTTTTGGC (SEQ ID NO: 48) |
| SL-130_mSnrpn_gRNA-2_Rev | AAAC GCCAAAAGGCAGCTACCAAA (SEQ ID NO: 49) |
| SL-131_mSnrpn_gRNA-3_For | TTGG CGCATGTGCAGCCATTGCCT (SEQ ID NO: 50) |
| SL-132_mSnrpn_gRNA-3_Rev | AAAC AGGCAATGGCTGCACATGCG (SEQ ID NO: 51) |
| SL-133_mSnrpn_gRNA-4_For | TTGG ACAAACCTGAGCCATTG (SEQ ID NO: 52) |
| SL-134_mSnrpn_gRNA-4_Rev | AAAC CAATGGCTCAGGTTTGT (SEQ ID NO: 53) | gRNAs targeting MyoD DMR-5 (distal enhancer region)

| | |
|---|---|
| SL-174_mMyoD_gRNA-1_For | TTGG agcatttgggggcatttatg (SEQ ID NO: 54) |
| SL-175_mMyoD_gRNA-1_Rev | AAAC cataaatgccccccaaatgct (SEQ ID NO: 55) |

SUPPLEMENTAL TABLE S2-continued

Primer sequences to construct guide RNAs

5' to 3'

| | |
|---|---|
| SL-176_mMyoD_gRNA-2_For | TTGG aagtatcctcctccagcagc (SEQ ID NO: 56) |
| SL-177_mMyoD_gRNA-2_Rev | AAAC gctgctggaggaggatactt (SEQ ID NO: 57) |
| SL-178_mMyoD_gRNA-3_For | TTGG acacagccagttgggggaag (SEQ ID NO: 58) |
| SL-179_mMyoD_gRNA-3_Rev | AAAC cttcccccaactggctgtgt (SEQ ID NO: 59) |
| SL-180_mMyoD_gRNA-4_For | TTGG ccagagtcagctgttcct (SEQ ID NO: 60) |
| SL-181_mMyoD_gRNA-4_Rev | AAAC aggaacagctgactctgg (SEQ ID NO: 61) | gRNAs targeting miR290 locus (CTCF target-1)

| | |
|---|---|
| SL-357_miR290-NIrp12_gRNA-1_For | TTGG GTTTTGAGGCCTCATTTGTA (SEQ ID NO: 62) |
| SL-358_miR290-NIrp12_gRNA-1_Rev | AAAC TACAAATGAGGCCTCAAAAC (SEQ ID NO: 63) |
| SL-359_miR290-NIrp12_gRNA-2_For | TTGG TTTTTGAAAAATTACCTTGT (SEQ ID NO: 64) |
| SL-360_miR290-NIrp12_gRNA-2_Rev | AAAC ACAAGGTAATTTTTCAAAAA (SEQ ID NO: 65) |
| SL-361_miR290-NIrp12_gRNA-3_For | TTGG CAGAGTCCTAGACATTTCCA (SEQ ID NO: 66) |
| SL-362_miR290-NIrp12_gRNA-3_Rev | AAAC TGGAAATGTCTAGGACTCTG (SEQ ID NO: 67) | gRNAs targeting Pou5f1 locus (CTCF target-2)

| | |
|---|---|
| SL-377_Pou5f1_gRNA-1_For | TTGG TCTCACCCTTGATAGTTTGA (SEQ ID NO: 68) |
| SL-378_Pou5f1_gRNA-1_Rev | AAAC TCAAACTATCAAGGGTGAGA (SEQ ID NO: 69) |
| SL-379_Pou5f1_gRNA-2_For | TTGG GGTAAATCTTTGAAGCCAAT (SEQ ID NO: 70) |
| SL-380_Pou5f1_gRNA-2_Rev | AAAC ATTGGCTTCAAAGATTTACC (SEQ ID NO: 71) |
| SL-381_Pou5f1_gRNA-3_For | TTGG ATTTTCTACCTACGGTGTGC (SEQ ID NO: 72) |
| SL-382_Pou5f1_gRNA-3_Rev | AAAC GCACACCGTAGGTAGAAAAT (SEQ ID NO: 73) |
| SL-383_Pou5f1_gRNA-4_For | TTGG TCTCCTGGAAGGACTCTGGG (SEQ ID NO: 74) |
| SL-384_Pou5f1_gRNA-4_Rev | AAAC CCCAGAGTCCTTCCAGGAGA (SEQ ID NO: 75) | gRNA targeting p16 locus

| | |
|---|---|
| SL-504_p16 promoter_sgRNA-1_For | TTGG tcctccttccttgccaacgc (SEQ ID NO: 76) |
| SL-505_p16 promoter_sgRNA-1_Rev | AAAC gcgttggcaaggaaggagga (SEQ ID NO: 77) | gRNA targeting RHOXF2 locus

| | |
|---|---|
| SL-506_RHOXF2 promoter_sgRNA-1_For | TTGG cccgctatttgctgtgggtt (SEQ ID NO: 78) |
| SL-507_RHOXF2 promoter_sgRNA-1_Rev | AAAC aacccacagcaaatagcggg (SEQ ID NO: 79) |

SUPPLEMENTAL TABLE S3 qPCR primers

| | |
|---|---|
| mBDNF_Exon IV_qPCR_For | CAG GAG TAC ATA TCG GCC ACC A (SEQ ID NO: 80) |
| mBDNF_Exon IV_qPCR_Rev | GTA GGC CAA GTT GCC TTG TCC GT (SEQ ID NO: 81) |
| β-Actin_qPCR_For primer | GCC TTC CTT CTT GGG TAT G (SEQ ID NO: 82) |
| β-Actin_qPCR_Rev primer | ACC ACC AGA CAA CAC TGT G (SEQ ID NO: 83) |
| mNpas4_qPCR_For primer | GCTATACTCAGAAGGTCCAGAAGGC (SEQ ID NO: 84) |

SUPPLEMENTAL TABLE S3-continued

| qPCR primers | |
|---|---|
| mNpas4_qPCR_Rev primer | TCAGAGAATGAGGGTAGCACAGC (SEQ ID NO: 85) |
| mMyoD_qPCR_For | ACT TTC TGG AGC CCT CCT GGC A (SEQ ID NO: 86) |
| mMyoD_qPCR_Rev | TTT GTT GCA CTA CAC AGC ATG (SEQ ID NO: 87) |
| CTCF target-1 | |
| SL-401_AU018091_for | AGGGGATTCTCCGTGGTACA (SEQ ID NO: 88) |
| SL-402_AU018091_rev | CTCTTCCCCTGTACTCGCAA (SEQ ID NO: 89) |
| SL-411_Pri-miR290-295_for | CGAGACGCGGATGGATGTAA (SEQ ID NO: 90) |
| SL-412_Pri-miR290-295_rev | GCGGCACTTTTCTTCCGATG (SEQ ID NO: 91) |
| SL-397_NIrp12_for | CCAGACCCTGCATGAGCTTTA (SEQ ID NO: 92) |
| SL-398_NIrp12_rev | AAACAGCCACAGGACTCGAA (SEQ ID NO: 93) |
| SL-429_Myadm_new_F | TCTGTTAAGGGAGCAGCCATGC (SEQ ID NO: 94) |
| SL-430_Myadm_new_R | GGATATTAGCTGCAGGAGGCG (SEQ ID NO: 95) |
| CTCF target-2 | |
| SL-423_H2Q10_CDS_F | CAGAGAGCCAAGGGCAATGA (SEQ ID NO: 96) |
| SL-424_H2Q10_CDS_R | GGACCCCACTTTACAGCCAT (SEQ ID NO: 97) |
| SL-421_Pou5f1_new_F | GCGTTCTCTTTGGAAAGGTGT (SEQ ID NO: 98) |
| SL-422_Pou5f1_new_R | TTGTTGTCGGCTTCCTCCAC (SEQ ID NO: 99) |
| SL-395_Tcf19_for | ATCTCTGGAGTCCATGCGGA (SEQ ID NO: 100) |
| SL-396_Tcf19_rev | CAAAGTCCCTTGGCTGCTGT (SEQ ID NO: 101) |
| ChIP-qPCR primers for CTCF target-1 | |
| SL-456_mCTCF_ChIP-qPCR_T1_2_For | CAGGTGTGCAAATCTTGGGT (SEQ ID NO: 102) |
| SL-457_mCTCF_ChIP-qPCR_T1_2_Rev | TGGTGGCTTGCAATCATCTG (SEQ ID NO: 103) |
| SL-458_mCTCF_ChIP-qPCR_T1_control_1_For | TGAGTCCTTGCTCGGTTCTT (SEQ ID NO: 104) |
| SL-459_mCTCF_ChIP-qPCR_T1_control_1_Rev | CAGGCACATTGCTGTGAGTT (SEQ ID NO: 105) |
| ChIP-qPCR primers for CTCF target-2 | |
| SL-446_mCTCF_ChIP-qPCR_T2_1_For | TGGCCTTGTACTGTTGCAAC (SEQ ID NO: 106) |
| SL-447_mCTCF_ChIP-qPCR_T2_1_Rev | AGTGTCACTATGGCCACCTT (SEQ ID NO: 107) |
| SL-452_mCTCF_ChIP-qPCR_T2_control_2_For | AATCTTCCCTTGGGGGTATG (SEQ ID NO: 108) |
| SL-453_mCTCF_ChIP-qPCR_T2_control_2_Rev | TAAGGAGCCATGCTGTACCC (SEQ ID NO: 109) |

SUPPLEMENTAL TABLE S4

| Bisulfite sequencing primers | |
|---|---|
| Dazl-Snrpn-GFP locus | |
| Dazl Nested F | GAAGTTTTTGTGAAATAAGTTTTGGGTAGG (SEQ ID NO: 110) |
| GFP Nested R | CTCGACCAAAATAAACACCACCCC (SEQ ID NO: 111) |
| Dazl-Snrpn F | CGAGTTGTAGGGTGTTTGGTAATTG (SEQ ID NO: 112) |
| Dazl-Snrpn R | ACGTTACAAATCACTCCTCAAAACC (SEQ ID NO: 113) |

SUPPLEMENTAL TABLE S4-continued

| Bisulfite sequencing primers | |
|---|---|
| Gapdh-Snrpn-GFP locus | |
| Gapdh Nested F | GGTTGTAGGAGAAGAAAATGAGATTAG (SEQ ID NO: 114) |
| GFP Nested R | CTCGACCAAAATAAACACCACCCC (SEQ ID NO: 115) |
| Gapdh-Snrpn F | TAGTTTAAGGGCGTAGAGGTTTGAG (SEQ ID NO: 116) |
| Gapdh-Snrpn R | ACGTTACAAATCACTCCTCAAAACC (SEQ ID NO: 117) |
| BDNF promoter IV | |
| SL-108_hBDNF_Exon IV_Nest_For | TTATTTATTGGTTGGATTAGAGGGGT (SEQ ID NO: 118) |
| SL-109_hBDNF_Exon IV_Nest_Rev | CATATACTTCCCAACAAACCAAAC (SEQ ID NO: 119) |
| SL-110_hBDNF_Exon IV_BS-Seq_For | GTGAATTTGTTAGGATTGGAAGTGAA (SEQ ID NO: 120) |
| SL-111_hBDNF_Exon IV_BS-Seq_Rev | ACTCTTACTATATATTTCCCCTTCTCTTCA (SEQ ID NO: 121) |
| DMR-5 for MyoD distal enhancer | |
| SL-253_mMyoD_DMR-5_Nest_For | GGTTTGAGGTAGGTAGGGGTTAGG (SEQ ID NO: 122) |
| SL-254_mMyoD_DMR-5_Nest_Rev | CCAACTCACTTTCTCCCAAAATTACACTAA (SEQ ID NO: 123) |
| SL-255_mMyoD_DMR-5_BS_For | GTAGAATTTGTTAGGTGGGTGAAAGGAAG (SEQ ID NO: 124) |
| SL-256_mMyoD_DMR-5_BS_Rev | CCTTCCTCCCAAAATACTAACCTCTCATAC (SEQ ID NO: 125) |
| CTCF target-1 locus (miR290) | |
| SL-431_miR290-NIrp12 locus_Nest_For | GATTTTTGGGTATTGTATTGGAAGTGGG (SEQ ID NO: 126) |
| SL-432_miR290-NIrp12 locus_Nest_Rev | CCAAAATATTTATTCCCTCTACTTTAAAACAC (SEQ ID NO: 127) |
| SL-433_miR290-NIrp12 locus_BS_For | TTTAGGATAGGATGGGAGTATTGGTTG (SEQ ID NO: 128) |
| SL-434_miR290-NIrp12 locus_BS_Rev | CAAAATCACTCAAAATCATCCTATTACATAAAAC (SEQ ID NO: 129) |
| CTCF target-2 locus (Pou5f1) | |
| SL-440_H2Q10-Pou5f1 locus_Nest_For | ATTAAGAGGTTAGGGGTTTTTTAGTTGGTTTTGTATTG (SEQ ID NO: 130) |
| SL-441_H2Q10-Pou5f12 locus_Nest_Rev | AAAAAAAACCTTCATCACATAATAAACTAAACCAACC (SEQ ID NO: 131) |
| SL-442_H2Q10-Pou5f1 locus_BS_For | GAAAGGATGTAATTAGAGGGTTTTTGGG (SEQ ID NO: 132) |
| SL-443_H2Q10-Pou5f1 locus_BS_Rev | AATCCTTTCTCAAAACCCCTTCCTC (SEQ ID NO: 133) |
| p16 | |
| SL-510_p16 promoter_Nest_For | Gtggggttttttataattaggaaagaatag (SEQ ID NO: 134) |
| SL-511_p16 promoter_Nest_Rev | ATTACAAACCCCTTCTAAAAACTCC (SEQ ID NO: 135) |
| SL-512_p16 promoter_BS_For | Atttggtagttaggaaggttgta (SEQ ID NO: 136) |
| SL-513_p16 promote_BS_Rev | CCAAAAAACCTCCCCTTTTTCC (SEQ ID NO: 137) |
| RHOXF2 | RHOXF2 BS-seq |
| SL-514_RHOXF2 promoter_Nest_For | GTGGATTTTTTTAAGGAGTGTGTTG (SEQ ID NO: 138) |
| SL-515_RHOXF2 promoter_Nest_Rev | CTTCTAATATCTAAACTCAACAACAATATATCCAC (SEQ ID NO: 139) |
| SL-516_RHOXF2 promoter_BS_For | GGAGATTTAGGAAGTATGGGGTTAGTG (SEQ ID NO: 140) |
| SL-517_RHOXF2 promoter_BS_Rev | AAAACCTCCTCTCTTACTTTTCTACTTC (SEQ ID NO: 141) |

SUPPLEMENTAL TABLE S5

| 3C assay primers | |
| --- | --- |
| SL-471_3Cassay_NIrp12_Rev | CACATCTTCAAAGCAAACACTATTGTT (SEQ ID NO: 142) |
| SL-472_3Cassay_NIrp12_SE_1_For | TTCCTGGAACCTGGGCAA (SEQ ID NO: 143) |
| SL-473_3Cassay_NIrp12_SE_2_For | TGATACAGCACAGCTTTCCTTCA (SEQ ID NO: 144) |
| SL-474_3Cassay_NIrp12_SE_3_For | CAGATTTTTATTTCCTTCAGTTCTGTG (SEQ ID NO: 145) |
| SL-475_3Cassay_NIrp12_Taqman Probe | TCTCCTACCCATTGCTTCTCTGCTACCTGC (SEQ ID NO: 146) |
| 3Cassay_NIrp12_NC_1_For | TGAAGTTTGAGGAGATGCCATGGTTG (SEQ ID NO: 147) |
| 3Cassay_NIrp12_NC_1_Rev | CACGCTAGGCTGAACACTGTGTCACTG (SEQ ID NO: 148) |
| SL_476_3C assay_H2Q10_For | AGGATGGCTCAGCGGTTAAG (SEQ ID NO: 149) |
| SL_477_3C assay_H2Q10_SE_Rev | AGGGCTCACCTTCAGTCAAGTT (SEQ ID NO: 150) |
| SL_478_3C assay_H2Q10_Taqman Probe | CGGCCTGTCTACTTTAGCCTCAGACTCCA (SEQ ID NO: 151) |
| 3C assay_H2Q10_NC-3_For | TGCCTTCCCTCTTACAAGGAGTTTTCTT (SEQ ID NO: 152) |
| 3C assay_H2Q10_NC-3_Rev | CGGTTAAGAAGAGCTCTTCTGGAGGCC (SEQ ID NO: 153) |
| SL-483_3C assay_Actin_For | GGGAGTGACTCTCTGTCCATTCA (SEQ ID NO: 154) |
| SL-484_3C assay_Actin_Rev | ATTTGTGTGGCCTCTTGTTTGA (SEQ ID NO: 155) |
| SL-485_3C assay_Actin_Taqman Probe | TCCAGGCCCCGCGTGTCC (SEQ ID NO: 156) |

SUPPLEMENTAL TABLE S6

Full length protein sequences of dCas9-Dnmt3a/Tet and mutants
dCas9-Dnmt3a (dC-D) (SEQ ID NO: 157)
MDKKYSIGLAIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIAQLPGEKKNGLFGNLIALS
LGLTPNFKSNFDLAEDAKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVSDFRKDFQ
FYKVREINNYHHAHDAYLNAVVGTALIKKYPKLESEFVYGDYKVYDVRKMIAKSEQEIGKATAKYFFYSNIMNFFKTEITL
ANGEIRKRPLIETNGETGEIVWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVKKDLIIKLPKYSLFELENGRKRML
ASAGELQKGNELALPSKYVNFLYLASHYEKLKGSPEDNEQKQLFVEQHKHYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGDEGADPKKKRKV
DPKKKRKVDPKKKRKVGSMPAMPSSGPGDTSSSAAEREEDRKDGEEQEEPRGKEERQEPSTTARKVGRPGRKRKHPP
VESGDTPKDPAVISKSPSMAQDSGASELLPNGDLEKRSEPQPEEGSPAGGQKGGAPAEGEGAAETLPEASRAVENGCC
TPKEGRGAPAEAGKEQKETNIESMKMEGSRGRLRGGLGWESSLRQRPMPRLTFQAGDPYYISKRKRDEWLARWKRE
AEKKAKVIAGMNAVEENQGPGESQKVEEASPPAVQQPTDPASPTVATTPEPVGSDAGDKNATKAGDDEPEYEDGRG
FGIGELVWGKLRGFSWWPGRIVSWWMTGRSRAAEGTRWVMWFGDGKFSVVCVEKLMPLSSFCSAFHQATYNKQP
MYRKAIYEVLQVASSRAGKLFPVCHDSDESDTAKAVEVQNKPMIEWALGGFQPSGPKGLEPPEEEKNPYKEVYTDMW
VEPEAAAYAPPPPAKKPRKSTAEKPKVKEIIDERTRERLVYEVRQKCRNIEDICISCGSLNVTLEHPLFVGGMCQNCKNCF
LECAYQYDDDGYQSYCTICCGGREVLMCGNNNCCRCFCVECVDLLVGPGAAQAAIKEDPWNCYMCGHKGTYGLLRR
REDWPSRLQMFFANNHDQEFDPPKVYPPVPAEKRKPIRVLSLFDGIATGLLVLKDLGIQVDRYIASEVCEDSITVGMVR
HQGKIMYVGDVRSVTQKHIQEWGPFDLVIGGSPCNDLSIVNPARKGLYEGTGRLFFEFYRLLHDARPKEGDDRPFFWL
FENVVAMGVSDKRDISRFLESNPVMIDAKEVSAAHRARYFWGNLPGMNRPLASTVNDKLELQECLEHGRIAKFSKVRT
ITTRSNSIKQGKDQHFPVFMNEKEDILWCTEMERVFGFPVHYTDVSNMSRLARQRLLGRSWSVPVIRHLFAPLKEYFAC
V dCas9-Dnmt3a_IM (dC-dD, an inactive mutant form of Dnmt3a) (SEQ ID NO: 158)
MDKKYSIGLAIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIAQLPGEKKNGLFGNLIALS
LGLTPNFKSNFDLAEDAKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQGDSLHEHIANLAGSPAI SUPPLEMENTAL TABLE S6-continued KKGILQTVKVVDELVKVMGRHKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVSDFRKDFQ
FYKVREINNYHHAHDAYLNAVVGTALIKKYPKLESEFVYGDKVYDVRKMIAKSEQEIGKATAKYFFYSNIMNFFKTEITL
ANGEIRKRPLIETNGETGEIVWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVKKDLIIKLPKYSLFELENGRKRML
ASAGELQKGNELALPSKYVNFLYLASHYEKLKGSPEDNEQKQLFVEQHKYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGDEGADPKKKRKV
DPKKKRKVDPKKKRKVGSMPAMPSSGPGDTSSSAAEREEDRKDGEEQEEPRGKEERQEPSTTARKVGRPGRKRKHPP
VESGDTPKDPAVISKSPSMAQDSGASELLPNGDLEKRSEPQPEEGSPAGGQKGGAPAEGEGAAETLPEASRAVENGCC
TPKEGRGAPAEAGKEQKETNIESMKMEGSRGRLRGGLGWESSLRQRPMPRLTFQAGDPYYISKRKRDEWLARWKRE
AEKKAKVIAGMNAVEENQGPGESQKVEEASPPAVQQPTDPASPTVATTPEPVGSDAGDKNATKAGDDEPEYEDGRG
FGIGELVWGKLRGFSWWPGRIVSWWMTGRSRAAEGTRWVMWFGDGKFSVVCVEKLMPLSSFCSAFHQATYNKQP
MYRKAIYEVLQVASSRAGKLFPVCHDSDESDTAKAVEVQNKPMIEWALGGFQPSGPKGLEPPEEEKNPYKEVYTDMW
VEPEAAAYAPPPPAKKPRKSTAEKPKVKEIIDERTRERLVYEVRQKCRNIEDICISCGSLNVTLEHPLFVGGMCQNCKNCF
LECAYQYDDDGYQSYCTICCGGREVLMCGNNNCCRCFCVECVDLLVGPGAAQAAIKEDPWNCYMCGHKGTYGLLRR
REDWPSRLQMFFANNHDQEFDPPKVYPPVPAEKRKPIRVLSLFDGIATGLLVLKDLGIQVDRYIASAVCEDSITVGMVR
HQGKIMYVGDVRSVTQKHIQEWGPFDLVIGGSPCNDLSIVNPARKGLYEGTGRLFFEFYRLLHDARPKEGDDRPFFWL
FANVVAMGVSDKRDISRFLESNPVMIDAKEVSAAHRARYFWGNLPGMNRPLASTVNDKLELQECLEHGRIAKFSKVRT
ITTRSNSIKQGKDQHFPVFMNEKEDILWCTEMERVFGFPVHYTDVSNMSRLARQRLLGRSWSVPVIRHLFAPLKEYFAC
V dCas9-Tet1CD (dC-T) (SEQ ID NO: 159)
MDKKYSIGLAIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIAQLPGEKKNGLFGNLIALS
LGLTPNFKSNFDLAEDAKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVSDFRKDFQ
FYKVREINNYHHAHDAYLNAVVGTALIKKYPKLESEFVYGDYKVYDVRKMIAKSEQEIGKATAKYFFYSNIMNFFKTEITL
ANGEIRKRPLIETNGETGEIVWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVKKDLIIKLPKYSLFELENGRKRML
ASAGELQKGNELALPSKYVNFLYLASHYEKLKGSPEDNEQKQLFVEQHKYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGDEGADPKKKRKV
DPKKKRKVGSLPTCSCLDRVIQKDKGPYYTHLGAGPSVAAVREIMENRYGQKGNAIRIEIVVYTGKEGKSSH
GCPIAKWVLRRSSDEEKVLCLVRQRTGHHCPTAVMVVLIMVWDGIPLPMADRLYTELTENLKSYNGHPTDRRCTLNEN
RTCTCQGIDPETCGASFSFGCSWSMYFNGCKFGRSPSPRRFRIDPSSPLHEKNLEDNLQSLATRLAPIYKQYAPVAYQNQ
VEYENVARECRLGSKEGRPFSGVTACLDFCAHPHRDIHNMMNGSTVVCTLTREDNRSLGVIPQDEQLHVLPLYKLSDTD
EFGSKEGMEAKIKSGAIEVLAPRRKKRTCFTQPVPRSGKKRAAMMTEVLAHKIRAVEKKPIPRIKRKNNSTTTNNSKPSSL
PTLGSNTETVQPEKVSETEPHFILKSSDNTKTYSLMPSAPHPVKEASPGFSWSPKTASATPAPLKNDATASCGFSERSSTP
HCTMPSGRLSGANAAAADGPGISQLGEVAPLPTLSAPVMEPLINSEPSTGVTEPLTPHQPNHQPSFLTSPQDLASSPME
EDEQHSEADEPPSDEPLSDDPLSPAEEKLPHIDEYWSDSEHIFLDANIGGVAIAPAHGSVLIECARRELHATTPVEHPNRN
HPTRLSLVFYQHKNLNKPQHGFELNKIKFEAKEAKNKKMKASEQKDQAANEGPEQSSEVNELNQIPSHKALTLTHDNV
VTVSPYALTHVAGPYNHWV dCas9-Tet1CD_IM (dC-dT, an inactive mutant form of Tet1) (SEQ ID NO: 160)
MDKKYSIGLAIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIAQLPGEKKNGLFGNLIALS
LGLTPNFKSNFDLAEDAKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVSDFRKDFQ
FYKVREINNYHHAHDAYLNAVVGTALIKKYPKLESEFVYGDYKVYDVRKMIAKSEQEIGKATAKYFFYSNIMNFFKTEITL
ANGEIRKRPLIETNGETGEIVWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVKKDLIIKLPKYSLFELENGRKRML
ASAGELQKGNELALPSKYVNFLYLASHYEKLKGSPEDNEQKQLFVEQHKYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGDEGADPKKKRKV
DPKKKRKVGSLPTCSCLDRVIQKDKGPYYTHLGAGPSVAAVREIMENRYGQKGNAIRIEIVVYTGKEGKSSH
GCPIAKWVLRRSSDEEKVLCLVRQRTGHHCPTAVMVVLIMVWDGIPLPMADRLYTELTENLKSYNGHPTDRRCTLNEN
RTCTCQGIDPETCGASFSFGCSWSMYFNGCKFGRSPSPRRFRIDPSSPLHEKNLEDNLQSLATRLAPIYKQYAPVAYQNQ
VEYENVARECRLGSKEGRPFSGVTACLDFCAHPYRAIHNMMNGSTVVCTLTREDNRSLGVIPQDEQLHVLPLYKLSDTD
EFGSKEGMEAKIKSGAIEVLAPRRKKRTCFTQPVPRSGKKRAAMMTEVLAHKIRAVEKKPIPRIKRKNNSTTTNNSKPSSL
PTLGSNTETVQPEKVSETEPHFILKSSDNTKTYSLMPSAPHPVKEASPGFSWSPKTASATPAPLKNDATASCGFSERSSTP
HCTMPSGRLSGANAAAADGPGISQLGEVAPLPTLSAPVMEPLINSEPSTGVTEPLTPHQPNHQPSFLTSPQDLASSPME
EDEQHSEADEPPSDEPLSDDPLSPAEEKLPHIDEMSDSEHIFLDANIGGVAIAPAHGSVLIECARRELHATTPVEHPNRN
HPTRLSLVFYQHKNLNKPQHGFELNKIKFEAKEAKNKKMKASEQKDQAANEGPEQSSEVNELNQIPSHKALTLTHDNV
VTVSPYALTHVAGPYNHWV SUPPLEMENTAL TABLE S6-continued dCas9-Dnmt3a-P2A-BFP (SEQ ID NO: 161)
```
MDKKYSIGLAIGTNSVGWAVITDEYKVPSKKFKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEKYPTIYHLRKKLVDSTDKADLRLIYLALAHMIK
FRGHFLIEGDLNPDNSDVDKLFIQLVQTYNQLFEENPINASGVDAKAILSARLSKSRRLENLIAQLPGEKKNGLFGNLIALS
LGLTPNFKSNFDLAEDAKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKEDYFK
KIECFDSVEISGVEDRFNASLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVENTQLQNEKLY
LYYLQNGRDMYVDQELDINRLSDYDVDAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVSDFRKDFQ
FYKVREINNYHHAHDAYLNAVVGTALIKKYPKLESEFVYGDYKVYDVRKMIAKSEQEIGKATAKYFFYSNIMNFFKTEITL
ANGEIRKRPLIETNGETGEIVWDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVKKDLIIKLPKYSLFELENGRKRML
ASAGELQKGNELALPSKYVNFLYLASHYEKLKGSPEDNEQKQLFVEQHKHYLDEIIEQISEFSKRVILADANLDKVLSAYNK
HRDKPIREQAENIIHLFTLTNLGAPAAFKYFDTTIDRKRYTSTKEVLDATLIHQSITGLYETRIDLSQLGGDEGADPKKKRKV
DPKKKRKVDPKKKRKVGSMPAMPSSGPGDTSSSAAEREEDRKDGEEQEEPRGKEERQEPSTTARKVGRPGRKRKHPP
VESGDTPKDPAVISKSPSMAQDSGASELLPNGDLEKRSEPQPEEGSPAGGQKGGAPAEGEGAAETLPEASRAVENGCC
TPKEGRGAPAEAGKEQKETNIESMKMEGSRGRLRGGLGWESSLRQRPMPRLTFQAGDPYYISKRKRDEWLARWKRE
AEKKAKVIAGMNAVEENQGPGESQKVEEASPPAVQQPTDPASPTVATTPEPVGSDAGDKNATKAGDDEPEYEDGRG
FGIGELVWGKLRGFSWWPGRIVSWWMTGRSRAAEGTRWVMWFGDGKFSVVCVEKLMPLSSFCSAFHQATYNKQP
MYRKAIYEVLQVASSRAGKLFPVCHDSDESDTAKAVEVQNKPMIEWALGGFQPSGPKGLEPPEEEKNPYKEVYTDMW
VEPEAAAYAPPPPAKKPRKSTAEKPKVKEIIDERTRERLVYEVRQKCRNIEDICISCGSLNVTLEHPLFVGGMCQNCKNCF
LECAYQYDDDGYQSYCTICCGGREVLMCGNNNCCRCFCVECVDLLVGPGAAQAAIKEDPWNCYMCGHKGTYGLLRR
REDWPSRLQMFFANNHDQEFDDPPKVYPPVPAEKRKPIRVLSLFDGIATGLLVLKDLGIQVDRYIASEVCEDSITVGMVR
HQGKIMYVGDVRSVTQKHIQEWGPFDLVIGGSPCNDLSIVNPARKGLYEGTGRLFFEFYRLLHDARPKEGDDRPFFWL
FENVVAMGVSDKRDISRFLESNPVMIDAKEVSAAHRARYFWGNLPGMNRPLASTVNDKLELQECLEHGRIAKFSKVRT
ITTRSNSIKQGKDQHFPVFMNEKEDILWCTEMERVFGFPVHYTDVSNMSRLARQRLLGRSWSVPVIRHLFAPLKEYFAC
VEFAYPYDVPDYAATNFSLLKQAGDVEENPGPMSELIKENMHMKLYMEGTVDNHHFKCTSEGEGKPYEGTQTMRIKV
VEGGPLPFAFDILATSFLYGSKTFINHTQGIPDFFKQSFPEGFTWERVTTYEDGGVLTATQDTSLQDGCLIYNVKIRGVNF
TSNGPVMQKKTLGWEAFTETLYPADGGLEGRNDMALKLVGGSHLIANIKTTYRSKKPAKNLKMPGVYYVDYRLERIKE
ANNETYVEQHEVAVARYCDLPSKLGHKLN
```

REFERENCES (THE CONTENTS OF WHICH ARE HEREBY INCORPORATED BY REFERENCE IN THEIR ENTIRETY)

Bell, A. C., and Felsenfeld, G. (2000). Methylation of a CTCF-dependent boundary controls imprinted expression of the Igf2 gene. Nature 405, 482-485.

Bernstein, D. L., Le Lay, J. E., Ruano, E. G., and Kaestner, K. H. (2015). TALE-mediated epigenetic suppression of CDKN2A increases replication in human fibroblasts. J Clin Invest 125, 1998-2006.

Bird, A. (2002). DNA methylation patterns and epigenetic memory. Genes Dev 16, 6-21.

Boch, J., and Bonas, U. (2010). Xanthomonas AvrBs3 family-type III effectors: discovery and function. Annual review of phytopathology 48, 419-436.

Brunk, B. P., Goldhamer, D. J., and Emerson, C. P., Jr. (1996). Regulated demethylation of the myoD distal enhancer during skeletal myogenesis. Dev Biol 177, 490-503.

Carroll, D. (2008). Progress and prospects: zinc-finger nucleases as gene therapy agents. Gene Ther 15, 1463-1468.

Cedar, H., and Bergman, Y. (2012). Programming of DNA methylation patterns. Annu Rev Biochem 81, 97-117.

Chen, B., Gilbert, L. A., Cimini, B. A., Schnitzbauer, J., Zhang, W., Li, G. W., Park, J., Blackburn, E. H., Weissman, J. S., Qi, L. S., et al. (2013). Dynamic imaging of genomic loci in living human cells by an optimized CRISPR/Cas system. Cell 155, 1479-1491.

Chen, W. G., Chang, Q., Lin, Y., Meissner, A., West, A. E., Griffith, E. C., Jaenisch, R., and Greenberg, M. E. (2003). Derepression of BDNF transcription involves calcium-dependent phosphorylation of MeCP2. Science 302, 885-889.

Choudhury, S. R., Cui, Y., Lubecka, K., Stefanska, B., and Irudayaraj, J. (2016). CRISPR-dCas9 mediated TET1 targeting for selective DNA demethylation at BRCA1 promoter. Oncotarget.

Cong, L., Ran, F. A., Cox, D., Lin, S. L., Barretto, R., Habib, N., Hsu, P. D., Wu, X. B., Jiang, W. Y., Marraffini, L. A., et al. (2013). Multiplex Genome Engineering Using CRISPR/Cas Systems. Science 339, 819-823.

Constantinides, P. G., Jones, P. A., and Gevers, W. (1977). Functional striated muscle cells from non-myoblast precursors following 5-azacytidine treatment. Nature 267, 364-366.

Davis, R. L., Weintraub, H., and Lassar, A. B. (1987). Expression of a single transfected cDNA converts fibroblasts to myoblasts. Cell 51, 987-1000.

Dawlaty, M. M., Breiling, A., Le, T., Barrasa, M. I., Raddatz, G., Gao, Q., Powell, B. E., Cheng, A. W., Faull, K. F., Lyko, F., et al. (2014). Loss of Tet enzymes compromises proper differentiation of embryonic stem cells. Dev Cell 29, 102-111.

Dawlaty, M. M., Ganz, K., Powell, B. E., Hu, Y. C., Markoulaki, S., Cheng, A. W., Gao, Q., Kim, J., Choi, S. W., Page, D. C., et al. (2011). Tet1 is dispensable for maintaining pluripotency and its loss is compatible with embryonic and postnatal development. Cell Stem Cell 9, 166-175.

De Jager, P. L., Srivastava, G., Lunnon, K., Burgess, J., Schalkwyk, L. C., Yu, L., Eaton, M. L., Keenan, B. T., Ernst, J., McCabe, C., et al. (2014). Alzheimer's disease: early alterations in brain DNA methylation at ANK1, BIN1, RHBDF2 and other loci. Nat Neurosci 17, 1156-1163.

Dixon, J. R, Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Doi, A., Park, I. H., Wen, B., Murakami, P., Aryee, M. J., Irizarry, R., Herb, B., Ladd-Acosta, C., Rho, J., Loewer, S., et al. (2009). Differential methylation of tissue- and cancer-specific CpG island shores distinguishes human induced pluripotent stem cells, embryonic stem cells and fibroblasts. Nat Genet 41, 1350-1353.

Dowen, J. M., Fan, Z. P., Hnisz, D., Ren, G., Abraham, B. J., Zhang, L. N., Weintraub, A. S., Schuijers, J., Lee, T. I., Zhao, K., et al. (2014). Control of cell identity genes occurs in insulated neighborhoods in mammalian chromosomes. Cell 159, 374-387.

Ebert, D. H., Gabel, H. W., Robinson, N. D., Kastan, N. R., Hu, L. S., Cohen, S., Navarro, A. J., Lyst, M. J., Ekiert, R., Bird, A. P., et al. (2013). Activity-dependent phosphorylation of MeCP2 threonine 308 regulates interaction with NCoR. Nature 499, 341-345.

Flavahan, W. A., Drier, Y., Liau, B. B., Gillespie, S. M., Venteicher, A. S., Stemmer-Rachamimov, A. O., Suva, M. L., and Bernstein, B. E. (2016). Insulator dysfunction and oncogene activation in IDH mutant gliomas. Nature 529, 110-114.

Gibcus, J. H., and Dekker, J. (2013). The hierarchy of the 3D genome. Mol Cell 49, 773-782. Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.

Gorkin, D. U., Leung, D., and Ren, B. (2014). The 3D genome in transcriptional regulation and pluripotency. Cell Stem Cell 14, 762-775.

Guo, J. U., Su, Y., Zhong, C., Ming, G. L., and Song, H. (2011). Hydroxylation of 5-methylcytosine by TET1 promotes active DNA demethylation in the adult brain. Cell 145, 423-434.

Hilton, I. B., D'Ippolito, A. M., Vockley, C. M., Thakore, P. I., Crawford, G. E., Reddy, T. E., and Gersbach, C. A. (2015). Epigenome editing by a CRISPR-Cas9-based acetyltransferase activates genes from promoters and enhancers. Nat Biotechnol 33, 510-517.

Hockemeyer, D., Soldner, F., Beard, C., Gao, Q., Mitalipova, M., DeKelver, R. C., Katibah, G. E., Amora, R., Boydston, E. A., Zeitler, B., et al. (2009). Efficient targeting of expressed and silent genes in human ESCs and iPSCs using zinc-finger nucleases. Nat Biotechnol 27, 851-857.

Hockemeyer, D., Wang, H., Kiani, S., Lai, C. S., Gao, Q., Cassady, J. P., Cost, G. J., Zhang, L., Santiago, Y., Miller, J. C., et al. (2011). Genetic engineering of human pluripotent cells using TALE nucleases. Nat Biotechnol 29, 731-734.

Jaenisch, R., and Bird, A. (2003). Epigenetic regulation of gene expression: how the genome integrates intrinsic and environmental signals. Nat Genet 33 Suppl, 245-254.

Ji, X., Dadon, D. B., Powell, B. E., Fan, Z. P., Borges-Rivera, D., Shachar, S., Weintraub, A. S., Hnisz, D., Pegoraro, G., Lee, T. I., et al. (2016). 3D Chromosome Regulatory Landscape of Human Pluripotent Cells. Cell Stem Cell 18, 262-275.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Kagey, M. H., Newman, J. J., Bilodeau, S., Zhan, Y., Orlando, D. A., van Berkum, N. L., Ebmeier, C. C., Goossens, J., Rahl, P. B., Levine, S. S., et al. (2010). Mediator and cohesin connect gene expression and chromatin architecture. Nature 467, 430-435.

Kang, J. Y., Song, S. H., Yun, J., Jeon, M. S., Kim, H. P., Han, S. W., and Kim, T. Y. (2015). Disruption of CTCF/cohesin-mediated high-order chromatin structures by DNA methylation downregulates PTGS2 expression. Oncogene 34, 5677-5684.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015). Genome-scale transcriptional activation by an engineered CRISPR-Cas9 complex. Nature 517, 583-U332.

Laird, P. W., and Jaenisch, R. (1996). The role of DNA methylation in cancer genetics and epigenetics. Annual Review of Genetics 30, 441-464.

Landau, D. A., Clement, K., Ziller, M. J., Boyle, P., Fan, J., Gu, H., Stevenson, K., Sougnez, C., Wang, L., Li, S., et al. (2014). Locally disordered methylation forms the basis of intratumor methylome variation in chronic lymphocytic leukemia. Cancer Cell 26, 813-825.

Lassar, A. B., Paterson, B. M., and Weintraub, H. (1986). Transfection of a DNA locus that mediates the conversion of 10T1/2 fibroblasts to myoblasts. Cell 47, 649-656.

Li, E., Bestor, T. H., and Jaenisch, R. (1992). Targeted mutation of the DNA methyltransferase gene results in embryonic lethality. Cell 69, 915-926.

Lin, Y., Bloodgood, B. L., Hauser, J. L., Lapan, A. D., Koon, A. C., Kim, T. K., Hu, L. S., Malik, A. N., and Greenberg, M. E. (2008). Activity-dependent regulation of inhibitory synapse development by Npas4. Nature 455, 1198-1204.

Lister, R., Mukamel, E. A., Nery, J. R, Urich, M., Puddifoot, C. A., Johnson, N. D., Lucero, J., Huang, Y., Dwork, A. J., Schultz, M. D., et al. (2013). Global Epigenomic Reconfiguration During Mammalian Brain Development. Science 341, 629-+.

Lister, R., Pelizzola, M., Dowen, R. H., Hawkins, R. D., Hon, G., Tonti-Filippini, J., Nery, J. R., Lee, L., Ye, Z., Ngo, Q. M., et al. (2009). Human DNA methylomes at base resolution show widespread epigenomic differences. Nature 462, 315-322.

Maeder, M. L., Angstman, J. F., Richardson, M. E., Linder, S. J., Cascio, V. M., Tsai, S. Q., Ho, Q. H., Sander, J. D., Reyon, D., Bernstein, B. E., et al. (2013). Targeted DNA demethylation and activation of endogenous genes using programmable TALE-TET1 fusion proteins. Nat Biotechnol 31, 1137-1142.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Martinowich, K., Hattori, D., Wu, H., Fouse, S., He, F., Hu, Y., Fan, G., and Sun, Y. E. (2003). DNA methylation-related chromatin remodeling in activity-dependent BDNF gene regulation. Science 302, 890-893.

Narendra, V., Rocha, P. P., An, D., Raviram, R., Skok, J. A., Mazzoni, E. O., and Reinberg, D. (2015). CTCF establishes discrete functional chromatin domains at the Hox clusters during differentiation. Science 347, 1017-1021.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Phillips-Cremins, J. E., Sauria, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295.

Phillips, J. E., and Corces, V. G. (2009). CTCF: master weaver of the genome. Cell 137, 1194-1211.

Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.

Robertson, K. D. (2005). DNA methylation and human disease. Nat Rev Genet 6, 597-610.

Schultz, M. D., He, Y., Whitaker, J. W., Hariharan, M., Mukamel, E. A., Leung, D., Rajagopal, N., Nery, J. R., Urich, M. A., Chen, H., et al. (2015). Human body epigenome maps reveal noncanonical DNA methylation variation. Nature 523, 212-216.

Seitan, V. C., Faure, A. J., Zhan, Y., McCord, R. P., Lajoie, B. R., Ing-Simmons, E., Lenhard, B., Giorgetti, L., Heard, E., Fisher, A. G., et al. (2013). Cohesin-based chromatin interactions enable regulated gene expression within pre-existing architectural compartments. Genome Res 23, 2066-2077.

Smith, Z. D., and Meissner, A. (2013). DNA methylation: roles in mammalian development. Nat Rev Genet 14, 204-220.

Sofueva, S., Yaffe, E., Chan, W. C., Georgopoulou, D., Vietri Rudan, M., Mira-Bontenbal, H., Pollard, S. M., Schroth, G. P., Tanay, A., and Hadjur, S. (2013). Cohesin-mediated interactions organize chromosomal domain architecture. EMBO J 32, 3119-3129.

Stelzer, Y., Shivalila, C. S., Soldner, F., Markoulaki, S., and Jaenisch, R. (2015). Tracing dynamic changes of DNA methylation at single-cell resolution. Cell 163, 218-229.

Sweatt, J. D. (2013). The emerging field of neuroepigenetics. Neuron 80, 624-632.

Tang, Z., Luo, O. J., Li, X., Zheng, M., Zhu, J. J., Szalaj, P., Trzaskoma, P., Magalska, A., Wlodarczyk, J., Ruszczycki, B., et al. (2015). CTCF-Mediated Human 3D Genome Architecture Reveals Chromatin Topology for Transcription. Cell 163, 1611-1627.

Vojta, A., Dobrinic, P., Tadic, V., Bockor, L., Korac, P., Julg, B., Klasic, M., and Zoldos, V. (2016). Repurposing the CRISPR-Cas9 system for targeted DNA methylation. Nucleic Acids Res 44, 5615-5628.

Wang, H., Maurano, M. T., Qu, H., Varley, K. E., Gertz, J., Pauli, F., Lee, K., Canfield, T., Weaver, M., Sandstrom, R., et al. (2012). Widespread plasticity in CTCF occupancy linked to DNA methylation. Genome Res 22, 1680-1688.

Wilson, M. H., Coates, C. J., and George, A. L., Jr. (2007). PiggyBac transposon-mediated gene transfer in human cells. Mol Ther 15, 139-145.

Wu, H., Luo, J., Yu, H., Rattner, A., Mo, A., Wang, Y., Smallwood, P. M., Erlanger, B., Wheelan, S. J., and Nathans, J. (2014a). Cellular resolution maps of X chromosome inactivation: implications for neural development, function, and disease. Neuron 81, 103-119.

Wu, H., and Zhang, Y. (2014). Reversing DNA methylation: mechanisms, genomics, and biological functions. Cell 156, 45-68.

Wu, X., Scott, D. A., Kriz, A. J., Chiu, A. C., Hsu, P. D., Dadon, D. B., Cheng, A. W., Trevino, A. E., Konermann, S., Chen, S., et al. (2014b). Genome-wide binding of the CRISPR endonuclease Cas9 in mammalian cells. Nat Biotechnol 32, 670-676.

Xu, W., Yang, H., Liu, Y., Yang, Y., Wang, P., Kim, S. H., Ito, S., Yang, C., Wang, P., Xiao, M. T., et al. (2011). Oncometabolite 2-hydroxyglutarate is a competitive inhibitor of alpha-ketoglutarate-dependent dioxygenases. Cancer Cell 19, 17-30.

Xu, X., Tao, Y., Gao, X., Zhang, L., Li, X., Zou, W., Ruan, K., Wang, F., Xu, G. L., and Hu, R. (2016). A CRISPR-based approach for targeted DNA demethylation. Cell discovery 2, 16009.

Yu, M., Hon, G. C., Szulwach, K. E., Song, C. X., Zhang, L., Kim, A., Li, X., Dai, Q., Shen, Y., Park, B., et al. (2012). Base-resolution analysis of 5-hydroxymethylcytosine in the mammalian genome. Cell 149, 1368-1380.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome Biol 9, R137.

Zuin, J., Dixon, J. R., van der Reijden, M. I., Ye, Z., Kolovos, P., Brouwer, R. W., van de Corput, M. P., van de Werken, H. J., Knoch, T. A., van, I. W. F., et al. (2014). Cohesin and CTCF differentially affect chromatin architecture and gene expression in human cells. Proc Natl Acad Sci USA 111, 996-1001.

PCT Application No. PCT/US2014/034387, filed Apr. 16, 2014, and U.S. application Ser. No. 15/078,851, filed Mar. 23, 2016.

What is claimed is:

1. A method of modulating the methylation of one or more CTCF binding sites in a cell comprising introducing into the cell
   a. a catalytically inactive site specific nuclease fused to an effector domain having methylation activity, wherein the effector domain comprises Dnmt3a; and
   b. one or more guide sequences or a nucleic acid that encodes the one or more guide sequences, wherein the one or more guide sequences target the CTCF binding sites, thereby modulating the methylation of one or more genomic sequences in the cell.

2. The method of claim 1, wherein the catalytically inactive site specific nuclease is a catalytically inactive Cas protein,
   wherein the catalytically inactive site specific nuclease is a catalytically inactive Cas9 protein, or
   wherein the catalytically inactive site specific nuclease is a catalytically inactive Cpf1 protein.

3. The method of claim 1, wherein the one or more guide sequences are ribonucleic acid guide sequences.

4. The method of claim 1, wherein the one or more guide sequences are from about 10 base pairs to about 150 base pairs in length.

5. The method of claim 1, wherein the one or more guide sequences comprises two or more guide sequences.

6. The method of claim 1, wherein 2, 3, 4, 5, 6, 7, 8, 9, 10, 11, 12, 13, 14, 15, 16, 17, 18, 19, or 20 genomic sequences are modified in the cell.

7. The method of claim 1, wherein the cell is a stem cell, a neuron, a post-mitotic cell, or a fibroblast.

8. The method of claim 1, wherein the cell is a human cell.

9. A method of modulating the methylation of one or more enhancers of MyoD in a cell comprising introducing into the cell
   a. a catalytically inactive site specific nuclease fused to an effector domain having demethylation activity, wherein the effector domain comprises Tet1; and
   b. one or more guide sequences or a nucleic acid that encodes one or more guide sequences, wherein the one or more guide sequences target the enhancers of MyoD, thereby modulating the methylation of one or more genomic sequences in the cell.

10. The method of claim 9, wherein the catalytically inactive site specific nuclease is a catalytically inactive Cas protein,
    wherein the catalytically inactive site specific nuclease is a catalytically inactive Cas9 protein, or
    wherein the catalytically inactive site specific nuclease is a catalytically inactive Cpf1 protein.

11. The method of claim 9, wherein the one or more guide sequences are ribonucleic acid guide sequences.

12. The method of claim 9, wherein the one or more guide sequences are from about 10 base pairs to about 150 base pairs in length.

13. The method of claim 9, wherein the one or more guide sequences comprises two or more guide sequences.

14. The method of claim 9, wherein 2, 3, 4, 5, 6, 7, 8, 9, 10, 11, 12, 13, 14, 15, 16, 17, 18, 19, or 20 genomic sequences are modified in the cell.

15. The method of claim 9, wherein the cell is a stem cell, a neuron, a post-mitotic cell, or a fibroblast.

16. The method of claim 9, wherein the cell is a human cell.

* * * * *

SEQUENCE LISTING

<160> NUMBER OF SEQ ID NOS: 167

<210> SEQ ID NO 1
<211> LENGTH: 23
<212> TYPE: DNA
<213> ORGANISM: Artificial
<220> FEATURE:
<223> OTHER INFORMATION: guide RNA sequence

<400> SEQUENCE: 1
gttttgaggc ctcatttgta agg                                           23

<210> SEQ ID NO 2
<211> LENGTH: 23

```
<212> TYPE: DNA
<213> ORGANISM: Artificial
<220> FEATURE:
<223> OTHER INFORMATION: guide RNA sequence

<400> SEQUENCE: 2
tttttgaaaa attaccttgt ggg                                    23

<210> SEQ ID NO 3
<211> LENGTH: 23
<212> TYPE: DNA
<213> ORGANISM: Artificial
<220> FEATURE:
<223> OTHER INFORMATION: guide RNA sequence

<400> SEQUENCE: 3
cagagtccta gacatttcca tgg                                    23

<210> SEQ ID NO 4
<211> LENGTH: 23
<212> TYPE: DNA
<213> ORGANISM: Artificial
<220> FEATURE:
<223> OTHER INFORMATION: guide RNA sequence

<400> SEQUENCE: 4
ggagagaggc ctcatttgta ggg                                    23

<210> SEQ ID NO 5
<211> LENGTH: 23
<212> TYPE: DNA
<213> ORGANISM: Artificial
<220> FEATURE:
<223> OTHER INFORMATION: guide RNA sequence

<400> SEQUENCE: 5
gttgtcagag catagcttgt agg                                    23

<210> SEQ ID NO 6
<211> LENGTH: 23
<212> TYPE: DNA
<213> ORGANISM: Artificial
<220> FEATURE:
<223> OTHER INFORMATION: guide RNA sequence

<400> SEQUENCE: 6
ctaaagcgat gttccttcca ggg                                    23

<210> SEQ ID NO 7
<211> LENGTH: 23
<212> TYPE: DNA
<213> ORGANISM: Artificial
<220> FEATURE:
<223> OTHER INFORMATION: guide RNA sequence

<400> SEQUENCE: 7
ttgctctcaa gacatttcca ggg                                    23

<210> SEQ ID NO 8
<211> LENGTH: 23
<212> TYPE: DNA
<213> ORGANISM: Artificial
<220> FEATURE:
<223> OTHER INFORMATION: guide RNA sequence

<400> SEQUENCE: 8
```

```
ttgctttcca ttttcttcca ggg                                              23

<210> SEQ ID NO 9
<211> LENGTH: 23
<212> TYPE: DNA
<213> ORGANISM: Artificial
<220> FEATURE:
<223> OTHER INFORMATION: guide RNA sequence

<400> SEQUENCE: 9
agcttctagc tctaccttct agg                                              23

<210> SEQ ID NO 10
<211> LENGTH: 23
<212> TYPE: DNA
<213> ORGANISM: Artificial
<220> FEATURE:
<223> OTHER INFORMATION: guide RNA sequence

<400> SEQUENCE: 10
tctgcgagtc cttaatttta ggg                                              23

<210> SEQ ID NO 11
<211> LENGTH: 23
<212> TYPE: DNA
<213> ORGANISM: Artificial
<220> FEATURE:
<223> OTHER INFORMATION: guide RNA sequence

<400> SEQUENCE: 11 aaagcattt cttctttcca ggg                                               23

<210> SEQ ID NO 12
<211> LENGTH: 23
<212> TYPE: DNA
<213> ORGANISM: Artificial
<220> FEATURE:
<223> OTHER INFORMATION: guide RNA sequence

<400> SEQUENCE: 12
agttgctgct cttttgtcca ggg                                              23

<210> SEQ ID NO 13
<211> LENGTH: 23
<212> TYPE: DNA
<213> ORGANISM: Artificial
<220> FEATURE:
<223> OTHER INFORMATION: guide RNA sequence

<400> SEQUENCE: 13
acgcaactgc gagctttcaa agg                                              23

<210> SEQ ID NO 14
<211> LENGTH: 23
<212> TYPE: DNA
<213> ORGANISM: Artificial
<220> FEATURE:
<223> OTHER INFORMATION: guide RNA sequence

<400> SEQUENCE: 14
tttaaagccc cttccttcca ggg                                              23

<210> SEQ ID NO 15
<211> LENGTH: 23
<212> TYPE: DNA
<213> ORGANISM: Artificial
```

-continued

```
<220> FEATURE:
<223> OTHER INFORMATION: guide RNA sequence

<400> SEQUENCE: 15
actgtcttca acttccttgg ggg                                              23

<210> SEQ ID NO 16
<211> LENGTH: 23
<212> TYPE: DNA
<213> ORGANISM: Artificial
<220> FEATURE:
<223> OTHER INFORMATION: guide RNA sequence

<400> SEQUENCE: 16
ggactactga gacatttcca ggg                                              23

<210> SEQ ID NO 17
<211> LENGTH: 23
<212> TYPE: DNA
<213> ORGANISM: Artificial
<220> FEATURE:
<223> OTHER INFORMATION: guide RNA sequence

<400> SEQUENCE: 17
tcaaccctga gacatttcca ggg                                              23

<210> SEQ ID NO 18
<211> LENGTH: 23
<212> TYPE: DNA
<213> ORGANISM: Artificial
<220> FEATURE:
<223> OTHER INFORMATION: guide RNA sequence

<400> SEQUENCE: 18
ccaagattga gacatttcca ggg                                              23

<210> SEQ ID NO 19
<211> LENGTH: 23
<212> TYPE: DNA
<213> ORGANISM: Artificial
<220> FEATURE:
<223> OTHER INFORMATION: guide RNA sequence

<400> SEQUENCE: 19
taaagtccca gtccctccc tgg                                               23

<210> SEQ ID NO 20
<211> LENGTH: 23
<212> TYPE: DNA
<213> ORGANISM: Artificial
<220> FEATURE:
<223> OTHER INFORMATION: guide RNA sequence

<400> SEQUENCE: 20
ctaagctctg tgttgttcca ggg                                              23

<210> SEQ ID NO 21
<211> LENGTH: 23
<212> TYPE: DNA
<213> ORGANISM: Artificial
<220> FEATURE:
<223> OTHER INFORMATION: guide RNA sequence

<400> SEQUENCE: 21
gtagagcatg ttgagctgta ggg                                              23
```

<210> SEQ ID NO 22
<211> LENGTH: 23
<212> TYPE: DNA
<213> ORGANISM: Artificial
<220> FEATURE:
<223> OTHER INFORMATION: guide RNA sequence

<400> SEQUENCE: 22
gagccgagct gtagggtgct tgg                                           23

<210> SEQ ID NO 23
<211> LENGTH: 23
<212> TYPE: DNA
<213> ORGANISM: Artificial
<220> FEATURE:
<223> OTHER INFORMATION: guide RNA sequence

<400> SEQUENCE: 23
cgggcagcct gtagggtgct ggg                                           23

<210> SEQ ID NO 24
<211> LENGTH: 23
<212> TYPE: DNA
<213> ORGANISM: Artificial
<220> FEATURE:
<223> OTHER INFORMATION: guide RNA sequence

<400> SEQUENCE: 24
gcgcaagggt tgtcgtgcct tgg                                           23

<210> SEQ ID NO 25
<211> LENGTH: 23
<212> TYPE: DNA
<213> ORGANISM: Artificial
<220> FEATURE:
<223> OTHER INFORMATION: guide RNA sequence

<400> SEQUENCE: 25
cgcatgtgca gccattgcct ggg                                           23

<210> SEQ ID NO 26
<211> LENGTH: 23
<212> TYPE: DNA
<213> ORGANISM: Artificial
<220> FEATURE:
<223> OTHER INFORMATION: guide RNA sequence

<400> SEQUENCE: 26
tttggtagct gccttttggc agg                                           23

<210> SEQ ID NO 27
<211> LENGTH: 20
<212> TYPE: DNA
<213> ORGANISM: Artificial
<220> FEATURE:
<223> OTHER INFORMATION: guide RNA sequence

<400> SEQUENCE: 27
acaaacctga gccattgcgg                                               20

<210> SEQ ID NO 28
<211> LENGTH: 23
<212> TYPE: DNA
<213> ORGANISM: Artificial
<220> FEATURE:
<223> OTHER INFORMATION: guide RNA sequence

```
<400> SEQUENCE: 28
ccctgcagct gtagggtgct agg                                          23

<210> SEQ ID NO 29
<211> LENGTH: 23
<212> TYPE: DNA
<213> ORGANISM: Artificial
<220> FEATURE:
<223> OTHER INFORMATION: guide RNA sequence

<400> SEQUENCE: 29
tctcttcagt gtaattggct tgg                                          23

<210> SEQ ID NO 30
<211> LENGTH: 23
<212> TYPE: DNA
<213> ORGANISM: Artificial
<220> FEATURE:
<223> OTHER INFORMATION: guide RNA sequence

<400> SEQUENCE: 30
tccatttgct gtagggtgct agg                                          23

<210> SEQ ID NO 31
<211> LENGTH: 23
<212> TYPE: DNA
<213> ORGANISM: Artificial
<220> FEATURE:
<223> OTHER INFORMATION: guide RNA sequence

<400> SEQUENCE: 31
tgctaatgtc cccatttggc agg                                          23

<210> SEQ ID NO 32
<211> LENGTH: 23
<212> TYPE: DNA
<213> ORGANISM: Artificial
<220> FEATURE:
<223> OTHER INFORMATION: guide RNA sequence

<400> SEQUENCE: 32
gcacagcact gtagggtgct ggg                                          23

<210> SEQ ID NO 33
<211> LENGTH: 23
<212> TYPE: DNA
<213> ORGANISM: Artificial
<220> FEATURE:
<223> OTHER INFORMATION: guide RNA sequence

<400> SEQUENCE: 33
ccatctctct gtagggtgct ggg                                          23

<210> SEQ ID NO 34
<211> LENGTH: 23
<212> TYPE: DNA
<213> ORGANISM: Artificial
<220> FEATURE:
<223> OTHER INFORMATION: guide RNA sequence

<400> SEQUENCE: 34
gtgagctgct gtagggtgct agg                                          23

<210> SEQ ID NO 35
```

```
<211> LENGTH: 23
<212> TYPE: DNA
<213> ORGANISM: Artificial
<220> FEATURE:
<223> OTHER INFORMATION: guide RNA sequence

<400> SEQUENCE: 35
gaatggacct gtagggtgct tgg                                              23

<210> SEQ ID NO 36
<211> LENGTH: 24
<212> TYPE: DNA
<213> ORGANISM: Artificial
<220> FEATURE:
<223> OTHER INFORMATION: guide RNA primer sequence

<400> SEQUENCE: 36
ttggcccccg ggggaaaaat tttt                                             24

<210> SEQ ID NO 37
<211> LENGTH: 24
<212> TYPE: DNA
<213> ORGANISM: Artificial
<220> FEATURE:
<223> OTHER INFORMATION: guide RNA primer sequence

<400> SEQUENCE: 37
aaacaaaaat ttttcccccg gggg                                             24

<210> SEQ ID NO 38
<211> LENGTH: 24
<212> TYPE: DNA
<213> ORGANISM: Artificial
<220> FEATURE:
<223> OTHER INFORMATION: guide RNA primer sequence

<400> SEQUENCE: 38
ttggctacaa agcatgcaat gccc                                             24

<210> SEQ ID NO 39
<211> LENGTH: 24
<212> TYPE: DNA
<213> ORGANISM: Artificial
<220> FEATURE:
<223> OTHER INFORMATION: guide RNA primer sequence

<400> SEQUENCE: 39
aaacgggcat tgcatgcttt gtag                                             24

<210> SEQ ID NO 40
<211> LENGTH: 24
<212> TYPE: DNA
<213> ORGANISM: Artificial
<220> FEATURE:
<223> OTHER INFORMATION: guide RNA primer sequence

<400> SEQUENCE: 40
ttggaatgcg cggaattctg attc                                             24

<210> SEQ ID NO 41
<211> LENGTH: 24
<212> TYPE: DNA
<213> ORGANISM: Artificial
<220> FEATURE:
<223> OTHER INFORMATION: guide RNA primer sequence

<400> SEQUENCE: 41
```
aaacgaatca gaattccgcg catt                                              24

<210> SEQ ID NO 42
<211> LENGTH: 24
<212> TYPE: DNA
<213> ORGANISM: Artificial
<220> FEATURE:
<223> OTHER INFORMATION: guide RNA primer sequence

<400> SEQUENCE: 42
ttgggtgggt gggagtccac gaga                                              24

<210> SEQ ID NO 43
<211> LENGTH: 24
<212> TYPE: DNA
<213> ORGANISM: Artificial
<220> FEATURE:
<223> OTHER INFORMATION: guide RNA primer sequence

<400> SEQUENCE: 43
aaactctcgt ggactcccac ccac                                              24

<210> SEQ ID NO 44
<211> LENGTH: 24
<212> TYPE: DNA
<213> ORGANISM: Artificial
<220> FEATURE:
<223> OTHER INFORMATION: guide RNA primer sequence

<400> SEQUENCE: 44
ttggggcagc gtggagccct ctcg                                              24

<210> SEQ ID NO 45
<211> LENGTH: 24
<212> TYPE: DNA
<213> ORGANISM: Artificial
<220> FEATURE:
<223> OTHER INFORMATION: guide RNA primer sequence

<400> SEQUENCE: 45
aaaccgagag ggctccacgc tgcc                                              24

<210> SEQ ID NO 46
<211> LENGTH: 24
<212> TYPE: DNA
<213> ORGANISM: Artificial
<220> FEATURE:
<223> OTHER INFORMATION: guide RNA primer sequence

<400> SEQUENCE: 46
ttgggagccg agctgtaggg tgct                                              24

<210> SEQ ID NO 47
<211> LENGTH: 24
<212> TYPE: DNA
<213> ORGANISM: Artificial
<220> FEATURE:
<223> OTHER INFORMATION: guide RNA primer sequence

<400> SEQUENCE: 47
aaacagcacc ctacagctcg gctc                                              24

<210> SEQ ID NO 48
<211> LENGTH: 24
<212> TYPE: DNA

```
<213> ORGANISM: Artificial
<220> FEATURE:
<223> OTHER INFORMATION: guide RNA primer sequence

<400> SEQUENCE: 48
ttggtttggt agctgccttt tggc                                          24

<210> SEQ ID NO 49
<211> LENGTH: 24
<212> TYPE: DNA
<213> ORGANISM: Artificial
<220> FEATURE:
<223> OTHER INFORMATION: guide RNA primer sequence

<400> SEQUENCE: 49
aaacgccaaa aggcagctac caaa                                          24

<210> SEQ ID NO 50
<211> LENGTH: 24
<212> TYPE: DNA
<213> ORGANISM: Artificial
<220> FEATURE:
<223> OTHER INFORMATION: guide RNA primer sequence

<400> SEQUENCE: 50
ttggcgcatg tgcagccatt gcct                                          24

<210> SEQ ID NO 51
<211> LENGTH: 24
<212> TYPE: DNA
<213> ORGANISM: Artificial
<220> FEATURE:
<223> OTHER INFORMATION: guide RNA primer sequence

<400> SEQUENCE: 51
aaacaggcaa tggctgcaca tgcg                                          24

<210> SEQ ID NO 52
<211> LENGTH: 21
<212> TYPE: DNA
<213> ORGANISM: Artificial
<220> FEATURE:
<223> OTHER INFORMATION: guide RNA primer sequence

<400> SEQUENCE: 52
ttggacaaac ctgagccatt g                                             21

<210> SEQ ID NO 53
<211> LENGTH: 21
<212> TYPE: DNA
<213> ORGANISM: Artificial
<220> FEATURE:
<223> OTHER INFORMATION: guide RNA primer sequence

<400> SEQUENCE: 53
aaaccaatgg ctcaggtttg t                                             21

<210> SEQ ID NO 54
<211> LENGTH: 24
<212> TYPE: DNA
<213> ORGANISM: Artificial
<220> FEATURE:
<223> OTHER INFORMATION: guide RNA primer sequence

<400> SEQUENCE: 54
ttggagcatt tgggggcatt tatg                                          24
```

<210> SEQ ID NO 55
<211> LENGTH: 24
<212> TYPE: DNA
<213> ORGANISM: Artificial
<220> FEATURE:
<223> OTHER INFORMATION: guide RNA primer sequence

<400> SEQUENCE: 55
aaaccataaa tgcccccaaa tgct                                            24

<210> SEQ ID NO 56
<211> LENGTH: 24
<212> TYPE: DNA
<213> ORGANISM: Artificial
<220> FEATURE:
<223> OTHER INFORMATION: guide RNA primer sequence

<400> SEQUENCE: 56
ttggaagtat cctcctccag cagc                                            24

<210> SEQ ID NO 57
<211> LENGTH: 24
<212> TYPE: DNA
<213> ORGANISM: Artificial
<220> FEATURE:
<223> OTHER INFORMATION: guide RNA primer sequence

<400> SEQUENCE: 57
aaacgctgct ggaggaggat actt                                            24

<210> SEQ ID NO 58
<211> LENGTH: 24
<212> TYPE: DNA
<213> ORGANISM: Artificial
<220> FEATURE:
<223> OTHER INFORMATION: guide RNA primer sequence

<400> SEQUENCE: 58
ttggacacag ccagttgggg gaag                                            24

<210> SEQ ID NO 59
<211> LENGTH: 24
<212> TYPE: DNA
<213> ORGANISM: Artificial
<220> FEATURE:
<223> OTHER INFORMATION: guide RNA primer sequence

<400> SEQUENCE: 59
aaaccttccc ccaactggct gtgt                                            24

<210> SEQ ID NO 60
<211> LENGTH: 22
<212> TYPE: DNA
<213> ORGANISM: Artificial
<220> FEATURE:
<223> OTHER INFORMATION: guide RNA primer sequence

<400> SEQUENCE: 60
ttggccagag tcagctgttc ct                                              22

<210> SEQ ID NO 61
<211> LENGTH: 22
<212> TYPE: DNA
<213> ORGANISM: Artificial
<220> FEATURE:

```
<223> OTHER INFORMATION: guide RNA primer sequence

<400> SEQUENCE: 61
aaacaggaac agctgactct gg                                              22

<210> SEQ ID NO 62
<211> LENGTH: 24
<212> TYPE: DNA
<213> ORGANISM: Artificial
<220> FEATURE:
<223> OTHER INFORMATION: guide RNA primer sequence

<400> SEQUENCE: 62
ttgggttttg aggcctcatt tgta                                            24

<210> SEQ ID NO 63
<211> LENGTH: 24
<212> TYPE: DNA
<213> ORGANISM: Artificial
<220> FEATURE:
<223> OTHER INFORMATION: guide RNA primer sequence

<400> SEQUENCE: 63
aaactacaaa tgaggcctca aaac                                            24

<210> SEQ ID NO 64
<211> LENGTH: 24
<212> TYPE: DNA
<213> ORGANISM: Artificial
<220> FEATURE:
<223> OTHER INFORMATION: guide RNA primer sequence

<400> SEQUENCE: 64
ttggtttttg aaaaattacc ttgt                                            24

<210> SEQ ID NO 65
<211> LENGTH: 24
<212> TYPE: DNA
<213> ORGANISM: Artificial
<220> FEATURE:
<223> OTHER INFORMATION: guide RNA primer sequence

<400> SEQUENCE: 65
aaacacaagg taattttca aaaa                                             24

<210> SEQ ID NO 66
<211> LENGTH: 24
<212> TYPE: DNA
<213> ORGANISM: Artificial
<220> FEATURE:
<223> OTHER INFORMATION: guide RNA primer sequence

<400> SEQUENCE: 66
ttggcagagt cctagacatt tcca                                            24

<210> SEQ ID NO 67
<211> LENGTH: 24
<212> TYPE: DNA
<213> ORGANISM: Artificial
<220> FEATURE:
<223> OTHER INFORMATION: guide RNA primer sequence

<400> SEQUENCE: 67
aaactggaaa tgtctaggac tctg                                            24
```

```
<210> SEQ ID NO 68
<211> LENGTH: 24
<212> TYPE: DNA
<213> ORGANISM: Artificial
<220> FEATURE:
<223> OTHER INFORMATION: guide RNA primer sequence

<400> SEQUENCE: 68
ttggtctcac ccttgatagt ttga                                          24

<210> SEQ ID NO 69
<211> LENGTH: 24
<212> TYPE: DNA
<213> ORGANISM: Artificial
<220> FEATURE:
<223> OTHER INFORMATION: guide RNA primer sequence

<400> SEQUENCE: 69
aaactcaaac tatcaagggt gaga                                          24

<210> SEQ ID NO 70
<211> LENGTH: 24
<212> TYPE: DNA
<213> ORGANISM: Artificial
<220> FEATURE:
<223> OTHER INFORMATION: guide RNA primer sequence

<400> SEQUENCE: 70
ttggggtaaa tctttgaagc caat                                          24

<210> SEQ ID NO 71
<211> LENGTH: 24
<212> TYPE: DNA
<213> ORGANISM: Artificial
<220> FEATURE:
<223> OTHER INFORMATION: guide RNA primer sequence

<400> SEQUENCE: 71
aaacattggc ttcaaagatt tacc                                          24

<210> SEQ ID NO 72
<211> LENGTH: 24
<212> TYPE: DNA
<213> ORGANISM: Artificial
<220> FEATURE:
<223> OTHER INFORMATION: guide RNA primer sequence

<400> SEQUENCE: 72
ttggattttc tacctacggt gtgc                                          24

<210> SEQ ID NO 73
<211> LENGTH: 24
<212> TYPE: DNA
<213> ORGANISM: Artificial
<220> FEATURE:
<223> OTHER INFORMATION: guide RNA primer sequence

<400> SEQUENCE: 73
aaacgcacac cgtaggtaga aaat                                          24

<210> SEQ ID NO 74
<211> LENGTH: 24
<212> TYPE: DNA
<213> ORGANISM: Artificial
<220> FEATURE:
<223> OTHER INFORMATION: guide RNA primer sequence
```

```
<400> SEQUENCE: 74
ttggtctcct ggaaggactc tggg                                              24

<210> SEQ ID NO 75
<211> LENGTH: 24
<212> TYPE: DNA
<213> ORGANISM: Artificial
<220> FEATURE:
<223> OTHER INFORMATION: guide RNA primer sequence

<400> SEQUENCE: 75
aaaccccaga gtccttccag gaga                                              24

<210> SEQ ID NO 76
<211> LENGTH: 24
<212> TYPE: DNA
<213> ORGANISM: Artificial
<220> FEATURE:
<223> OTHER INFORMATION: guide RNA primer sequence

<400> SEQUENCE: 76
ttggtcctcc ttccttgcca acgc                                              24

<210> SEQ ID NO 77
<211> LENGTH: 24
<212> TYPE: DNA
<213> ORGANISM: Artificial
<220> FEATURE:
<223> OTHER INFORMATION: guide RNA primer sequence

<400> SEQUENCE: 77
aaacgcgttg gcaaggaagg agga                                              24

<210> SEQ ID NO 78
<211> LENGTH: 24
<212> TYPE: DNA
<213> ORGANISM: Artificial
<220> FEATURE:
<223> OTHER INFORMATION: guide RNA primer sequence

<400> SEQUENCE: 78
ttggcccgct atttgctgtg ggtt                                              24

<210> SEQ ID NO 79
<211> LENGTH: 24
<212> TYPE: DNA
<213> ORGANISM: Artificial
<220> FEATURE:
<223> OTHER INFORMATION: guide RNA primer sequence

<400> SEQUENCE: 79
aaacaaccca cagcaaatag cggg                                              24

<210> SEQ ID NO 80
<211> LENGTH: 22
<212> TYPE: DNA
<213> ORGANISM: Artificial
<220> FEATURE:
<223> OTHER INFORMATION: qPCR primer sequence

<400> SEQUENCE: 80
caggagtaca tatcggccac ca                                                22

<210> SEQ ID NO 81
<211> LENGTH: 23
```

```
<212> TYPE: DNA
<213> ORGANISM: Artificial
<220> FEATURE:
<223> OTHER INFORMATION: qPCR primer sequence

<400> SEQUENCE: 81
gtaggccaag ttgccttgtc cgt                                          23

<210> SEQ ID NO 82
<211> LENGTH: 19
<212> TYPE: DNA
<213> ORGANISM: Artificial
<220> FEATURE:
<223> OTHER INFORMATION: qPCR primer sequence

<400> SEQUENCE: 82
gccttccttc ttgggtatg                                               19

<210> SEQ ID NO 83
<211> LENGTH: 19
<212> TYPE: DNA
<213> ORGANISM: Artificial
<220> FEATURE:
<223> OTHER INFORMATION: qPCR primer sequence

<400> SEQUENCE: 83
accaccagac aacactgtg                                               19

<210> SEQ ID NO 84
<211> LENGTH: 25
<212> TYPE: DNA
<213> ORGANISM: Artificial
<220> FEATURE:
<223> OTHER INFORMATION: qPCR primer sequence

<400> SEQUENCE: 84
gctatactca gaaggtccag aaggc                                        25

<210> SEQ ID NO 85
<211> LENGTH: 23
<212> TYPE: DNA
<213> ORGANISM: Artificial
<220> FEATURE:
<223> OTHER INFORMATION: qPCR primer sequence

<400> SEQUENCE: 85
tcagagaatg agggtagcac agc                                          23

<210> SEQ ID NO 86
<211> LENGTH: 22
<212> TYPE: DNA
<213> ORGANISM: Artificial
<220> FEATURE:
<223> OTHER INFORMATION: qPCR primer sequence

<400> SEQUENCE: 86
actttctgga gccctcctgg ca                                           22

<210> SEQ ID NO 87
<211> LENGTH: 21
<212> TYPE: DNA
<213> ORGANISM: Artificial
<220> FEATURE:
<223> OTHER INFORMATION: qPCR primer sequence

<400> SEQUENCE: 87
```
tttgttgcac tacacagcat g                                          21

<210> SEQ ID NO 88
<211> LENGTH: 20
<212> TYPE: DNA
<213> ORGANISM: Artificial
<220> FEATURE:
<223> OTHER INFORMATION: qPCR primer sequence

<400> SEQUENCE: 88
aggggattct ccgtggtaca                                            20

<210> SEQ ID NO 89
<211> LENGTH: 20
<212> TYPE: DNA
<213> ORGANISM: Artificial
<220> FEATURE:
<223> OTHER INFORMATION: qPCR primer sequence

<400> SEQUENCE: 89
ctcttcccct gtactcgcaa                                            20

<210> SEQ ID NO 90
<211> LENGTH: 20
<212> TYPE: DNA
<213> ORGANISM: Artificial
<220> FEATURE:
<223> OTHER INFORMATION: qPCR primer sequence

<400> SEQUENCE: 90
cgagacgcgg atggatgtaa                                            20

<210> SEQ ID NO 91
<211> LENGTH: 20
<212> TYPE: DNA
<213> ORGANISM: Artificial
<220> FEATURE:
<223> OTHER INFORMATION: qPCR primer sequence

<400> SEQUENCE: 91
gcggcacttt tcttccgatg                                            20

<210> SEQ ID NO 92
<211> LENGTH: 21
<212> TYPE: DNA
<213> ORGANISM: Artificial
<220> FEATURE:
<223> OTHER INFORMATION: qPCR primer sequence

<400> SEQUENCE: 92
ccagaccctg catgagcttt a                                          21

<210> SEQ ID NO 93
<211> LENGTH: 20
<212> TYPE: DNA
<213> ORGANISM: Artificial
<220> FEATURE:
<223> OTHER INFORMATION: qPCR primer sequence

<400> SEQUENCE: 93
aaacagccac aggactcgaa                                            20

<210> SEQ ID NO 94
<211> LENGTH: 22
<212> TYPE: DNA
<213> ORGANISM: Artificial

```
<220> FEATURE:
<223> OTHER INFORMATION: qPCR primer sequence

<400> SEQUENCE: 94
tctgttaagg gagcagccat gc                                              22

<210> SEQ ID NO 95
<211> LENGTH: 21
<212> TYPE: DNA
<213> ORGANISM: Artificial
<220> FEATURE:
<223> OTHER INFORMATION: qPCR primer sequence

<400> SEQUENCE: 95
ggatattagc tgcaggaggc g                                               21

<210> SEQ ID NO 96
<211> LENGTH: 20
<212> TYPE: DNA
<213> ORGANISM: Artificial
<220> FEATURE:
<223> OTHER INFORMATION: qPCR primer sequence

<400> SEQUENCE: 96
cagagagcca agggcaatga                                                 20

<210> SEQ ID NO 97
<211> LENGTH: 20
<212> TYPE: DNA
<213> ORGANISM: Artificial
<220> FEATURE:
<223> OTHER INFORMATION: qPCR primer sequence

<400> SEQUENCE: 97
ggaccccact ttacagccat                                                 20

<210> SEQ ID NO 98
<211> LENGTH: 21
<212> TYPE: DNA
<213> ORGANISM: Artificial
<220> FEATURE:
<223> OTHER INFORMATION: qPCR primer sequence

<400> SEQUENCE: 98
gcgttctctt tggaaaggtg t                                               21

<210> SEQ ID NO 99
<211> LENGTH: 20
<212> TYPE: DNA
<213> ORGANISM: Artificial
<220> FEATURE:
<223> OTHER INFORMATION: qPCR primer sequence

<400> SEQUENCE: 99
ttgttgtcgg cttcctccac                                                 20

<210> SEQ ID NO 100
<211> LENGTH: 20
<212> TYPE: DNA
<213> ORGANISM: Artificial
<220> FEATURE:
<223> OTHER INFORMATION: qPCR primer sequence

<400> SEQUENCE: 100
atctctggag tccatgcgga                                                 20
```

```
<210> SEQ ID NO 101
<211> LENGTH: 20
<212> TYPE: DNA
<213> ORGANISM: Artificial
<220> FEATURE:
<223> OTHER INFORMATION: qPCR primer sequence

<400> SEQUENCE: 101
caaagtccct tggctgctgt                                                   20

<210> SEQ ID NO 102
<211> LENGTH: 20
<212> TYPE: DNA
<213> ORGANISM: Artificial
<220> FEATURE:
<223> OTHER INFORMATION: qPCR primer sequence

<400> SEQUENCE: 102
caggtgtgca aatcttgggt                                                   20

<210> SEQ ID NO 103
<211> LENGTH: 20
<212> TYPE: DNA
<213> ORGANISM: Artificial
<220> FEATURE:
<223> OTHER INFORMATION: qPCR primer sequence

<400> SEQUENCE: 103
tggtggcttg caatcatctg                                                   20

<210> SEQ ID NO 104
<211> LENGTH: 20
<212> TYPE: DNA
<213> ORGANISM: Artificial
<220> FEATURE:
<223> OTHER INFORMATION: qPCR primer sequence

<400> SEQUENCE: 104
tgagtccttg ctcggttctt                                                   20

<210> SEQ ID NO 105
<211> LENGTH: 20
<212> TYPE: DNA
<213> ORGANISM: Artificial
<220> FEATURE:
<223> OTHER INFORMATION: qPCR primer sequence

<400> SEQUENCE: 105
caggcacatt gctgtgagtt                                                   20

<210> SEQ ID NO 106
<211> LENGTH: 20
<212> TYPE: DNA
<213> ORGANISM: Artificial
<220> FEATURE:
<223> OTHER INFORMATION: qPCR primer sequence

<400> SEQUENCE: 106
tggccttgta ctgttgcaac                                                   20

<210> SEQ ID NO 107
<211> LENGTH: 20
<212> TYPE: DNA
<213> ORGANISM: Artificial
<220> FEATURE:
<223> OTHER INFORMATION: qPCR primer sequence
```

```
<400> SEQUENCE: 107
agtgtcacta tggccacctt                                              20

<210> SEQ ID NO 108
<211> LENGTH: 20
<212> TYPE: DNA
<213> ORGANISM: Artificial
<220> FEATURE:
<223> OTHER INFORMATION: qPCR primer sequence

<400> SEQUENCE: 108
aatcttccct tgggggtatg                                              20

<210> SEQ ID NO 109
<211> LENGTH: 20
<212> TYPE: DNA
<213> ORGANISM: Artificial
<220> FEATURE:
<223> OTHER INFORMATION: qPCR primer sequence

<400> SEQUENCE: 109
taaggagcca tgctgtaccc                                              20

<210> SEQ ID NO 110
<211> LENGTH: 30
<212> TYPE: DNA
<213> ORGANISM: Artificial
<220> FEATURE:
<223> OTHER INFORMATION: bisulfite sequencing primer sequence

<400> SEQUENCE: 110
gaagtttttg tgaaataagt tttgggtagg                                   30

<210> SEQ ID NO 111
<211> LENGTH: 24
<212> TYPE: DNA
<213> ORGANISM: Artificial
<220> FEATURE:
<223> OTHER INFORMATION: bisulfite sequencing primer sequence

<400> SEQUENCE: 111
ctcgaccaaa ataaacacca cccc                                         24

<210> SEQ ID NO 112
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 112
cgagttgtag ggtgtttggt aattg                                        25

<210> SEQ ID NO 113
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 113
acgttacaaa tcactcctca aaacc                                        25

<210> SEQ ID NO 114
```

```
<211> LENGTH: 27
<212> TYPE: DNA
<213> ORGANISM: Artificial
<220> FEATURE:
<223> OTHER INFORMATION: bisulfite sequencing primer sequence

<400> SEQUENCE: 114
ggttgtagga gaagaaaatg agattag                                              27

<210> SEQ ID NO 115
<211> LENGTH: 24
<212> TYPE: DNA
<213> ORGANISM: Artificial
<220> FEATURE:
<223> OTHER INFORMATION: bisulfite sequencing primer sequence

<400> SEQUENCE: 115
ctcgaccaaa ataaacacca cccc                                                 24

<210> SEQ ID NO 116
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 116
tagtttaagg gcgtagaggt ttgag                                                25

<210> SEQ ID NO 117
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 117
acgttacaaa tcactcctca aaacc                                                25

<210> SEQ ID NO 118
<211> LENGTH: 26
<212> TYPE: DNA
<213> ORGANISM: Artificial
<220> FEATURE:
<223> OTHER INFORMATION: bisulfite sequencing primer sequence

<400> SEQUENCE: 118
ttatttattg gttggattag aggggt                                               26

<210> SEQ ID NO 119
<211> LENGTH: 24
<212> TYPE: DNA
<213> ORGANISM: Artificial
<220> FEATURE:
<223> OTHER INFORMATION: bisulfite sequencing primer sequence

<400> SEQUENCE: 119
catatacttc ccaacaaacc aaac                                                 24

<210> SEQ ID NO 120
<211> LENGTH: 26
<212> TYPE: DNA
<213> ORGANISM: Artificial
<220> FEATURE:
<223> OTHER INFORMATION: bisulfite sequencing primer sequence

<400> SEQUENCE: 120
```

-continued gtgaatttgt taggattgga agtgaa                                      26

<210> SEQ ID NO 121
<211> LENGTH: 30
<212> TYPE: DNA
<213> ORGANISM: Artificial
<220> FEATURE:
<223> OTHER INFORMATION: bisulfite sequencing primer sequence

<400> SEQUENCE: 121
actcttacta tatatttccc cttctcttca                                  30

<210> SEQ ID NO 122
<211> LENGTH: 24
<212> TYPE: DNA
<213> ORGANISM: Artificial
<220> FEATURE:
<223> OTHER INFORMATION: bisulfite sequencing primer sequence

<400> SEQUENCE: 122
ggtttgaggt aggtaggggt tagg                                        24

<210> SEQ ID NO 123
<211> LENGTH: 30
<212> TYPE: DNA
<213> ORGANISM: Artificial
<220> FEATURE:
<223> OTHER INFORMATION: bisulfite sequencing primer sequence

<400> SEQUENCE: 123
ccaactcact ttctcccaaa attacactaa                                  30

<210> SEQ ID NO 124
<211> LENGTH: 29
<212> TYPE: DNA
<213> ORGANISM: Artificial
<220> FEATURE:
<223> OTHER INFORMATION: bisulfite sequencing primer sequence

<400> SEQUENCE: 124
gtagaatttg ttaggtgggt gaaaggaag                                   29

<210> SEQ ID NO 125
<211> LENGTH: 30
<212> TYPE: DNA
<213> ORGANISM: Artificial
<220> FEATURE:
<223> OTHER INFORMATION: bisulfite sequencing primer sequence

<400> SEQUENCE: 125
ccttcctccc aaaatactaa cctctcatac                                  30

<210> SEQ ID NO 126
<211> LENGTH: 28
<212> TYPE: DNA
<213> ORGANISM: Artificial
<220> FEATURE:
<223> OTHER INFORMATION: bisulfite sequencing primer sequence

<400> SEQUENCE: 126 gattttggg tattgtattg gaagtggg                                     28

<210> SEQ ID NO 127
<211> LENGTH: 32
<212> TYPE: DNA

```
<213> ORGANISM: Artificial
<220> FEATURE:
<223> OTHER INFORMATION: bisulfite sequencing primer sequence

<400> SEQUENCE: 127 ccaaatatt tattccctct actttaaaac ac                              32

<210> SEQ ID NO 128
<211> LENGTH: 27
<212> TYPE: DNA
<213> ORGANISM: Artificial
<220> FEATURE:
<223> OTHER INFORMATION: bisulfite sequencing primer sequence

<400> SEQUENCE: 128
tttaggatag gatgggagta ttggttg                                   27

<210> SEQ ID NO 129
<211> LENGTH: 34
<212> TYPE: DNA
<213> ORGANISM: Artificial
<220> FEATURE:
<223> OTHER INFORMATION: bisulfite sequencing primer sequence

<400> SEQUENCE: 129
caaaatcact caaaatcatc ctattacata aaac                           34

<210> SEQ ID NO 130
<211> LENGTH: 38
<212> TYPE: DNA
<213> ORGANISM: Artificial
<220> FEATURE:
<223> OTHER INFORMATION: bisulfite sequencing primer sequence

<400> SEQUENCE: 130
attaagaggt tagggttttt ttagttggtt ttgtattg                       38

<210> SEQ ID NO 131
<211> LENGTH: 37
<212> TYPE: DNA
<213> ORGANISM: Artificial
<220> FEATURE:
<223> OTHER INFORMATION: bisulfite sequencing primer sequence

<400> SEQUENCE: 131
aaaaaaaacc ttcatcacat aataaactaa accaacc                        37

<210> SEQ ID NO 132
<211> LENGTH: 28
<212> TYPE: DNA
<213> ORGANISM: Artificial
<220> FEATURE:
<223> OTHER INFORMATION: bisulfite sequencing primer sequence

<400> SEQUENCE: 132
gaaaggatgt aattagaggg tttttggg                                  28

<210> SEQ ID NO 133
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 133
aatcctttct caaacccct tcctc                                      25
```

```
<210> SEQ ID NO 134
<211> LENGTH: 29
<212> TYPE: DNA
<213> ORGANISM: Artificial
<220> FEATURE:
<223> OTHER INFORMATION: bisulfite sequencing primer sequence

<400> SEQUENCE: 134
gtggggtttt tataattagg aaagaatag                                    29

<210> SEQ ID NO 135
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 135
attacaaacc ccttctaaaa actcc                                        25

<210> SEQ ID NO 136
<211> LENGTH: 23
<212> TYPE: DNA
<213> ORGANISM: Artificial
<220> FEATURE:
<223> OTHER INFORMATION: bisulfite sequencing primer sequence

<400> SEQUENCE: 136
atttggtagt taggaaggtt gta                                          23

<210> SEQ ID NO 137
<211> LENGTH: 22
<212> TYPE: DNA
<213> ORGANISM: Artificial
<220> FEATURE:
<223> OTHER INFORMATION: bisulfite sequencing primer sequence

<400> SEQUENCE: 137
ccaaaaaacc tcccctttt cc                                            22

<210> SEQ ID NO 138
<211> LENGTH: 25
<212> TYPE: DNA
<213> ORGANISM: Artificial
<220> FEATURE:
<223> OTHER INFORMATION: bisulfite sequencing primer sequence

<400> SEQUENCE: 138
gtggattttt ttaaggagtg tgttg                                        25

<210> SEQ ID NO 139
<211> LENGTH: 35
<212> TYPE: DNA
<213> ORGANISM: Artificial
<220> FEATURE:
<223> OTHER INFORMATION: bisulfite sequencing primer sequence

<400> SEQUENCE: 139
cttctaatat ctaaactcaa caacaatata tccac                             35

<210> SEQ ID NO 140
<211> LENGTH: 27
<212> TYPE: DNA
<213> ORGANISM: Artificial
<220> FEATURE:
```

<223> OTHER INFORMATION: bisulfite sequencing primer sequence

<400> SEQUENCE: 140
ggagatttag gaagtatggg gttagtg                                    27

<210> SEQ ID NO 141
<211> LENGTH: 28
<212> TYPE: DNA
<213> ORGANISM: Artificial
<220> FEATURE:
<223> OTHER INFORMATION: bisulfite sequencing primer sequence

<400> SEQUENCE: 141
aaaacctcct ctcttacttt tctacttc                                   28

<210> SEQ ID NO 142
<211> LENGTH: 27
<212> TYPE: DNA
<213> ORGANISM: Artificial
<220> FEATURE:
<223> OTHER INFORMATION: 3C assay primer sequence

<400> SEQUENCE: 142
cacatcttca aagcaaacac tattgtt                                    27

<210> SEQ ID NO 143
<211> LENGTH: 18
<212> TYPE: DNA
<213> ORGANISM: Artificial
<220> FEATURE:
<223> OTHER INFORMATION: 3C assay primer sequence

<400> SEQUENCE: 143
ttcctggaac ctgggcaa                                              18

<210> SEQ ID NO 144
<211> LENGTH: 23
<212> TYPE: DNA
<213> ORGANISM: Artificial
<220> FEATURE:
<223> OTHER INFORMATION: 3C assay primer sequence

<400> SEQUENCE: 144
tgatacagca cagctttcct tca                                        23

<210> SEQ ID NO 145
<211> LENGTH: 28
<212> TYPE: DNA
<213> ORGANISM: Artificial
<220> FEATURE:
<223> OTHER INFORMATION: 3C assay primer sequence

<400> SEQUENCE: 145
cagatttttt atttccttca gttctgtg                                   28

<210> SEQ ID NO 146
<211> LENGTH: 30
<212> TYPE: DNA
<213> ORGANISM: Artificial
<220> FEATURE:
<223> OTHER INFORMATION: 3C assay primer sequence

<400> SEQUENCE: 146
tctcctaccc attgcttctc tgctacctgc                                 30

```
<210> SEQ ID NO 147
<211> LENGTH: 26
<212> TYPE: DNA
<213> ORGANISM: Artificial
<220> FEATURE:
<223> OTHER INFORMATION: 3C assay primer sequence

<400> SEQUENCE: 147
tgaagtttga ggagatgcca tggttg                                   26

<210> SEQ ID NO 148
<211> LENGTH: 27
<212> TYPE: DNA
<213> ORGANISM: Artificial
<220> FEATURE:
<223> OTHER INFORMATION: 3C assay primer sequence

<400> SEQUENCE: 148
cacgctaggc tgaacactgt gtcactg                                  27

<210> SEQ ID NO 149
<211> LENGTH: 20
<212> TYPE: DNA
<213> ORGANISM: Artificial
<220> FEATURE:
<223> OTHER INFORMATION: 3C assay primer sequence

<400> SEQUENCE: 149
aggatggctc agcggttaag                                          20

<210> SEQ ID NO 150
<211> LENGTH: 22
<212> TYPE: DNA
<213> ORGANISM: Artificial
<220> FEATURE:
<223> OTHER INFORMATION: 3C assay primer sequence

<400> SEQUENCE: 150
agggctcacc ttcagtcaag tt                                       22

<210> SEQ ID NO 151
<211> LENGTH: 29
<212> TYPE: DNA
<213> ORGANISM: Artificial
<220> FEATURE:
<223> OTHER INFORMATION: 3C assay primer sequence

<400> SEQUENCE: 151
cggcctgtct actttagcct cagactcca                                29

<210> SEQ ID NO 152
<211> LENGTH: 28
<212> TYPE: DNA
<213> ORGANISM: Artificial
<220> FEATURE:
<223> OTHER INFORMATION: 3C assay primer sequence

<400> SEQUENCE: 152
tgccttccct cttacaagga gttttctt                                 28

<210> SEQ ID NO 153
<211> LENGTH: 27
<212> TYPE: DNA
<213> ORGANISM: Artificial
<220> FEATURE:
<223> OTHER INFORMATION: 3C assay primer sequence
```

<400> SEQUENCE: 153
cggttaagaa gagctcttct ggaggcc                                            27

<210> SEQ ID NO 154
<211> LENGTH: 23
<212> TYPE: DNA
<213> ORGANISM: Artificial
<220> FEATURE:
<223> OTHER INFORMATION: 3C assay primer sequence

<400> SEQUENCE: 154
gggagtgact ctctgtccat tca                                                23

<210> SEQ ID NO 155
<211> LENGTH: 22
<212> TYPE: DNA
<213> ORGANISM: Artificial
<220> FEATURE:
<223> OTHER INFORMATION: 3C assay primer sequence

<400> SEQUENCE: 155
atttgtgtgg cctcttgttt ga                                                 22

<210> SEQ ID NO 156
<211> LENGTH: 18
<212> TYPE: DNA
<213> ORGANISM: Artificial
<220> FEATURE:
<223> OTHER INFORMATION: 3C assay primer sequence

<400> SEQUENCE: 156
tccaggcccc gcgtgtcc                                                      18

<210> SEQ ID NO 157
<211> LENGTH: 2309
<212> TYPE: PRT
<213> ORGANISM: Artificial
<220> FEATURE:
<223> OTHER INFORMATION: dCAS9-Dnmt3a (protein)

<400> SEQUENCE: 157

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe

```
                995              1000             1005
    Val  Tyr  Gly  Asp  Tyr  Lys  Val  Tyr  Asp  Val  Arg  Lys  Met  Ile  Ala
        1010             1015             1020

Lys  Ser  Glu  Gln  Glu  Ile  Gly  Lys  Ala  Thr  Ala  Lys  Tyr  Phe  Phe
        1025             1030             1035

Tyr  Ser  Asn  Ile  Met  Asn  Phe  Phe  Lys  Thr  Glu  Ile  Thr  Leu  Ala
        1040             1045             1050

Asn  Gly  Glu  Ile  Arg  Lys  Arg  Pro  Leu  Ile  Glu  Thr  Asn  Gly  Glu
        1055             1060             1065

Thr  Gly  Glu  Ile  Val  Trp  Asp  Lys  Gly  Arg  Asp  Phe  Ala  Thr  Val
        1070             1075             1080

Arg  Lys  Val  Leu  Ser  Met  Pro  Gln  Val  Asn  Ile  Val  Lys  Lys  Thr
        1085             1090             1095

Glu  Val  Gln  Thr  Gly  Gly  Phe  Ser  Lys  Glu  Ser  Ile  Leu  Pro  Lys
        1100             1105             1110

Arg  Asn  Ser  Asp  Lys  Leu  Ile  Ala  Arg  Lys  Lys  Asp  Trp  Asp  Pro
        1115             1120             1125

Lys  Lys  Tyr  Gly  Gly  Phe  Asp  Ser  Pro  Thr  Val  Ala  Tyr  Ser  Val
        1130             1135             1140

Leu  Val  Val  Ala  Lys  Val  Glu  Lys  Gly  Lys  Ser  Lys  Lys  Leu  Lys
        1145             1150             1155

Ser  Val  Lys  Glu  Leu  Leu  Gly  Ile  Thr  Ile  Met  Glu  Arg  Ser  Ser
        1160             1165             1170

Phe  Glu  Lys  Asn  Pro  Ile  Asp  Phe  Leu  Glu  Ala  Lys  Gly  Tyr  Lys
        1175             1180             1185

Glu  Val  Lys  Lys  Asp  Leu  Ile  Ile  Lys  Leu  Pro  Lys  Tyr  Ser  Leu
        1190             1195             1200

Phe  Glu  Leu  Glu  Asn  Gly  Arg  Lys  Arg  Met  Leu  Ala  Ser  Ala  Gly
        1205             1210             1215

Glu  Leu  Gln  Lys  Gly  Asn  Glu  Leu  Ala  Leu  Pro  Ser  Lys  Tyr  Val
        1220             1225             1230

Asn  Phe  Leu  Tyr  Leu  Ala  Ser  His  Tyr  Glu  Lys  Leu  Lys  Gly  Ser
        1235             1240             1245

Pro  Glu  Asp  Asn  Glu  Gln  Lys  Gln  Leu  Phe  Val  Glu  Gln  His  Lys
        1250             1255             1260

His  Tyr  Leu  Asp  Glu  Ile  Ile  Glu  Gln  Ile  Ser  Glu  Phe  Ser  Lys
        1265             1270             1275

Arg  Val  Ile  Leu  Ala  Asp  Ala  Asn  Leu  Asp  Lys  Val  Leu  Ser  Ala
        1280             1285             1290

Tyr  Asn  Lys  His  Arg  Asp  Lys  Pro  Ile  Arg  Glu  Gln  Ala  Glu  Asn
        1295             1300             1305

Ile  Ile  His  Leu  Phe  Thr  Leu  Thr  Asn  Leu  Gly  Ala  Pro  Ala  Ala
        1310             1315             1320

Phe  Lys  Tyr  Phe  Asp  Thr  Thr  Ile  Asp  Arg  Lys  Arg  Tyr  Thr  Ser
        1325             1330             1335

Thr  Lys  Glu  Val  Leu  Asp  Ala  Thr  Leu  Ile  His  Gln  Ser  Ile  Thr
        1340             1345             1350

Gly  Leu  Tyr  Glu  Thr  Arg  Ile  Asp  Leu  Ser  Gln  Leu  Gly  Gly  Asp
        1355             1360             1365

Glu  Gly  Ala  Asp  Pro  Lys  Lys  Lys  Arg  Lys  Val  Asp  Pro  Lys  Lys
        1370             1375             1380

Lys  Arg  Lys  Val  Asp  Pro  Lys  Lys  Lys  Arg  Lys  Val  Gly  Ser  Met
        1385             1390             1395
```

-continued

```
Pro Ala Met Pro Ser Ser Gly Pro Gly Asp Thr Ser Ser Ser Ala
    1400            1405            1410

Ala Glu Arg Glu Glu Asp Arg Lys Asp Gly Glu Glu Gln Glu Glu
    1415            1420            1425

Pro Arg Gly Lys Glu Glu Arg Gln Glu Pro Ser Thr Thr Ala Arg
    1430            1435            1440

Lys Val Gly Arg Pro Gly Arg Lys Arg Lys His Pro Pro Val Glu
    1445            1450            1455

Ser Gly Asp Thr Pro Lys Asp Pro Ala Val Ile Ser Lys Ser Pro
    1460            1465            1470

Ser Met Ala Gln Asp Ser Gly Ala Ser Glu Leu Leu Pro Asn Gly
    1475            1480            1485

Asp Leu Glu Lys Arg Ser Glu Pro Gln Pro Glu Glu Gly Ser Pro
    1490            1495            1500

Ala Gly Gly Gln Lys Gly Gly Ala Pro Ala Glu Gly Glu Gly Ala
    1505            1510            1515

Ala Glu Thr Leu Pro Glu Ala Ser Arg Ala Val Glu Asn Gly Cys
    1520            1525            1530

Cys Thr Pro Lys Glu Gly Arg Gly Ala Pro Ala Glu Ala Gly Lys
    1535            1540            1545

Glu Gln Lys Glu Thr Asn Ile Glu Ser Met Lys Met Glu Gly Ser
    1550            1555            1560

Arg Gly Arg Leu Arg Gly Gly Leu Gly Trp Glu Ser Ser Leu Arg
    1565            1570            1575

Gln Arg Pro Met Pro Arg Leu Thr Phe Gln Ala Gly Asp Pro Tyr
    1580            1585            1590

Tyr Ile Ser Lys Arg Lys Arg Asp Glu Trp Leu Ala Arg Trp Lys
    1595            1600            1605

Arg Glu Ala Glu Lys Lys Ala Lys Val Ile Ala Gly Met Asn Ala
    1610            1615            1620

Val Glu Glu Asn Gln Gly Pro Gly Glu Ser Gln Lys Val Glu Glu
    1625            1630            1635

Ala Ser Pro Pro Ala Val Gln Gln Pro Thr Asp Pro Ala Ser Pro
    1640            1645            1650

Thr Val Ala Thr Thr Pro Glu Pro Val Gly Ser Asp Ala Gly Asp
    1655            1660            1665

Lys Asn Ala Thr Lys Ala Gly Asp Asp Glu Pro Glu Tyr Glu Asp
    1670            1675            1680

Gly Arg Gly Phe Gly Ile Gly Glu Leu Val Trp Gly Lys Leu Arg
    1685            1690            1695

Gly Phe Ser Trp Trp Pro Gly Arg Ile Val Ser Trp Trp Met Thr
    1700            1705            1710

Gly Arg Ser Arg Ala Ala Glu Gly Thr Arg Trp Val Met Trp Phe
    1715            1720            1725

Gly Asp Gly Lys Phe Ser Val Val Cys Val Glu Lys Leu Met Pro
    1730            1735            1740

Leu Ser Ser Phe Cys Ser Ala Phe His Gln Ala Thr Tyr Asn Lys
    1745            1750            1755

Gln Pro Met Tyr Arg Lys Ala Ile Tyr Glu Val Leu Gln Val Ala
    1760            1765            1770

Ser Ser Arg Ala Gly Lys Leu Phe Pro Val Cys His Asp Ser Asp
    1775            1780            1785
```

-continued

Glu Ser Asp Thr Ala Lys Ala Val Glu Val Gln Asn Lys Pro Met
1790            1795            1800

Ile Glu Trp Ala Leu Gly Gly Phe Gln Pro Ser Gly Pro Lys Gly
1805            1810            1815

Leu Glu Pro Pro Glu Glu Glu Lys Asn Pro Tyr Lys Glu Val Tyr
1820            1825            1830

Thr Asp Met Trp Val Glu Pro Glu Ala Ala Tyr Ala Pro Pro
1835            1840            1845

Pro Pro Ala Lys Lys Pro Arg Lys Ser Thr Ala Glu Lys Pro Lys
1850            1855            1860

Val Lys Glu Ile Ile Asp Glu Arg Thr Arg Glu Arg Leu Val Tyr
1865            1870            1875

Glu Val Arg Gln Lys Cys Arg Asn Ile Glu Asp Ile Cys Ile Ser
1880            1885            1890

Cys Gly Ser Leu Asn Val Thr Leu Glu His Pro Leu Phe Val Gly
1895            1900            1905

Gly Met Cys Gln Asn Cys Lys Asn Cys Phe Leu Glu Cys Ala Tyr
1910            1915            1920

Gln Tyr Asp Asp Asp Gly Tyr Gln Ser Tyr Cys Thr Ile Cys Cys
1925            1930            1935

Gly Gly Arg Glu Val Leu Met Cys Gly Asn Asn Cys Cys Arg
1940            1945            1950

Cys Phe Cys Val Glu Cys Val Asp Leu Leu Val Gly Pro Gly Ala
1955            1960            1965

Ala Gln Ala Ala Ile Lys Glu Asp Pro Trp Asn Cys Tyr Met Cys
1970            1975            1980

Gly His Lys Gly Thr Tyr Gly Leu Leu Arg Arg Arg Glu Asp Trp
1985            1990            1995

Pro Ser Arg Leu Gln Met Phe Phe Ala Asn Asn His Asp Gln Glu
2000            2005            2010

Phe Asp Pro Pro Lys Val Tyr Pro Pro Val Pro Ala Glu Lys Arg
2015            2020            2025

Lys Pro Ile Arg Val Leu Ser Leu Phe Asp Gly Ile Ala Thr Gly
2030            2035            2040

Leu Leu Val Leu Lys Asp Leu Gly Ile Gln Val Asp Arg Tyr Ile
2045            2050            2055

Ala Ser Glu Val Cys Glu Asp Ser Ile Thr Val Gly Met Val Arg
2060            2065            2070

His Gln Gly Lys Ile Met Tyr Val Gly Asp Val Arg Ser Val Thr
2075            2080            2085

Gln Lys His Ile Gln Glu Trp Gly Pro Phe Asp Leu Val Ile Gly
2090            2095            2100

Gly Ser Pro Cys Asn Asp Leu Ser Ile Val Asn Pro Ala Arg Lys
2105            2110            2115

Gly Leu Tyr Glu Gly Thr Gly Arg Leu Phe Phe Glu Phe Tyr Arg
2120            2125            2130

Leu Leu His Asp Ala Arg Pro Lys Glu Gly Asp Asp Arg Pro Phe
2135            2140            2145

Phe Trp Leu Phe Glu Asn Val Val Ala Met Gly Val Ser Asp Lys
2150            2155            2160

Arg Asp Ile Ser Arg Phe Leu Glu Ser Asn Pro Val Met Ile Asp
2165            2170            2175

Ala Lys Glu Val Ser Ala Ala His Arg Ala Arg Tyr Phe Trp Gly

```
                2180                2185                2190
Asn Leu Pro Gly Met Asn Arg Pro Leu Ala Ser Thr Val Asn Asp
        2195                2200                2205
Lys Leu Glu Leu Gln Glu Cys Leu Glu His Gly Arg Ile Ala Lys
    2210                2215                2220
Phe Ser Lys Val Arg Thr Ile Thr Thr Arg Ser Asn Ser Ile Lys
    2225                2230                2235
Gln Gly Lys Asp Gln His Phe Pro Val Phe Met Asn Glu Lys Glu
    2240                2245                2250
Asp Ile Leu Trp Cys Thr Glu Met Glu Arg Val Phe Gly Phe Pro
    2255                2260                2265
Val His Tyr Thr Asp Val Ser Asn Met Ser Arg Leu Ala Arg Gln
    2270                2275                2280
Arg Leu Leu Gly Arg Ser Trp Ser Val Pro Val Ile Arg His Leu
    2285                2290                2295
Phe Ala Pro Leu Lys Glu Tyr Phe Ala Cys Val
    2300                2305

<210> SEQ ID NO 158
<211> LENGTH: 2309
<212> TYPE: PRT
<213> ORGANISM: Unknown
<220> FEATURE:
<223> OTHER INFORMATION: dCAS9-Dnmt3a_IM

<400> SEQUENCE: 158

Met Asp Lys Lys Tyr Ser Ile Gly Leu Ala Ile Gly Thr Asn Ser Val
1               5                   10                  15
Gly Trp Ala Val Ile Thr Asp Glu Tyr Lys Val Pro Ser Lys Lys Phe
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
    50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
```

```
            225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
```

-continued

```
Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065
```

```
Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Glu Gly Ala Asp Pro Lys Lys Lys Arg Lys Val Asp Pro Lys Lys
    1370                1375                1380

Lys Arg Lys Val Asp Pro Lys Lys Arg Lys Val Gly Ser Met
    1385                1390                1395

Pro Ala Met Pro Ser Ser Gly Pro Gly Asp Thr Ser Ser Ser Ala
    1400                1405                1410

Ala Glu Arg Glu Glu Asp Arg Lys Asp Gly Glu Gln Glu Glu
    1415                1420                1425

Pro Arg Gly Lys Glu Glu Arg Gln Glu Pro Ser Thr Thr Ala Arg
    1430                1435                1440

Lys Val Gly Arg Pro Gly Arg Lys Arg Lys His Pro Pro Val Glu
    1445                1450                1455

Ser Gly Asp Thr Pro Lys Asp Pro Ala Val Ile Ser Lys Ser Pro
```

```
              1460                1465                1470

Ser Met Ala Gln Asp Ser Gly Ala Ser Glu Leu Leu Pro Asn Gly
         1475                1480                1485

Asp Leu Glu Lys Arg Ser Glu Pro Gln Pro Glu Glu Gly Ser Pro
         1490                1495                1500

Ala Gly Gly Gln Lys Gly Gly Ala Pro Ala Glu Glu Gly Gly Ala
         1505                1510                1515

Ala Glu Thr Leu Pro Glu Ala Ser Arg Ala Val Glu Asn Gly Cys
         1520                1525                1530

Cys Thr Pro Lys Glu Gly Arg Gly Ala Pro Ala Glu Ala Gly Lys
         1535                1540                1545

Glu Gln Lys Glu Thr Asn Ile Glu Ser Met Lys Met Glu Gly Ser
         1550                1555                1560

Arg Gly Arg Leu Arg Gly Gly Leu Gly Trp Glu Ser Ser Leu Arg
         1565                1570                1575

Gln Arg Pro Met Pro Arg Leu Thr Phe Gln Ala Gly Asp Pro Tyr
         1580                1585                1590

Tyr Ile Ser Lys Arg Lys Arg Asp Glu Trp Leu Ala Arg Trp Lys
         1595                1600                1605

Arg Glu Ala Glu Lys Lys Ala Lys Val Ile Ala Gly Met Asn Ala
         1610                1615                1620

Val Glu Glu Asn Gln Gly Pro Gly Glu Ser Gln Lys Val Glu Glu
         1625                1630                1635

Ala Ser Pro Pro Ala Val Gln Gln Pro Thr Asp Pro Ala Ser Pro
         1640                1645                1650

Thr Val Ala Thr Thr Pro Glu Pro Val Gly Ser Asp Ala Gly Asp
         1655                1660                1665

Lys Asn Ala Thr Lys Ala Gly Asp Asp Glu Pro Glu Tyr Glu Asp
         1670                1675                1680

Gly Arg Gly Phe Gly Ile Gly Glu Leu Val Trp Gly Lys Leu Arg
         1685                1690                1695

Gly Phe Ser Trp Trp Pro Gly Arg Ile Val Ser Trp Trp Met Thr
         1700                1705                1710

Gly Arg Ser Arg Ala Ala Glu Gly Thr Arg Trp Val Met Trp Phe
         1715                1720                1725

Gly Asp Gly Lys Phe Ser Val Val Cys Val Glu Lys Leu Met Pro
         1730                1735                1740

Leu Ser Ser Phe Cys Ser Ala Phe His Gln Ala Thr Tyr Asn Lys
         1745                1750                1755

Gln Pro Met Tyr Arg Lys Ala Ile Tyr Glu Val Leu Gln Val Ala
         1760                1765                1770

Ser Ser Arg Ala Gly Lys Leu Phe Pro Val Cys His Asp Ser Asp
         1775                1780                1785

Glu Ser Asp Thr Ala Lys Ala Val Glu Val Gln Asn Lys Pro Met
         1790                1795                1800

Ile Glu Trp Ala Leu Gly Gly Phe Gln Pro Ser Gly Pro Lys Gly
         1805                1810                1815

Leu Glu Pro Pro Glu Glu Glu Lys Asn Pro Tyr Lys Glu Val Tyr
         1820                1825                1830

Thr Asp Met Trp Val Glu Pro Glu Ala Ala Ala Tyr Ala Pro Pro
         1835                1840                1845

Pro Pro Ala Lys Lys Pro Arg Lys Ser Thr Ala Glu Lys Pro Lys
         1850                1855                1860
```

-continued

Val Lys Glu Ile Ile Asp Glu Arg Thr Arg Glu Arg Leu Val Tyr
1865                1870                1875

Glu Val Arg Gln Lys Cys Arg Asn Ile Glu Asp Ile Cys Ile Ser
1880                1885                1890

Cys Gly Ser Leu Asn Val Thr Leu Glu His Pro Leu Phe Val Gly
1895                1900                1905

Gly Met Cys Gln Asn Cys Lys Asn Cys Phe Leu Glu Cys Ala Tyr
1910                1915                1920

Gln Tyr Asp Asp Asp Gly Tyr Gln Ser Tyr Cys Thr Ile Cys Cys
1925                1930                1935

Gly Gly Arg Glu Val Leu Met Cys Gly Asn Asn Cys Cys Arg
1940                1945                1950

Cys Phe Cys Val Glu Cys Val Asp Leu Leu Val Gly Pro Gly Ala
1955                1960                1965

Ala Gln Ala Ala Ile Lys Glu Asp Pro Trp Asn Cys Tyr Met Cys
1970                1975                1980

Gly His Lys Gly Thr Tyr Gly Leu Leu Arg Arg Arg Glu Asp Trp
1985                1990                1995

Pro Ser Arg Leu Gln Met Phe Phe Ala Asn Asn His Asp Gln Glu
2000                2005                2010

Phe Asp Pro Pro Lys Val Tyr Pro Pro Val Pro Ala Glu Lys Arg
2015                2020                2025

Lys Pro Ile Arg Val Leu Ser Leu Phe Asp Gly Ile Ala Thr Gly
2030                2035                2040

Leu Leu Val Leu Lys Asp Leu Gly Ile Gln Val Asp Arg Tyr Ile
2045                2050                2055

Ala Ser Ala Val Cys Glu Asp Ser Ile Thr Val Gly Met Val Arg
2060                2065                2070

His Gln Gly Lys Ile Met Tyr Val Gly Asp Val Arg Ser Val Thr
2075                2080                2085

Gln Lys His Ile Gln Glu Trp Gly Pro Phe Asp Leu Val Ile Gly
2090                2095                2100

Gly Ser Pro Cys Asn Asp Leu Ser Ile Val Asn Pro Ala Arg Lys
2105                2110                2115

Gly Leu Tyr Glu Gly Thr Gly Arg Leu Phe Phe Glu Phe Tyr Arg
2120                2125                2130

Leu Leu His Asp Ala Arg Pro Lys Glu Gly Asp Asp Arg Pro Phe
2135                2140                2145

Phe Trp Leu Phe Ala Asn Val Val Ala Met Gly Val Ser Asp Lys
2150                2155                2160

Arg Asp Ile Ser Arg Phe Leu Glu Ser Asn Pro Val Met Ile Asp
2165                2170                2175

Ala Lys Glu Val Ser Ala Ala His Arg Ala Arg Tyr Phe Trp Gly
2180                2185                2190

Asn Leu Pro Gly Met Asn Arg Pro Leu Ala Ser Thr Val Asn Asp
2195                2200                2205

Lys Leu Glu Leu Gln Glu Cys Leu Glu His Gly Arg Ile Ala Lys
2210                2215                2220

Phe Ser Lys Val Arg Thr Ile Thr Thr Arg Ser Asn Ser Ile Lys
2225                2230                2235

Gln Gly Lys Asp Gln His Phe Pro Val Phe Met Asn Glu Lys Glu
2240                2245                2250

```
Asp Ile Leu Trp Cys Thr Glu Met Glu Arg Val Phe Gly Phe Pro
    2255                2260                2265

Val His Tyr Thr Asp Val Ser Asn Met Ser Arg Leu Ala Arg Gln
    2270                2275                2280

Arg Leu Leu Gly Arg Ser Trp Ser Val Pro Val Ile Arg His Leu
    2285                2290                2295

Phe Ala Pro Leu Lys Glu Tyr Phe Ala Cys Val
    2300                2305

<210> SEQ ID NO 159
<211> LENGTH: 2115
<212> TYPE: PRT
<213> ORGANISM: Unknown
<220> FEATURE:
<223> OTHER INFORMATION: dCAS9-Tet1CD

<400> SEQUENCE: 159

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
```

```
                725                 730                 735
Ile Leu Gln Thr Val Lys Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
```

```
Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

Glu Gly Ala Asp Pro Lys Lys Lys Arg Lys Val Asp Pro Lys Lys
    1370            1375            1380

Lys Arg Lys Val Asp Pro Lys Lys Arg Lys Val Gly Ser Leu
    1385            1390            1395

Pro Thr Cys Ser Cys Leu Asp Arg Val Ile Gln Lys Asp Lys Gly
    1400            1405            1410

Pro Tyr Tyr Thr His Leu Gly Ala Gly Pro Ser Val Ala Ala Val
    1415            1420            1425

Arg Glu Ile Met Glu Asn Arg Tyr Gly Gln Lys Gly Asn Ala Ile
    1430            1435            1440

Arg Ile Glu Ile Val Val Tyr Thr Gly Lys Glu Gly Lys Ser Ser
    1445            1450            1455

His Gly Cys Pro Ile Ala Lys Trp Val Leu Arg Arg Ser Ser Asp
    1460            1465            1470

Glu Glu Lys Val Leu Cys Leu Val Arg Gln Arg Thr Gly His His
    1475            1480            1485

Cys Pro Thr Ala Val Met Val Val Leu Ile Met Val Trp Asp Gly
    1490            1495            1500

Ile Pro Leu Pro Met Ala Asp Arg Leu Tyr Thr Glu Leu Thr Glu
    1505            1510            1515

Asn Leu Lys Ser Tyr Asn Gly His Pro Thr Asp Arg Arg Cys Thr
    1520            1525            1530
```

| | | | | | | | | | | | |
|---|---|---|---|---|---|---|---|---|---|---|---|
| Leu | Asn 1535 | Glu | Asn | Arg | Thr 1540 | Cys | Thr | Cys | Gln 1545 | Gly | Ile | Asp | Pro | Glu |

Leu Asn Glu Asn Arg Thr Cys Thr Cys Gln Gly Ile Asp Pro Glu
1535                1540                1545

Thr Cys Gly Ala Ser Phe Ser Phe Gly Cys Ser Trp Ser Met Tyr
1550                1555                1560

Phe Asn Gly Cys Lys Phe Gly Arg Ser Pro Ser Pro Arg Arg Phe
1565                1570                1575

Arg Ile Asp Pro Ser Ser Pro Leu His Glu Lys Asn Leu Glu Asp
1580                1585                1590

Asn Leu Gln Ser Leu Ala Thr Arg Leu Ala Pro Ile Tyr Lys Gln
1595                1600                1605

Tyr Ala Pro Val Ala Tyr Gln Asn Gln Val Glu Tyr Glu Asn Val
1610                1615                1620

Ala Arg Glu Cys Arg Leu Gly Ser Lys Glu Gly Arg Pro Phe Ser
1625                1630                1635

Gly Val Thr Ala Cys Leu Asp Phe Cys Ala His Pro His Arg Asp
1640                1645                1650

Ile His Asn Met Asn Asn Gly Ser Thr Val Val Cys Thr Leu Thr
1655                1660                1665

Arg Glu Asp Asn Arg Ser Leu Gly Val Ile Pro Gln Asp Glu Gln
1670                1675                1680

Leu His Val Leu Pro Leu Tyr Lys Leu Ser Asp Thr Asp Glu Phe
1685                1690                1695

Gly Ser Lys Glu Gly Met Glu Ala Lys Ile Lys Ser Gly Ala Ile
1700                1705                1710

Glu Val Leu Ala Pro Arg Arg Lys Lys Arg Thr Cys Phe Thr Gln
1715                1720                1725

Pro Val Pro Arg Ser Gly Lys Lys Arg Ala Ala Met Met Thr Glu
1730                1735                1740

Val Leu Ala His Lys Ile Arg Ala Val Glu Lys Lys Pro Ile Pro
1745                1750                1755

Arg Ile Lys Arg Lys Asn Asn Ser Thr Thr Thr Asn Asn Ser Lys
1760                1765                1770

Pro Ser Ser Leu Pro Thr Leu Gly Ser Asn Thr Glu Thr Val Gln
1775                1780                1785

Pro Glu Val Lys Ser Glu Thr Glu Pro His Phe Ile Leu Lys Ser
1790                1795                1800

Ser Asp Asn Thr Lys Thr Tyr Ser Leu Met Pro Ser Ala Pro His
1805                1810                1815

Pro Val Lys Glu Ala Ser Pro Gly Phe Ser Trp Ser Pro Lys Thr
1820                1825                1830

Ala Ser Ala Thr Pro Ala Pro Leu Lys Asn Asp Ala Thr Ala Ser
1835                1840                1845

Cys Gly Phe Ser Glu Arg Ser Ser Thr Pro His Cys Thr Met Pro
1850                1855                1860

Ser Gly Arg Leu Ser Gly Ala Asn Ala Ala Ala Asp Gly Pro
1865                1870                1875

Gly Ile Ser Gln Leu Gly Glu Val Ala Pro Leu Pro Thr Leu Ser
1880                1885                1890

Ala Pro Val Met Glu Pro Leu Ile Asn Ser Glu Pro Ser Thr Gly
1895                1900                1905

Val Thr Glu Pro Leu Thr Pro His Gln Pro Asn His Gln Pro Ser
1910                1915                1920

Phe Leu Thr Ser Pro Gln Asp Leu Ala Ser Ser Pro Met Glu Glu

-continued

```
            1925                1930                1935

Asp Glu Gln His Ser Glu Ala Asp Glu Pro Ser Asp Glu Pro
        1940                1945                1950

Leu Ser Asp Asp Pro Leu Ser Pro Ala Glu Glu Lys Leu Pro His
    1955                1960                1965

Ile Asp Glu Tyr Trp Ser Asp Ser Glu His Ile Phe Leu Asp Ala
    1970                1975                1980

Asn Ile Gly Gly Val Ala Ile Ala Pro Ala His Gly Ser Val Leu
    1985                1990                1995

Ile Glu Cys Ala Arg Arg Glu Leu His Ala Thr Thr Pro Val Glu
    2000                2005                2010

His Pro Asn Arg Asn His Pro Thr Arg Leu Ser Leu Val Phe Tyr
    2015                2020                2025

Gln His Lys Asn Leu Asn Lys Pro Gln His Gly Phe Glu Leu Asn
    2030                2035                2040

Lys Ile Lys Phe Glu Ala Lys Glu Ala Lys Asn Lys Lys Met Lys
    2045                2050                2055

Ala Ser Glu Gln Lys Asp Gln Ala Ala Asn Glu Gly Pro Glu Gln
    2060                2065                2070

Ser Ser Glu Val Asn Glu Leu Asn Gln Ile Pro Ser His Lys Ala
    2075                2080                2085

Leu Thr Leu Thr His Asp Asn Val Val Thr Val Ser Pro Tyr Ala
    2090                2095                2100

Leu Thr His Val Ala Gly Pro Tyr Asn His Trp Val
    2105                2110                2115

<210> SEQ ID NO 160
<211> LENGTH: 2115
<212> TYPE: PRT
<213> ORGANISM: Unknown
<220> FEATURE:
<223> OTHER INFORMATION: dCAS9-Tet1CD_IM

<400> SEQUENCE: 160

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
```

```
                165                 170                 175
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590
```

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
        995                 1000                1005
```

```
Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Glu Gly Ala Asp Pro Lys Lys Lys Arg Lys Val Asp Pro Lys Lys
1370                1375                1380

Lys Arg Lys Val Asp Pro Lys Lys Arg Lys Val Gly Ser Leu
1385                1390                1395

Pro Thr Cys Ser Cys Leu Asp Arg Val Ile Gln Lys Asp Lys Gly
```

```
                1400              1405              1410
Pro Tyr Tyr Thr His Leu Gly Ala Gly Pro Ser Val Ala Ala Val
    1415              1420              1425

Arg Glu Ile Met Glu Asn Arg Tyr Gly Gln Lys Gly Asn Ala Ile
    1430              1435              1440

Arg Ile Glu Ile Val Val Tyr Thr Gly Lys Glu Gly Lys Ser Ser
    1445              1450              1455

His Gly Cys Pro Ile Ala Lys Trp Val Leu Arg Arg Ser Ser Asp
    1460              1465              1470

Glu Glu Lys Val Leu Cys Leu Val Arg Gln Arg Thr Gly His His
    1475              1480              1485

Cys Pro Thr Ala Val Met Val Val Leu Ile Met Val Trp Asp Gly
    1490              1495              1500

Ile Pro Leu Pro Met Ala Asp Arg Leu Tyr Thr Glu Leu Thr Glu
    1505              1510              1515

Asn Leu Lys Ser Tyr Asn Gly His Pro Thr Asp Arg Arg Cys Thr
    1520              1525              1530

Leu Asn Glu Asn Arg Thr Cys Thr Cys Gln Gly Ile Asp Pro Glu
    1535              1540              1545

Thr Cys Gly Ala Ser Phe Ser Phe Gly Cys Ser Trp Ser Met Tyr
    1550              1555              1560

Phe Asn Gly Cys Lys Phe Gly Arg Ser Pro Ser Pro Arg Arg Phe
    1565              1570              1575

Arg Ile Asp Pro Ser Ser Pro Leu His Glu Lys Asn Leu Glu Asp
    1580              1585              1590

Asn Leu Gln Ser Leu Ala Thr Arg Leu Ala Pro Ile Tyr Lys Gln
    1595              1600              1605

Tyr Ala Pro Val Ala Tyr Gln Asn Gln Val Glu Tyr Glu Asn Val
    1610              1615              1620

Ala Arg Glu Cys Arg Leu Gly Ser Lys Glu Gly Arg Pro Phe Ser
    1625              1630              1635

Gly Val Thr Ala Cys Leu Asp Phe Cys Ala His Pro Tyr Arg Ala
    1640              1645              1650

Ile His Asn Met Asn Asn Gly Ser Thr Val Val Cys Thr Leu Thr
    1655              1660              1665

Arg Glu Asp Asn Arg Ser Leu Gly Val Ile Pro Gln Asp Glu Gln
    1670              1675              1680

Leu His Val Leu Pro Leu Tyr Lys Leu Ser Asp Thr Asp Glu Phe
    1685              1690              1695

Gly Ser Lys Glu Gly Met Glu Ala Lys Ile Lys Ser Gly Ala Ile
    1700              1705              1710

Glu Val Leu Ala Pro Arg Arg Lys Lys Arg Thr Cys Phe Thr Gln
    1715              1720              1725

Pro Val Pro Arg Ser Gly Lys Lys Arg Ala Ala Met Met Thr Glu
    1730              1735              1740

Val Leu Ala His Lys Ile Arg Ala Val Glu Lys Lys Pro Ile Pro
    1745              1750              1755

Arg Ile Lys Arg Lys Asn Asn Ser Thr Thr Thr Asn Asn Ser Lys
    1760              1765              1770

Pro Ser Ser Leu Pro Thr Leu Gly Ser Asn Thr Glu Thr Val Gln
    1775              1780              1785

Pro Glu Val Lys Ser Glu Thr Glu Pro His Phe Ile Leu Lys Ser
    1790              1795              1800
```

```
Ser Asp Asn Thr Lys Thr Tyr Ser Leu Met Pro Ser Ala Pro His
    1805            1810                1815

Pro Val Lys Glu Ala Ser Pro Gly Phe Ser Trp Ser Pro Lys Thr
    1820            1825                1830

Ala Ser Ala Thr Pro Ala Pro Leu Lys Asn Asp Ala Thr Ala Ser
    1835            1840                1845

Cys Gly Phe Ser Glu Arg Ser Thr Pro His Cys Thr Met Pro
    1850            1855                1860

Ser Gly Arg Leu Ser Gly Ala Asn Ala Ala Ala Asp Gly Pro
    1865            1870                1875

Gly Ile Ser Gln Leu Gly Glu Val Ala Pro Leu Pro Thr Leu Ser
    1880            1885                1890

Ala Pro Val Met Glu Pro Leu Ile Asn Ser Glu Pro Ser Thr Gly
    1895            1900                1905

Val Thr Glu Pro Leu Thr Pro His Gln Pro Asn His Gln Pro Ser
    1910            1915                1920

Phe Leu Thr Ser Pro Gln Asp Leu Ala Ser Ser Pro Met Glu Glu
    1925            1930                1935

Asp Glu Gln His Ser Glu Ala Asp Glu Pro Pro Ser Asp Glu Pro
    1940            1945                1950

Leu Ser Asp Asp Pro Leu Ser Pro Ala Glu Glu Lys Leu Pro His
    1955            1960                1965

Ile Asp Glu Tyr Trp Ser Asp Ser Glu His Ile Phe Leu Asp Ala
    1970            1975                1980

Asn Ile Gly Gly Val Ala Ile Ala Pro Ala His Gly Ser Val Leu
    1985            1990                1995

Ile Glu Cys Ala Arg Arg Glu Leu His Ala Thr Thr Pro Val Glu
    2000            2005                2010

His Pro Asn Arg Asn His Pro Thr Arg Leu Ser Leu Val Phe Tyr
    2015            2020                2025

Gln His Lys Asn Leu Asn Lys Pro Gln His Gly Phe Glu Leu Asn
    2030            2035                2040

Lys Ile Lys Phe Glu Ala Lys Glu Ala Lys Asn Lys Lys Met Lys
    2045            2050                2055

Ala Ser Glu Gln Lys Asp Gln Ala Ala Asn Glu Gly Pro Glu Gln
    2060            2065                2070

Ser Ser Glu Val Asn Glu Leu Asn Gln Ile Pro Ser His Lys Ala
    2075            2080                2085

Leu Thr Leu Thr His Asp Asn Val Val Thr Val Ser Pro Tyr Ala
    2090            2095                2100

Leu Thr His Val Ala Gly Pro Tyr Asn His Trp Val
    2105            2110                2115
```

<210> SEQ ID NO 161
<211> LENGTH: 2573
<212> TYPE: PRT
<213> ORGANISM: Unknown
<220> FEATURE:
<223> OTHER INFORMATION: dCAS-Dnmt3a-P2A-BFP

<400> SEQUENCE: 161

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30
```

-continued

```
Lys Val Leu Gly Asn Thr Asp Arg His Ser Ile Lys Lys Asn Leu Ile
         35                  40                  45
Gly Ala Leu Leu Phe Asp Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
```

```
Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
```

```
            865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
```

```
Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

Glu Gly Ala Asp Pro Lys Lys Arg Lys Val Asp Pro Lys Lys
    1370            1375            1380

Lys Arg Lys Val Asp Pro Lys Lys Arg Lys Val Gly Ser Met
    1385            1390            1395

Pro Ala Met Pro Ser Ser Gly Pro Gly Asp Thr Ser Ser Ser Ala
    1400            1405            1410

Ala Glu Arg Glu Glu Asp Arg Lys Asp Gly Glu Gln Glu Glu
    1415            1420            1425

Pro Arg Gly Lys Glu Glu Arg Gln Glu Pro Ser Thr Thr Ala Arg
    1430            1435            1440

Lys Val Gly Arg Pro Gly Arg Lys Arg Lys His Pro Pro Val Glu
    1445            1450            1455

Ser Gly Asp Thr Pro Lys Asp Pro Ala Val Ile Ser Lys Ser Pro
    1460            1465            1470

Ser Met Ala Gln Asp Ser Gly Ala Ser Glu Leu Leu Pro Asn Gly
    1475            1480            1485

Asp Leu Glu Lys Arg Ser Glu Pro Gln Pro Glu Glu Gly Ser Pro
    1490            1495            1500

Ala Gly Gly Gln Lys Gly Gly Ala Pro Ala Glu Gly Glu Gly Ala
    1505            1510            1515

Ala Glu Thr Leu Pro Glu Ala Ser Arg Ala Val Glu Asn Gly Cys
    1520            1525            1530

Cys Thr Pro Lys Glu Gly Arg Gly Ala Pro Ala Glu Ala Gly Lys
    1535            1540            1545

Glu Gln Lys Glu Thr Asn Ile Glu Ser Met Lys Met Glu Gly Ser
    1550            1555            1560

Arg Gly Arg Leu Arg Gly Gly Leu Gly Trp Glu Ser Ser Leu Arg
    1565            1570            1575

Gln Arg Pro Met Pro Arg Leu Thr Phe Gln Ala Gly Asp Pro Tyr
    1580            1585            1590

Tyr Ile Ser Lys Arg Lys Arg Asp Glu Trp Leu Ala Arg Trp Lys
    1595            1600            1605

Arg Glu Ala Glu Lys Lys Ala Lys Val Ile Ala Gly Met Asn Ala
    1610            1615            1620

Val Glu Glu Asn Gln Gly Pro Gly Glu Ser Gln Lys Val Glu Glu
    1625            1630            1635

Ala Ser Pro Pro Ala Val Gln Gln Pro Thr Asp Pro Ala Ser Pro
    1640            1645            1650

Thr Val Ala Thr Thr Pro Glu Pro Val Gly Ser Asp Ala Gly Asp
    1655            1660            1665
```

```
Lys Asn Ala Thr Lys Ala Gly Asp Asp Glu Pro Glu Tyr Glu Asp
1670                1675                1680

Gly Arg Gly Phe Gly Ile Gly Glu Leu Val Trp Gly Lys Leu Arg
    1685                1690                1695

Gly Phe Ser Trp Trp Pro Gly Arg Ile Val Ser Trp Trp Met Thr
    1700                1705                1710

Gly Arg Ser Arg Ala Ala Glu Gly Thr Arg Trp Val Met Trp Phe
    1715                1720                1725

Gly Asp Gly Lys Phe Ser Val Val Cys Val Glu Lys Leu Met Pro
    1730                1735                1740

Leu Ser Ser Phe Cys Ser Ala Phe His Gln Ala Thr Tyr Asn Lys
    1745                1750                1755

Gln Pro Met Tyr Arg Lys Ala Ile Tyr Glu Val Leu Gln Val Ala
    1760                1765                1770

Ser Ser Arg Ala Gly Lys Leu Phe Pro Val Cys His Asp Ser Asp
    1775                1780                1785

Glu Ser Asp Thr Ala Lys Ala Val Glu Val Gln Asn Lys Pro Met
    1790                1795                1800

Ile Glu Trp Ala Leu Gly Gly Phe Gln Pro Ser Gly Pro Lys Gly
    1805                1810                1815

Leu Glu Pro Pro Glu Glu Glu Lys Asn Pro Tyr Lys Glu Val Tyr
    1820                1825                1830

Thr Asp Met Trp Val Glu Pro Glu Ala Ala Ala Tyr Ala Pro Pro
    1835                1840                1845

Pro Pro Ala Lys Lys Pro Arg Lys Ser Thr Ala Glu Lys Pro Lys
    1850                1855                1860

Val Lys Glu Ile Ile Asp Glu Arg Thr Arg Glu Arg Leu Val Tyr
    1865                1870                1875

Glu Val Arg Gln Lys Cys Arg Asn Ile Glu Asp Ile Cys Ile Ser
    1880                1885                1890

Cys Gly Ser Leu Asn Val Thr Leu Glu His Pro Leu Phe Val Gly
    1895                1900                1905

Gly Met Cys Gln Asn Cys Lys Asn Cys Phe Leu Glu Cys Ala Tyr
    1910                1915                1920

Gln Tyr Asp Asp Asp Gly Tyr Gln Ser Tyr Cys Thr Ile Cys Cys
    1925                1930                1935

Gly Gly Arg Glu Val Leu Met Cys Gly Asn Asn Asn Cys Cys Arg
    1940                1945                1950

Cys Phe Cys Val Glu Cys Val Asp Leu Leu Val Gly Pro Gly Ala
    1955                1960                1965

Ala Gln Ala Ala Ile Lys Glu Asp Pro Trp Asn Cys Tyr Met Cys
    1970                1975                1980

Gly His Lys Gly Thr Tyr Gly Leu Leu Arg Arg Arg Glu Asp Trp
    1985                1990                1995

Pro Ser Arg Leu Gln Met Phe Phe Ala Asn Asn His Asp Gln Glu
    2000                2005                2010

Phe Asp Pro Pro Lys Val Tyr Pro Pro Val Pro Ala Glu Lys Arg
    2015                2020                2025

Lys Pro Ile Arg Val Leu Ser Leu Phe Asp Gly Ile Ala Thr Gly
    2030                2035                2040

Leu Leu Val Leu Lys Asp Leu Gly Ile Gln Val Asp Arg Tyr Ile
    2045                2050                2055

Ala Ser Glu Val Cys Glu Asp Ser Ile Thr Val Gly Met Val Arg
```

```
                2060                2065                2070
His Gln Gly Lys Ile Met Tyr Val Gly Asp Val Arg Ser Val Thr
        2075                2080                2085

Gln Lys His Ile Gln Glu Trp Gly Pro Phe Asp Leu Val Ile Gly
        2090                2095                2100

Gly Ser Pro Cys Asn Asp Leu Ser Ile Val Asn Pro Ala Arg Lys
        2105                2110                2115

Gly Leu Tyr Glu Gly Thr Gly Arg Leu Phe Phe Glu Phe Tyr Arg
        2120                2125                2130

Leu Leu His Asp Ala Arg Pro Lys Glu Gly Asp Arg Pro Phe
        2135                2140                2145

Phe Trp Leu Phe Glu Asn Val Val Ala Met Gly Val Ser Asp Lys
        2150                2155                2160

Arg Asp Ile Ser Arg Phe Leu Glu Ser Asn Pro Val Met Ile Asp
        2165                2170                2175

Ala Lys Glu Val Ser Ala Ala His Arg Ala Arg Tyr Phe Trp Gly
        2180                2185                2190

Asn Leu Pro Gly Met Asn Arg Pro Leu Ala Ser Thr Val Asn Asp
        2195                2200                2205

Lys Leu Glu Leu Gln Glu Cys Leu Glu His Gly Arg Ile Ala Lys
        2210                2215                2220

Phe Ser Lys Val Arg Thr Ile Thr Thr Arg Ser Asn Ser Ile Lys
        2225                2230                2235

Gln Gly Lys Asp Gln His Phe Pro Val Phe Met Asn Glu Lys Glu
        2240                2245                2250

Asp Ile Leu Trp Cys Thr Glu Met Glu Arg Val Phe Gly Phe Pro
        2255                2260                2265

Val His Tyr Thr Asp Val Ser Asn Met Ser Arg Leu Ala Arg Gln
        2270                2275                2280

Arg Leu Leu Gly Arg Ser Trp Ser Val Pro Val Ile Arg His Leu
        2285                2290                2295

Phe Ala Pro Leu Lys Glu Tyr Phe Ala Cys Val Glu Phe Ala Tyr
        2300                2305                2310

Pro Tyr Asp Val Pro Asp Tyr Ala Ala Thr Asn Phe Ser Leu Leu
        2315                2320                2325

Lys Gln Ala Gly Asp Val Glu Glu Asn Pro Gly Pro Met Ser Glu
        2330                2335                2340

Leu Ile Lys Glu Asn Met His Met Lys Leu Tyr Met Glu Gly Thr
        2345                2350                2355

Val Asp Asn His His Phe Lys Cys Thr Ser Glu Gly Glu Gly Lys
        2360                2365                2370

Pro Tyr Glu Gly Thr Gln Thr Met Arg Ile Lys Val Val Glu Gly
        2375                2380                2385

Gly Pro Leu Pro Phe Ala Phe Asp Ile Leu Ala Thr Ser Phe Leu
        2390                2395                2400

Tyr Gly Ser Lys Thr Phe Ile Asn His Thr Gln Gly Ile Pro Asp
        2405                2410                2415

Phe Phe Lys Gln Ser Phe Pro Glu Gly Phe Thr Trp Glu Arg Val
        2420                2425                2430

Thr Thr Tyr Glu Asp Gly Gly Val Leu Thr Ala Thr Gln Asp Thr
        2435                2440                2445

Ser Leu Gln Asp Gly Cys Leu Ile Tyr Asn Val Lys Ile Arg Gly
        2450                2455                2460
```

```
Val Asn Phe Thr Ser Asn Gly Pro Val Met Gln Lys Lys Thr Leu
    2465                2470                2475

Gly Trp Glu Ala Phe Thr Glu Thr Leu Tyr Pro Ala Asp Gly Gly
    2480                2485                2490

Leu Glu Gly Arg Asn Asp Met Ala Leu Lys Leu Val Gly Gly Ser
    2495                2500                2505

His Leu Ile Ala Asn Ile Lys Thr Thr Tyr Arg Ser Lys Lys Pro
    2510                2515                2520

Ala Lys Asn Leu Lys Met Pro Gly Val Tyr Tyr Val Asp Tyr Arg
    2525                2530                2535

Leu Glu Arg Ile Lys Glu Ala Asn Asn Glu Thr Tyr Val Glu Gln
    2540                2545                2550

His Glu Val Ala Val Ala Arg Tyr Cys Asp Leu Pro Ser Lys Leu
    2555                2560                2565

Gly His Lys Leu Asn
    2570

<210> SEQ ID NO 162
<211> LENGTH: 579
<212> TYPE: DNA
<213> ORGANISM: Unknown
<220> FEATURE:
<223> OTHER INFORMATION: Daz1-Snrpn locus

<400> SEQUENCE: 162
cgactagaga gcaggccgcc tggccgggcc cccaccctct cagccacaga gaagggagtc      60
cgggtgcatg tggaaggcgc acctcatgcc tcacgggccg gcccgtcagc catcaggaca     120
gtcccgctcc cccccccccg cccccaaata aatgcccgaa atccggtaca aaggacacag     180
cagtgaccag accacacgag agaatatccc tccccgtgga ataggggcagt gtgagcgtct     240 cgtaggctac agaaacaagc taggccagct gagagaacta gaacactcaa ggccagagaa     300
acggggccta cctacctaca gcagagccga gctgtagggt gcttggcaag acgctcaaat     360
ttccgcagta ggaatgctca agcattcctt ttggtagctg cctttggca ggacattccg      420 gtcagaggga cagagacccc tgcattgcgg caaaaatgtg cgcatgtgca gccattgcct     480
gggacgcatg cgtagggagc cgcgcgacaa acctgagcca ttgcggcaag actagcgcag     540
agaggagagg gagccggaga tgccagacgc ttggttctg                            579

<210> SEQ ID NO 163
<211> LENGTH: 274
<212> TYPE: DNA
<213> ORGANISM: Unknown
<220> FEATURE:
<223> OTHER INFORMATION: Gapdh-Snrpn locus

<400> SEQUENCE: 163
ctacgtgcac ccgtaaagcc gcgagtagct gggcctctct ccaagacgct caaatttccg      60
cagtaggaat gctcaagcat tccttttggt agctgccttt tggcaggaca ttccggtcag     120
agggacagag acccctgcat tgcggcaaaa atgtgcgcat gtgcagccat tgcctgggac     180
gcatgcgtag ggagccgcgc gacaaacctg agcattgcg gcaagactag cgcagagagg     240
agagggagcc ggagatgcca gacgcttggt tctg                                 274

<210> SEQ ID NO 164
<211> LENGTH: 199
<212> TYPE: DNA
```

<213> ORGANISM: Unknown
<220> FEATURE:
<223> OTHER INFORMATION: BDNF IV locus

<400> SEQUENCE: 164

| ctacaaagca tgcaatgccc tggaacggaa cctaataaaa gatgtatcat taaatgcgcg | 60 |
| gaactgactg gtaacgtgca ctagagtgtc tatcgaggca gaggaggtat catatgacag | 120 |
| ctcacgtcaa ggcagcgtgg agccctctcg tggactccca cccactccca caccgaggag | 180 |
| aggactgctc tcgctgccg | 199 |

<210> SEQ ID NO 165
<211> LENGTH: 253
<212> TYPE: DNA
<213> ORGANISM: Unknown
<220> FEATURE:
<223> OTHER INFORMATION: MyoD DE (DMR-5) locus

<400> SEQUENCE: 165

| ccacagcatt tgggggcatt tatgggtctt cctataaact tctgagacag taattttatc | 60 |
| ctgcttcttt cggccaagta tcctcctcca gcagctggtc acaaagccag ttaatctccc | 120 |
| agagtgctca gcttaaaacc cgtgactcac aacacagcca gttgggggaa ggggacagcc | 180 |
| gcctccaaac gtggcgccca gactcagctg ttcctgggtc ttctccggtt tctctagctc | 240 |
| aggcctaggg ctg | 253 |

<210> SEQ ID NO 166
<211> LENGTH: 543
<212> TYPE: DNA
<213> ORGANISM: Unknown
<220> FEATURE:
<223> OTHER INFORMATION: CTCF miR290 locus

<400> SEQUENCE: 166

| gttttgaggc tcatttgta aggtgcctta tacctttagc cccagcccac tttttttcc | 60 |
| ccctgctgta taaaattcag gtgtgagtac aattttctt tttaaagatt tataagtgtt | 120 |
| ctgtagctat cttcagattc acccaaagaa ggcattggat cccattacag atgattgcaa | 180 |
| gccaccatgt agttgctggg aattgaactc aggacctctg acttaaccac tccagcccct | 240 |
| gagtacaatt tttgaaaaat taccttgtgg gtctttatgc tgtgacttgg ccagtagatg | 300 |
| gcagtcttgg tccatggaaa tgtctaggac tctggatatt tttccttttc tgtggtcttt | 360 |
| actgatcttc aaacctgcta accagccaat ccccgtccta aattatctgc gtggaatcta | 420 |
| catcaaaccc agtgagctcc atcaaaggtt gagtgtttag gtctcaagca gaacaatttt | 480 |
| gtcaacctgc acttactggg cctcctgacc taagacggtc ccatgtaaca ggatgacctt | 540 |
| gag | 543 |

<210> SEQ ID NO 167
<211> LENGTH: 461
<212> TYPE: DNA
<213> ORGANISM: Unknown
<220> FEATURE:
<223> OTHER INFORMATION: CTCF Pou5f1 locus

<400> SEQUENCE: 167

| tctcacccctt gatagtttga gggatatgag caaattacac ggttatcaga aggtggccat | 60 |
| agtgacactg aaaattggcc cattggcttc aaagatttac caaagtaccg tccgtatttt | 120 |
| ctacctacgg tgtgctggag cctagaggac actagggggc gcgctgagct cgcggaagcc | 180 |

```
acccagagtc cttccaggag actcccttaa aggttgatca aattgttctt tgccaaactg    240
aatttatcat aaaaattata ctttattttg tattactttg tgtacatggg tgttttgcct    300
tcacagatgc gtctggtgca cctgagaagc cagaaaagag aacaggagtg aacaggtttg    360
tgggggctga cactcaaact cgaggactct gggaaagcat cgagtgctct taaccattga    420
gccatctctc cagcccatct gttttctttt gccggaggaa g                       461
```